US007595156B2

(12) United States Patent
Lee et al.

(10) Patent No.: US 7,595,156 B2
(45) Date of Patent: Sep. 29, 2009

(54) GENES FOR SYNTHESIS OF FR-008 POLYKETIDES

(75) Inventors: Sang Yup Lee, Daejeon (KR); Zixin Deng, Shanghai (CN); Shi Chen, Shanghai (CN); Ki Jun Jeong, Daejeon (KR); Xiufen Zhou, Shanghai (CN)

(73) Assignee: Korea Advanced Institute of Science and Technology, Daejeon (CN)

( * ) Notice: Subject to any disclaimer, the term of this patent is extended or adjusted under 35 U.S.C. 154(b) by 675 days.

(21) Appl. No.: 10/819,386

(22) Filed: Apr. 6, 2004

(65) Prior Publication Data

US 2005/0089884 A1 Apr. 28, 2005

(30) Foreign Application Priority Data

Oct. 23, 2003 (KR) ..................... 10-2003-0074035

(51) Int. Cl.
*C12Q 1/68* (2006.01)
*C07H 21/04* (2006.01)

(52) U.S. Cl. ........................... 435/6; 435/76; 435/69.1; 435/252.3; 435/320.1; 435/193; 536/23.2

(58) Field of Classification Search ................ 435/69.1, 435/183, 252.3, 325, 193, 6, 76; 536/23.2
See application file for complete search history.

(56) References Cited

U.S. PATENT DOCUMENTS 4,874,748 A 10/1989 Katz et al.
5,063,155 A 11/1991 Cox et al.
5,098,837 A 3/1992 Beckmann et al.
5,149,639 A 9/1992 Katz et al.
5,252,474 A 10/1993 Gewain et al.
5,672,491 A 9/1997 Khosla et al.
5,712,146 A 1/1998 Khosla et al.
5,830,750 A 11/1998 Khosla et al.
5,843,718 A 12/1998 Khosla et al.

FOREIGN PATENT DOCUMENTS

WO WO 93/13663 A1 7/1993
WO WO 95/08548 A1 3/1995
WO WO 96/40968 A1 12/1996
WO WO 97/02358 A1 1/1997
WO WO 98/27203 A1 6/1998
WO WO 98/49315 A2 11/1998

OTHER PUBLICATIONS

Fu, H. et al., Engineered Biosynthesis of Novel Polyketides: Stereochemical Course of Two Reactions Catalyzed by a Polyketide Synthase, *Biochem*., 33:9321-6, 1994.

McDaniel, R. et al., Engineered Biosynthesis of Novel Polyketides, *Science*, 262:1546-50, 1993.

Kuhstoss, S. et al., Production of a Novel Polyketide Through the Construction of a Hybrid Polyketide Synthase, *Gene*, 183:231-6, 1996.

Khosla, C., Harnessing the Biosynthetic Potential of Modular Polyketide Synthases, *Chem. Rev*., 97:2577-90, 1997.

Hopwood and Sherman, Molecular Genetics of Polyketides and Its Comparison to Fatty Acid Biosynthesis, *Annu. Rev. Genet*., 24:37-66, 1990.

Hopwood, Genetic Contributions to Understanding Polyketide Synthases, *Chem. Rev*., 97:2465-97, 1997.

Cortes et al., An Unusually Large Multifunctional Polypeptide in the Erythromycin-Producing Polyketide Synthase of *Saccharopolyspora Erythraea, Nature*, 348:176-8, 1990.

Donadio et al., Modular Organization of Genes Required for Complex Polyketide Biosynthesis, *Science*, 252:675-9, 1991.

Ikeda, et al., Organization of the Biosynthetic Gene Cluster for the Ployketide Anthelmintic Macrolide Avermectin in *Streptomyces avermitilis PNAS USA*, 96:9509-14, 1999.

Motamedi & Shaflee, The Biosynthetic Gene Cluster for the Macrolactone Ring of the Immunosuppressant FK506, *Eu. I. Biochem*., 256:528-34, 1998.

Schwecke, et al., The Biosynthetic Gene Cluster for the Polyketide Immunosuppressant Rapamycin, *PNAS USA*., 92:7839-43, 1995.

August, et al., Biosynthesis of the Ansamycin Antibiotic Rifamycin: Deductions from the Molecular Analysis of the *rif*Biosynthetic Gene Cluster of *Amycolatopsis mediterranei* S699, *Chem. Biol*., 5:69-79, 1998.

Cundliffe, et al., The Tylosin-Biosynthetic Genes of *Streptomyces fradiae, Ant. van Leeuwen*., 79:229-34, 2001.

Brautaset, et al., Biosynthesis of the Polyene Antifungal Antibiotic Nystatin in *Streptomyces noursei* ATCC 11455: Analysis of the Gene Cluster and Deduction of the Biosynthetic Pathway, *Chem. Biol*., 7:395-403, 2000.

Aparicio, et al., A Complex Multienzyme System Encoded by Five Polyketide Synthase Genes is Involved in the Biosynthesis of the 26-membered Polyene Macrolide Pimaricin in *Streptomyces natalensis, Chem. Biol*., 7:895-905, 2000.

Caffrey, et al., Amphotericin Biosynthesis in *Streptomyces nodosus*: Deductions from Analysis of Polyketide Synthase and Late Genes, *Chem. Biol*., 8:713-23, 2001.

Campelo & Gil, The Candicidin Gene Cluster from *Streptomyces griseus* IMRU 3570, *Microbiol*., 148:51-9, 2002.

(Continued)

*Primary Examiner*—Chih-Min Kam
(74) *Attorney, Agent, or Firm*—Boyle Fredrickson S.C.

(57) ABSTRACT

The present invention relates to the base sequence of whole genes involved in the biosynthesis of FR-008 polyketides derived from *Streptomyces* sp. FR-008. This base sequence comprises genes coding for ketosynthase (KS), acyl transferase (AT), acyl carrier protein (ACP), ketoreductase (KR), dehydratase (DH) and enoyl reductase (ER) domains, and genes coding for modifier enzymes, such as ABC transporter, cytochrome P450 monooxygenase, ferredoxin, thioesterase, sugar synthetic protein, FAD-dependent monooxygenase, 4-amino-4-deoxychorismate (ADC) synthase and ADC lyase. The gene base sequence according to the present invention can be used to increase the productivity of the existing FR-008 polyketides or produce new FR-008 polyketides, through modification of its parts.

4 Claims, 7 Drawing Sheets

OTHER PUBLICATIONS

Hu et al., Repeated Polyketide Synthase Modules Involved in the Biosynthesis of a Heptaene Macrolide by *Streptomyces* sp. FR-008, *Mol. Microbiol*., 14:163-72, 1994.

Aparicio, J.F. et al., The Biosynthetic Gene Cluster for the 26-Membered Ring Polyene Macrolide Pimaricin, *I Biol. Chem*., 274:10133-9, 1999.

Tang, L. et al., Characterization of the Enzymatic Domains in the Modular Polyketide Synthase Involved in Rifamycin B Biosynthesis by *Amycolatopsis mediterranei, Gene*, 216:255-65, 1998.

Haydock, S.F. et al., Divergent Sequence Motifs Correlated with the Substrate Specificity of (methyl)malonyl-CoA:acyl Carrier Protein Transacylase Domains in Modular Polyketide Synthases, *FEBS Lett*., 374:246-8, 1995.

Butler, et al., Impact of Thioesterase Activity on Tylosin Biosynthesis in *Streptomyces fradiae, Chem. Biol*., 6:287-92, 1999.

Tang, et al., Elucidating the Mechanism of Chain Termination Switching in the Picromycin/Methymycin Polyketide Synthase, *Chem. Biol*., 6:553-8, 1999.

O'Keefe & Harder, Occurrence and Biological Function of Cytochrome P450 Monooxygenases in the Actinomycetes, *Mol. Microbiol*., 5:2099-105, 1991.

Boihuis et al., Mechanisms of Multidrug Transporters, *FEMS Microbiol. Rev*., 21:55-84, 1997.

Janssen and Bribb, Derivatives of pUC18 that have *Bg*/II Sites Flanking a Modified Multiple Cloning Site and that Retain the Ability to Identify Recombinant Clones by Visual Screening of *Escherichia coli* Colonies, *Gene*, 124:133-4, 1993.

Sun et al, 'Streptomyces nanchangensis', A Producer of the Insecticidal Polyether Antibiotic Nanchangmycin and the Antiparasitic Macrolide Meilingmycin, Contains Multiple Polyketide Gene Clusters, *Microbiology*, 148:361-71, 2002.

MacNeil et al., Complex Organization of the *Streptomyces avermitilis* Genes Encoding the Avermectin Polyketide Synthase, *Gene*, 115:119-25, 1992.

Mazodier et al., Intergeneric Conjugation between *Escherichia coli* and *Streptomyces* Species, *J. Bacteriol*., 171:3583-5, 1989.

Altschul et al, Iterated Profile Searches with PSI-BLAST—A tool for Discovery in Protein Databases, *Trends Biochem. Sci*., 23:444-7, 1998.

Pearson, Rapid and Sensitive Sequence Comparison with FASTPand FASTA, *Methods Enzymol*., 183:63-98, 1990.

Robinson, J.A., Polyketide Synthase Complexes: Their Structure and Function in Antibiotic Biosynthesis, *Philos. Trans. R. Soc. Lond. B. Biol. Sci*., 332:107-14 (1991).

Hopwood, D.A., Genetic Engineering of *Streptomyces* to Create Hybrid Antibiotics, *Curr. Opin. Biotechnol*., 4:531-7 (1993).

Yuan and Zhou, The Killing Activity to Mosquito Lervae of a New Antibiotic Produced by FR-008, an Intra-Specific Fusant of *Streptomyces Hygroscopicus Var. Yingchengensis, J. Huazhong Agricult. Univ*., 9:209, 1990 and English Abstract.

Liang and Zhou, *Chinese J. Biotech*., 3:130-6 (1987), English abstract only.

Yuan and Zhou, *Chinese J. Biotechnol*., 7:142-7 (1991), English abstract only.

SEQUENCE LISTING

```
<160> NUMBER OF SEQ ID NOS: 28

<210> SEQ ID NO 1
<211> LENGTH: 138203
<212> TYPE: DNA
<213> ORGANISM: Streptomyces sp. FR-008

<400> SEQUENCE: 1

ccaatggcga gatggccggg ggagtacggc atgagggccg gggggcacga tgggggggcgg      60

cgatcgtggc gggagggacc cagcgggggg gtcgtacctg ttccacgcgg ggcgcacggc     120

acggggcgcc tggtgggggg acgagacgtc cgtggggaag gaggcgtacg tcgaccgctt     180

caccgcgctg taggggctct cccgcgaaac ggcgcgagac cgagtgtttc agcggccgga     240

tcgacgcgga ccggctgacg cggctgctga ccctgttggg cgcccggccc ggccccggga     300

cccggttcgc ggtgtgcgga ccgtacggcc tggtggagac ggtccgctcc acgctcgacg     360

ggtgggggc cgagccggac accgtccgtt tcgagctgtt ctccaccgac ggggcaccgc     420

cggagccgga gcccgaggcg cccgccgtcc gcaggggccg ggtcaccacc gtgctcgccg     480

ggcgcaccgg cacggtgacg acggcaccgg aggacaccac gctcctcgac accgtgctgc     540

ggtgccgcgc ccactcacgt acgaggtcct cggttacctg gacttcaggc tgtgtccgcc     600

gaagccgctg cgccggtcgg agccgttgtt ctgctcctgc caccacgcgt cgaactcggc     660

ctggcccatc gcggaccagt cgggggtctc ctcgacctgg gcactgccca tccggcgggc     720

gagtcccacc atggccgtgc cgacgggacc ccgagccgcg tggtacccct ccaggatctc     780

cttccagctc tccccggcca cccaggcggc ttccagcgcg gtggcgtcct ggagtgcctt     840

cacactgccg gcgccgaggt gcggccgggc cacgctcgcg gcgtccccga tgagcaccat     900
```

-continued

```
ccggtcggtg gcgtagtgcg gcacgtccag gtcgtagatg ggctggatga aggtggtctc    960
ggccggggtg gagaggagct tggcggccca gaagggcggg aagtgctctg ccaccagggc   1020
gcgcaggtgc tccgtcagtt ccgcgttgag ccggcccggc ggcagggagg tgggggtccg   1080
caggtcgggg tggaggccgt cgatccgcgg gggtgccgtg tagagcaccc agttgaggcg   1140
gtggccgccg gagccgtccg ggatgcggta ggccatgcag tggccgccgg ggaaggtgat   1200
gttgtgcgcg tcgagcccgt ccgagggaag accggagacg tccggggagg tcccgcgcca   1260
gccgatgtag ccggcgtacg cggcgccggt gcccgggtac atggcctcac ggacgacgga   1320
gcggtagccg tcggcgccta tgaccaggtc gaagcgttcc ggctcgccgt cggcgagacg   1380
taccgtgacc ccgtcggcgt cctgctccac cgcttccacc ttggcgcctg cccgataggt   1440
ggcggtctcg ggcacccggc ggcgcaactc gctccacagc gaaccccagt tgtaggcccg   1500
gaaggggaac ggctgggtgc cgatggctct gccgtgctcg gcgtcgccgt cgcgcacgct   1560
ccacaccctg cggttcagcg gcgcccacgg catctcgtcc gccatgtaac cggcgtcgcg   1620
cagttcggcg taccgggcgt cgtggacacc gatgcccact cccctgtcgc ggagtcgcgc   1680
gtcggcgcgt tcgaagacgg tgatcctctc cgccccgccg cgcgacgccg ccaatgcggc   1740
ggcgcatccc gcgatactgc cgccgacgac ggcgacactg cctccacgca tactgactct   1800
ccacttcttc gcgtgctggt gccctttccg gactttcccg caggggcgcg tcggaacggc   1860
gatccgccgt ccccgacttg tccgcccttt cctgcggtga ggacacccgc gaaaccctat   1920
cgaggtgggt gccgggcatg tcgagggcat tcgccggtcc gtcaggccgc cctggacgca   1980
ggcgtatacg cggggcctgg cgcattcacc gttcccggcg cggaagggcc ggcctctccg   2040
gaccgtacac acggttcgcg acgccgcgat gcacacgaga tcatttcttc ccgcatccgc   2100
tttccccaca tgccgtgcag ggaaatgtcc gggtgctgcc gaaaaggaga gcgggtgggc   2160
gaatggcgaa tgccgggcgg catggaggaa atgggcgatc gaccgtccgc ccgaggactc   2220
ctgcgcgagc ggcggaacgg agcgccccgg cgccgccgcc ccgtcagagc ggggagccgg   2280
gaagtgcctg gtagatctcc gcgagccggg tcaccgagtg atgggccgcc gggaactcac   2340
ggtcgtcgat gccggtgacg ggacggaccc cgacgcggcg ttggtcgcga agaccgcctc   2400
gactgagtcg aggtccgcga ggccgaccag ttcggtggga ccgtcggtgg ccccgccgca   2460
gcagctgccg ggtcgtgccg gccagcacct ccccgccggg ccagaccacc tcgccgtcgc   2520
gcaccaggcc gacgttccag gtgccgccct ccaggatgtc gccgtcgggg cccgtgaaca   2580
gcacgtcgtc gtaacccgcc cgttgggcct gcctgcgcag ccgcagggtg ggacagaggc   2640
cgaccgactt cacctcggga aggtcgcggc ggtggaccac cgaacgtacc cgcagcggac   2700
caggggggctt gtcgggggcg ggccgggagg tcaccaggat gcccggccgg gcgtcggcgg   2760
cgatgttccc caggttcagc gccgggtcga agacggtgac acggacggtg gcccggccgt   2820
ctgttggtgc cgcccggcgg gcgagcttcc gcacccggtc cgggtcgagc gccgcgtcga   2880
agagggtccg gcagtcgcgg atgaggcgtt ccaggtggag gtcgagcccg cgcacccggc   2940
cgttctcgac gagcagcgtg gtgaaatggc cgtagttggt gagggcgagc gaggccagcg   3000
cctcgggccc ggcgggttcc ccgtccagtt cgatcatgac gtcaccctgt cactgtgacc   3060
gccgtaccgt gcgcggagcg cgcgacgggg acgagcgggg gtgcggaccg gcggccgggc   3120
tgccgccggc ggggcacacg gtgtacggat cacttgatga agtcctcgac gaccttcggc   3180
ggccaggtgc cgaccttgag gacgcccatg gagtaggcgc gggagacgag agcggcacgg   3240
ttgggcacct tgagcttccg cagcagcccg gtgacgtggt actccacgcc ctggcggctg   3300
```

-continued

```
aggtagaggc gggaggcgag cgggatggtc gagaccccgg cggctatgcc ctccaggatg   3360
cgtgcgtcga tctcgctgag gagcttcttg cggggcgcca tgacgtccgc gtccccggcc   3420
tcctcctccg cggcgttcat caccacgagg atcgcggcca cgtcgggcgt acggccaccg   3480
cgtaccgcga gcgcgttcag cggcagcgtg gacgccgtgc gttcctggtc gaccgcgatg   3540
acctcggtgg cgaagcggtg ccgcttgccg tccagcatcc gcgcgaactg gtgcatgagg   3600
ggctgctgga cgctcgggtg gacgaggtcg cagaagcggc tgccgcagag ttcggaggac   3660
gagccgccga agcggcgctc gaactcctgg ttgacctgct ggatcgtgag agacgggtcg   3720
aggcaggcga cataggcacc ggcccggtcg aacccgtccg cgagaacggc ggcccgttcc   3780
ggcgagccgg ccgggtcggc cgccggcgcg ggatccatga gcgtgctgtg gggggtggcg   3840
ggcatcaagg aactcataac ctttcatcgt ttcgcattac gggggtgggg tggcgcggcc   3900
cgcgctcagg aaaaggcgac cgcgcccagg gcccttgagt aagggccagc gacgagaaag   3960
aagatgtttt ggatcctacg aaagcggcta tcggcggtca acgcggtcca gggctgaccg   4020
gccaatactg tggtagcccc ttcggtaggt acggtcccgt accgaagagg ttcgggcggg   4080
gagggttcgg tgtgcgtacc tcaccgcccc gcaccgcgtc cacctgcgaa gaagggtcga   4140
actcgggcgc cgttccccgc cccgggggcc ggacggccct agccgtcccc gcaccgtggc   4200
cccgcacacc gcggaaatgg tgacgaacgt tcatccagat ttcccggccc ggggcgcaaa   4260
cgacattctg gggggacgccg gatgtcctgg ccgcaccatg gccggaaaac aaggacgccc   4320
ggggtccttc cgcgaatatg cggcggaagg agcccgggcg tttccctcgg cgcgtatcag   4380
tcgccggtgc cggcgtattc cgcgcgggag aagaggacga tcagttcccg gcggccggag   4440
atgcccaggc gccggtaggc gtgggtcagg tgcttctcca cggcgcgcga gctgaccccg   4500
agggcgccgg cgatctcctg gttggtcagc ccccggcagg ccagccccac cacgcggcgc   4560
tcggtcgggg tgagcacgtc ctccggtgtg gccggcgggc cggagcgatg accggcaccc   4620
cgggccgccc gttcggccag cccgggggcg ccgcacgagg tggccagggt ggcggcctcc   4680
cgggcgagcg cctcggtctc ggcgccgccg cccaggcgtt cggcgagggt ggacagggcg   4740
cgggccagtt cgagctggtt ggcggagcca cgcagcacgg tgacggcctc gcgcagcaga   4800
ccgatgcccc ggccgccgtc ctccaggcgg ccgagcagcc gcagcgcgcg gcccaccccg   4860
acgggggcgc cccactgctc ggcccgcgcg tactcctcct cggcgaggct ccgggcggtg   4920
cggatgtcac ccaggcggcg gtggacgccg acggcccagg ggcgccaggg gaagagcacc   4980
gggttgtgcc agccggcggc ttcgagctgg cggccgcagg agtgcagcga gtcgagggct   5040
ccggtctggt cgcccgcggc gatctcccgg gtggcctcca gcaggcgcag gatcccggtg   5100
agggtcaggc cctgcggcct gatgcggctc gcgcgccgca gcaccttctc ggcgagcgag   5160
gggtcgcggg actccagcgc gacgatcgcg tgcgtcatcg tcgccgcggt gtccaggccc   5220
tggtgggcgg gctccgtcat cccgagggcc gtctcggact gctcgcgggc ctgggcgagc   5280
cggccgcgcc cgaggtggac gagggcctgc tcgatgtgga ccagggcgtt ggcgggggtg   5340
gtaccccgct cgttggcacg gtgctcgacg gcgagccagg agtcgacggc ctccaccgag   5400
tcggcggcga tcatcgtgat gatcgccagc gggagggtgg agtggatgcg ggcggaggtg   5460
gcgggctcgc ggtccaggac gcgcccggcg aggcgcacca cctcggaggc gggcaggtga   5520
cagccgaggg tcgcggcacc gagcagcgcg atcgtcagct cccgctcgcc tccggtgtcc   5580
accgggggct cggggcccag ttccttcaac cggtgcgccg aggcggcgag ttcgtggggg   5640
```

-continued

```
tcctcgtggc cgcagtggcg cagcctggct tccagacgga gcgcgagatc gcggtcggtg   5700
ccggtgagcc cgtcggcggg cccgaggtcc tcggcggcct ggcgcagcag gtcgacggcg   5760
gtgagcgggg cggggcccag cgcggtcggg gagatgcgca gggcggcgac ggcccggtcc   5820
cgtggttcgg ggagcagggt catggcctgg gcgatgtggc gttcgcaggc gagtgggtcg   5880
aaccctctct ccgcggtgcc cagttcgacg aggaggcggc cgcggccgac gccggcggcg   5940
gggctgtcca gcagggcgcg gcacaggtag ccggcggcgg tgtcgggggc gccgcggcgc   6000
agcgcggtgt cggcggcggc gcgcaggacg tcgacggccc acggctggcg ccgggtgacg   6060
acggccatga gctgggcggc gacctgttcg gccggggagc cggcggcgta gaggagggcg   6120
gcggcctcgt cgtgcatccg ctcccgctgg accatggtga gggtggactc ggcggcgtcg   6180
cggacggacc ggtggatgaa gcgcggttcg tcgggggcgg cgagggcgcc gagcgcgccg   6240
agggcgcgca gggcccccgc gtagccgatc gagtcgagcc cggccagccg ggccagggtg   6300
ggcgcgtcgc tctgttcgcc gaggatggcg atggcggcgg cgaggtcgcg gaccggggcc   6360
ggctgggtgc gcaggatgct ggcgagccgt tcgcgcagtt gggaagggcg cagccggcgt   6420
gcggtctcgg cgtgttcggc gagcgggcgg cggccgagga agccggtgcc gacgaggatc   6480
gacagcagga agagcgggtt gccgacggac gcctcgtggc aggcctggac gaactcgtcg   6540
tcgcccgcct cgccgaagtg ctcccggacc agctcgtggg tggccgtcag gctgagggag   6600
gcggggcgca gggtttgggt gccggcctct cggatctcgc gggcgagggt gtggtggctg   6660
cgggggtccc cgtcgcgcag ggcgcagacg acgacggccc gcagcccgtg cagccgcttg   6720
gcgaggtagg tgagccagcg cagcgagggc acgtcggacc actgcaggtc gtcgacgagg   6780
atgagcaggc ggctgtcggc gctcacgttg gcgagcagcg agagcagtcc gtgcagcacg   6840
gcctcggtgg cggcgatggc ctggtcggcg ccgggcgggg cggcgtcgtc ggccaggacg   6900
tggcgggcga aggaggcgtg cgcgtccatc cagcggtccc gggcgtcctc gggcgagtcg   6960
ccgagcagcg tctcgaagag ctgccgtacg actccgaagg cgaagtcctg ttccatgggg   7020
gccgcgtggg cccgcagcac ccggacgtcg tcccggtcgt cggccaggca ggacagccgc   7080
tgcaggaggg cggagcggcc gatgccgagg gggccggtga ggaggacgag ggaggacctg   7140
ccttcggtcg cggcgcccag ggcggcgtcg accagggcga tctcggtggt gcgctccagc   7200
aacatgcgat cagctgccct ccgcttcttg tacgagtgcg cgcagttcct cacgtccgcg   7260
gatgcggagt ttgcggtaga cgccgctgag gcgcagctcc acggcgcgcg tggtcacggc   7320
gagttccgtg gcgatctccc ggttgcccag gccctgggcg gcgagggccg cggtctcccg   7380
ttcgacggcg gtcaggccgt gccagacggc cgcgtcgtgg cccggggcct tcgcggtccg   7440
ccgaccggtc agcaccgccg ggcgcgggcc ggggggcctg gccaccgcgg aggggacgtg   7500
cggaccgggg ggtggggcga ccggcgggag caccgtggcg gccgggccga gggcgacggc   7560
ggtccggcgc tcgttctcct cgcgttcggc ggcggccagt tcgatgacgg cccgggtgta   7620
ggcggtgcgg gccgatgccg cgctgagcgt ggtgacggcg gcacggaggt tttcgacccg   7680
gttctcctcg gtgacgacgg cgaggctgag ctgggcgcgg ccgagcgggg cggcggcgcc   7740
ccagcggcgg gcgaggcgga cttcctcgtg gaccagccgg gcggcctcct cggtgtcgcc   7800
gagggtgtgg gcggcctcgg cggcgaggga gcgccagggc tggacggccg ggttggcgca   7860
gccgtgccgc aggagccagc gaccgcaggc gcggaagtgt tccctggcct ggtggggctc   7920
gtcgtccgtg cgggccagca ccccccgggc gaagagcagt tgggcggtgg tggcgctctc   7980
gtgggcgagc ggcggcagcg gccgggcggc ggtctcgcgg gcccgttcgg tgtggccgtt   8040
```

-continued

```
ctgcagatcg gtgatcatgc tcagggcgag ccagtacggg aggaagagcg ggtggaggcg   8100
gtccagcggg agttccgcct gggcggcggc caggtcacgg gcggcggcgt cggggcggcc   8160
gtggcggatg tgcagctcgg cgcggacggt gaggatgtgg gcgaccgaga tcgccgcgcg   8220
ctcccggtgg gactcgtcga gcagggcacc gaggtggttc tccgcctcgt cgccgtcgtc   8280
ggtgagcagg agggcgcggc agccgagcag ccggggtacg acgaggagcg ggcggccggt   8340
ggcggcgggg acgaaggcgg agcgggcgag tctgcgtact tcctcgcggt ggacgccggc   8400
cacgccgtgt tcccaggccc agacccccgc gacggccggg ttgtgcaccg cgtcgggcag   8460
ggcggggacg gggaggacgt cgaggtcggc gtcgtcgtgg cggaggaagg aggcgacgcg   8520
gcacaggacg gtcagttcgt gccgttcggc gacggccggg tcctcgtccg gcccggcggt   8580
gtccggtcgt cctgcggcct cggggccggg agagcggggg gcgtcgtggg cgcggggggt   8640
gccgggaagg tccggcgcgg cggatcttct accgtccggc ccggtggcgc cgggcggggt   8700
gcccgcgtag gggcggtgag ggacgaggtg ggtgcgggga gtcgaggcgg gctccgcctc   8760
gggcggcacg gccggggcgc cggtcgggcc acgtcgtggt tcgggggcgg ccggggccga   8820
gtcgatggct ccggcgaggg cgtggcgggc cgcgcgggtg tctccgccga ggaggcacag   8880
gtcggtggcg cgggcccgca gtccggcgcc ggggccgggc cgggtggccc ggatgagccc   8940
gcccagccgg cgttcggcgg ccgtgggggc ggtgaccatc tccacggagg ccagctggaa   9000
ctcgatccgg gcgcggtcct cggcggccag tggttcgtcc agggcgcgcg ccaggtaggc   9060
gacggccagg tcgcggcggc cgccgcgcag cgcggaggtg aagccccgcc gcagggtgtc   9120
gacggcccag gggtcgccga cggggcgggc cagcagcagc aggtcggcta tgccctggtc   9180
gtcggcggcg acgcgctggg cgagcccggc ggcgcgtgcg tacagctcgg cccggtccgc   9240
tgcgggcatc tcctccagga cgcgggcgcg tacgacggcg tcctggaccc gggggtggcc   9300
gtcgcgcagg gtggtcaggc cgctggccgc cagggcggcg cgcaggcggg actcggagac   9360
ggagtgcggt ccggcgagcg tgcagacgag ggggaagtcg aggaggtcgc cgcagacggc   9420
gagggcgcgc agggcgtcga cggcggccgg gtcgcgcagg tcgctgaggg cgcgggtggc   9480
gtggtcgccg acgacctccg cggtcagggc gcgcaggggg tcgatccggt cggcccgggg   9540
gctgtacccc gcgcgggcga aacggtccag cacgtcgtgg acgacggccg ggatgccccg   9600
ggtcgcctcg gcgagggcct cggtgaaggc ggggtccccc ggggcgccga aggcccgcag   9660
gacggcggtg gcggtgccgc cggaggtgag gggcggcagc gccagctcga tggtggtggc   9720
cagtccggtc agggggggtgc cgacgctcca ctcgggccgg gtcagggcgg tgccggtggt   9780
gctggtgagc agggcgaccg gggcgcgggg cagccgccgg gcgagggctt ccagccagcg   9840
cagggaggcc gggtcgagcc actgggtgtc gcgtaccacg agcagggtgg gccggtcgcg   9900
gacggcgttg agcaggccgt tgaggcccgg cagcccgccg ggctgctcgt cggtgaggaa   9960
gaggcgcggg gcgagtgcgc ggttctcctc cgcgaggagc tgggccacca cgccgtaccg  10020
cacctcgtgt tcggcggggg tggcgtgggc gctgaggacg cgcagtccgg cgtcggtggc  10080
gtacgcggcc gcccagcgca gcagatcgtt ctggccgagc cccggttctc cggtcaccgt  10140
caccaccgcg ggacggccgg atccgagctc gccgatgacg gcggagaggg cggccagttc  10200
gcggtcgcgc tccaggagcg ggagctcgat gggcggcatg tgaagatcat acatttgcgc  10260
agtgcagcag gtgggcgtct gtaacccact gttcttccta tggatttctc cgcttcgcat  10320
gtcccggccg cctctccgca gccggccggg cggtggcgcc ggcctcgcgc agggcctcgg  10380
```

-continued

```
tcagatcgcc ccggcgggcg actcccagtt tccggtagac gctggtgagg tggagttcca  10440
cggtccgcac ggtgacgaag agggattccg ccacttcgcg gttgccggcg cccgaggcga  10500
ccagcccggc cacggtgcgc tcggtgccgg tgagcatgtc cagcggtgag gcggtgacct  10560
cgcgcatccg tccgccggcc gcgatcagct cgtcgcgggc gcgccgggcg agggcgacgc  10620
acccgcaccg ccgggccagc ccgacggcct cccgtagatg ctcccggccc tcccgcacgg  10680
ccccgtcctc caccagggcg cgtcccagca gcaacaggcc gcgggcgtgc ccgctccgcg  10740
cgggcgagtc cgccagcagg gcgaccgcct cccgcagcgc cccggtgcgc gccgtgccgc  10800
gcgccgccgc gccccgggcg agcgcggcgt accccagggc ccggcgggtg ccccagcgtt  10860
cggcgagccg ggtgccgtgc gcggcggccc gccccgcctc ctcgccgcgt ccggcctcgc  10920
ccagcagaca ggccgtctcc agccaccacg gcgcgaggac cgggttggtg agtccggcct  10980
ccgccatcga ggcgccgcag gacccgaaga cctgcagggc tccgtccagg tcgccgtcgg  11040
cggcaagcgc ccggccacgc gccatcaggt accagtggta ctcccagacg aaccggtcca  11100
ggtgggggcg tttgatggcg tccagcgcct ccagcgcgcg ccccggatca ccccgctcgg  11160
tgaggacgga ggcgtacgcc gtgtgcggca tcgtggcggt gtcgccccag cgttcctggc  11220
cgaggatctc cagcgcggtc tgcgcgtcgg ccatcgcgtc cggcaccgcc ccgttctcca  11280
ggcggaacag cgaccgggtg gagagcgcga gcacgtacgt ccagaccgcg gcggtgtcgc  11340
cgctgccgcg cagcacggtc tccaggacct cctcggcggc ctcgttctcg tcggccagcg  11400
acagggcgag cgaggtgggc agcagtgacc agacgcccag cggcaccccg ggggcgcgca  11460
gcgcgcggcg ggcccggccc acggtctcct ccgctccccc gccctcggcg gcggagagca  11520
cactcagcat ggcgagttgc tgacgctggg cgggggtgtc cccggctgc ggggtgaggc  11580
cctcggtccg gcgcaggatg tcgggcaggg tggccttctc gtcggagccc acgatcagca  11640
gggccgactc cgtgagggtg cgcagttcgc ggtcggcggg ttcgggctcg ggacccagct  11700
cggcgtcgag ggcgtccagc gcctcggtga gggcccgggc accgtccggc gactgctgca  11760
cggcgaggca ggtcaggccc agctgaaccg ctgtggcggc gcgggcgcgg acgtccgtgg  11820
tcagggagtg ggcctcgtgc agcagggtca ccgagcgggc cgggtcggtc tcggccagcg  11880
ccttgccgag ccgggagagg acgtcggggt ccttcggctc ggcctcgcgg acgcgctcca  11940
ggtagcgggc ggcggcctca caggcgccgc gctgttcggc ctgggcggcg gcgtcccgga  12000
gcacggagac cgcccagtcg tcgggggtgc ccgggaccag cagcagctgc gtggcgatct  12060
cctcggggga ccgtccgacg tcgctgagga gccgggcggc gcgtctgcgc aggacggcga  12120
cgcccgacgc gccgacggcg tcgaggaccg cggcgcgcac caggtcgtgg gagagctcca  12180
ggtggccggg gtggatcagc ccggcgtcgc gcaggatctc cacggcctcc tccacgtgga  12240
cgacggagac cctgccgagg gcggccaggt acgtccggtc ctcgtcgccg agcacggcca  12300
cggcacgcgc gacctggcgc acccagtccg gctggtgttc cagcacaccc cggacggagg  12360
cggcgacgac cttcccgccg gcctgggcga ggcgtgccgt cccggtgtcg tcggggccca  12420
gtccggcgga gcgcaggtcg cgcaggagcc ggacgatctc cagcgggctg ccgccggtca  12480
cggagaggag gcggccgacg aacgacggca gggggtcctg ctccgggaag gagtgggcgg  12540
tcagctccgc cacctcggcg gtgtccagcg ggccgagccc gagtgaggcc ggcaggtggt  12600
gggcgaccag gtcggcgagg gcgtcgggag cggtgaggcc ggtgccggtg cggtgggcgg  12660
cgacgacgag cagcggcagg ccgtccgcgc ggcgcagcag gaagtcgagc cagcgcaggg  12720
accgctcgtc gcaccagtgg acgtcgtcga ggacgagcac caggggggccg tccgccatga  12780
```

-continued

```
ggttggccgc gagccagtac aggccctgga ggacggagaa ggtgctgccg gggtcggcgt  12840
ccagctcccc cgggtcggcg gcgagggcgg gcagcgcgcg ccgggcgccg ccgacaagga  12900
gcggcgaggt acggcccttg cggccggtca ggccgagtcc gccgaacagg gcgcggaccc  12960
cgctgtagcc cgtggcgacg tcgacggcgc ggcaggagcc gtacagggtg gtcatgccgg  13020
cgaggggggcc gtcctcggcc agggcggcgc gcagcagtgc ggtcttgccg attccggcgg  13080
gaccgtccag gagcaccagg cggggtcttc ccgcgcgggc ggcgtccgcg tgccgggcga  13140
ggacgtcgag ctggtgggcc ctgccgacga ggggcggggc cgggggcacg gcacgggacc  13200
ggtgaggcac agggctctcc ctcgcgtcgg acggggccag ggacggcggc ccggcggaac  13260
cggaacggcc cggggcggcg ccccgggacc ggtcacctgc ccaccggagc cacatctacg  13320
cacacccggg tggccggcgc agcggtccgg cgccgaatct aaggatttcc ccggtgccgg  13380
acgtgagatc aagtggtggt gcggtcgggg ccgcccctgt ccggcccggc cggcgggcgg  13440
catccgccac cgccccgcgc ccgtccgcgc gtgaccggcg ggccgcgacg actgtcgccg  13500
tcacttcgtg aaagggctcc catggactcc gccgcccggc cgatcctctt cgtcagtctc  13560
cccgagagcg ggctgctcaa cccgttgctg gtgctggccg gggagcttgc ccggcgcggt  13620
gtgccggacc tgtggttcgc caccgacgag caccggcgcg aggaggtgga ggcgctctcc  13680
gacgtctcca aggtgtcgtt cgcctcgctg ggcgaggtgg tccccgaact gtcggcggtg  13740
acctgggacg acgaggtgta ccgcgaggtc acccagtcct cccgcttcaa ggcccaccgc  13800
gcggtcgtcc ggcagtccta ccggcccgcg ctccaggcgc gcaagtaccg cgagctggag  13860
caggtcgtcg acgaggtccg gccggcgctg atggtcgtcg actgcgtcgc gggcttcggc  13920
gtcgacctgg ccctggcccg gggcatcccg tacgtgctga acgtgccgtt cgtcgccagc  13980
aacgtgctga cctcgcacaa cccgttcggc gcctcgtaca cccccaagag cttcccggtg  14040
cccaactcgg ggctgcccgc gcggatgtcg gtgcggcaga agctggccaa cacgctgttc  14100
aagtggcgga cgctcggcat gttcctgcac ccggacatgg cggcactgct gcgcgaggac  14160
gccgcgatac gcaaggaact gggcatcgcc ccgccgaacg ccatgacccg ggtcgacgag  14220
gccgccgccg tggtgtgctc ctccgtcgcg gaactggact accccttcga catcccggac  14280
cgggtgagcc tggtgggcgc cgtgctgccg ccgctgcccg aggcaccgga cgacgacgag  14340
gtcaccaggt ggctcgacgc gcagtcgtcg gtggtctaca tgggcttcgg caccatcacg  14400
cgcctcaccc gcgaggaggt cgcggcgctg gtggaggtgg cccggcggat gtccggcacc  14460
caccagttcc tgtggaagct gcccaaggag cagcagcacc tgctgcccga ggccgggtcg  14520
ctgccggaca acctgcgggt ggagagctgg gtgccctcgc agctcgatgt gctggcccac  14580
ccgaacgtct ccgtcttctt ctcgcacggc ggcggcaacg cctaccacga gggcgtctac  14640
ttcggtaagc cgcaggtcgt gcggcccctg tgggtggact gcttcgacca ggcggtccgc  14700
ggccgcgact tcggcatcag cctgaccctg gacaagccgc acaccgtcga ccccgacgac  14760
gtggtggaca agctgacccg ggtcacctcc gaccccgcct tccgtaccga ggccgaacgc  14820
ctgggcgccc tgcagcgggc ggccggaggc cgtgcggccg ccgccgatct cgtgaccggc  14880
ctgctcccgg cggcatgaca gcggccgcgc ccgaggccgc ctgacccatc gaccgacagc  14940
agcgaggacc ccatggcctt cacccatccc gtctcccggc ccgctctgga cggccgggaa  15000
ctggagtacg tctccgacgc cgtctccggc ggctggatct cctcccaggg accgtacgtc  15060
cggcgtttcg aggaagcctt cgccgagtgg aacggcgtgg cgcacggggt ggcctgctcc  15120
```

-continued

```
tccggcaccg ccgccctcac cctggcgctg cgcgcgctga acatcggccc gggtgacgag  15180
gtgatcgtgc cggagttcac gatggtcgcc tccgcgtggg cggtgaccta caccggcgcc  15240
accccggtct tcgtggactg cggcgacgac ctgaacatcg acgtcacccg catcgaggag  15300
aagatcactc cgcgcacccg ggcggtcatg ccggtgcacg tctacggccg gcgctgcgac  15360
atggacgccg tgatggacct cgccctgcag tacaacctgc gggtggtcga ggactcggcg  15420
gaggcgcacg gggtccgccc ggtcggcgac atcgcctgct tctcgctctt cgccaacaag  15480
atcatcacgg ccggcgaggg aggcgtctgc ctcaccgacg atccccggct cgccgaacag  15540
ctggcccatc tgcgggcgat ggccttcacc cgcgaccaca gcttcctgca caagaaactg  15600
gcctacaact accggatgac ggccatgcag ggcgccgtcg ccctggccca gaccgagcgg  15660
ctcgacgaga tcctcgccac ccgccgggag atcgaggccc gctacgacgc ggggctcaag  15720
gacctccccg gcatcaccct gatgcctgcc cgcgacgtcc tgtggatgta cgacctgcgt  15780
gccgagcgcc gcgaggaact ccgcgcccac ctggacgcac gcggcatcga gacccggctg  15840
ttcttcaagc cgatgagccg ccagcccggc tacctcgacc cggtgtggcc gacgctcaac  15900
gcccaccggt tcagcgagga cggcctgtac ctgcccaccc acaccgggct gaccgccgcc  15960
gaccaggagt acatcaccgg cgccgtccgg gacttctacc gcgcgggctg accgacggcc  16020
cgtgcagcgg gccgcgcaga ccgcccgccg ccggcccgac cgggcgcggc accagccgac  16080
gcaggaagag aaacgaggag cggacatgac gaccagcccc ggcccgacgg tggtcgactt  16140
cccacggcgc acgccccggg aaccgctgcc gctgtcccag tacgccgaac accggaagca  16200
gaacggcctg gtccagacgc acctgccgaa cggccggccg atctggctgg tgacccggca  16260
cgaggacgtg cgcgcggtcc tcacccatcc ccggatcagc gccaaccccg acaacgaggg  16320
cttccccaac gtcggcgaga cgatgggggt gcccaagcag gagcagatcc ccggctggtt  16380
cgtcggtctg gactcccccg agcacgaccg tttccgcaag gtgctgatcc ccgagttcac  16440
cgtgcgccgc gtccgtgagc tgcggccggc gatcgaacgg accgtggacg agcggatcga  16500
cgcgatgctg gccggcggga acaccgcgga cctggtgaac gacttcgcgc tgcccgtgcc  16560
gtccctggtc atctccgcgc tgctgggggt gccgtcggcg gaccgggact tcttcgagtc  16620
ccgcacccgc acgctggtcg ccatccgcac ctcgaccgac gaggagcgcg ccgaggccac  16680
ccggcagctc ctgcggtaca tcaaccggct catcgtcatc aagaagaagt ggcgcggcga  16740
ggacctcatc agccgcctgc tgtcgaccgg caagctctcg gacgaggagc tgtcgggcgt  16800
cctgctgctc ctgctgatcg cgggccacga gaccacggcg aacaacatcg ggctcggcgt  16860
cgtcacgctg ctctcgcacc gggagtggat cggcgacgac cggctcgtgg aggagctgct  16920
gcgcctgcac tcggtggccg acatggtggc gctgcgcgtc gccgtggacg acgtggagat  16980
cgccggccag accatccgca agggcgaggg catcgtgccg ctgctcgcct ccgccaacca  17040
cgacaccgag gcgttcggct gcccgcacgc cttcaacccg gagcgcaccg agcgccgtca  17100
cgtggcgttc ggctacggcg tccaccagtg cctgggccag aacctggtcc gggtcgagat  17160
ggagatcgcc taccgcaagc tcttcgagcg catcccggag ctgcggctgg ccgtgcccga  17220
ggaccagctc gcctacaagt acgacgggat cctgttcggg ctgcacgagc tgccggtgcg  17280
ctggtagccg ggcgccgccg acggaccccc catccaccga ggagccaacg atcatgcgtg  17340
tcaccgtcga cagcgagcag tgcgtaggag cgggccagtg cgtcctgaac gcgccggagg  17400
tcttcgacca ggacgacgac ggcgtcgtgg tcctgctccg cgcggagccc gacgagcggg  17460
accacgaggc ggtccgcacg gcgggcgacc tgtgcccgtc ggcctcggtc gtcctccagg  17520
```

-continued

```
aggactgaac cagccggctg cgcggaccgg caccggtgcc ccgtccggcc cggccctcgc  17580
acccgcggac ccgtcgccgg cggaacaccg accggcgcca gaaccatcga agggactccc  17640
ccgtgaccac cgctgacgac accgcggccc gctggctgcg gcggtaccac ccggccgagg  17700
ccgacgcggt acggctggtg tgcttcccgc acgccggcgg ctccgccagc ttctaccacc  17760
cggtctcggc gcggttcgcg ccgggcgccg aggtcgtctc gctccagtac ccgggccggc  17820
aggaccgccg caaggagccc tgtgtcccgg acctcggcac gctggccgac ctgatcaccg  17880
agcagctgct cccgctggac gagcggccca ccgtcttctt cgggcacagc atgggggccg  17940
cgctcgcctt cgagacggcg tggcggctgg agcagaaggg cgccggtccc cgcaccgtca  18000
tcgcctccgg acggcgcggc ccctccacca cccgcgccga acgggtccac acgagggacg  18060
acgacgggat cgtcgcggag atgaagcggc tgaacggcac ggcggccggt gtcctcggcg  18120
acgaggagat cctccgcatg gcgctgcccg cgctgcgcgg cgactaccgc gccatcgaga  18180
cctacacctg ccctccggac cgccggctgg cctgcgggct gaccgtgctg acgggcgagg  18240
acgacccgct gaccaccgtc gaggaggcgg agcggtggcg cgaccacacc accgggccgt  18300
tccggctgcg ggtcttcacg ggcgggcact tcttcctcac ccagcacctc gacgcggtca  18360
acacggagat cgcccaggcc ctccaccccg accgggccgc cccggccgcc tgagcgtccg  18420
gcccggccgg cggcgggacc gccggccggg caggcgctgg agccgtgacc gacgcaccgc  18480
cgacggcgta cgcgcgtacg cggcggacgt cgtccgcacc accggagagc ccgcacaggc  18540
ccggacggcg atcccgtccg accgcctccc ccgtcacttt ccgctcacgc gcctgaggga  18600
caaggacaca tgcgcaccct tctcgtcgac aactacgact cgttcaccta caacctcttc  18660
cactacctct cccgggccaa cggccgggaa cccgaggtca tccgcaacga cgacccggcc  18720
tggcggcccg gtctgctcga cgcgttcgac aacgtggtgc tctccccggg gccgggtacc  18780
ccacaccgcc cggccgactt cggcctgtgc gcccggatcg ccgaggaggg ccggctgccg  18840
gtgctcggcg tctgcctggg ccaccagggc atggccctcg cccacggcgc ccgggtgggc  18900
cgggcccccg agccccgtca cggccgcacc tcggcggtac ggcacgacgg caccgggctc  18960
ttcgaggggc tgccgcagcc gctggaggtg gtgcggtacc actccctcgc ggtgacggaa  19020
ctgccgccgg agctggaggc caccgcctgg tcggaggacg gggtcctgat ggcgctgcgc  19080
caccgcacgc tgccgctgtg gggggtgcag ttccaccccg agtcgatcgg cacccaggac  19140
ggccaccggc tgctggccaa cttccgcgac ctcaccgagc gccacggccg aacgcgcccg  19200
ggcggccggg cggggcacgg cacgctcccg ccccccgcgc ccgcccggga gacgacggcc  19260
accaccggca cgccacggcg gctccgggtc atcgccgagt cgctgcccac gcgctgggac  19320
gccgaggtcg ccttcgactc gctgttccgc accggcgacc accccttctg gctcgacagc  19380
agccgtcccg gggcgagct gggccagctc tccgtgatgg gcgacgcctc aggtcccctc  19440
gcccggaccg ccaaggccga cgtgcacgcc ggaacggtca cggtgagagc cgacggcgcc  19500
agcagcacgg tcgagagcgc cttcctgacc tggctggaga acgacctggc ggggctgcgc  19560
accgaggtgc ccgaacttcc cttcgcgttc gcgctcggct gggtcggctg cctgggctac  19620
gagttgaagg ccgagtgcga cggcgacgcc gcgcaccgct cacccgatcc cgacgccgtg  19680
ctggtcttcg ccgaccgggc cctggtgctg gaccaccgca cccgcaccac ctacctgctg  19740
gcgctggtgg aggacgacgc cgaggccgag gcacgcgcct ggctcgcggc ggcctccgcc  19800
accctggagg ccatcgccgg gcgggagccc gagccgtgcc ccgaggcgcc cgtgtgcacg  19860
```

-continued

```
acgggtccgg tggagctgcg ccacgaccgg gacggctacc tgaagctgat cgacgtctgc  19920
cagcaggaga tagccgccgg ggagacctac gaggtctgcc tgaccaacat ggccgaggcg  19980
gacaccgacc tcaccccgtg ggcggcctac cgcgcgctgc gccgggtgag ccccgccccg  20040
ttcgccgcgt tcctggactt cggccccatg gccgtgctca gcagctctcc ggagcggttc  20100
ctgcgcatcg accggcacgg gcggatggag tccaagccga tcaagggcac gcggccacgc  20160
ggcgccaccc cgcaggagga cgccgcgctc gtacgcgccc tggccacctg cgagaaggac  20220
cgcgccgaga acctgatgat cgtcgacctg gtccgccacg acctggggcg gtgcgccgag  20280
gtcggctcgg tcgtcgccga cccggtgttc caggtcgaga cgtacgcgac cgtgcaccag  20340
ctggtcagta ccgtcacggc gcggctgcgc gaggacagca gcccggtggc ggcggtccgg  20400
gcggccttcc ccggcggatc gatgaccggg gcgccgaaga tccgcaccat gcagatcatc  20460
gaccggctgg aaggcgggcc gcgcggtgtc tactcgggcg ccatcggcta cttctccctc  20520
accggcgcgg tggacctgtc catcgtgatc cgcacggtgg tgctcagcgg cggcaggctg  20580
cgctacggcg tcggcggcgc cgtcatcgcg ctctccgacc cggccgacga gttcgaggag  20640
acggcggtca aggccgcccc gctgctgcgt ctcctcgaca ccgccttccc gggccgtgag  20700
gctcccggca aggacctcga cggggaaccc gacgacggca cggacgcggg tgctccgaag  20760
gacctcgtcc tgcccgggtg acctcacggg tgccccggcg gtccggcggg ccgccggggc  20820
cccgcgcggc cggcaccggc cgcatctcta gggaaaacac gggccccgtg gcaagagcct  20880
ggaaccgttc ccccctctga cggcgacgct cgacatcccg ggagtgatgg tgcccgtcca  20940
cgcacacgac tacgtgaccg atccgccctc caccaccggc aggaccctgg acgggctgac  21000
gctgccacgg gtgttcgccg acgccgtaca ccggggcggc gacgccgtgg ccctggtgga  21060
cggggagtac gccctgacct ggagcgcctg gcggacggcg gtggacgcgc tggcgcgcgg  21120
cctccaggag tccggcgtcg tctccggcga cgtggtggcc ctgcacctgc ccaacagctg  21180
ggagtacctg acgctccatc tggccgccgc ctcggtcggg gcggtcacga tgccggtgca  21240
ccagggcaac gctccctcgg acgtccgggc cctgctggaa cgggtccggc ccgcagccgt  21300
cgtcctgccg gcgcggaccc aggagggtgg gggcccgctc accggcacgg cgctgcgcga  21360
ggtcctgccc gagctgcgcg ccgtgctcgt cacgggcgac gcggcgggcg agggcaccga  21420
gacggtgacc gagatgctgg agcggtggtc cggagaggac ccgctgcccg tcgaggtgcg  21480
cccggactcg ccgttcctgc tgctgccgtc ctcgggcacc acctcggcgc ggcccaagat  21540
ctgcctccac tcgcacgagg ggctgctcac caactcccgg gccgccaccg aggacaccgc  21600
ggacgcctac gccggcaccc tgatcaccgc gtgccccctg acccactgct tcggcctcca  21660
gtcggcgtac tcggcgctct tccgcgccgg ccgccaggtg ctgctgtccg ggtgggacgt  21720
cggccggttc ctggagctgg cccgccggga gcggcccagc gtggtggtgg cggtccccgc  21780
ccaactgcac gacctggtca cccgggtgcg cgaggacgcg gacggccccg gcttccggcc  21840
cggccggatc ctcaccgccg gagcggccct gccccccggcg ctcgtccgcg acgtgcggga  21900
ggcgctggac accacgctgg tggtggtgtg gggcatgtcg gaggccggca acggcaccag  21960
cagcctctcc gccgacgcgc cggaggtggt ctcccgcagc gtcggccggc ccacccgcga  22020
cgccgagatg cgcgtcgtgg acgaggacgg cgcccccgtgc ccgcccgggc agcccggcga  22080
gctgtactac cgcagtccca gcatgttccg tggctacttc ggcgagccgg agctgacccg  22140
gtcggtggtg tcggaggacg gctggctgcg caccggcgac ctcgcctcga tcggcgagga  22200
cggcctggtc accttccacg gccggtcggc cgaactgatc aacgtcggcg gccgcaagtt  22260
```

-continued

```
caacgcggtg gagatccagg cgctcctcgc ggacctgccg gacatcggcc cgctcgccgt  22320
ggtcgccgcg ccggacccgc gtctgggcga gtacccggtc ctggtggtca ccgaacggcc  22380
ggccgccgca ccggcggacg gcacggcacc gcgcccgcgc ggcacggtcg ggctcgacga  22440
ggtgacggct catctccggg gcctgggcac cgccgagtac aagattccgc tggagctggt  22500
ggcccttccc gagctgcccc gcactcccgc ggggaagatc aaccggcggg cgctggagca  22560
gtacctcgcc gacgccgccg agcggaccgc cgttactccc gccgaggcgc cgcgccccgg  22620
tctccggacg gcgctggagc tggtggtgac cgccgtcgcc gaggtgctgg ccgccgtgcc  22680
cggcgaggac ggcgcgcggc ccgccgccgc cggtccgatc gggccggaca ccaccttccg  22740
cgcccacggt ctggactcgg tcgcctccgt acggctgcgc aacgcgctcg ccgaggccac  22800
ggggctgacg ctgcccgccg gactcgcctt cgacttcccc accccggccg ccctggcccg  22860
ggaactggcc gggctctcct ccccggccgc agaggagagc ccgggtgcgt ccgcccacga  22920
ggacgagccc gtcgcgatcg tctccatggc ctgccgcctg cccggcggcg ccacctcccc  22980
cgaggcgctg tgggagctgc tgcgcgacgg cgtcgacgcc gtgtccggct tccccgagga  23040
ccggggctgg gacctggacg ccctcttcgg cgacgacccc gacgcaccgg gcacctcggt  23100
ggcgcgcgag ggcgggttcc tgcgcgacgc ggcccacttc gacgccggct tcttcgggat  23160
gtccgcgcgg gaggccctcg ccaccgaccc gcagcagcgg ctgctgctgg agacggcctg  23220
ggaggccgtg gagcgcgccg gcatcgcccc gcgaaccctg cggggcagcc gtaccggtgt  23280
gttcaccggc gcgatgtacc acgactacgc ggccggcgcg tccgacccgg ccggggagct  23340
ggagagcctg ctgccggtgg gcaccgcggg cggcgcgctc tccgggcgga tcgcctacac  23400
cctcgggctg agcggtccgg cgctcaccgt ggacaccgcc tgctcctcct cgctggtcgc  23460
cctgcacctc gcctgccgct ccctgcgctc cggcgagtcg gacctggcgc tggccggcgg  23520
cgtcgccgtg atggccaccc cggccgcgtt cgtgggcttc tcccggctgc ggggcctttc  23580
ccccgacggc cgctgcaagt ccttcggcga gggagccgac ggagccgcct ggtcggaggg  23640
ggccggcctg ctcatgctgg agcggctctc cgacgcccgc cgcaacggcc accctgtcct  23700
cgcggtgatc cgcggctccg ccgtcaacca ggacggcgcc tccaacggac tgaccgcccc  23760
ccacgggccg gcccagcgcc gggtcgtccg gcaggccctg gccgacgccg gtgtccgcgc  23820
cgccgaggtg gacgtggtcg aggcgcacgg aaccggtacc gccctcggcg accccatcga  23880
ggccgaggcg ctgctcgaca cctacggacg ggaccggccg gagggccgtc cgctgtggct  23940
gggttcggtg aagtccaacc tgggacacac gcaggccgcc gccggcgccg ccgccgtgat  24000
caagatggtg ctggccctgc ggcacgacct gctcccggcc accctgcacg ccgacacccc  24060
cacctcccgg gtggactggt cccccggcac cgtgcagctg ctgacgcggg cccgcgactg  24120
gccccgcgag gagggcaggc cgcgccgcgc gggcgtctcg tccttcggca tcagcggcac  24180
caacgcccac ctcgtcctgg aggaggcacc cgtgcccgcc gccggcacgg agcggagcgc  24240
ggacgcggga gccgccggcc tccgtgccgc cgtgccgtgg ctggtgtcgg ccaaggacgc  24300
ggacgcgctg cgcggccagg cccggcgcct ggccgcacac gccgccgccc acccggaggt  24360
gtccgcacgc gacctcgcct actccctgct caccacccgg gcgctgcacc cccgcaccgc  24420
cctgctgacc ggcggcgacc gggacgcgct ggtcgcgtcc gccgacgcct tcgcccgtgg  24480
cgaggcaccc gggagcatcg tccgtggccc gctcggtccc gcccccggga ccgccttcgt  24540
cctcaccggg cagggcagcc agcggctcgg catggggcgc gggctcgccg ccgccttccc  24600
```

-continued

```
ggtcttcgac gacgctctgc gcgaggtgtg cgcgctcctc gacccgctgc tggaacggcc  24660
gctgaccgag gtcatgtggg ccgcgccgga cagtgacgag gcggggctcc tcggcggcac  24720
gggctacgcc cagcccgcgc tcttcgcgtt cgaggtcgcc ctgtaccggc ttctggagtc  24780
gtgggggatc gtccccgacc ggctggtggg gcactcggtc ggcgagatcg ccgccgccca  24840
cgtggccggg gtgctctccc tgccggacgc ctgcgccctg gtcgccgcgc gggggcggct  24900
gatgcaggcg ctgccgccgg gcggcgccat ggcggcggtg cgctgctccg aggcggagat  24960
tctgccgctc ctggccggac gcaccgccgg ggccaccgtc gccgccgtca acggcccgcg  25020
gtccgtggtg ctgtcgggca ccgaggaggc cgtggccgag gtcgtcacgg aggtctccgc  25080
cgccgggcac aagacgcgtc ggctcatggt cagccacgcc ttccactcgc cgctgatgga  25140
gccgatgctc gcggagttcc gggcgacggt cgccgggctg tcgttcgccg cgccccaggt  25200
tccgctggtc tccggcgtca ccggacggcc gctcaccgcc gaggaggccc gcgacccgga  25260
ccactgggta cgccatgcca gggacaccgt ccgcttcgcc gacgcgatca gccatcttgc  25320
cggagaacac accgagatct acgtcgagtt gggcccggag gccgcactca ccccgatggt  25380
cgaggagtgc ctgggcgagc cggagagcgg cgacggtccc gccgtggagc cggtggtacg  25440
gggcgacgtg gacgaggagc gggcggcact ggccgccgcc gtacggctgc acgcgctcgg  25500
cctggacgtg cagtggcggg cggtgctgcc ggaggcccgc gcggtgccgc tgccgaccta  25560
cgccttccag cacgaggcct actggctggc cacgtccggt tccgtggtcg cggggctgtc  25620
gctgccgggc ggccgggcgg ccgacaccgt tccggacctg gccgggcggc tggcggggct  25680
ctccggcggt gaggcggagg cgctcgtcac cgaactggtg cggaccgagc tggcggcggt  25740
gaccggtggt gagatctccg ccgccggagc cggcacggcc ttcaccgagc tgggcgtcac  25800
ctccgtcacg gcggtggagc tgcgcaaccg gctgaccgcc gtcaccggcg tgcggcttcc  25860
cccgaccctg atcttcgacc accccacccc cacggccgtg gcccgcctca tcggcgagac  25920
ggtccggggg agttcggtcc cgggccgccg ggacgccgtg tccctggtgg acgagttgga  25980
ggcgctgctc gtctcgggcg ccgaggtcga ctcggacacg gcggcgcggc tgcggtccct  26040
ggccggccgg tgggctccgt cggccaccgg aacggcggcc gacgcgaacg gtccgctgga  26100
tctggacgac gcctccgacg aggagctgtt ccgcctcatg gacggcggcg ccccgtgact  26160
ctctccgccc ggcggctcct cggcggcgtc cgcccccggc gagccgtcgg gcacccctga  26220
ccgaccgcgt tccgggcggc cccgttgctc cggcgccccg gccggaacgc ggccccgcca  26280
ggcggtccgc cggtcgccca ccttcacaga cccacgagcg gaagtacctc tcatgaacgg  26340
gctccacctg ccccccgccc ccttgcccgc cccgggcgtg agcgccgccg gttccggcga  26400
tctgatgatc gaggcggagg gcgtcagcaa ggcatacggc acggtccacg ccctggactc  26460
ggtcagcctc gccgtccccc ggggcaccgt gctgggactc ctcggccaca acggcgccgg  26520
gaaaaccacc ctggtcgaca tcctcaccac ggcgctgccg cccacctcgg ggcgggcgag  26580
ggtcgccggg tacgacgtgg ccgacaagcc ggtcgagatc cgccggcgca tcgggctcac  26640
cgggcagttc gcctcggtgg acgcgcagct cagcgggtac gacaacctcg tcctgatcgc  26700
ccgtctgctg ggcgccgggc gccgggcggc ccgcgtgcgc gcgagggagc tgctggagct  26760
gttccggctg acggaggtcg cggaccggcg tgcgagcagc tactcgggcg ggctgcggcg  26820
gcgcctggac ctggccgtgt cgctggtcgg cgcgccggag gtgctcttcc tcgacgagcc  26880
caccaccggc ctggacccct ccagccgcat caacctgtgg gagatcgtcg aggggctggt  26940
cgagcagggc accacggtgc tgctgaccac gcagtacctg gaggaggccg accggctggc  27000
```

-continued

```
ggaccggatc gcggtgctct ccgcgggccg ggtcgtcgcg gcgggcacgg cgcccgagct  27060
gaaggccacc gtggggcgcc gcacggtgac gctcaccctg gagaccggcg aggacgtgag  27120
cgcggcgcgc acggcgctgc gcggggcggg cttcgccccg gtcgacggcg aggcccgcac  27180
cgtggtcgtc ccgatcgacg ccacacggga gatcgccgac atcatcagga gcctggacca  27240
ggccggcgtc gaggcgagcg agctgaactt cggcgaaccc acgctcgacg acgtgtacct  27300
gaccctcgcc gagcaggccg ccggccggac ccgggcatga ccgcgcggaa ccccgtcccc  27360
cgcgggcccc gcctcccgcg ccccgacacc ccggcgggcg ctgccgccgg ccgacgacgc  27420
ctttcacgga ggaccccttg accactcagc tcgccccgcc gctgcctccg gccgtgccac  27480
ggcccgcggc ggtgcctgcc ttcggcggga gttcactgtt cacccagatc cgggtgctca  27540
ccgggcggtc cctgcgggcc atggtgaccg acccgggcat cgtgctcttc ggcctgatcc  27600
agccggtggt catcctcttc gtgctgaccc aggtcttcag caagatgggt atgccgcccc  27660
acttcccgga cggcgtcagc tacctcgact acgtcctgcc cgccgtcctg gtggacaacg  27720
ccgcccagtc ggcgatgcag tcgggcgtgg gcctggtgga ggaccagaag aacggcatcg  27780
tggcccggct gcgctccctg cccgtccacc cgggcgcgct gctggccgcc cgcagcctgg  27840
tcggcctggt gcgcagcgcc gtgcaggtcg cggtcatcat ggcgctggcg atgaccgtcc  27900
tcggctactc ccccaacggc ggtgccgccg aactggccct ctccgcgggg ctgacgctct  27960
tcatcagctt ctcgctgggc tgggcgttca tcgcggccgg cgcctggctg cggcgggccg  28020
agccgctgca gaacctcgcc ctgatcgtga tcttcccgct gatgttcgcc tccagcgcct  28080
acgtcccggt cgcggacctg ccctcctggc tgggcgcggt cgcgagcgtc aaccccctga  28140
cgtacgcgat cgacgcgacc cgggcactgg cgctggacgt gcccggcctg gaccacgcga  28200
tcccggcggt ggtgatctgc gccgtgatcg cggtggtcgg catgatcgcc gccgtacgcg  28260
gcttccgccg gcctctctga ctccccgcac gaactccccc cgtgcgtgcg gggacggggc  28320
ccgtggacgc ctctcgcgtc cacgggcccc gttccttgcc cggaggaggc ggagacagcc  28380
cctggcagga ggaaacaggc gacttcggac cgtccctggc tcccggacgg cgcccgtccg  28440
gaccacagcg cgggcacccg aacgggcagc ggacgacggt cggtccggac cagggccgtg  28500
gaacaccgga gcatacggag gtgcgcaccg gtatgtcggc cccgagtagc gggcaaaaac  28560
gggcacagct ccgcacggaa acggaccgag agactcccat atctgtctca cttctgtcag  28620
gagcgctcgt ccgcagcccc tgagacggtc tcggcacccg gctcaacggc gtccggaacc  28680
cactgcggcg accccgaaac cgggcggtgg tgatccccac cgcgaggctg gagccgctcg  28740
gtcactccct gcccgcaacg ggcacggctc acgtgccgag gggcgcacgg aacgcacacg  28800
gcccacgccc gaaactctct gaccagcggg gcaagctccg catccccaca gcaaagcagt  28860
ccgcgtcggg ccgggaacgg gcagaatcgg gcctcttcgc ttccggacgg cgggcaggag  28920
aacggccctg gggccggcac cgtggtgccg gccccagggc cgttcgttcg cggcctgtgc  28980
ggtcaggaga gtccgagttc gttgtcgagc atgtcgaaca tgtcctcgtc ggaggcggag  29040
gcgaagtcga aggactcctc cgccttctcc ccgcccttga gggcctcggc ccgcatctcc  29100
tgccacttgc cgcggagaac ctccagccgg cccgccacct ggtcgaagag ctcggcgccg  29160
acctcggcgc ccgcgaaagc cctctccagc ttgtccagtt ccgccaggac caccgccgac  29220
ccgtcggccg gtgccggggc cacccgcgtg tacaggtggg cgacgagttc gccgggcgtc  29280
gggtagtcga acagcagcgt ggccgggagc cgcaccccgg tgagcgcgcc gagccggttc  29340
```

-continued

```
cgcagctcga ccgaggtcag cgaatcgaag cccaggtcct ggaaggcacg ggcgggttcg  29400
atgtcggcct ggcccgcgtg gcccagtacg gtcgcgatct ggccgcgtac caggtccagc  29460
aggacctcct cgccctcggt ccgggtgagg ccggtgaggc gccgggtgag gtcggcggcg  29520
gccgccgctc ccccgtcgga ggcggcacgg cgggcctggg tccggatcag tgaccggaac  29580
agcggcggca cctcgccgag ggagcgcagg gcccccaggt cgagccggac cgggaggacg  29640
gccggggcct gctcggcggc gccggtgacc gcgtcgaaca gggccaggcc ctgctcgggg  29700
tcgatcgggg gcatgcccgc ccgcgccatc cgggcggtgt ccgcctcggt cagctcaccg  29760
gtcatgccgc tcccccgggt ccacgggccc caggccatcg acaccgcggg cagtccacgg  29820
tcccggcggt ggcgggccag tgcgtcgagg aaggcgttgc ccgccgcgta gttggcctgt  29880
cccgcgctgc cgagcgtgcc ggcgacggag gagaagagca cgaaggcgtc gagcgtaagc  29940
ccctcggtcg cctcgtggag gtgccaggcg gcgtccgcct tgggccgcag cacggcggcg  30000
aggcgttccg ggtgagggga gtcgagaacc ccgtcgtcca ggacaccggc cgcgtggatc  30060
accgcccgca gcggacggtc ggcggggatc tccgccagca gcgcgtcgac ggccgtacgg  30120
tcgccgacgt cgcaggcggc gacggtgacg tgggcgccgg actcctccag cgcggcggcc  30180
agttcaccgg caccctcggc ggccggacca cgacggctga ccaggagcag gctccggacc  30240
ccgtgctcgg cgaccaggtg ccgggcgacg gtggcgccga ggccgccggt gccgcccgtg  30300
atcagcacgg tgccctccgg gtcccagccg gccgcgtcgc tctcggcggg cgtcaccgcg  30360
cgcaccaggc gaggtgccag caggcggtcc tcgcgcaggg cgagctgcgg ttcgcccgag  30420
gccagcgccg cccgcagggc ggacatcccg agcggagagg tggccgaggg ctccaggtcg  30480
aggaggatga accggcccgg gttctccgcc tgcgcggcgc gcaccagccc ccagaccgcc  30540
gcggcggccg ggtcggcgcc gtcggaggca ccccgggtga cgacgaccag gcgggaggcg  30600
gcgaaccgct cctgggccga ccagtcgcgg agggtctcca ggacccgggc ggtggcggcg  30660
tgggcggcgg cggccacgtc cccggtgccg gacccggcct ccggggcggt ggcgaccggc  30720
agcagcacca cggacggcac gtcctccccg ggcccggtgc cggtgacgag gtccgccaga  30780
ccggtcacgc cctccgtccc ggcttcggcg aggaggtcgc cgccgccgag gagcgcggtg  30840
tccgggccga gcacggcgac cggccgggc gtctcggcgt cccgcgtggc ggggtccccg  30900
gcagccgccc agtccagctg gaacagggag tcgcggcccg cgccgcccgc gccgccgaac  30960
tgcccggcgg agagcgggcg ggtcaccagg gacccgaccg aggcgaccgg ggtgccggcg  31020
gtgtcggtga cggcgatcgc gagggtgccg tcgtcggtac gggagagccg cagccgtacc  31080
gaggaggcgc ccacggcgtg cacggagacc ccgttccagg agaacgggac gccgccggtg  31140
ccttcggact ccccgccgtc gccggccagg gcggtggcgt ggagtccggc gtcgaagagc  31200
gccgggtgca gggtgaacgc gtcgccgtcg gtgccgtcgg gcagcgacgc ctcggcgaag  31260
acctcgccgt cgcggctcca ggcggcacgc agcccctgga agacgggccc gtaggcgaac  31320
ccggcgtcct cgaaacgctc gtacagcccg gtggtgtcga gcggctcggc cttctccggc  31380
ggccacacgg tggcgtcgaa gtcggtggcg gggcctgtg ccggtccggc ggccagggtg  31440
ccctcggcgt gcgaggtcca cggggcgccg gagtcgtcgg cgggccggga gtggatggtg  31500
atcccgcgcc ggccctcctc gtcgggggcg ccgacgccga cctgcacctg gacggtgccc  31560
tgctcgggca ggaccagcgg ggccgccagg gtcagttcct ccaccacgtc gcagccgagc  31620
acgccgcccg cgtggactgc gagttccagc agggcggtgc cgggcaccag gacggcgccc  31680
atgacacggt ggtcggagat ccagccgtgg gtgccctggg aaagacgtcc ggtgaacagg  31740
```

-continued

```
tggccgtccg tgccggccag ttcgaccgcg ccgccgagca gcgggtggcc ggcgggcgcg 31800
agcccggcgg cctccgcccc ggcgcccagg ggcatcatcc cggcgggcca gaaccggcgc 31860
cgctggaagg cgtacgtggg cagctccacc cggcgggcgc cgcggccggc gaagaacgcg 31920
ggccagtcga cgcggacacc gtggccgtgc agccgggcga ccgcctcgac cagggcctgc 31980
tcgccgggga cggtgcggcg ctgggcggcg accgtcacgg cggactcggg cagggactcg 32040
cgggccatgg cgcaggcgac accgtcgggg cccagttcca ggtagcgggt ggcaccggcc 32100
tcgtgcaggg cccggacgcc gtcggcgaag cggacggcct cccggacgtg gcgcacccag 32160
tactcggcgg agcacagttc ctccgcgcgg gccgtggtcc cggtgaggtt ggagacgacg 32220
ggtatcacgg gtgcctgcgg ggagaggccg gcgacgacgg cccggaactc ggcgagcatc 32280
ggttccatca gcggcgagtg gaaggcgtgc gagacgcgca gcgcggtcgt ccggcgaccg 32340
cgctcccgca gggcctcggt caccttctcc accccttcgg cggtgcccga caccacgacg 32400
gacgtgggtc cgttgacggc ggcgaccgag accccgtcgg tgaggtgcgc gagcacctcg 32460
tcctcggtgg cctggacggc ggccatcgcg ccgccctccg gcagtgcctg catcaggcgg 32520
ccccgcgcgg cgaccagggc gcaggcgtcg gccagcgaga agaccccggc gacgtgcgcg 32580
gcggcgatct cgccgatcga gtggcccgcc accaggtcgg gggtgacgcc ccacgaggcg 32640
acgagccggt ggaggcccac tccgagggcg aagagcgcgg cctgcgcgta ggcggtggcg 32700
ttcagggcgt cctcgtcgtc gccccagacc acctcccgca gcgggcggtc caggtgcgcg 32760
tcgagtccgg cgcagaccgc gtcgaacgcc tcggcgaaca ccgggaagcg ctcgtagagg 32820
tcgcggccca tgccgagccg ctgggagccc tgccccggga agaggagggc gagcagcccc 32880
tcaccggtcg tcgtggccgg ttcctcgccc cgggccacgg agccgagcgc ggccagcaga 32940
ccgtcccggc cggcgcccgt gacggcgacc cggtgctcga acgcggtacg ggcggtggcc 33000
agagagtagg cgacgtccag cgggcgcgcc tcggttccgc cggcggccgg gtggtccccc 33060
gtcaggtggt ggaggagccg ctcggcctgg gcgcgcaggg cgtcccggtc gcgggcggac 33120
agcagccacg ggacgacagg ggcgacgccg tcgtcgtccg cgccggtcgc gggctcgtcg 33180
gacggcacgg ccgcgggcgc ctgctcgacg atgacgtggg cgttggtgcc gctgatcccg 33240
aaggaggaga tcccggcgcg gcgcgggcgg ccggagccgg tccactgccg ggcctcggtc 33300
agcagctcca ccgacccggt ggtccagtcg acctggtcgc tgggggcgtc gacgttcagc 33360
gtggcgggca gcagcccgtt gcgcagcgcc agcaccatct tgatgacgcc ggcgactccc 33420
gccgcggcct gggcgtgccc gatgttcgac ttgaccgagc cgagcagcag cggccggtcc 33480
tcggggcggt cctggccgta ggtggcgagg agcgcctggg cctcgatggg gtcgcccagg 33540
gtggtgccgg tgccgtgcgc ctcgacggcg tcgacctggt cggcggcgag ccgggcgttg 33600
gccagggcct gccggatgac gcggcgctgg gacgggccgt tgggcgcggt gaggccgttg 33660
ctcgcgccgt cctggttgac ggcggagccg cggacgacgg cgagtacctc gtggccgttg 33720
cgcaccgcgt cggagagccg ctcgacgacg aggaagcccg cgccctcgga gaagccggtg 33780
ccgtcggccg ccgacgcgaa ggacttgcag cggccgtcgg gggcgaggcc gccctggcgg 33840
ccgaactcgg cgaacacggc cggtgtcgac agcacggtga caccaccggt gaccgccagg 33900
gagcactcgc cctgccggag cgcctgcacg gcgaggtgca gggcgaccag cgaggaggag 33960
caggccgtgt cgacggagac ggcggggccc tccagtccga gcttgtaggc gacgcggccg 34020
gtgaccacgc tgccgttgcc gtcgctgccc gggtagtcgt ggtacatcac gccggtgaag 34080
```

-continued

```
acgccggtcc ggctgccctt gagcgaggcc gggtcgatcc cggcccgctc cagggcctcc  34140
caggacatct ccagtgccag gcgctgctgc gggtccatgc cgagcgcctc gcgcggcgag  34200
atgccgaaga aggcggggtc gaagtcggcc gccccgtcga ggaagccgcc ttcccgggcg  34260
tacaggccgt ccgggtggtc gccgtcgggg tcgcggagga tcgacaggtc ccagccgcgg  34320
tcctggggga aggggacgat cgcgtcgtcg ccggaggtga ccaggcgcca gaggtcctcg  34380
ggcgagctga cgccgcccgg gtagcggcag gccatgccga cgatggcgat gggttcgtgc  34440
tgggccgagg tgagcctgcg gttgtcgcgg cgcagccggg cggtctcggc acgggcggca  34500
cggagcgcgt cggcgcccgg ttcggtggcc gtgccggtcc cggcggtctc ggccgcgccg  34560
tcgctctcgt cgtacggtcc ggaggcgtcg tcctcgtcgt cgccgtcgaa ggcggcgagc  34620
agggcgtccc ggtcggtgtc ggacatctcg tcggagtccg cggcgagttc gagcagcgtc  34680
tccgccagcc ccgcgtcacg caggcggcgg gccgggatgg cggagagggc gcggcgcacc  34740
ccgtcgtcgt cgccggtggc accgcccgcg ccggaggcgg ggtgggcggc ggcgagttcc  34800
tcctcgacga cctcggtgac ggcgagggcg ttggggtggt cgaagacgag ggtggcgggc  34860
agcctcagtc cggtcagcgt gttgagctgg ttgcgcagct cggtcgcggc cagggagtcg  34920
aagcccagtt cctggaatgc ccggtcagcg ccgatcgcct ccgccgaacc gtgccccagc  34980
accgccgcga cctgcgaccg gacgagatgc agcaccgcgc ggtgccgttc gggcgcgggc  35040
agttcggcga gcctgcggga cggggagtcg tccgggcccg gcgcggcagc cgaacccgag  35100
gccgcggtgg cgcggcgggc gggagccagc gcgcgcagga gggcggggat ctcgtcggtg  35160
cgggtgcgca gcgcggcggt gtcgacgcgc agcggcacga cggtcgcctc gcttcggtcc  35220
aggccggccg cgaacagctc cagccccgcc tcgtgcgaca gcaacggcag cccctgcgac  35280
gccatccgac gccggtccac ctccgacaga tactccccca gacccgcacc cacgtcccag  35340
aacccgaacg ccatggacgt ggccaccaga ccctcggccc gacgccgcga cgccaacgcg  35400
tccaggaaca cattggccgc cgcgtaattg ccctgccccg ccgtcagcac cagaccaccc  35460
gccgacgaca ccagcacgaa cgccgccagc tccacacccg ccgtcgcctc gtgcaaccac  35520
cacgccgcat cagccttcgc acccagcacc gcatcgaacc ggtcgggagt gagggagccc  35580
aggagcccgt tgtcaccgac tccggccgcg tggaccacgg ccagcagccc gcgcccggag  35640
acgagagagc cgacgaggtc cacgaccgat tcgcggtcgg acaggtcgca cgcgacgacc  35700
tccaccgccg caccggcctc acgcagttcc ccggccagct ccgccgcacc cggggcgtcc  35760
ccgccccgcc gcgacaccag caccagatcc cgcaccccac gctcagccac cagataccgg  35820
gccatcaccg cacccagacc acccgtacca cccgtcacca gcaccgcacc ctcaccatcc  35880
aacgacggca cggacagcgg cagttcggca gcgggtgcgt cggcggtcag ccgcgtcagc  35940
ctcggtacga ggaccacgcc gtcccggacg gcgacctcgg cctcgcccga gaggacagcc  36000
gcgaccgcac agtccaccgc cgcatcatcc gcgtccacgg cgacatcggc cagggcgaac  36060
cggcccggat tctccgcgag cgccgcccgc accagacccc acacaggggc ctgcacgacg  36120
tcgccctcgg ccggggcgcc gccggaaccc acgggcatag cgccccgggt caccacgacg  36180
agccgggagg cggcgaaccg ctcctcggtc agccagcgct gtgccacggt cagcacaccg  36240
tccagcgcgg agcgcaccga gccgggcacg tcggccccgg ccggagcgga ggcgtccagc  36300
acgaccacgg cgggcacctc ggtaccggcc tcctcgaccc gggaccaggt ggcccaggcc  36360
gtgtcggtgt cgtcgagccg ggtcacgggg acccactcgg gggcgtagag cgcgcccgcg  36420
tcacggggcg ccgcaccgag ctggccggcg gagacggtgc ggctcaccat ggagccgacc  36480
```

-continued

```
gtcaggaccg gggctccggt gacgtcggtg acgcggatgt ccataccgcc gtcggcggcg  36540
gtggcgatcc ggacgcggac ggcggcggcg ccgaccgcgt gcagggcgac ccggttccac  36600
gcgaacggga tgacggtccc gccgctcccg ccctcggcgt tgtcgttgct gtcgttgctg  36660
tcgttgctgt cgttgaggat cgcgacgtgc atggcggcgt cgagcagcgc cgggtggagg  36720
ccgaagcggc ccgcctccga ggcagcctcc tccgggagcg ccacctcggc gaagagttcc  36780
ccgccccggc gccaggcggc gcgcagcccc tggaagaccg gcccgtagcc gtagccacgc  36840
tcgcggaaga tctggtacgc gctgtccacg ggcacgctcg cggccccggt cggcggccac  36900
tgctccagtg cggcctcggc ccctgccacg agggcgttgt cggtgaggaa gccggtggcg  36960
tgggtggccc actcctgccc ggtgccctcg gggcgtgagt agacggcgac cgtgcggcgt  37020
tcggcggtgc gcggtccgac gaccacgcgg acctgggcgc cgccgtgctc gggaagtacc  37080
aggggtgtcg ccagggtcag ttcgtcgagt acggcgcagt cgacggactc tccggcggcg  37140
agggccagtt ccacgaggac ggcgccgggc agcatgaccc ggccgaggac cacgtggtcg  37200
gcaagccacg gctgcgcctc caccgacagc aggcccgtca gcaccgcgcc tccggagtcc  37260
ggcagcgaca ccaccgcgcc cagcaacgga tggtcggccg cgtcgagtcc ggctccggcc  37320
gcggccgggg ctccgtcggt ggcggtcagc cagtaccgct ggcgctggaa ggcgtaggtg  37380
ggcaggtcga cggggccggc gccggagccg gcgaagaagc cggcccagtc gacggccgtg  37440
cccgcggtgt gcagctgcgc gagcgcggtg agcagggcgt cgggctcctc ccgtcccttg  37500
cgggccgacg gcaccagcag gactgcggtg tcctcgtcgc cgtcgaggca ggtgcgggcc  37560
atgccggtga gtacggcgtc ggggccgatc tcgacacagc ggtccacgcc cgcggcgcgc  37620
agtgcccgga cgccgtcgcc gaagcggacg gcctcgcgga cgtgggtgac ccagtagtca  37680
ggtgtggcca gttcaccgga ctccgcgatc cggcccgaga cgttcgagac gaccggcagc  37740
gacggctccg cgtacgacac cccggacaga acctctcgga agtcagcgag catcggttcc  37800
atcagcggcg agtggaaagc gtgcgacacc cgcagctggc tgacccgccg tccctgctca  37860
cggaacacct cagccaccgc ctcaacggct tccccggcgc ccgagacgac caccgacgac  37920
ggaccgttga ccgcagcgac cgacacacct tcgacggact ccagatgcgg cagcacctcc  37980
gtctcggacg cctccacggc caccatcgcg ccgccctccg gcaacgcctg catcagccgc  38040
ccacgagcag ccaccagagc acaggcgtcc gccagcgaga acacacccgc cacatgcgcg  38100
gccgccacct caccgatcga atggccggcc accaggtcag gcgtgacgcc ccatgaggcg  38160
agaagccgga agagggcgac ttcgtaggcg aacagggcgg actgggcgta cgccgtgccg  38220
tcgaggtccg gcgcgttctc gccccaggcc acctcgcgca gcgggcggtc caggtgctcg  38280
tcgagcccgg cgcagaccgc gtcgaacgcc tccgcgaaga cggggaacgc ctcgtggagg  38340
ccgcgcccca tctccaggcg ctgtgcgccc tgcccggaga agaggaaggc cgtggtaccg  38400
acggagcggg cggttccggt gatgaccccg ggggcgtgct cgccggccgc gagggcgcgc  38460
aggccggtca ggaggtcgtc ccggccggtg ccgaggacca ccgcgcgggc ctccagcggg  38520
gtgcgggagg tggccagcgc gtgggcgacg tccagcggac gggtgccggg ccggtccgcc  38580
aggtggtcca gaaggcgggt ggcctgggcg cgcagggcgt ccggggtggc cgccgagacc  38640
gtccacggga ggacggcggg ggcgcggccc tcctcggccg tgctcggcgc gtcggctgcg  38700
gcgtcggggc cctgttccag gacgacgtgc gcgttggtgc cgctgaggcc gaacgccgag  38760
acgctcgccc ggcgcgggcg gccggtgacc ggccacggcc ggtcctcggt gacgagttcg  38820
```

-continued

```
gcgcggccct cggtccagtc gacgtgcggg gacggccggt cgacgtgaag ggtgcgcggc  38880
acggtgccgt gctccatcgc catgaccatc ttgatgacgc cggcgactcc cgccgcggcc  38940
tgggcgtgcc cgatgttgga cttgaccgag ccgagcagca gcggccggtc ctcggggcgg  39000
tcctggccgt aggtggcgag gagcgcctgg gcctcgatgg ggtcgcccag ggtggtgccg  39060
gtgccgtgcg cctcgaccac gtcgacttcg gaggcgggga ccccggcgcc gtgcagagcc  39120
tggcggatca cgcgctgctg ggaggggccg ttgggggcgg tgaagccgtt ggaggcgccg  39180
tcctggttga cggccgtgcc cttgacgacg gccagcacgc ggtggccgtt gcgcacggcg  39240
tcggagagcc gctccaccag gaggacgccg acgccctcgg accagcccac gccgtccgcc  39300
gcgcccgcga acgccttgca gcggccgtcc accgacaggc cacgctggcg gctgaactcg  39360
acgaacattc cgggcgtcga catcacggtg gcgccgccgg ccacggccag cgagcactcg  39420
cccgagcgca gggcctgtac cgcgaggtgc agcgcgacca gggacgagga gcaggccgtg  39480
tccacggtga cggctgggcc ctcccagccg aaggtgtacg acaggcggcc ggagaccacg  39540
ctgccgccgg cggtgccgga gggcgagacg ttcagcgcgt agtcgtggta catgacgccg  39600
gcgaagacgc cggtgcggct gccccgcagc gtcgccgggt cgatcccggc gcgttccagc  39660
gcctcccagg aggtctccag gagcaggcgc tgctgcgggt ccatgtacag ggcctcgcgg  39720
ggcgagatgc cgaagaagcc ggggtcgaac tgggcggcgt cgtgcaggaa gctgccgcgc  39780
ctggtgtagc tcttgccctc cttgccgggc tcggggtcgt agaggccctc gatgtcccag  39840
ccccggtcac cggggaggtc ggagacggtg tcgacgccgt cggtgaccag gcgccacagc  39900
tcctcggggg tggtgacgcc gccggggtag cggcaggcca tgccgacgat ggcgatgggc  39960
tcgtcgtcgg ccggtgctgc cgtgcccgta cggacggggg tctccgcccg cgcggactcc  40020
ccggccagtc gcgccgagag gtgatcggtg acggcgaggg cgttggggtg gtcgaagacg  40080
agggtggcgg gcagcctcag tccggtcagc gtgttgagct ggttgcgcag ttcggtcgcg  40140
gccagcgagt cgaagcccag ttcctggaag gcccggtcag cgccgatcgc ctccgccgaa  40200
ccgtgcccca gcaccgccgc cacctgcgac cggacgaggt ggagcagggt gcggtgccgc  40260
tccgcctccg gaagcgaggc cagccggtgg gccggcgagc cctcgacggt ggccgggggg  40320
accacggccg cggagcgccg cacgggagcg agggacttga gcagggcggg gatctcgtcg  40380
gtgcgggtgc gcagcgcggc ggtgtcgacg cgcagcggca cgaccgtcgc ctcgccccgg  40440
tccaggccgg ccgcgaacag ctccagcccc gcctcgtgcg acagcaacgg cagcccctgc  40500
gacgccatcc gacgccggtc cacctccgac agatactccc ccagccccgc acccacgtcc  40560
cagaacccga acgccatgga cgtggccacc agaccctcgg cccgacgccg cgacgccaac  40620
gcgtccagga acacattggc cgccgcgtaa ttcccctggc ccgccgtcag caccagacca  40680
cccgccgacg acaccagcac gaacgcagcc agctccacac ccgccgtcgc ctcgtgcaac  40740
caccacgccg catcagcctt cgcacccagc accgcatcga accggtcgga cgacagcgtg  40800
cccaccaggc cgccgccgcc gaccccggcc gcgtgcacga cggcgcgcag cccacgcccg  40860
gcgacgaggg actcgaccag gccgacgacc gattcgcggt cggacaggtc gcacgcgacg  40920
acctccaccg ccgcgccggc ctcacgcagt tccccggcca gctccgccgc gcccggggcg  40980
tccccgcccc gccgcgacac cagcaccaga tcccgcacac cacgctcagc caccagatac  41040
cgcgccatca ccgcacccag accacccgta ccacccgtca ccagcaccgc accctcacca  41100
tccagcgacg gcacggacag gggcagttca ggctcggcga gacgactgag cctcggcacc  41160
agcacaacac cgtcacggac ggcgacctcg gcctcgcccg agagggcagc cgcgaccgca  41220
```

-continued

```
cggtccaccg ccgcgtcatc cgcgtccacg gagacatcgg ccagggcgaa ccggcccggg  41280
ttctccgcga gtgccgcccg caccagaccc cacacggggg cctggacgac gtcggcggat  41340
gaaccggccg gggcggcgcc acgggtgacg acgaccagac gcgaggaggt gaagcgctcg  41400
tcgcggagcc actgctggat cgcgggaagg acctggtcca ggacggcccg gacggcggca  41460
gggacgtccg gaccggcggg ctcgcgcacc tccaggacga ccgcgcccgg cgccgtggtg  41520
tccgcctcca gggcttcggc ccaggagacg tgggcggggg ccgtggaggt gtccacggtg  41580
accggcgtcc actcgatgcc gtagagggcg cccgcgccgg cggaggcgct gccgagctgt  41640
tcggcggaga ccgggcggct cgccagggag cccacggtca ggaccggcgc gccggtggag  41700
tcggcgaggg tcagggagac ggtgtgggcg tcgacgcggc tcacgcgtac gcggacggcg  41760
gaggcgccga cggcgtggag agtcacgtcg ttccaggcga acgggacgac cgcctggccc  41820
tcctcctcgt tcaggatgcc ggcgtgcatg gcggcgtcga gtacggccgg gtgcaggccg  41880
aaccggcccg cctcacctgc cgcgtcctcg gggagcgcca cttccgcgaa catcgcgtcg  41940
tcgcgccgcc aggcggcgcg caggccctgg aagaccggcc cgtagccgta tccccggtgg  42000
cggaactcct cgtaggcgtg ctcgaccggt accgggtcgg cgccgggcgg gggccactcg  42060
gtcagcgctt cgccggagcc tgccggggcg tcggtgagga agccgtgcgc gtgggccgtc  42120
cacggcgcgt cctccgcgcc ctcgggacgg gagtggacgg ccacggtgcg gcgtccgtcg  42180
gtcttcggcc ccgcgacgac gcggagctgg aggccggtgt cctcgggcag caccagcggc  42240
gcggcgaggg tcagctcctc gagagcggtg gagccggccg cgtccccggc cgcgagggcc  42300
agttccacca ggcccgtacc gggcagcagg acccggccga ggaccacgtg gtcggcgagc  42360
cacggctgcg cctccaccga cagccggccc gtcagcacca cgccacccga gtccggcagt  42420
gacaccaccg cgcctagcaa cggtggtcg gccgcgtcga cccccgccga cctggggtcg  42480
gcggcggcgc ggaccgtggt ctccggccag aagcgccgct tctggaaggc gtaggtcggc  42540
aggtccacgg tgcgggccgc ggtaccggcg aagaagccgg tccacttcac ctcggcgccc  42600
accgtgtgga gacgggccag cgcggcgagc gccgtcgacg tctcctcacg gtccttgcgc  42660
aggagcggga cgaggacggc gtcctcaccg gcgccctcgc gcgccatgcc gctgagcacc  42720
ccgtccggac ccagctccac gaaccgggtg acgccctcct ccgcgagggc ccggacaccg  42780
tcgtcgaagc ggacggcctc gcggacgtgg gtgacccagt agtcaggcgt ggtcagttca  42840
ccgggttccg cgatccggcc cgagacgttc gagacgaccg gcagcgaagg ctccgcgtac  42900
gacaggccgg acagaacctc tcggaagtca ccgagcatcg gctccatcag cggcgagtgg  42960
aaagcgtgcg acacccgcag cctgctgacc cggcgtccct gctcacggaa gacctcggcg  43020
accgcctcga cggcgtcctc ggcgcccgag acgaccacgg aggaagaccc gttgacggcg  43080
gcgacggaca ccccctcgac ggattccagt cgcggcagca cctccgcctc cgacgcctcc  43140
agggcgacca tggcgccccc ctcgggcagc gcctgcatca gacggccacg ggcggcgacg  43200
agcgcggcgg cgtcggcgag ggtgaacacc ccggccacgt gcgcagcggc gacctcaccg  43260
atggagtgac cggccacgaa ctccggccgc accccccacg actcgaccag ccggaacaac  43320
gccacctcga cggcgaagag accggcctgc gcgtacgccg tcccgtccag aaccgacgtg  43380
tcgtcgcccc agaccacctc acgcagcggg cgctccaggt gctcgtccaa cccggcgcag  43440
accgcgtcga acgcctccgc gaacaccggg aaacgctcgt acagcccacg ccccattccc  43500
agacgctgcg acccctgtcc cgagaacagg aacgcggtac ggcctccggt ggccacgcct  43560
```

-continued

```
tccacgacgc ccgcgtcggg cagacccgag gccagggctt ccagggccgc ttcacggtcg  43620
gtgcccagga ccaccgcccg gtggtcgaag gtggcgcggc cggagaccag cgagaaggcc  43680
acgtccggcg cgctcaccgg ttcggcggcc acgtgcacgc gcagccgctc ggcctgggcg  43740
cgcagcgccg gggccgaccg tgcggagagc acccacggca cgtcgacggc gggcgccacc  43800
gtgggcgcgg gctcctgcgc ctcctccggc tgttcgagga tgacgtgggc gttggtgccg  43860
ctgatcccga acgaggacac accggcccgg cgcagccgct cctcccccgg ccacacccgc  43920
tcaccggtca gcaactccac agcaccggcc gaccagtcga cgtgcgacga cggagcatcc  43980
acatgcagcg tgcgcggtag cctgccgtga cgcatcgcca tcaccatctt gatcacaccc  44040
gccacaccgg cggcagcctg cgtgtgcccg atgttggact tgacggaacc gagcagcaac  44100
ggccgctcct cgtcccggcc ctgcccgtac gtcgccagga gcgcctgtgc ctcgatcggg  44160
tcacccaacg tcgtccccgt accgtgcgcc tccacgacat ccacatcacc ggcggacaga  44220
ccaccgctcg ccagagcctg acggatgacc cgctgctggg aaggaccgtt gggcgccgtc  44280
agaccgttcg acgcaccgtc ctggttcacc gccgaaccac gcaccaccgc cagcacacga  44340
tgaccgttgc gccgggcatc cgacagacgc tccagcacca ccatgcccac gccctcggac  44400
cagcccgcgc cgtcggcggc gtcggagaac gccttgcagc ggctgtccgg ggagagggcg  44460
ccctggcggg agaactccac gaaggcggtg ggggtggcca tgacggtgac gccgccggcc  44520
acggccagcg agcactcacc ggagcgcagc gcctgcgccg cccagtgcat ggcgacgagc  44580
gacgaggagc aggcggtgtc gaccgtgacc gcgggtcctt cgaagccgaa ggtgtaggag  44640
acacggcccg aggcgatgct gcccgcgctg ccgttgccgc gatagccctc gtactggtcg  44700
tcggtgagga tgctgccgta gtcgttgtac atgacaccgg cgaagacacc ggtctggctg  44760
ccgcgcaggg agaccgggtc gataccggac cgctcgatcg cttcccacgt cgtctccagc  44820
aggagacgct gctgcgcgtc cgtggagacg gcctcacgcg ggctcatccc gaagaactcc  44880
gggtcgaact cgggcgcgtc gtgcaggaag ccaccggacc gggtgtacgt ggtgccgggc  44940
acgccccggt cctcgctgta gagggattcc acgtcccagc cacggtcgga ggggaagtcc  45000
ccgaccgcgt cgacgccgtc ggagacgacg ctccacaggt cctcggggga cgtgacgccg  45060
cccgggtagc ggcaggccat gccgacgatg acgaccgggt cgtcggccac ggagggcagc  45120
gccgcgacgg ggaccgccac ggccggctcg gtgccgagga cgccgtcgag gaggtgaccg  45180
gcgaggaggt cggcggtcgg gtagtcgaag acgaccgtcg cgggcaggcg caggccggtg  45240
accttgccga gccggttgcg cagttccaca gccgtcaggg aatcgaaacc gaggtcctgg  45300
aaggcgcggt gcgggttgac ggtctgggca ccggaatggc cgaggacgac ggcgatctgg  45360
ccacggacca ggtcgagcag cacctcgcgg cgctcggcct ccgcgaggcc ggcgaggcgc  45420
gcggccaggc cggtggcggc ggcaccggct gcggcggcgg tgcggcggac ggaggtgcgg  45480
atcagcccgc tgagcagcgg cggcacctca ccctgggcgc gcagcgccgg gaggtcgagg  45540
cggacgggaa gcacgaccgg ctcacccgaa gccagggccg cgtcgaacag ggcggtcccc  45600
tgctcggcct cgaccggcgg cagaccggac cgggcgatac gccgccggtc ggtctccgac  45660
aactcccgcg tcatccccgc gtcctgcgcc cacggacccc agacaagaga gacaccaggg  45720
agccccaggg cccgccggta ctccaccaac gcgtccagga acacgttccc cgccgcgtac  45780
gcgccctgcc ccgcactccc gaacgtcccc gccaccgacg agaacaccac gaacgcctca  45840
aggcccaggt cccgcgtcgc ctcgtgcagg ttccacgccg cgtccacctt cggacgcaac  45900
accgccgcga cgcgctccgc cgtcagcgat gcgagcgtgg cgtcgtcgat gacgccagcc  45960
```

```
gcgtgtacca ccgcgcgcac gccgtgccgg gtgacgagcc cggcgacggc atcggcgtcg  46020
gcggcgtcgc atgcctcgac ggccacgtgt gcgccggcct ccgtcagttc ggtgacgagt  46080
tccccggcgc cctcggcgtt ggcaccgctc cggctgacca gcagcaggtc ccgcactccg  46140
tgcgtcatga cgaggtggcg ggccagtacc cggcccaggc cgccggtacc gccggtgatc  46200
agcaccggac cggtgagggc gtcccagcgc aggccctcgg ttgcttccgg tgtgacgcgg  46260
gccaggcgcg gcacccgcac ctcgccgtcc cgcaccaccg actccgcctc gccggaggcg  46320
agcgcggagc ggagggacgc ggtgtccgcg tcggccggaa gctccaacag gccgaatcgg  46380
cccgggtgtt cggagatcgc ggagcgcacc agcccccggg cggcggcgtc ggcgagtccg  46440
gtggtgcggt cggtggaggc cgtgacgaag accaggcggg atccggcgaa ccggtcctcg  46500
gccagccacg accgcaccag ggcgagagcc cgggcggcgg cggtgtgcgc ggcctgggcc  46560
ggatcggtcc cgtcggcgtc gtcggaggcg gccaccagca ccgtggaggg catctcctcg  46620
gcggccgcca gctcctccaa ggtggcgtac gtgacgaagt cgtcggcggc cggcacggcg  46680
ctccgggcct cgccgaggac ggccaccgca ccggtgtcgg caggaccgtc cagcggccgg  46740
gccgggaccc actccacctg gtagagggag tcccgcgccg gggtggtgag ctgtcccgtg  46800
gcgagcgggc gcaccgtcag ggagtggaca gtggcgaccg gggaaccagc ggggtcggcg  46860
agggcgaggg ccatggtgcc gtcggcgtcc cgggtgagac ggacgcggag ggccgtggcg  46920
ccggaggcat ggagggaaac gccgccccag gagaacggga cacctccacg gccgtcgtcg  46980
gcgagggcga aggcgtgcag cgcggcgtcg aagagcgcgg gatgcaggcc gaaggcgtcg  47040
ccgtcggtcc ccccgtccag ggcgacctcg gcgtacaggg cgtcgccgtg ccgccaggcg  47100
gcccgcagcc cccggaaggc ggggccgtag gcgaagccgg cctcggccag gcgctcgtag  47160
cagtcggtca cgtcgacctg ggccgcgtcg cgcggcggcc agacggtggc gtcgaagggg  47220
tcgggggcga gggtctcggg ggcgagggtt ccggtggcgt ggacggtcca cggagcaccg  47280
tcgtcgtcct cggtgcgcgc gtgtacgccg agggcacggc ggccgtcctc gtcgggagcg  47340
gcgacccgta tctggatctg gagggcgccg cgttcgggca ggaccagcgg ggcggagagc  47400
gtcagttcct cgaccgatcc gcagcccgcc tcgtcggcgg cacggacggc catctccagc  47460
agggccgtgc ccggcaccag cacggtgccc tggacgacgt ggtccgcgag ccacgggtgc  47520
gaccgcgtcg acaggcgtcc ggtgaggacc accccgtccg cgccgtcggc gccggcgagt  47580
tcgacggccg cgccgagcag cgggtgaccg gcggagccga gacccgcgaa gcgcacgtca  47640
ccggcgcgcg ggagcgtggc ctcgggccag tagcgctgct tctggaaggc gtaggtcggc  47700
aggtcgacgg ggcgggcgcc cacgaggaag ccggaccagt cgacgtccac gccgacggtg  47760
tggagccggc cgagggcgct gagcgccgag cccgtctcct cgcggtcctt gcgcaggagc  47820
gggacgagga cggcgtcctc accggcgctc tcgcgcgcca tgccgctgag cacgccgtcg  47880
gggcccacct ccacgaaccg ggtgacgccc tcttccgcga gggcccggac accgtcgtcg  47940
aaccggacgg cctcgcggac gtgggtgacc cagtactcgg gctcgtccac ctgtcccggt  48000
tcggcgagcg tgccggtgat gttcgagacc agcgggatcc tcggcgccgc gaaggacagc  48060
ccctccacca cctcgcggaa cgcgtggagc atcggctcca tcagcgggga gtggaaggcg  48120
tgcgagacgc gcagccggct gacccggcgg cccagctccc ggaagacctc ggcgaccgac  48180
tcgacggagg cctcggagcc cgagacgacc accgaggacg ggccgttgac ggcggcgatg  48240
gacaggttgc cggtgaggtg cggcagtacc tcggcgcacg tggcctcgac cgccgccatg  48300
```

-continued

```
gcgccgccct cgggcagcgc ctgcatcaga cggccacggg cggcgacgag cgcggcggcg  48360
tcggcgaggg tgaacacccc ggccacgtgc gcagcggcga cctcaccgat ggagtgaccg  48420
gccacgaact ccggccgcac cccccacgac tcgaccagcc ggaacaacgc cacctcgacg  48480
gcgaacagac ccggctgggc gtacgccgtg cggttcagga gttcggcgtc gtcgccccac  48540
acgacctcgc ggagcgggcg gtccaggtgc tcgtccagct cggcgcagac cgcgtcgaac  48600
gcctcggcga ggacggggaa ccgttcgtac aggtcacgcc ccataccgag ccgctgggag  48660
ccctgcccgg ggaagaggaa ggcggtgcga ccgttcccgg ccacgccttc cgcgacggcg  48720
gcgtcgggag ccccggcggc cagcgcgcga agggacgtca gcgccgtttc caggtcggcg  48780
cccaggacca ccgcgcggtg gtcgaagagg gtgcgctgcg tggccagaga gagcgccacg  48840
tcccgtacgt ccgccggcgc gtcggtgagg aagtcggcca ggcgggcggc ctgggcgcgc  48900
agtgcctcct cggtacgagc cgacaggacc cacggctgga caccggacga tgcctccgtc  48960
ccgtctgcct ctcccgggcc cgacccggtg accggctcgg gctgttcgag gatgacgtgg  49020
gcgttggtgc cgctgatccc gaacgaggac acaccggccc ggcgagcccg ctcctccccc  49080
ggccacaccc gctcaccggt cagcaactcc acagcaccgg ccgaccagtc gacgtgcgac  49140
gacggagcat ccacatgcag cgtgcgcggc agcctgccgt gacgcatcgc catcaccatc  49200
ttgatcacac ccgccacacc ggcggcagcc tgcgtgtgcc cgatgttgga cttgacggaa  49260
ccgagcagca acggccgctc ctcgtcccgg ccctgcccgt acgtcgccag gagcgcctgc  49320
gcctcgatcg ggtcacccaa cgtcgtcccc gtaccgtgcg cctccacgac atccacatca  49380
ccggccgaca gaccaccact cgccagagcc tgacggatga cccgctgctg ggaaggaccg  49440
ttgggcgccg tcagaccgtt cgacgcaccg tcctggttca ccgccgaacc acgcaccacc  49500
gccagcacac gatgaccgtt gcgccgggca tccgacagac gctccagcac caccatgccc  49560
acgccctcgg accagcccac accgtcagcc gagtccgcga acgaacggca ccgcccgtcc  49620
gccgacagac caccctgacg cgagaactcc acgaacgtcg atggcgtcga catcaccgtc  49680
acaccaccgg ccaccgccaa cgagcactca cccgaacgca acgcctgcgc agcccagtgc  49740
aacgccacca acgacgacga gcacgccgtg tccaccgtca ccgccggacc ctcgaacccg  49800
aacgtgtacg aaacacggcc cgaggccaca cttccggcac taccgctgcc ctggtacccc  49860
tcgtactccg gggaggccag caggttggcg tagtcgtggt acatgacgcc ggcgaagaca  49920
ccggtctggc tgccgcgcag ggagaccggg tcgataccgg accgctcgat cgcctcccac  49980
gtcgtctcca gcagaagacg ctgctgcgcg tccgtggaga cggcctcacg cgggctcatc  50040
ccgaagaact ccgggtcgaa ctcgggcgcg tcgtgcagga agccaccaga acgcgtgtag  50100
gaggtgcccg gcacagcgcg gtcggggttg tagagcgcgt ccacgtccca gcctcggtcc  50160
gaggggaagt ccgagaccgt gtcgacgccc tcggagacga cgcgccacag gtcctccggc  50220
gaggagacgc caccggggta gcggcaggcc atgcccacga tcacgatcgg gtcctcggcc  50280
accgacggca gcgccgacac cggcaccacc gccgccggct ccacccccacc gaacagttcc  50340
tccagcaggt accccaccaa cgcgttgacc gtcggatagt cgaacaccac cgtcgccggc  50400
aaccgcaacc ccgtcgactt ccccaaccgg ttccgcaact ccaccgcagt caacgaatca  50460
aaacccagat cctgaaacgc acgccccgga tccaccgact gcacacccgc atgacccaac  50520
accacagcga cctgaccacg caccagatcc agcaacacct cacgacgctc atctacgccc  50580
aacgccccaa gacgctgcac cagaccagcc gccgccaccg aaccacccgc agccgcacga  50640
cgaccacgcc gccgcaccag accccggaag agagccggta cgtcctcctc accgcgcagg  50700
```

-continued

```
gcggccaggt cgaggcggac ggggaggacg accggctcac ccgaggccag ggccgcgtcg  50760
aagagcgcgg tcccctgctc ggcctcgacc ggcggcagac cggaccgggc gatacgccgc  50820
cggtcagtct ccgacagtcc tcgtgtcatc cccgcgtcct gcgcccacgg accccacacc  50880
agcgacacac cgggaagacc cagagaacgc cggtactcca ccaacgcgtc caggaacacg  50940
ttccccgccg cgtacgcgcc ctgccccgca ctcccgaacg tccccgccac cgacgagaac  51000
accacgaacg cctcaagatc aaggccacgc gtcgcctcgt gcaggttcca cgccgcgtcc  51060
accttcggac gcaggaccgc agcaacccgc tccgccgtca gcgactcggc catgccgtcg  51120
tccaggacgc ccgccgcgtg cacgacggcg cgcaccgggc ggtcggccgg tactccggcc  51180
agcagggcgt cgagcgcggt gcggtcggcc aggtcgcagg cggcgaccga cacccgggcg  51240
ccgaggccgg tcagctccgc ggtgaaggcg tcgacgccct cggcggcggc accgctccgg  51300
ctcacgagca gcaggtcccg caccccgcgc tcgaccacca ggtgccgggc gacgatccgc  51360
cccagcccac ctgtgccgcc ggtcagcagc acggtgccgg agccgagacc ggccgacgat  51420
cccgcggtct cctctccccc ggcgtccggc gtcgtgcgga ccaggcgcgg gacgcacacc  51480
tcgctgtcca gcacggccgt ctccggctcg tccacggcga gggccgcgaa cagccgcccc  51540
gcgtccgtac ccgccgggag gtgcagcagg ccgaagcggc cggggtgttc cagcgccacg  51600
gaacgcacca gaccgcgtac gggcgcgcta gtcagagcgg aggcgggctc cgtgacgtga  51660
ccgcctcggg tgatgaagac cagccgggag ccggcgaacc gctcctgcgc cagccactcc  51720
ttgaccaggg cgagcgccca ggcggccgag gcgtgcgcgg agcccacgac gccctcggtg  51780
tccggggcgg gcggaacggc gaccacgacc gtctccggca ccgcctcggc cgcggccagc  51840
tcctgcaggt cggcgcggac ggctgcgccg tcgcccgcga gatcggcgag gccctcgccg  51900
aggaggacga cggatcccgc tgcgggagtc gcacgcgtgc cccgggccgg gacccactcc  51960
acgcggtaca gcggttcggc ggtgtcggcc gcgcgggcac cggcggcggc gcggacggtg  52020
agggagccga ccgaggcgac gggggctccg gtcgggtcgg ccacgtgcac ggccagcgtg  52080
tcgtcaccgg tccgggtcag ccgggtccgc aggacggagg cgccggacgc gtgcagggtg  52140
gcgttctccc agacgaaggg caccccgccg ggcgcgtcgt cgccgccgaa ggcgaaggag  52200
gcgtgcaggg cggcgtcgaa gagggccggg tgcaggccga aggcggtggc gtcgacaccg  52260
tcgggcaggg cgacctcggc gaacacctcg tcgtcccggc gccaggcggc ccgcagcccc  52320
tggaagacgg ggccgtagcg cagtccggcc tcggccaggc tctcgtagca gtcggtcacg  52380
tcgaccggca cggcgtcccg tgggggccat acggaggcgt cgaagccttc ggccgccggg  52440
tccgcgtcga tggtctccgg ggcgagtacg ccctgggcgt gcaggctcca gggctgccgt  52500
tcgtcgccgt cgtcccggga gtggatcgcg acggtgcggc ggccggattc gtcaggttcg  52560
ccgacgccca cctggacgcg cacggcgccg cgctcgggca gcaccagggg cgcggacagg  52620
gtcagctcct cgaccgatcc gcagcccgcc tcgtcggcgg cgcgcacggc catctccagc  52680
agggccgtcc ccggcaccag cacggcaccc tggacgacgt ggtcggcgag ccacgggtgc  52740
gaccgtgtcg agaggcgtcc ggtgaggatc agaccgtcgg cgccggccag ctccacggcc  52800
gcgccgagca acgggtgccc ggccgcaccg agtccggcga ggcggatgtc cccggtcccg  52860
gtggtcgttc ccgtgggcca gtagtgctcg tgctggaacg cgtaggtggg caggtcgacc  52920
gcgcggccgc ccgtgccgtc gaggacggcg ccccagccgg cggagacgcc ccgcacgtgc  52980
agttcggcga gggcgctcag tgcgacggcc acttcctcgc ggtccttgcg caggagcggg  53040
```

-continued

```
acgaggacgg cgtcctcacc ggcactggcc cgcgccatgc cactgagcac cccgtcggga  53100
cccagctcca cgaaccgagt gacgccctct tccgcgaggg cccgcacacc gtcgtcgaac  53160
cggacggcct cacggacatg ccgcacccag tagtccggcg cggtcagttc acccggctcg  53220
gcaatccggc ccgagacgtt cgagacgacc ggcaggcgcg gctcggcgaa cgacagatcc  53280
cgcaggacct cgtggaacgc gtcgagcatg ggctccatga gcggcgagtg gaaagcgtgc  53340
gacacgcgca gtcggctgac ccgacgcccc agctcacgga acacctccgc caccgcctcg  53400
acggcttcct cggcgcccga gacgaccacg gacgacggac cgttgaccgc agcgaccgac  53460
acaccctcga cggactccag acgcggcagc acctccgcct ccgacgcctc cacagccacc  53520
atcgcgccgc cctccggcaa cgcctgcatc aaccgcccac gagcagccac cagaacacac  53580
gcgtccgcca gcgagaacac acccgccaca tgcgcagccg ccacctcacc gatcgaatga  53640
ccggcaacga actccggccg cacaccccac gactcgacca gccggaacaa cgccacctcg  53700
acggcgaaga gaccggcctg cgcgtacgcc gtcccgtcca gaaccgacgt gtcgtcgccc  53760
cagaccacct cacgcagcgg gcggtccagg tgcgcgtcga gtccggcgca gaccgcgtcg  53820
aacgcctccg cgaacaccgg gaaacgctcg tacagaccac gccccatccc cagacgctgc  53880
gacccctgcc ccgagaacag gaacgcggtg cggccgggct cgacggcgcc gaggacgacg  53940
gcggggtcgg gctcaccgac gcagacggcc gcgaggccac ggacggcggt ctcgcggtcg  54000
tccgtcagga ccacggcgcg gtggtcgaag agggaacgct gcgtggccag ggagagcgcc  54060
aggtccacgg gacgcaggcc ggggtggccc tcgacctggg ccagcagccg ggcggcctgg  54120
gcgcgcagcg cctcctcggt acggcccgac aggacccacg gcacgatgcc gggggcgagg  54180
gcggcgatcc cgtccccgcc ggtctcgggt tccgcgaccg gctcgggctg ttcgaggatg  54240
acgtgggcgt tggtgccgct gatgccgaac gaggacacac cggcccggcg cagccgctcc  54300
tcccccggcc acacccgctc accggtcagc aactccacag cgcctgccga ccagtcgacg  54360
tgcgacgacg gagcatccac atgcagcgtg cgcggcagcc taccgtgacg catcgccatc  54420
accatcttga tgacacccgc gacacccgcc gcagcctgcg tgtggccgag gttcgacttc  54480
accgaaccga gccagagcgg ccggccctcc tcacgctcct gcccgtacgt ggccaggagt  54540
gcctgcgcct cgatcgggtc acccagcgtc gtccccgtgc cgtgcgcctc cacgacgtcc  54600
acatcaccgg ccgacagacc accactggcc agagcctgac ggatgacacg ctgctgggag  54660
ggaccgttgg gcgccgtcag accgttcgac gcaccgtcct ggttcaccgc cgaaccacgc  54720
accaccgcca gcacacgatg accgttgcgc cgggcgtcgg agagacgctc cagcaccacc  54780
atgcccacac cctcggacca gcccacaccg tcagccgagt ccgcgaacga acggcaccgc  54840
ccgtccgccg acagaccacc ctgacgcgag aactccacga acgtcgtcgg cgtcgacatc  54900
accgtcacgc caccggccac cgccaacgag cactcacccg aacgcaacgc ctgcgcagcc  54960
cagtgcaacg ccaccaacga cgacgagcac gccgtgtcca ccgtcaccgc cggaccctcg  55020
aacccgaacg tgtacgagac acggccggac gcgatgctgg gtgcgctgcc gttgctgcgg  55080
aagccctcat accgctcgtc ggcgagcatg ttgccgtagt cgttgtacat gacaccggcg  55140
aagacgcccg tctggctgcc gcgcagggag gccgggtcga taccggaccg ctcgatcgcc  55200
tcccacgtcg tctccaggag aagacgctgc tgggagtcgg tcgccaccgc ctcgcgcggg  55260
ctcatcccga agaactcgga gtcgaaggct ccggcgtcgt gcaggaagcc accggccttg  55320
gtgtaggtgg taccggacgc gtcccggtcg gggttgtaga gcgcgtcgac gtcccagcct  55380
cggttgacgg ggaactcgga gacggtgtcg acgccttcgg agacgacggt ccagagatcc  55440
```

-continued

```
tccggcgagg agacaccgcc cgggtagcgg caggccatgc ccacgatcac gatcgggtcc  55500
tcggccaccg acggcagcgc cgacaccggc acgaccgacg caggctccac cccgccgaac  55560
agctcctcca gcagataccc caccaacgcg ttgaccgtcg gatagtcgaa caccaccgtc  55620
gccggcaacc gcaaccccgt cgacttcccc aaccggttcc gcaactccac cgcggtcaac  55680
gaatcgaaac ccagatcctg aaacgcacgc cccggatcca ccgactgcac acccgcatga  55740
cccaacacca cagcgacctg accacgcacc agatccagca acacctcacg acgctcatct  55800
acgcccaacg ccccaagacg ctgcaccaga ccagccgccg ccaccgaacc acccgcagcc  55860
gcacgacgac cacgccgccg caccagaccg agcatcatcg ggtgcaggtc accctgcccc  55920
cgcagggcgg ccaggtcgag gcggacaggg aggacgaccg gctcaccgga ggccagggcc  55980
gcgtcgaaga gcgcggtccc ctgctcggcg gtcagctcgg gcatgcctgc gcgggcgacg  56040
cggtgccggc tggtcccgga gagggtgccg atcatgccgg cgtcctgggt ccacgggccc  56100
caggcgagcg aggtcgcggg caggccgagg ctgcggcggt ggcgtaccag ggcgtcgagg  56160
aaggtgttgc cggccgcgta gttggcctgg ccggggccgc cgaggatgcc ggacatcgag  56220
gagaagacga cgaaggcttc gaggtcgagg gcgcgggtgg cctcgtgcag gttccacgcg  56280
gcgtccgcct tcgggcgcag gacgcgggtc acgcgctcgg ccgtgagtga ttccaccgtg  56340
ccgtcgtcca gcaccccggc ggagtggacg accgcgcgca ccgggtggcg ggcgaccagc  56400
tccgcgacgg cggcggggtc ggagacgtcg cacgcctcga cggtcacgtg cgcaccggtc  56460
tcggacagtt cggcgaccag ttgcccggcg ccgtcggcgg cggcgccgct gcggctcacc  56520
agcagcaggt cccgcacccc gcgctcgacc accaggtgcc gggcgacgat ccgccccagc  56580
ccacccgtac cgccggtcag cagcacagtg ccgtcgatgc tgtcccagcg cgggcccgtc  56640
gtggtgccgg aggtgatccg ggccagtcgc ggggcgagca cctcgccgtc gcgtgcggcg  56700
gtctccggct cgcccgtggc gacggcggcc agcacggtcg cggtgtcggt gccgcgtccc  56760
acctccatca ggccgaagcg gccggggtgc tcggagacgg cggagcgcac caggccccgg  56820
agggccgcgt cggccaggtc gccgccgtcg acggcgtccg aggtgacgaa gaccaggcgg  56880
gagtcggtga accgctcctg cgccagccac tcgcgcacca gctccaggcc acgggcggcc  56940
agggcgtgga cggcgtccac caccgcgtcg ggccgcgtcg cggcgtcggg acgcacccgg  57000
accagcaccg tcgccggtac ctcttcggcg gcggccaggt cctccaggtc ggggaaggcc  57060
acgaacccgc cgtccgacag cccgtcggcc cggaggactc ccgcaagggc cgtggacgcg  57120
tcggaatccc cgaggacgcc gaccggaccg gtgccggccg cgtcaccagg tgcctcggtc  57180
cggacccagt ccacccggaa gagggcgtca cgggtcaggg cgtcgacacc ggtggcgtcg  57240
ggggcgaccc ggcggagcac caggttctcg acgctggcga cgggcgcacc ggtggggtcg  57300
gccacggcga ccgtcacggt ctcgtcgccg gtccgggtca tccggacccg gacctcccgg  57360
gcgccggtgg cgtgcaggca cacccccttcc caggagaacg ggaccacacc gtgcgcgaga  57420
ccacccaggg ccgagacgtg gagggaggcg tcgaggagcg ccgggtggag gccgtaggcg  57480
gtggcgtcgc gctcggcgga gtcgggcagg gcgacctcgg cgaagacgtc gtcgccccgg  57540
cgccaggcgg cccgcagacc ctggaagagc ggcccgtacc ggtagccgcc ctcggccatg  57600
cgctcgtaca ggccggtgag gtcgagggat tcggcgtcgg cggggggcca caccgaggtg  57660
tcgaactcca cggtgcgctc cccgggagcg aggacaccgg tggcgtgctc ggtccagggc  57720
tggtcgtcgg cgcccctcggc gcgggagcgg gccgcgagga cgcggcggcc ggcggcgtcg  57780
```

-continued

```
gcggggccca cgtgcaggtg gagctggacg ccgccctgct cgggcaggac cagcggggcg 57840
gcgagggtca gttcctcgac acggtcgcag ccgacctcgt cgccggcgcg gaccgcgagt 57900
tccacgaagg ccgtgccggg cagcagcgcg ttgcccatga cgacgtgctc gccaagccag 57960
gggtgggtgc gcagcgacag ccgggtggtg agcaggaggc cgccggagtc ggagagttcg 58020
acggcggcgc tgagcagggg gtgcccggcg gcgcgcagtc cggcggactc cacgtccccg 58080
gcgggtgcag gtgcgggcac gggccagtag tgctcgtgct ggaaggcgta cgtgggcagg 58140
tcgacgaggc gggcgccggt cccggcgagg acggcggtcc agtcgacggg cgcaccggtg 58200
gcgtggaggc ggcccagcgc ggcgagcgcg gtgacctcct cgtcacggtc cttgcgcagg 58260
agcgggacga ggacggcgtc ctcaccggca ctgacccgcg ccatgccact gagcaccccg 58320
tcgggcccca gctccacgaa ccgcgcgaca ccctccgccg ccagagcctg gacaccgtcg 58380
tcgaaacgca cggcctcgcg gacatgccgc acccagtagt ccggcgtggt cagttcaccc 58440
ggctccgcga tccggcccga gacgttcgag acgaccggca gcgaaggctc cgcgtacgac 58500
aggccggcca gagcctcacg gaagtcaccg agcatcggct ccatcagcgg cgagtggaaa 58560
gcgtgcgaca cccgcagcct gctgacccgg cgtccctgct cacggaacac ctccgccacc 58620
gcctcgaccg cgtcctcggc gcccgaaacg accaccgacg acggaccgtt gaccgcagcg 58680
accgacacac cctcgacaga ctccagacgc ggcaacacct ccgcctccga cgcctccaca 58740
gccaccatcg cgccgccctc cggcaacgcc tgcatcaacc gcccacgagc agccaccaga 58800
acacacgcgt ccgccagcga gaacacaccc gccacatgcg cagccgccac ctcaccgatc 58860
gaatgaccgg caacaaactc cggccgcaca ccccacgact caaccagccg gaacaacgcc 58920
acctcgacgg cgaagagacc cgcctgcgcg tacgccgtcc cgtccagaac cgacgtgtcg 58980
tcgccccaga ccacctcacg cagcgggcgc tccaggtgct cgtccaaccc ggcgcacacc 59040
gcgtcgaacg cctccgcgaa caccgggaaa cgctcgtaca gaccacgccc catccccaga 59100
cgctgcgacc cctgccccga gaacaggaac gcggtggagg cgctgcggac ggcgtcctcc 59160
aggacagcgg ggtggggttc gtcggcggcg agggaggtga gagctgcttc ggtggttccg 59220
gggtcggtgg cgaggacgac cgcgcggtgc gggagcgggg cgcggctggt ggcgagggag 59280
agggcgatgt ccgccgggcg cggggactcg gggccggtgt ggtcggtgag gtgggccagg 59340
agtcgtgccg cctgggcgcg tagcgcggtc tgcgaacggg cggagaggag ccagggggtg 59400
accgccgggt cggtggccgt caccggttcg gcgggggtgg cgtcctgagg ggtgtcctcg 59460
gccccggcgg gttcgggggt ggcctgttcg agcaggacgt gggcgttggt gccgctgatg 59520
ccgaaggcgg agacgccggc ccggcgggga cggtcggcgt cgggccagtc gacggcctcg 59580
gtgaggagtt cgacggcgcc ggccgtccag tcgacgtgcg gggtgggggt gtcgacgtgg 59640
agggtggcgg gcagcaggcc gtgccggatg gccatgacca tcttgatgac gccggcgaca 59700
ccggcggcgg cctgggcgtg gccgatgttc gacttgatgc cgcccagccg cagcgggcgg 59760
tcctccgggc ggttctggcc gtaggtggcg aggagtgcct gggcctcgat ggggtcgccc 59820
agggtggtgc cggtgccgtg cgcctcgacg gcgtcgacct ggtcggcggc gaggcgggcg 59880
tcggcgagcg cggcctcgat gacgcggcgc tgggagggcc cgttgggcgc ggtgaggcgg 59940
ctgctggcac cgtcctggtt gacggcggtg ccgcggacga cggcgaggac ggggtggccg 60000
ttgcggcggg cgtcggagag ccgctcgacg agcagcacgc cgacgccttc gccccaggaa 60060
gtgccgtcgg cggcctcggc gaagggcttg cagcggccgt cggtggcgag gccgcgctgg 60120
cgggagaact cggtgaagag ttcggtggtc ggcatcatgg cgacgccgcc ggcgagggcg 60180
```

-continued

```
agggagcact cccccgcgcg cagggcgcgg accgcgaggt gcagggcgac cagggaggag  60240
gagcaggcgg tgtcgacggt gaccgccggg ccctccaggc cgagggtgta ggagatccgg  60300
ccggagagga cgctcatggc gccgccggtg aggttgtggc cctcggtctc ctcggcggtg  60360
cgggccaggg agccgtagtt ggtgtcggcg ccgccgacga agacgccggt gtcggtgttg  60420
cgcagggagg cggggctgat gcgggcgcgc tccacggcct cccaggcggt ttccaggagc  60480
aggcgctgct gggggtccat ggcgagggct tcacgcgggg cgatgccgaa caggtccgcg  60540
tcgaagtcgg ccgcgccttc gaggaagccg ccctcacgga catagctctt gccgggggtg  60600
cccgggtccg ggtcgtagag gccgtccagg tcccagccac ggtccgcggg gagggggccg  60660
atggcgtcgg tgccgtcggc gaccagctgc cacaggtcct ccggggagcg gacaccgccg  60720
gggaaccggc aggccatgcc gatgacggcg atgggctcgc tctcccgtgc ctcgaccgtc  60780
tccagccgct gccgggtgcg gcgaaggtcg gtggtgacct tcttgaggta gtcgcggagc  60840
ttggcttcgg agcttgccat ggggtggatc ctctgaattc gggaaggacg cggtggccgg  60900
ggcgggggac gggagcggtg gccgccggcg cgctcgtgga cgcgccggcg gccaggcgcc  60960
gtcaggcgag cccgagttcg ttgtcgatga ggtcgaacat ctcgtcgtcc gtggtggtgt  61020
cgaggtcgga gtcgtcgtcg ggctcgtcgg cgtcctggga ggtggcgtcg agcttccacc  61080
cgagggcctt gagtcgctgc gccaggcggg cgcggtcctg gtcgtcgagg gcggccccgc  61140
cgacggcggc ctccagggcg gccagttcgg cgaagacggc ctggtcgggt tcgccggcgc  61200
ctgtgccgag ttcggtctgg aggtggcgaa cgagggcggc cgggtccggg tggtcgaaga  61260
tcagggtggt gggcagggag agcccggtgt cggcgttgag ccggttgcgg agttcgaccg  61320
cggtcagcga ggacatcccg aggtcgagga agccgcggtc cgcgtcgagg gacgcggcgg  61380
aggcgtggcc gaggacggcg gcgaggtgac cgaggaccgt acggtgcagc agcgcccgct  61440
gctgggggcc gctgaggccg gccagccgct cacggaggtc cgccggagcg ccggtggccg  61500
cgccgggccc ggagtcggcg gcgcgtcgta cggccgggcg tgccagggcc cgcagcagcg  61560
ggggcacctc gtcggcgcgc agggtgcggg tgtcgagccg tacggggacg aggtgggcgg  61620
tgtccagggc ggtgctcgcg tcgaggaggg cgagcccctg tccggcggtg agggggcgga  61680
tgccggagcg ttccaggcgg gccagaccgg tggtgtcgag ggcgccggtc aggtcgctgc  61740
ggtcctccca gaggccccag gcgagggagt gcgcgggcag gccgctcgcc cggcggtgct  61800
gcgcgagggc gtcgaggaag gcgttggcgg ccgcgtagtt ggcctggccg gggccaccgg  61860
cgacgcccgc gtaggaggag aacatcacga aagcggtgag tttggtgtcg cgggtgagct  61920
cgtggaggtg ccaggcggcg tcggccttgg gccgcaggac gtgggcgacg cggtcggcgg  61980
tgaggccgtc cagtgtgccg tcgtccagga caccggccgt gtggacgacg gcggtcaggg  62040
ggtgttcggc cggtacggcg tcgaggacgc cggccagttg ctcgcggtcg gcgacgtcgc  62100
aggcgacgat ctctgcctcg gcgccgagcg cggcgagttc ctcgcgcagg gccgcagctc  62160
cgggggcgcc gggcccgcgg cggctggtga gcaacaggtg gcgtacgccg tggcgggtga  62220
cgaggtgacg ggcgacgagg gcgccgaggg tgccggttcc gcccgtgatc agcacggtgc  62280
cggcgccggt tccctcgccc cacggagcgg tggcggcggg cgcgggggcg ccctccgggt  62340
gaccggcggg gaccaggcgc ggcacggtga cggtgccggc ccgtacggcg aactggtgct  62400
cgccggtgcg cgcggccgcc gcggcggcgg cgatcagggc gtcggcggcg ctgtcctcgt  62460
cggtgtcgcc gggggcaggg tcgaggtcgg ccaggaggaa gcgtccgggg tgctcggtct  62520
```

-continued

```
gggcggagcg gagcaggccc caggcggtgg cgtcggcgag gccggggacg gtgtcgtccg  62580
ggccggtggc gacggcgccc tcggtgacca ggaggagccg ggcgtcggcc aggcgcggct  62640
cccggagcca ggcggtggac agcgttaggg cacgggccgc agaggtgtgc gctgccttcg  62700
tcgggtcctc gccgctgtcg tggccgtgga aggcgacgac cagggcggga ggtgcggcct  62760
cgtcgttgtc gagggcggtg gtgagggcgg ccaggtcggg gtggagctgg acggtggcgc  62820
cgctgcgttc gagggcggcg gtgagccgtc cgggggcacc gatgacggcc cacggaccgt  62880
gtggttcggg ggtggcggag gaggttgtgt cggtccacgg gagccaggcg acccggtgcg  62940
gggcgtcggg gccggcggtg gcggggagcc ggtcggggcc ggccgagcgg gtcacggcgg  63000
tgccggtgag gacgaggtcg cctgcggcgt cgcgggcttc gacgctccag gtggcgtcgt  63060
cccccggggt gaggcgtacg cggagcctgc tggcgccggt ggcgtgcacg gtgacgtccc  63120
gccaggcggc gggcaggacc ggtgcggtcg cctcctcggt ggtcgcggcg agggcgagcg  63180
gggtctgcag gagcgccggg tggaggcgga agcgcgccgc gtcggcgtgc gcggcgtcgg  63240
gaagtgcgac ctcggcgagg acgtcggtgc cggcgcgcca cagggagcgc accgtgtcga  63300
agggcgcggc gaggtcgagg ccgcggtcct cggcgagggc gcgcacgggg gcggggtcgg  63360
ccgcgacggc gtcggcgggc ggccaggttc cggaagcctg cggggtggtg gtggggcggt  63420
cggtgaggtc gccggtcgcg ttccgcgtcc agggggtggc gggctcaccg gcgtcggcgg  63480
cgtggagcct tgagtggacg gagaacggcc gggagtcggt gtcggcggcg gagacggtga  63540
gctggatctc gacgtgcccc tcctcgggca cgacgagcgg gctgtgctcg tcgagtgcgg  63600
cgaccacggg caggccggtc tcgtcgccgg cccggaccgc ccagtccagc agggcggtgg  63660
tggggacgac ggcggcgccg tgggtccggt gggcgtccag ccagggctgg gtggtgaggg  63720
acagggagcc gctgaggacg gctccgccgt cggccaggcg gacgacggag tcgaggccgg  63780
ccgggtcgcc ctgggggggtg ccggcgtcca gccagtaccg ccggcgctgg aaggcgtagg  63840
tcggcaggtc gacggcggtg ccgtgggaca cggcggggcg ccagtcgacg gggacgcctt  63900
cgacgtgggc ggcggcgagg gcggtcagga cacgggcggg gccgccgtcg tcgcggcgca  63960
gcgagccgag ggccaccgcg tcggcgccga gggcggcgac ggtgtcctcg atgccgacgg  64020
tgagcaccgg gtgcgggccg cactcgacga agacgtcgtg gccctgctcg acgagggccc  64080
gcagggactc ctccaggcgg acggtgccgc gcaggttgcg gtgccagtag gcggcgccga  64140
gtccggtgcc ggggtgccag tccgcggtga cggtggagaa gaaggggatg tcgccgtcgc  64200
ggggctcgat gccgtcgagg gcggcgggca ggctctcggc gagccggtcg acgtgggccg  64260
agtgggaggc gtagtcgacg gggacgcggc gggcgcggac gccctgttcc tcgcaggcgg  64320
cgaggagggt gtcgagcccg ccggtgtcgc cggagaccac cacggaggag gggccgttga  64380
cggcggcgac gcagacgccg ggcagatcgg cgaggagggc ggtcacctcg tcgtgcgggg  64440
cggtgacggc caccatgccg ccgtgtccgg agagttcgcg ggcgatggcc cggctgcgga  64500
ccgcgacgat cctggcggcg tcggcgaggg agagggcccc ggcgacggcg gccgcggcga  64560
tctcgccctg ggagtggccg aggacggcgg ccggacgcag gccgtgggcg cgccacacct  64620
cggcgagggc gaccatcacg gcccaggtga cgggctggac gacgtcgacg cggtcgaggg  64680
cgggggcacc ctcctcctgg cgcaggacgg cggtcaggga ccagtcgacg tacggggcga  64740
gcgcctcctc gcaggcggcg acgcggtcgg cgaaggcggg gctggcgtcg aggagttcgg  64800
cgcccatgcc ggcccactgg gagccctgtc cggggaagac gaggacggtc cggcggtcgc  64860
gaccggcacc ccggccgccg gtcaccacgt gggcggcggg actgccctcg gcgagggcgg  64920
```

-continued

```
cgaggccggc gcggaagtcg ccggtggcgc tcccgacgac gacggcccgc ttctccagct  64980
gggcgcggcg cgtgaccagg gtgtgggcga tgtcggcggg gtcggtcccg gggtgggcgt  65040
cgaggtgggt gaggagggcc ttggcctggc cgcgcagggc ggcctcgctg cgggcggaca  65100
gcacccacgg caggggcgcg gggcgggtct ccgccgcgtc cggcgccggt gggctccggc  65160
tcgccgccgt ccgggccggg ggcggcgggg gccctcctcc aggatgacgt gggcgttggt  65220
gcccgctgat gccgaaggag gagacggcgg cgcggcgcgg gcgggaggcg ggcgcctcgg  65280
gccacgcggt ggcctcggtc agcaggcgca cgccggagtc cgcccagtcg acgtgcgggg  65340
tcggcgcgtc aatgtgcagg ctctcgggga gcaggcggtg gcgcagggcc agcaccatct  65400
tcatcacccc ggcgacaccg gccgcggcct gggtgtggcc gaggttggac ttgacggagc  65460
cgaggaacag cgggtggccg ccgtcccggt cgcggccgta cgtggcgagg agcgcctggg  65520
cctcgatcgg gtcgccgagg cgggtccccg tgccgtgcgc ctcgacgacg tcgacctcgg  65580
cggcgccgac acccgcgtcg gcgagggcct ggcggatcac ccgctgctgg gcggggccgt  65640
tgggggcgct gaggccgttg ctggcaccgt cctggttgac ggcggagccc cggaccacag  65700
cgaggacctg gtggccgttg cggcgggcgt cggagagccg ctcgacgagg atcaggccga  65760
cgccctcgga gaagccggtg ccgtcggcgg cctcggcgaa gggcttgcag cggccgtcgg  65820
cggcgaggcc gcgctgccgg gagaagtcca cgatgatctc gggcgaggac atgacggtga  65880
cgccgcccgc cagggccatg gtgcattcgc cgcgtcgcag ggcctgcagc gccatgtgca  65940
gcgcgacgag ggaggaggag caggcggtgt cgacggtgac ggccgggccc tccaggccga  66000
gggtgtagga gacgcggccg gagacgatgc tgttggcgtt gccgttgttg acgtatccgg  66060
cgatctcgtc ggggacgtgg gtgacgcgct tgaggtagtc gctggaggag aggccggcga  66120
agacgccggt gcggctgccg cgtaccgagc gggggtcgat gccggcgcgt tcgaaggtct  66180
cccaggccgt ctccaggagg aggcgctgct gcgggtccat ggcgagcgcc tcgcgggggg  66240
agatgccgaa gaagtcggcg tcgaagtcgg cggcgtcgtg gaggaagccg ccctcgcggg  66300
tgcgggagct gccctggccc tcggggacgg agtcgtagag gcgggcgagg tcccagccac  66360
ggtcgtcggg gaagggcgcg acggcgtcgg cgccgtcggc cagcagccgc cacaggtcct  66420
cgggcgagtg gatgtcgccg gggaggcggc aggccatgcc gacgatggcg aaggggtcgt  66480
cgtcgccggg cgcggcggga gcgggtgcgg gcgcggcggg gagcgcggcc ggggtgccgt  66540
cggagagttc gccgtcgagg tgggcggcga gggcggcgac ggtcgggtgg tcgaagacga  66600
gggtggcggg cagccgcaga ccggtggcgg cgctgaggcg gttgcgcagt tcgacggcgg  66660
tcagcgagtc gaagccgagg tcgcggaagg cgcggccggc gtggaacggc tcggtgtcgt  66720
cgtggccgag gacggcggcc gcgtgggcac cgaccaggtc gcgcagggtg ctgagccggt  66780
cctcggcgga acggccggcc aggcgggcgc gcaggccgtc ggtaccggtg gcggcgccgg  66840
cctcggcggt gcgccggacc gggccccggt acagggagcg cagcaggggc gggacctcgt  66900
cgccggatgc gcgcagctgt ccggtctcca ggcggaccgg caccaggtgg gggcgctgct  66960
cggtgagggc ggcgtcgaag aggaccatgc cgtcggcggc ggagagcggc aggacgccgg  67020
agcggcgcac ccgggcgagg tcggtgtcgt cgagctgtcc ggtcagggca ctggtgtcgg  67080
cccacagacc ccaggagagg gaggtggtgg gcaggccgtc ggcgcggcgc cggtgggcga  67140
gggcgtcgag gtaggtgttg gcggcggcgt agttggcctg tccggcgttg ccgaagacgc  67200
cggcgcccgc ggagaacagc accaggtccg tgagatcgag gtcgcgggtg aggcggtgca  67260
```

-continued

```
ggtggcgggc ggcgtcggcc ttcggggcga ggacggtgcg cagccggtcg ggggtgaggg  67320
attcgaggac gccgtcgtcg aggacgcccg cggcgtggac gacggcggtc agcgggtgct  67380
cggcggggac ggcggcgagc accgcggcga gggcgtcggc gtcggccgcg tcgcaggcgg  67440
caagggtgac ctcggcgccc agctcccgca gctcggcggc gagttccccg gcgccggggg  67500
tgtcggggcc ccggcggccg gtgaggacga ggtggcgcat gccgtggcgg gtgacgaggt  67560
ggcgggcgag gatgccgccg aggacaccgg cgccgccggt gacgaggacg gtgccctcgg  67620
ggtcccaggc gcgcggcagg gtgagcacga tcttgccgta gtgcttggcc tgggccatgt  67680
ggcggaaggc ttcgcgggcg tgccgcacgt cccaggtgac ggtgggcagg ggccgcaggg  67740
ctccggaggc gaagagttcc gacaggtcgc ggaacatctc ctggatgcgg tcctcaccgg  67800
cctcacgcag ttcgtacgcc tggtagaggg cggcggcggg gtggtcgcgg agaacctgcc  67860
cgggatcgcg gacatcggtc ttgcccatgt cgacgaggcg cccgccgggg gcgagcagcc  67920
gcagggaggc gtcgatgtag tcgccggcca gggagttgag gacgacgtcg acgccacggc  67980
cgccgctggt ggtgcggaag cggtcctcga aggcgagggt gcgggaggag gcgaggtggg  68040
cgtcgtccca gccgtcggcg cgcagcaggg tgcgcttgtg gtcgccggcg gtgccgtaga  68100
cctcggcgcc ccagtggcgg gcgagctggg cggcggccat gccgacaccg ccggcggcgg  68160
cgtggacgag gacggactcg ccggcgtcga ggtgggcgag gtcgcgcagt ccgtagtagg  68220
cggtgaggaa ggcgacgggg acggaggcgg cctgcgccca ggtccagccg tcgggtacgg  68280
gggcgagcat gcgggcgtcg gcgacggcgc ggggggcgaa gccgccggag accaggccca  68340
tgacgcggtc gcccggggcg aagccggtga ctccctcgcc gacggcggtg accacaccgg  68400
ccgcctcggc gccgaggagc acggcggggc cggggtacat gccgagggtg ttgaggacgt  68460
cgcggaagtt gagtccggcg gctcgcacct cgatcaccac ctcgccggcg gcgggctcct  68520
cggccgtccc gggggcggcg acgaggtcca gccggtcgac ggatcccttc tcggggatgt  68580
cgaggcgcca gttcccggtc ccctcgggca cggtgagggc gtcggaggta cggggccgga  68640
ccaggcgcgg cgcgtacgcg gcgccctggc ggagggcgag ttgcggctca ccggcggcga  68700
gtgcggccgg cagggcgagc caggagtcgt cgtggatgtc gaggtccacc aggacgaggc  68760
ggcccgggtg ctgggactgg gcggagcgca ccaggcccca gacggcggcg ccgggcaggt  68820
cgtgggcggg gtcggcgggg ccggtgggga cggcgccgcg ggtgacgacg accagcggaa  68880
cgccctcggt ggtctcgtcg gcgagccagc tctggacggt ggcgagcacg tcgtcgagga  68940
cggcgtccgg gacgcccggc tcggcgtcgg gggcggcggc cgtgcccgac gcggcggccc  69000
cggcgaacag caggacggcg tccggccggt gaccgttggc ctcggtgtgc tcggccagtg  69060
cgccgggggt ggcgaaggcg ggcagtgtgg ttccgctgcc gtcgggtgcg gtgaccgggt  69120
cggccggggt gccgaggacg gcccagccgg tggcggccgg gacggcggcg ggcggcgtga  69180
ccggtgtcca gtcgaggcgg aacagccagt cgcgggcggc gcgggcggac ggatcgaggg  69240
tgtccggcgc gatctcgcgt acggccaggg cgtcgatggt ggcgacgggg gcgccggtcg  69300
ggtcggtgag ctggacggag atggcgtcct gccctgccgg ggagacgcgg acgcgcagcg  69360
cggtcgctcc ggcggcgtgc aggcagaccc cgctccaggt gaacgggacg accgtgcgcc  69420
cggcgctgcc gggggcgagg tgggcggcgt gcagggcggc gtcgaggagc gcggggtgga  69480
tgccgaaccg tccggcgtca ccgcggacct gctcgggcag gacgacctcg gcgtagaggt  69540
cctcgccgcg gctccaggtg gcgcgtacgc cctggaagac gggcccgaac tcgtagccac  69600
ggccggcgag cagctcgtag aagccctcgg cggcgacggc ggtggcgccg gggggcggcc  69660
```

-continued

```
aggaggtgaa ctcctcgggc cggtcgacgg cgggggcgcc gggctcggtg agggtgccct  69720
gggcgcggag cgtccagagg tcctcggtgg cgccgtcggg gccggtggtg cgggtgtgga  69780
cggtgacggg acggcggccg gaggcgtcgg gttcgccgac gccgatctgg acctgtgcct  69840
cgccgcgttc ctggaggacc acgggggcct ggagggccag ttcctcgatc cggccgcagc  69900
cgaggacgtc tccggcccgg atcacggact ccacgagcgc ggtcccgggg acgatcacgg  69960
tgccggacac cgcgtggtcc gcgagccagg ggtgggtacg cagcgaccac cgtgccgtgg  70020
ccaccaggcc gtcgccgccc gcgagttcga cggaggcacc gagcaggggg tgatcgggcg  70080
agtcgaggcc ggccgagctg acgtcaccgc ccagctcggc gaaacgcggc cagtagtgct  70140
gccgctggaa ggcatacgtg gggaggtcga cgtggcgggg ccgggtgccc gcgtaatgcg  70200
tctcccagtc cacctcggca cccagcgccc acgcctcacc cagcgacagc gcgaaccgct  70260
ccagaccacc ctcgtcacgc cgcagcgtgc cgacgacacc ggcctgcacg ctcgcgtcct  70320
cgatggtctc ctgcaccccg gtggccacca ccggatgcgc actcacctcg acaaacaccc  70380
ggaacccgtc ggccagcaac gcacgcgtcc ccgcctcgaa ctccaccgtc ccccgcaggt  70440
tccggtacca gtacccggcg tccagaccag cggtgtcgat cacgccaccc gacaacgtcg  70500
agtagaacgg cacatcacac gagcgcggcg ccaccggcgc cagaagcccg gcaagctcct  70560
cctcgatgcg ctccacatgc gcggagtgcg acgcgtagtc caccgccacc cgacgcgccc  70620
gcacacccga cgcgtcacac gcggccacga actcgtccaa cgcctccgca tcacccgaca  70680
ccaccaccga cgacggccca ttgaccgccg ccacactgat acgcccctcc cagcccgcca  70740
gcagaccacg aacctcgtcc acgttccttg cgaccgacac catgccgccc agacccgaca  70800
gcgcacgcaa cgcacgcgac cgcagcgcca ccacacgcgc cccgtcctcc aacgacagac  70860
cacccgccac caccgcggcc gcgatctcgc cttgcgaatg accgatcacc gcacccggct  70920
ccacaccctg agcccgccac acctccgcca acgacaccat caccgcccac aacaccggct  70980
gcaccacatc cacccgctcc aacgacgcag caccctccac accgttcagc acatccagca  71040
acgaccactc cgtgaacggc tccaacgccg ccgcacactc cgccacccga cccgcgaaca  71100
ccggcgacga acccaacaac tccaccgcca tacccaccca ctgcgaaccc tgacccggga  71160
acacgaaggc gaccttgccg gagccgtccc cgaccgagcc ttccaccaga cgcggggaag  71220
gctccccggc ggcgagcgcg tccagcccgg cgagcagttc ctcgccgtcc cggccgacga  71280
ccaccgcacg ccggtccatc gccacgcggg aggagaccag cgcatgtgcc acgtccagca  71340
ccgacgcgtc ggacgtacgc accgacgccg ccagacgcgc cgcctgctcc cccaccgccg  71400
cacgcgactt gcccgacacc atccacgacc ggacggtgtc ggccgagtcg tccgcggagg  71460
gctcggtgaa cgggtcggcc ggctcgtcct cggcgggttc gggggccggg gcctcctcca  71520
ggatgaggtg gccgttggtg ccgctgatgc cgaacgagga gacgccggcg cggcgcggac  71580
ggccggtctc gggccagggg gtggactcgg tgacgaggcg gacggcgccg ctcgaccagt  71640
ccacgacgga ggtcggccgg gtgatgtgga ggctcttggg cagggtgccc tgccgcatcg  71700
ccaggatcat cttcatcatg ccggcgacgc cggcggcggc ctgggtgtgg ccgatgttgg  71760
acttcagcga accgagcagc agcggccggg ccgggtcgcg gtcctggccg taggtggcga  71820
ggatggcctg cgcctcgatg ggtcaccga gcggcgtgcc ggtgccgtgc gcctcgacca  71880
cgtcgacctc gcccggggcg aggcccgcgt tggcgagggc ctggcggatg acgcgctgct  71940
gggaggggcc gttgggggcg gtcagaccgt tggacgcacc gtcctggttc agggcggagc  72000
```

-continued

```
cgcggaccac ggcgaggacc gggtgaccgt tgcggcgtgc gtcggagagc cgctccagca  72060
ggaccaggcc gacgccctcg gcgaagccca tgccgtcggc gccctcggcg aaggccttgc  72120
agcgcccgtc ggccgccagg ccccgctgcc gggagaactc gacgtagggc tcgggtgtgg  72180
acatgacggt gacaccgccg gccagggcca tcgtgcactc gccggtgcgc agcgactgca  72240
gggccaggtg gagggcgacc atggacgagg agcagccggt gtccatggtg acggcagggc  72300
cttcgaagcc gtacgtgtac gacaggcggc cggaggcgat gctggaggcg ttgccggtca  72360
tgaggtggcc ggcgagttgt tcctgggcgg cggcgccgcc caggcggacc tggtagtccg  72420
tggtgatgct gccgacgaag accccggtgg cgctgttgcg cagggttccc gggtcgatgc  72480
cggcgcgttc gaaggtctcc caggaggtct ccagcaggag ccgctgctgc gggtccatgg  72540
ccagggcctc gcgcggcgag atcccgaaga acaccgggtc gaatccggcg acgtcctgga  72600
tgaagccgcc ctcacggctg taggtggtgc cgtggcgctc ggggtccggg tcgtacaggg  72660
cgtcgaggtc ccagccacgg tcctcgggcg gcgtggagac ggcgtccacc tcggcggcca  72720
tgaggtgcca cagttcctcg ggcgtggtga cgccgccggg gaagcggcag gccatggcga  72780
cgaccgccat cggctcgtcg gtgacgcccg cggagacgac gacgggcgcg gcgacggggc  72840
gctcgtcgcc gaggagcagg gtgcgcaggt gggcgacgac cgccgtggtg ttggggtagt  72900
cgaagaggag ggtggtgggc agcttgacgt cggtggcggc ggtgatccgg ttacggacct  72960
ccacggcggt cagcgagtcg aagcccaggt ccttgaaggc acggttgacg tccacggcct  73020
ccggtgagga gtggcgcagc gcggtggcga cctcggcgcg gaccaggtcg gtgagcagcc  73080
ggtcctgttc ggcgggggcg aggccgcgca gccggtcgcg cagggcgtgg gtgtcgggcg  73140
cggtggcggc ggctgcctcc agggcgcggc ggacctcggg gaggtcgccg acgagcgggc  73200
tgggccgggc cgcggtcatg gcggtgccgt aggcccgcca gtccacgtcg aggacggtgg  73260
cgtgcgggac gccctcggcg acggcggcgc gcagcgcggc gacggcggtg acggggtcca  73320
tcggggcgag gccgtcgtgg ctcatccggt cggcgagcac gtcggcggtg gccatgcccg  73380
cgtcggccca cgggccccag gccacggagg tgacgggcag gccctcggcc cgccgctgct  73440
cggctacggc gtccagatag gcgttggcgg cggcgtagtt ggcctgcccg gcgttgccga  73500
ggacaccgac gatcgaggag aagaggacga acagggtgac gtcgtggtcg cgggtcagct  73560
cgtgcaggtg ggcggtgccg agggtcttgg ggcgcaggac ggcttcgaag cggtccaggg  73620
tgagggcgtc gaggacaccg tcgtccagga caccggcggc gtgcacgacg ccggtgaggg  73680
ggaggccggc ggggagggag tccagcagac gggcgagctg gtcgcggtcg gccacgtcgc  73740
agtcggcgac ggtgacccgg gcacccagct cctccagctc ggcgacgagt ccgactgcac  73800
cggggctgcc gggtccgcgt cggctggtga gcaccaggtg gcgggcgccg gaggcggcga  73860
gcgagcgggc cacgtgggcg ccgagcgcac cggtaccgcc ggtgatcagg acggtgtcgt  73920
ggtcgcccca gcccccgatc ccgtcgtcgt cggccgcccg cacggcgagt tccgcgtcca  73980
cgtcggtgac ccgggccggc tcgggcagcg gcattcgggc cagccgacgg gcgtacgcgc  74040
cggaggagcg tacggcgatc tggtcctcgg ggccgccgag gagcgtggcg aggcgggcga  74100
ggctgcgggc gtcggggtcg gcgggcaggt cggcgaggcc gccccaggcg tcggggagtt  74160
ccagggcgac ggcgcgtccg aagccccagg tctcggcctg gacgggcgag gtcagccggt  74220
cgcggctgtc gacggcgacg gcgccgcggg tcagcgccca cacggaggct tcggtgccgg  74280
acagcgcgtg cagcagctcc ttggcggtgg cgaggccgcg cggtacggcg gggtggtcgg  74340
ggtgggggcg ctcgtcgagg gcgaggagcg agaggacgcc cgcgatgcct tcggcgccgt  74400
```

-continued

```
cgggctcggt gtcaccggtt ccggtgagca gggcggtgag cgcggcggtg tcctcgtcgc  74460
cggtgaggtc gtggcgctcg acacgcaggc cgcgccccgt gagagccccc agcaccgcgt  74520
gcacccaggg gtcgtcggcg tggccggcgg ggacgagggc gggccagcgg ccggcgggga  74580
cggcgtcgtc ggcgccggtc agcgcggtcc aggtgacgcg gtggcgccag gtgtcgaggg  74640
tggagcgcag ggtgcggcga cggcgccagg acgccagcgc gggcagcagc gtgccgaacg  74700
cctccacgtc gtcgccggtg acctccagca cggaggagag ccgggtgaga tcgccgctct  74760
cgacggccga ccagaagtcg ccgtcggcgg ggtcgccggt ggccgccgcc gcggccgact  74820
cggcgggcgt cagccagtac cagtcacggc ggaacgggta ggtggggagg tcgacgtggc  74880
ggggccgggt gcccgcgtaa tgcgtctccc agtccacctc ggcacccagc gcccacgcct  74940
cacccaacga cagcgcgaac cgctccagac caccctcgtc acgccgcagc gtgccgacga  75000
caccggcctg cacgctcgcg tcctcgatgg tctcctgcac cccggtggcc accaccggat  75060
gcgcactcac ctcgacaaac acccggaacc cgtcggccag caacgcacgc gtccccgcct  75120
cgaactccac cgtcccccgc aggttccggt accagtaccc ggcgtccaga ccagcggtgt  75180
cgatcacgcc acccgacaac gtcgagtaga acggcacatc acacgagcgc ggcgccaccg  75240
gcgccagaag cccggcaagc tcctcctcga tgcgctccac atgcgcggag tgcgacgcgt  75300
agtccaccgc cacccgacgc gcccgcacac ccgacgcgtc acacgcggcc acgaactcgt  75360
ccaacgcctc cgcatcaccc gacaccacca ccgacgacgg cccattgacc gccgccacac  75420
tgatacgccc ctcccagccc gccagcagac cacgaacctc gtccacgttc cttgcgaccg  75480
acaccatgcc gcccagaccc gacagcgcac gcaacgcacg cgaccgcagc gccaccacac  75540
gcgccccgtc ctccaacgac agaccacccg ccaccaccgc ggccgcgatc tcgccttgcg  75600
aatgaccgat caccgcaccc ggctccacac cctgagcccg ccacacctcc gccaacgaca  75660
ccatcaccgc ccacaacacc ggctgcacca catccacccg ctccaacgac gcagcaccct  75720
ccacaccgtt cagcacatcc agcaacgacc actccgtgaa cggctccaac gccgccgcac  75780
actccgccac ccgacccgcg aacaccggcg acgaacccaa caactccacc gccataccca  75840
cccactgcga accctgaccc gggaacacga aggccacatc acccgcaccc tcaccggcgg  75900
tgccctcgac cacacgcacg gacggctcac ccgccgccag cgcgtccagc cccgcgagca  75960
gctcctcacg gtcggacccc acgaccaccg cacgccggtc catcgccaca cgcgacgaca  76020
ccagcgcatg cgccacgtcc agcaccgacg cgtcggacgc acgcaccgac gccgccagac  76080
gcgccgcctg ctcccccacc gccgcacgcg acttacccga caccatccac gaccggacgg  76140
tgtcggccga gtcgtccgcg gagggctcgg tgccgggctc ctccgcgcgg ggggtctggt  76200
cctcgggggc ctgttccagg atgaggtggg cgttggtgcc gctgacgccg aaggaggaca  76260
cggcggcgcg gcggggccgg ccggtctcgg gccaggtggt ggactcggtg agcagttcca  76320
cgcccccggt cgcccagtcg gcgtgcgggg tgggcgcgtc gacgtggagg ctcttgggca  76380
gggtgccgtg gcgcatggcc tgcaccatct tgatgacccc ggcgacgccg gaagcggcct  76440
gggtgtggcc ggtgttggac ttcagcgagc cgagcagcag cgggtgcgcg tcaccgcggt  76500
cctgcccgta cgtgttgagg agggcctgcg cctcgatggg gtcaccgagg gtggtgccgg  76560
tgccgtgcgc ctcgaccacg tcgacctcgc ccgaggtgag accggcgtcg atgagggcct  76620
ggcggatcag ccgctgctgg gaggggccgt tgggggcggt caggccgttg gacgcgccgt  76680
cctggttgat ggcggaaccc cggatgacgg cgaggatctc gtggccgttg cgctgcgcgt  76740
```

-continued

```
cggagagccg ctccagcagg atcaggccga cgccctcgga ccaggcggtg ccgtcggcgc  76800
cggcggcgaa gggcttgcag cgcccgtcgg ccgccaggcc ctgctggcgg gagaactcgg  76860
tgaacatctt gggcgtcgac atgacggtgg cgccgccggc cagggccagc gagcattcgc  76920
cctgtcgcag cgaacggacg gccaggtgca gggcgacgag cgaggaggag caggcggtgt  76980
ccaccgtcac ggcgggcccc tcgaagccgt acgtgtacga caggcggccg gaggcgacgg  77040
cgaccgtgtt gccggtgagc aggtgcccgg cgacctcttt ctggcgcccg cgcgaggcgc  77100
cgtcgtagtc gccgtgcccg gtgccgacga agacaccggt ggtgctgccc gcgagggtgt  77160
cgggcaggat gccggcgcgc tccagcgcct cccaggaggt ctccagcagg agccgctgct  77220
gcgggtccat ggccagggcc tcgcgcggcg agatcccgaa gaacgccggg tcgaactcac  77280
cggcgtcgtg gaggaatccg ccttcacgcg tgtaggtggt gccgtggtgg gcggggtccg  77340
ggtggaacag gtggtcgagg tcccagccgc ggttcgcggg gaacgcggag atggcgtcca  77400
cgccgtcgcg ggccagttcc cacaggtcct gggggtgcg cacgccgccg gggtagcggc  77460
aggccatggc gacgacggcg acgggctcgc ggtcgcggtt ctcggcgtcg ctgagctgct  77520
gccgggcctc ctggagatcg gtgacggccc gcttgagata tgcgcggagc ctgtcctcgt  77580
tcgacatcag gtgcccacct ctccatgaga taccggaaaa cgcggaggcg gcgattcccg  77640
aattccacgc cccgacccag ttcgcgctcc cggaagtcag gggacccgtc cgggaaagcg  77700
gccacgggcc gtacgggacg gcccggtgcg agagccagtc tggccgtctt ggactgcggg  77760
tttccctaaa gcatggggag gctggtgggg acgcgcgttc cggtcgaggc gggttctccg  77820
tccgaggtct ggtgaattcc ctcgtcggtt tccgatatcg gcggggcgga tcgccgggcg  77880
gggaattcgc gacggcggag ggcggaacgg ctcggtcgtg gagccgacga ggccccgctc  77940
cgtcgaaggt gacggaacgg ggcctcgctg ggtgggggc agtcagccgg cgggggcggt  78000
ctccggcgcg tcggtggtgg ccgtggtctc cagggcggtc agccacgcgt ccatgaggtc  78060
ggcggcgggg ccggagtcct cacggatgag ggagaggtgg tcggagtcca gggggcggac  78120
ctccgcgtcg gggacgaccg gaaggtgcag gcgctcgggg tcgggggcgg ggacgccctc  78180
gatgagcgcc cgggtgcact tgatctccag gacggggacg gtggtggggt gcacgtcgag  78240
ggcgttgagg agcaccatcc agcggcccat ggcggacagg cgggagttgg tcaggcgcac  78300
cggggagtcg tcgacggcgg tgaagttgaa cttcatcatg ccgttgtagt cgacgccctc  78360
gtcgctcttg tgctggatgc tgagggtgtc gaggaggacg acggcctcgg gccggatgcc  78420
ccaggtgtgt tccaggactc cggccgccgc gtaggcgagg gagccgccgg aggagtggcc  78480
gaccaggacg aagggcttgc cgtcggcggc ctggagggtg cagtcggcga tgatccgcgc  78540
ggccgcctcg gcgtgggcgg gcagggcctc gccggtgttg aagccgatga ggggcagcgc  78600
ggtgacgtcg cggcggcccc ggaagtggcc ggagagagtg gcgtactggt ggacgccgcc  78660
gttggcggtg gggcgctga cgcacaccag gcgggtcggt gcggggccct cggcgagcgt  78720
caccggccag ggcaggtcct ccagttcggc ggtcacctcg aaggaggggc gcagcgccgc  78780
gacggtggcc agcatgcgct gtgcctcgcg caccttgccc tgggccaggc cgtcgaggaa  78840
cagccgctcc atggagtcgt tctcggtggg gccgccggcg gcgccggtct gcggggcgcc  78900
gctgccctgg gcgccgagtt cggtgcgcag ccaggcggtg agcccgttcg gggagccgct  78960
gtcgtagacg atgctcgcgg ggagctggag accggtgatc tcgctgagct tgcggcgcag  79020
ttcgataccg atcagggagt cgaagccgag ctccaggaag tcgcggtcgg ggtcgatctc  79080
cgaggtgtcg gtgtggccga ggagtgccgc ggcgcaggcc acgaccgtct cgcgcagggt  79140
```

-continued

```
ggtctcctgc tcccccgcgc cgaggttcgc gaagttctcg cggaaggagg ccgcgtccag  79200
gacgcgggcc ggggcgtcgg tcgtggcggc ggcggtccgg cgcgggggac ggaccaggcc  79260
ccgcatgagc ggcggcacct cgtcgaggtg ggcggtggcg ggcggtgcgg ccaggttggt  79320
ggcgaccacc aggggttcgc cgagcgtgag cgcggtgtcg agaaggtcca gggcgcggtc  79380
gccgggcagg gtgtcgatgc cgccggagcg gatgcggcgg cggccggtgt cggtgaggag  79440
gtcgccggcc atgccctcgt cgaggtccca ggcgccccag gccacggaga gggccggcag  79500
gccctgggcg gcccggtgct gggcgagggt gtcgaggaag aggttggcgg cgacgtagtt  79560
ggcctggccg gcgcgggcgg tgacgccgga gatggaggag tagaggacga aggcgtcgag  79620
gccgaggccg cgggtgaggt cgtgcaggtg ccaggcggcg tccgccttgg accgcaggac  79680
ggtggccagg cggtccggtg tgagggaggt gacgacggcg tcgtcgagga ctccggcggc  79740
gtgcacgacg gcggtgagcg ggtgctcggc ggggatgccg ccgagcagtg cggccagggc  79800
gtcgcggtcg gagacgtcgc aggcggcgac ggtgacatgg gcgccgaggg cggtcagttc  79860
ctcgcgcagg gcggcggcgc cgggggcgtc ggggccccgg cggcccgcca gcaggagccg  79920
ggtgacgccg tggcgggtga cgaggtggcg ggcggtgcgg gcgccgaggg tgccggtgcc  79980
tccggtcacc aggacggtgc cgtcacgggt gacaccgaac gggtcggtgt tctccgggcc  80040
gtcctggggc gtgggcgggg gcagttgggt gaggcggccg acgaggacct gtccgtcgcg  80100
gacggcggcc tgcggctcgt cgacggcgag gacggcctcc agggggaacg gggcgcccgg  80160
ttcgacgtcg accagggtga agtcggcggg gtgctcggcc tgggcggtgc ggaccatgcc  80220
ccacaccgcg gccccggcca ggttggcggc cgggtcgccg ggacgggcgg ccacgacgcc  80280
gcgtgcgacg aagaccagcc gggcgcccgc cgggcggggg ccgtccagcc actcctggag  80340
gagggcgagg gtggcgcggg tcgcctcgtg ggtggcggtg accgggtcct cgcctccgtc  80400
ggggacgggt acgaggacct gggtgcccgt ctcggtgacc tcgtcgagcc cggccaggac  80460
cgtaccggtg ccgaacgggt cggtgccgag ggcgacccgg gggcctccgg cggcgggccc  80520
ggtgggttcg gcggggaccc agtcgaggcc gaggagggtg gagcggtcgg ttccgggctt  80580
gagcaggcgg gccgccccgg agggccgcag ggccagcgac tcgaccgaca gcacgggccg  80640
gccggcggtg tcgacggcgg cgatgctgac ggtgtcctca ccggccttgg tgatacggac  80700
ccggagccgg gcggccccgg aggcgtgcag ggtgacgccg gaccaggaga acggcaggag  80760
tccctggtcg gcgtccttca gctcgacgta ctccacggcg tggagggcgg cggtgagcag  80820
ggcggggtgg agaccgaaga gggcggcgtc gtcggcgcgg gcgggcagtt cgagttcggc  80880
gaggacctcg tcgccccggg tccacacggc acgcagcccc tggaagagcg ggccgtactc  80940
ggtgcgctcg tagaagccgt ccaggtcgac gggggtggcg tcggcggggg gccaggcgct  81000
ctggccgaag gcgacctggc gtgctccggc gaccaggacg ccggtggcgt gctgggtcca  81060
gggctcgtcg tcggcggcgt cctcgggccg ggagtggatg gcgagcgggc ggcagccggc  81120
cgcgtcgggg ggaccgacgc cgacctgtac ggaggcggcg cctcgcgggt cgagggcgag  81180
cggggtggtg agggtcagtt cctggacgcg gccgcagccg gcctggtcgc ccgcgcggac  81240
ggcgagttcg aggaaggccg tggcggggaa gaggacgagg ccgcccatga cgtggtcggc  81300
gagccaggga tgggtgcgca ggcccacgcg cccggtcagc aggacgccct cggaaccggc  81360
gagggagacc gcggcaccga gcagggggtg ctcggccggg gtgagcccgg ccccggggat  81420
gtcggcggcg tgggcgagcg ggcgcggcca gtagcggcgg tgctgccagg cgtacgtggg  81480
```

-continued

```
caggtcggtg cggcgggcgc cggtaccggt gaaccaggcg gcccagtcga cgcggacacc  81540
cgcgacgtgc agctgggcga gaccggtgag cagggcctcc tgctcggggc ggcgggagcg  81600
cagcgccggg gctgccacgg cgccggtacc gccgtcgagc gtgtcgaggc tctgccgggc  81660
gagggcggtc aggaccccgc cggggccgat ctccaggaag gcgtcggctc ccgcctcggc  81720
gagggtacgg acgccgtcgg cgaagcggac ggtctcgcgg acgtgccgca cccagtactc  81780
ggggtcggtg agctgaccgg gcgcggcgag ggcgccggtg acgttggaga ccaccgggac  81840
gcgcggctcg gcgtactcca gcgagcgggc gacctcgcgg aaggcgtcga gcatcggctc  81900
catcagcgcc gagtggaagg cgtggctgac ggacagacgc tggatcttcc gcccttcggt  81960
ctcgaactcg gcggcgaggg ccgtcacttc accttcggga ccggacacga cgacggagtc  82020
gggaccgttc acggcggcca gggacaagcc ctcggtcagc cggggcgtca cctcggcctc  82080
cgtcgcccgt acggccacca tcgccccgcc cgtggggagt tcctgcatca ggcgggcgcg  82140
ggcggcgacc agccggcagg cgtcgtcgag cgagaagacc cccgccacgt gcgccgccgc  82200
gatctcaccg accgaatgcc ccgccacgaa ctccggcgag acaccccacg actccaccag  82260
ccggaacagc gccacctcca ccgcgaacag cgccggctgc gtgtacccgg tcacgtccag  82320
cagcgccgcc gcctcggagc cctcctccac gaacagcacc tcccgcagcg aacgctccag  82380
ccccgtgtcc agacgggcca ccaccgcgtc aagcgcctcc gcgaacaccg ggaaacgctc  82440
gtacaactcc cggcccatcc ccgcacgctg cgaaccctgg cccgagaaga ggagagcgag  82500
tgtgcgctcg gtggcccgtc cccgcgcggc ctcggccggt tcgccctcgg ggcccgcgag  82560
gagcaccgca cggtgttcga aggtggagcg tccggtggcc agggagtgac cgatgtcgag  82620
cggcgcggcg ccggtgaccg aggtgacgcg ggcgagctgc gcgtcgagcg cctcgcgggt  82680
cttcgcggac accggccagg ggacgagggt gggcctggcg gtgggcgtcc cgtcctcggg  82740
cgtcgcgggc tcctcgggct cgggcgcctg ctcgatcacg acgtgggcgt tggtgccgct  82800
gatgccgaag gaggagaccc cggcacggcg ggggcggccg gtctcgggcc aggcggtgtt  82860
ctcggtgagc aggcggacgt tgcccgcgcc ccagtcgacg tggctggagg cctcgtcgat  82920
gtggagggag cggggaagga cgccgtgctg gatggcgagc acggtcttga tgacgcccgc  82980
gacgccggcg gcggcctggg agtgcccgat gttcgacttc accgagccga gcagcaacgg  83040
ccggtcctcg ggccggtcct gcccgtacgt cgccagcagc gcctgcgcct cgatcgggtc  83100
gcccagcggg gtgcccgtcc cgtgtgcctc cacggcgtcc acgtcggcgg cggagagtcc  83160
ggcgcccgcc agggcctggc ggatgacgcg ctgctgggac gggccgttgg gggcggtcag  83220
cccgttggag gcaccgtcct ggttgacggc cgagccgcgc accacggcca gtacctggtg  83280
gccgttgcgg cgggcgtcgg agagccgttc caggacgagg acgccggcgc cctcggccca  83340
gccggtcccg tcggcggagt cggcgaacgc cttgcagcgg ccgctggtgg agatgccgcc  83400
ctggcgggtg aagcccgaga agcccatcgg ggtggacatc acggtgacgc cgcccgccag  83460
ggcgaggccg cactcgccgt tgcgcagcgc ctgggccgcc aggtggatgg cgaccagcga  83520
ggcggagcag gcggtgtcga cggtgacggc gggcccggcg aggtcgaagg cgtacgacag  83580
gcggccggag accacgctgg cggtgaggcc ggtggtggcg tggccctcgg cgtcctcccg  83640
ggagttcatg acgacgccga cgtagtcgac gccggccgtg ccgacgtaga cgccggtgcg  83700
gctgccgcgc agggagaccg ggtcgatgcc cgccctctcc accgcctccc aggtggtctc  83760
cagcaggatc cgctgctgcg ggtccatggc gaccgcctcg cggggcgaga tcccgaagaa  83820
gcccgcgtcg aaggcggcgg cgtcgacgaa gccgccctcg cccgccgcgc tgctgccggc  83880
```

-continued

```
gccctcgccg ttcagggcgt cgaggtccca gccccggtcg gcggggaagg gcgcgatgcc  83940
gtcacggccc tcctccagga gccgccagta ctcctcgggg gtcgcgacgc ctccgggcag  84000
ccggcaggcc atgccgacga ccgcgatggg ttcgcggcgg tgggcctccg cctcctccag  84060
ccgccggcgg gtcttgtgca gatcggccgt gacccacttg aggtagtcga cgagcttctt  84120
gtcatcgggc atgacgtggg gaaccttcct gtggtggatc aagctcgtct cagaggtcgc  84180
ccaggcggcc gagctcgttg tcgatgaagg cgaagacctc gtcggtgctg gccgactcga  84240
agtcgtcgtc gagggaggaa ccggcctgct cgggggcgtt gccgcgcacc tggtcgagca  84300
tctggcccag tcgcagggcg aggcccgcgc gggtgatctc gtccgggtcc ccggccgaca  84360
gcagcgtctc gaagcggtcg agttcggcga ggagcgacgg tccctgcggg acggcgtcgt  84420
caccggccag ctcggcgacg aagtgttcgg cgagcgcggt gggggtcggg tagtcgaaga  84480
ccagcgtggc gggcagccgc agcccggtcg cggtcgccag gtggttacgg agttccagcg  84540
ccgtcagcga gtcgacgccc agctcgcgga actcctggct gacgtcgacg gacttcggtg  84600
aggcgtggcc caggacccgg gcggcctgtt cgcggaccag gtcggtgacg taccggacgc  84660
gctcggcggc accgagcccg gcgagcttgg cgccgagcgc ggccgaagcg ccggccgcgt  84720
ccgtggaggc ggcggtacgg cggccgctgc ggaccatgga gcggaacagc gggggcaggt  84780
cctccggcgc cgcgcccctc atcgctccgg cggcgagacc gaccaggacg aggaaggact  84840
cgtccgagcc ccgggcgatg tcgaacagtt ccaggccctg gtcgacggcg agcggcggga  84900
gtccgccgga ctgcatgcgg cgcatgtccg tgtcggacag ggtgctggtc atgccgccgt  84960
cgtgggccca ggggccccag gccagcgagg tgccggccag gccgaggtgg cgccggtgcc  85020
gggtgagggc gtccaggaag gagttggccg cggcgtagtt gccctggccg gggctgccca  85080
tgacgcccgc gacggacgag aagggcagga aggcggcgag gtcgaggtcg cgggtcagct  85140
cgtgcaggtg ccaggcggcg tccaccttgg gccgcaggac ggcggcgagg cgttcgggcg  85200
tgagggaggc gatcaccccg tcgtcgagga tgcccgcggt gtgcacgacg gcggtgagcg  85260
ggtgtgcggc cgggaccgcg tcgaggagcg cggccgtggc ctcgcggtcg gcggtgtcgc  85320
aggcggcgac ggtgacctcg gcgcccagtt cccgcagctc ggcggcgagt tcggcggcgc  85380
cgggggcgtc cgcgccgcgc cggctggtca gcagcaggtg gcgcatgccg gcccgggcga  85440
agcggcgggc gaggtggccg ccgagtgcgc cggtgccgcc ggtgatgagg acggtgccct  85500
cggggttcca gcggggcggc atggtcagca cgatcttgcc ggtgtgcttg gcctggctca  85560
tgaagcggaa cgcctcgcgg gcccgccgga cgtcccaggt gcgcaccggg agcggccgca  85620
gcgcgccctc ggcgaagagg tcgaggagtt cgccgaggag ggccttgttc cgctccggtc  85680
cggcctcgcc gaggtcgaag gcctggtagc ggacctcgcc cgtggtctgc gggtcgcgga  85740
tgtcggtctt gcccatctcc aggaaccggc caccgggagc cgtgatccgc aacgacgcgt  85800
ccacgaagtc accggcgagc gcgttcagga ccacgtccat ccccgcgcca ccggtgacct  85860
cccggaactt ctcctcgaag cccaggtcac gcgaggacgc gatgtgagcg tcgtcgagcc  85920
ccagactccg cagcgtctcc cacttgggct cgctcgccgt ggcgaagacc tcggcgccca  85980
cgtgccgcgc gagctggatc gccgccatac cgacaccacc cgcaccggcg tggatcagca  86040
cccgctcccc cgcctggacc gaggccaggt cacggaaggc gtacagggcg gtgaggaaga  86100
ccagcggcac cgaggccgcg tcccgcatgg tccagccttc ggggacctgg gtgacgtagt  86160
gctggtcggc gacgacgacg gggccgaatc cgccgggcac ggtgccgagg acgcggtcgc  86220
```

-continued

```
cgggggcgag gccggtgacg gcctcgccga cggcggtgac cacgccggcg gcctcggtgc  86280
ccatggggcc ggactcgccc gggtacatgc cgagcgcgtt cagcacgtcg cggaagttga  86340
ggccggccgc ctcgacgtcg atgcggacct cgtgggcgcc gagtggctgg aggacctccg  86400
ggcacggggc gaggaccagg ttgtccaggc tgcccttgcc ggtggtgtcc aggcgccacg  86460
gggtgccggt gggggcgagg aggccgggtg ccgtggtgag ccgttcgagc cggccgacca  86520
gcgcggtgcc ctcgcggacg gcgaactggg cgtcgccgct gcccagcagc cccggcaggt  86580
cgggcaggag cgcgcgcagg gtgtccgggg cgtccgctcc gtcgaggtcc agcaggacga  86640
agcggtccgg gttctcggac tgggcggagc gcaccaggcc ccaggcggca ccggccgcga  86700
ggtcgcggac ggtctcggtg tcgtgggcgg cgaccgctcc cgtggtgacg aagaccaggc  86760
gggagtggcc gagccgctcg gcggcctgcc actgctggag caggtcgagc gtccgcgtgg  86820
tcagcgcgtg gacggccgcc ggcacgtcgg cgccgtgggc gtccgggtcc ccggcccccg  86880
ccgcgtcacc ggcaccggcg agcgggacga ggacgaagtc gggtgctgcg gacgggtcgg  86940
cgtcggggcc ggtcagctcg gtgagggagg ccagggcggt gcccacgccg aagacgtcct  87000
cgccgagggt cgccgcggtc aggccctcgg tgggcttgac cgcgggtgcg gccgtccagt  87060
ccaggcggaa gaccggctcc tggccaccgg tggcgaccgg ggcgctgggc accgtggggg  87120
cgcgcaggac cagggactcg gcgcagagca ccgggacgcc ctccgcgtcg acggcggtca  87180
gccggaccga ctcgtccccg agccgggtga tccgcacccg cagcgtggtg gcgcccctgg  87240
cgtgcaggga gacgccgttc caggcgaagg gcagcagcgg gttctcctcg ctgcccaccc  87300
cgaggtagcc gttggcgtgc tggacggcgt ccaggagcgc ggggtgcatg ccgaagtact  87360
gggcgtcccc ggcgacctcc tcggggaggg cgacctccac gaaggcctcc tcaccgcgga  87420
gccacacctg gcgcaggccc tggaaggacg gcccgtaccc ggtacggctg tagtcgccgt  87480
cgaactccac ggagaccgcg tccgccgggg gccagacggg ggcttcgaag gagtcggtgc  87540
gctcctgaac ggccaggaac ccgtcggcgt gccgggacca cggcgcgtcg acggcgtcgg  87600
agggacggga gtagaaggtg accggcctgg tgccggtgtc gtcgggagcg ccgacgacga  87660
cctggacgga gaccgggtgc ttctcgtcga ggaccatcgg cgcggcgagg acgagttcct  87720
cgacgcgggc gcagccgacc tggtcggctg cgcggatggc catctccagg tagccggtgc  87780
ccggcatgat gacggtgccg ccgacacggt ggtcgaggag ccaggggtgg acctgcatgg  87840
agatctggct ggtgaacagg acgccctcgg agtcggcgag cgggacggcc gcgccgagca  87900
gggggtgttc ggcggagatg aggccggccg tgctgatgtc gccggtgagg gcggccgggc  87960
gcggccagta ccgctcgcgc tggaaggcgt aggtgggcag ctcggtgcgg cgggcgccgg  88020
tgccggtgaa ccaggcggac cagtccaccc ggacgccgct gacgtggagc ccggcgaccg  88080
cggtcagcag cgcggtctcc tcgtcgcggt ccttgcgcag ggccgggagg acgaccgcct  88140
cgtcccggtc gtcggcttcg aggacgctct gggccagggc ggtcaggaca ccgccgggtc  88200
cgatctccag gaaggcgttg gcgccggcgc cggccagggc gcggacaccg tcggcgaagc  88260
ggacggtggc gcggacgtgc tcgacccagt acgcggcccg ggtgagctgt ccgggttcgg  88320
cgagggcgcc ggtgacgtcg gagaccaccg ggatacgcgg ctccgcgtac tccaggctct  88380
ccgccacctg ccggaacgcg tcgagcatcg gctccatgag cggggagtgg aaggcgtggc  88440
tgaccggcag gcgctgcgtc ttgcggccct cggccgcgaa cgcctccgcc agggcgaggg  88500
cttcgtcctc ggtgccggcg atcaccacgg agtcggggcc gttcacggcc gccagggaca  88560
ggccctcggt gagccggggc acgacctcgg cctcggtcgc ccgcacggcc accatcgccc  88620
```

```
cgcccgaggg cagttcctgc atcagacggg cacgggcggc gaccagccgg caggcgtcct  88680
ccagcgagaa gactcccgcc acgtgcgccg ccgcgatctc gccgaccgag tggcccgcga  88740
cgtggccggg gcgcacgccc cacgactcga cgaggcggta cagggcgacc tcgacggcga  88800
acagcgcggg ctgcgtgtac ccggtcgtgt ccaggagtgc cgccgtcccg gagccctcct  88860
ccgcgaacag cacctcccgc agcgaggggg tcaggccggt gtccagccgg gcgaggacgg  88920
cgtccagcgc ctcggcgaag accgggaaac ggtcgtacag ttcgcggccc atgccggcac  88980
gctgcgatcc ctggccggag aagagcaggg cgagcgagcg caccgcggcc cggccccggg  89040
cggcctccca cggcgtcgtg ccggggcgcg cgaggagcac ggcgcggtgg tcgaagcggg  89100
cgcggccggt ggccagggag tggccgacgt cgagcggggc cgcgccgtcc agggcggtga  89160
cggccgcgat ctgcccgtcg agggcctcct cggacttggc cgacaccggc cacgggacga  89220
cggtgggtgt gggccccggc aggagggccg caccgggctc ggcgggctcc ggggccgggg  89280
cctgctcgat gatggtgtgc gcgttggtgc cgctgatgcc gaaggacgag atgcccgccc  89340
gccagggccg gccgctgtcg ggccaggccg actcctccgt gagcagccgt atcgccccgg  89400
actcccagtc gacgtgggtc gagggccggt cgacgtggag ggtgcgcggc aggacgccgt  89460
ggcgcatcgc catgacggtc ttgatgatgc cggcgacgcc ggcggcggcc tgggtgtggc  89520
cgatgttcga cttgatggag ccgagcagca gtggccggtc cgcgggccgg tcctgcccgt  89580
acgtcgccag cagggcctgg gcctcgatcg ggtcgcccag cggggtgccc gtgccgtggc  89640
cctcgaccgc gtcgatgtcg gagggggtca ggccgccgcc ggccagcgcc tggcggatga  89700
cgcgctgctg ggaggggccg ttgggggcgg tgaggccgtt ggaggcgccg tcctggttga  89760
tggccgagcc gcgcacgacg gcgaggacct cgtgaccgtt gcggcgggcg tcggagagcc  89820
gctcgacgac gatcaggccg accccctccg accagccggt gccgtccgcc gcgtccgcgt  89880
acgccttgca gcggccgtcg acggccaggc cgttctggag ggtgaagccg gagaaggcgg  89940
acggggtgct catcatggtg atgccgcccg ccacggcgag gtcgcactca cccgcgcgca  90000
gcgcctgcat cgcccagtgg agggcgacca gtgaggagga gcaggcggtg tcgacggtga  90060
ccgccgggcc ttccaggccg aaggtgtagg ccagccggcc cgagacgacg ctggcggcga  90120
ggcccgttcc ggcgtggccc tccaggtcct cgcgggagtt catgacgagc gtggagtagt  90180
cctggccgtt ggtgccgacg aagacaccgg tacggctgcc gcgcagttgg tcggcgtcga  90240
tgccggaccg ttcgaacgcc tcccaggtgg tctccaggag caggcgctgc tgcgggtcca  90300
tcgccagcgc ctcacgcggg gagatgccga agaaggccgc gtcgaagtcg gctgccccgg  90360
agaggaatcc gccgcgcagc gtggcgctgc ggcccccggcc gtcggccccg ccggtcgtca  90420
gggtggcgag gtcccagcct cggtcctcgg ggaatgcctc gatgccgtcg cggccctcgc  90480
tgaccatggc ccacaggtcc tgcggggagc ggaccccgcc gggcaggcgg caggccatgc  90540
cgacgatgac gaccgggtcc tcggccagtg ccgccggggt ggcccggccg gagcccgggg  90600
tgtcctgctc gcccagcagt tcggcgagga ggtgttcggc gagggcctgg gcggtcgggt  90660
agtcgtagac ggtggtggcg ggcaggcgca ggccggtcgc gagggcgatc cggttgggca  90720
gctcgatggc ggtgagcgag tcgaagccca ggtcgcggaa gttccggtcg gcggcgacgg  90780
cctccggtcc tgggtggccg aggacggctg ccgcgtgggt gcgcaccagt tccgtgacgc  90840
tgtcggtgcg ttcgtcggcg gggaggccgc gcagccgctc ggcgagtccg gaggcggccg  90900
tgcgggcacg gtcgcgggtg gtctcggcgt cggcgagggc ctgccgggcg tcgggcaggt  90960
```

-continued

```
cgcgcaggag cgcgttgccg cgcatgccga tcaggccgtc caggacctgc ggctggcgcg  91020
ggtcgaacag gacgggtgcg gcctcgggcc gggtcacggc ctgccgcagt gcggccaggg  91080
ccagatccgg gtggaccgcc gggtgcccgg ctcctgccct cggggcggcg gggggcgtcgt  91140
cccctccggt ctcgtcggcg tccccgatcc aggcgcccca ggccatcgag gtggcgggca  91200
gcccctcact ccggcggctc cgggcgaggg cgtcgagtac ggcggtggcg gcggcgaggt  91260
tggcccggcc cgccgtgccg acggtcccgg cgacggagga gcagagggcg aagacgtcga  91320
ggtcaaggcc gcgggtcagc tcgtccaggt ggagggcggg cgcggtccgc gcgtggtgcg  91380
gagcggcgaa tcgttccggg gtcaggtcgt cgaggactcc gtcgtcgacg actgcggcgg  91440
cgtggacgac ggcggagagc ggggtgtcgg cggggatgcc gtcgaggacg gccgcgaggg  91500
cgtcccggtc ggcggcgtcg caggcgacga gggtgacgcg ggcaccggcc gcctccagtt  91560
cggcgcggag cgcgtcggcg ccgggggcgt cgggaccgcg tcggccgagg agcaccaggt  91620
gcgcggcgcc ggctccggcg agccagcgcg cgacgtgggc gccgcgtccg ccggtgccgc  91680
cggtgacgag gacggttccg cggggctgcc agccgtcgcc gggctccgcg gccggtgccg  91740
ggacgagccg gcgtgcgaag gcggcggagg agcggacggc cacctggtcc tcgccgtcat  91800
gtccggcgag gacggcggcg aagcggcggg cggcgcgttc gtcccacgcg gagggcaggt  91860
cgacgagccc gccccacacg gcggggtgtt cgagggcggc gacccggccc aggccccaga  91920
cggcggcctg ggcgggggcg gtgacggcct cggaacccgc caccgcgacg gctccccggg  91980
tcaggcacca cagggggcg tcgaccccgg cgtcgagcag ggcctggaac aggacggcgg  92040
tcggggcggc gggggctccc gccgggtcgc cggagacggc tgcctccggc gtgtcggcga  92100
gggccagcag ggagaccaca ccggcgaggg cggcgccgtc ggcggagagg gcgcgcaggc  92160
ggtcggcgag cgcgtggcgc tcgacggtgt ccacggtgag gcggacgacg tcggtgccga  92220
cggcgtcgag gacggcggcg gtccaggggt cctcgccgta cgcggcgggc acgacggcca  92280
gccaggttcc ggccggggcg ggcgcaccgg gcggcagcga cagcggcttc cacgtctcgt  92340
ggtggcggtt ggagtcgacc atggcctggt cccggcgccg gcgccgccag gtggagaggg  92400
ccgggagtac cgcgccgagc gcctcggtgt ccacggccag gtcggtggcg agacgggtca  92460
ggtcctcgcc ctcgacggcg gtccagaagg cgccgtcgag cgggtcggag gagccgccgc  92520
ccgtaccggg gcgccgggtg tcgggccagt ggcggacgcg ctggaaggcg taggtgggca  92580
ggtcgacgcg gcgggcgccg gtgccctcga agcaggcggc ccagtcgacg gggacgccgg  92640
tgacgtggag cgtggcgagc gcggtgagca gggcgggctc ctcggcccgg tccttgcgca  92700
gcgcgggcgc ggtgacggcc tcggagtcgg tgcccagggt ctgccgggcg agggcggtga  92760
ggacgccgcc ggggccggcc tccaggtagg cgtcggctcc cgcctcggcg agggcgcgga  92820
cgccgtcggc gaagcggacg gtctcacgga cgtgccgcac ccagtactcg gggtcggtga  92880
gctgaccggg cgcggcgagg gcgccggtga cgttggagac gacggggaga cgcggttcgg  92940
cgtacgccag cgagcgggcg acctcgcgga acgcgtcgag catcggctcc gtgagcgcgg  93000
agtggaaggc gtggctgacc tgcaggcgct gggtcttgcg tccctcggcc acgaactcgg  93060
cggccagcgc ggtcacttcg ctctccgggc cggacacgac cacggagtcc gggccgttga  93120
ccgcggcgag ggagagtccc tcggtcagcc gtggggcgat ctccgcctcg gtggcctgca  93180
cggccgccat ggcgccgccg gcgggcagtt cctgcatcag gcgggcgcgg gcggcgacca  93240
gccggcaggc gtcctccagg gagaagaccc cggccacgtg cgcggcggcg atctcgccga  93300
cggagtgacc ggccacgtac tccggcgaca cgccctgcga ctccagcagg cggtgcaggg  93360
```

-continued

```
ccacctccac ggcgaagagc gcgggctggg tgtagccggt ggtgtccagg agagcggccg  93420
tctcggagcc ctcctccgcg aagagcacct cacgcagcgg acggtccagc tccgggtcga  93480
gcagggcggt gatctcgtcg agtgccttcg cgaacaccgg gtaacgctcg tacagttcac  93540
ggcccattcc ggcccgctgg gaaccctggc ccgggaacag caccgcgagc ctgcgctcca  93600
cggcacggcc ccgcgccacc tccaccggct cgtcctcggc accggtgccc gccagcagga  93660
ccgcgcggta ctcgaaggag gcgcggccgg tggccaggga gtggccgatg tcgagcgggg  93720
tggcgccggt gacggtggcg atccgggcga gctgtgcgtc gagcgcctcc ggggacttcg  93780
cggagaccgg ccaggggacg gccgccggag ccggggcgga cgcggcggcc ggcgtggcct  93840
ccacgatctc cggggcctgc tcgatgatgg tgtgcgcgtt ggtgccgctg atgccgaagg  93900
aggagacggc ggcgcggcgt ggacggccgg tctcgggcca ctccgtggtc tcggtcagca  93960
ggcggacgtc gccctcggtc cagtccacgt gcgtggaggg ccggtcgatg tggagcgagc  94020
ggggcaggac accgtgccgg atcgccatga cggtcttgat gaccccggcg acaccggcgg  94080
cggcctgcgc gtggccgatg ttcgacttga tggagccgag cagcagcggc cggtcgccgg  94140
gccggtcctg cccatacgtc gccagcagcg cctgggcctc gatcgggtca cccagggtgg  94200
taccggtgcc gtgtgcctcc acggcgtcga cctcgtcggt cgagagcccg gcgctcgcga  94260
gggcctgacg gatgacccgc tgctgcgagg gtccgttggg cgcggtcagg ccgttggagg  94320
cgccgtcctg gttgacggcg gagccgcgca gtaccgcgag gaccgggtgg ccgttgcggc  94380
gggcgtcgga gaggcgctcg acgacgagca tgcccacgcc ctcggaccag ccggtgccgt  94440
ccgccgcgtc cgcgaacgcc ttgcagcggc cgtcggtggc caggccgccc tgccgggtga  94500
agcccgcgta ccccatggcg gtggacatga cggtgacgcc gccggcgagc gccaggtcgg  94560
cttcgccgga gcgcagcgcg tgcgcggccc agtggagggc gacgagcgag gaggagcagg  94620
cggtgtcgat ggtgaccgcc gggccctcca gtccgaaggt gtaggacagc cggccggaga  94680
tgacactggt ggcgaggccg gtgggggcgt ggccctcggc gtcctgacgg gagttcatga  94740
ccagggtggt gtagtcctgg ccactggtgc cgacgaaaac accggtacgg ctgccgcgca  94800
cctcggtggg ggtgatgccg gcgcgctcga acgcctccca ggtggtctcc aggagcaggc  94860
gctgctgggg gtccatcgcc agcgcctcgc gcggggagat gccgaagaag ccggcgtcga  94920
agtcggcgac gtcgtagagg aatccgcctt cggaggtggc gctgcggccg tggccgctct  94980
cgccgccgcg ctggagggtg tcgaggtccc agccccggtc ggtcgggaag gcggagatgc  95040
cctcctggcc gtcgaggacg agctgccaca gctcctcggg agagctgacg ccgcccggca  95100
tccggcaggc catgccgacg atgacgacgg ggtcctcggc gagggccgcg gcgacgggcg  95160
tcggggcggt ggcgccagtg gcgcgctgct cgtcgagcag ggcggcgatc aggtgctccg  95220
ccagcacgcc gggcgtgggg tggtcgaaga cgagggtggc gggcagccgc aggccggtgg  95280
cgccggtgag gcggttgcgc agttcgacgg cggtgaggga gtcgaagccc aggtcgtgga  95340
agtcgcgttc ggcgtcgatg gcctgggcgg aggagtggcc gaggaccgag gcggcctcgg  95400
cccggatcag gttcacggcg aagcggagcc gctcgtcctc gcgcaggtcg aggaggcgcc  95460
gggtgagctc gtcggcggta cccgcgccgc cgacggcggt cgcggcggcg cgccgggtgc  95520
cgcggaccag gttgcgcagc agcggcggca cctccccggg catccgggtg gagcccgagg  95580
ctccgagggg gacgaggtgc ggctcgtcgg agacgacggc ggcgtcgagg agggcgagcc  95640
cctgctcgac ggtgagggcg ggggccgccg acgccgacat gcgccgcacg cccgcgtcgg  95700
```

-continued

```
tgagggtgcc ggtcatgccg ctggtctgtt cccaggcccc ccaggccagg gagagcccgg  95760
ccagaccctc ggcccggcgg tactgcgcca acgcgtccat gaacacattg gcggcggcat  95820
agttgccctg ccccgcactg cccatcacac cggacacgga cgagaacatc acgaaccctg  95880
cgagacccat gtcccgcgtc aactcgtgca ggtgccacgc agcgtccacc ttcggacgca  95940
acacccccga caaccgctcc ggcgacaacc ccgtcaccac accgtcgtcc agcacacccg  96000
ccgtatgcac cacagccgtc aacggatgcc ccaccggcac cgacgccaac agccccgcca  96060
cggcagcacg gtccgccaca tcacacgcca ccacgtccac gtgggcaccc agcccggcca  96120
actcctcacg gaaagcgtcc acaccctccg ccgccggacc acgccgcgac accagcagca  96180
gacgccgcac cccacgcgcc gacaccagat gacgcgccac ctcacgcccc agaccacccg  96240
tcccaccagt gaccaggacc gtgccctcgg ggttccagcg cggcggcatc gtcagcacga  96300
tcttgcccac atgcctcgcc tggctcatga aacggaacgc ctcacgcgcc cgacgcacat  96360
cccacgcacg caccggcaac gggcgcaacg ccccctccgc gaacaggccg aggagttcgc  96420
tcagcatctc gccggtccgg tccggtcccg cctcgccgag gtcgaaggcg cggtaccgca  96480
cgtcaccgac cgcgtgcggg tcgcggatgt cggtcttgcc catctccagg aaccggccgc  96540
cggaagccgt gatccgcaac gacgcgtcca cgaagtcacc ggcgagcgcg ttcaggacca  96600
cgtccatgcc cgcgccacca gtctcctccc ggaacttctc ctcgaagccc aggtcacgcg  96660
aggacgcgat gtgagcgtcg tccagcccca gaccccgcag cgtctcccac ttgggctcac  96720
tcgccgtcgc gaagacctcg gcacccatgt gccgcgcgag ctggatcgcc gccataccga  96780
cgccacccgc accggcgtgg atcagcaccc gctcccccgc cgacaggccg gcgagttcgg  96840
tgagcgcgta gtaggcggtg aggaagacca ggggcaccga ggcggcgtcc tcgtcgctcc  96900
actcctcggg tacgcgggtg aggaagcgtt cgtcgatcag ggtctccgtg gcgaggccgc  96960
cggggaccat gcccatgacg cggtcgccga cggagagccc ggtgacctcg gggcccacgg  97020
cggtgacgaa cccggccgct tccgcgccga gcagtccggc ctcgccgggg tacatgccga  97080
gcgcgttcag cacgtcacgg aagttcaggc cggcggctcg tacctcgacc cggacctggc  97140
gctcctgagg ctccgccagc tcctcggggc aggggcgcag ggtgagcgcg tccaggctgc  97200
cgcgtgacgg ggagtccagg cgccaggggc cgtcggcggg cggcaggagg gacggggcgg  97260
tcacggcccg gtcgagacgg ccgaccagga cggcgccctc gcggacgacg aactgggcgt  97320
ctccgcccga gagcggaccg aggagttgcg gcagagcggt ctcgacgggg gtggtgtcgt  97380
ccaggtcgag gagggcgaac cgggtggggt tctccgactg ggcggcgcgg acgaggcccc  97440
agacggcggc ggcggggagg tcgtcgaccc gctcgccggg gcgggcacag accgcgcccc  97500
gggtgacgaa gacgaggcgg gtgtcggcga accgttcgtc ggccagccac tcctgcgcca  97560
gggcgagggc ctgtgcggcg cgctcgtggg tggcggcggg cacgtcggca ccctcggccg  97620
gtgcggggac ctcgaccagg acgaggtcct cctcgccggt cagcggggcg agggtggccg  97680
cggccccgcc ggtgccgagg gcaccggcgg tcgtgtgacg ggcggcgggg gcgtcgccgg  97740
tctcggggcc ggcggtccac tccaggcgga gcagcgagtc gagttcggtg cggcgggcgg  97800
ccggggcgtg gtccccggcg ggaacacgca gcaccagcga ctcggcggag agcaccgggg  97860
cgccctcgac gtccacggcg gcgatggaga cggagtcctc gccggtccgg gcgacgcgga  97920
agcggaccac ggaggcgccg ccggcgtgca gggagactcc ggcccacagg aacgggagca  97980
gctggtgctc gtcgtcgagc ccggcgaagc cgacggactg gacggcggcg tcgagcagcg  98040
cggggtgcat cccgtagtac tcggcgtcgt cggcctgcgg gggcagggcc gcctcgacga  98100
```

-continued

```
acgcctcgtc gccgcgcttc cagacggcgc ggatggtgcg gaagaccggg ccgtactcgg  98160
tgcggtcgta gaagtcctcc aggccgacgg cgaccgcgcc cttggggggc catatctcgg  98220
cgacggcggg gagggtgacg gcgccgctgg tcaggacgcc ggtcgcgtgc tgtgtccagg  98280
tggcgtccgg aacgtcggcg gaccgggagt acaggctgac cgtgcgggcg ccgctctcgt  98340
cgggggcgcc ggcccagacc tggacgacca cggcggtgtc cgcgggcagc agcagcgggg  98400
tggcgagggt gaattcctcg acgcggtcgc agccgacctc gtcggcggcg cgtacggcca  98460
gttccaggaa gccggtggcg gggaagagca ccatgccccc gccgacggtg tggtcggcga  98520
gccaggggtg cgtggtgagg gagaggcgtc cggtgaagag gacgccttcg gaggcggcga  98580
ggccggtggc ggcgcccagc agcgggtgcg cggcggggct cagaccggcg ccggtgacgt  98640
ccccgccgtg tgcggagggg cgcggccagt accgctcgtg ctggaaggcg taggtgggca  98700
gctcgacgcg gcgggcgccg gtgccctcga agcagccggc ccagtcgacg gggacgccgg  98760
tgacgtggag cgtggcgagc gcggtgagca gggcgggctc ctcggcccgg tccttgcgca  98820
gcgcgggcgc ggtcacgctg tcgctcgcgg tgccggcggc gtcgagggtc tgctgggcga  98880
ggacggtgag gacgccgccg gggccgatct ccagataggc gttggcgccg gcctggtcga  98940
gggcgtggac ggcgtcggcg aagcggacgg tagagcggac gtgctcgacc cagtactcgg  99000
gcctgctgag ctgcccgggc tcggcgaggg tgccggtcac gtcggagacg acagggatgc  99060
gcggttcgcc gtaccccagg cccttggcca cgtcgtggaa ggcgtcgagc atcggctcca  99120
tgagcgccga gtggaaggcg tggctgaccg ccaggcgctg gaccttgcgt ccttcggcgg  99180
cgaactccga cgccagcgcg tcgacctcgt ggtccggacc ggcgatcacc acggagtccg  99240
ggccgttgac cgcagccagg gacaggcccc cggtcagtcg gcctgcggtc tccgcctcgg  99300
tcgcctggac ggccaccatg gcgccgccgg cgggcagttc ctgcatcagg cgggcgcggg  99360
cggcgaccag cgtgcacgcg tcctccaggg agaggacgcc cgcgatgtgg gcggcggaga  99420
tctcgccgac ggagtggccc gcgacgaact ccgggacgac cccgaaggac tcgaccaggc  99480
ggtagagggc gacctccacg gcgaagagcg cgggctgcgt gtagccggtg gtgtccagga  99540
gagcggccgt ctcggagccc tcctccgcga agagcacctc gcgcagcgga cggtccagct  99600
tcgggtcgag cagggccagg acttcgtcca gcgccttcgt gaacaccggg aaacggccgt  99660
acagttcccg gcccatcccg gcgcgctgcg aaccctggcc ggagaacagc accgcgagcc  99720
tgcgctcgac ggcgcggccc cgcgccacct ccaccggctc gtcctcaccg tcggcgcccg  99780
ccagcaggac cacccggtgg tcgaaggagg cgcggccggt ggccagggag tgaccgatgt  99840
ccaggggtgc ggcgtcgagt gcggtgatcc gggcgagctg gccgggcagt gcctcctcgg  99900
tacgggcgga gacgggccac ggcacgaccc gcgcgagcgc ctcgggctcc gcctggggct  99960
cgggggactc cgtgtcggcg gtctccggct ccggctgttc gaggatcacg tgggcgttgg 100020
tgccgctgag cccgaaggag gagactccgg cgcgccaggg gcggccggtc tcgggccagc 100080
cggtcgtctc ggtgaggagc cggaccgctc cggcctccca gtcgacgtgg gtggagggct 100140
ggtcgatgtg gagggaccgc ggcagggcgc cgtggcgcat ggcgagcacc atcttgatca 100200
cgcccgcgac gccggcggcg gcctgggtgt ggccgatgtt cgacttgatg gagccgagca 100260
gcagcggccg gtcctcgggc cggtcctgcc cgtacgtcgc cagcagcgcc tgggcctcga 100320
tcgggtcacc cagggtggta ccggtgccgt gtgcctccac ggcgtcgacc tcgtcggcgg 100380
agagcccggc cgtcgccagc gcctggcgga tgacccgctg ctgggacggg ccgttgggcg 100440
```

-continued cggtcaggcc gttggaggca ccgtcctggt tgatggccga gccgcgcacg acggcgagga 100500
cgtcgtggcc gttgcggcgg gcgtcggaga ggcgctccag gacgagcatg cccacgccct 100560
cggaccagcc ggtcccgtcg gcggcgtcgg cgaacgcctt gcacaggccg tcgccggcca 100620
gcccgccctg acgggtgaac ccgaagaagt tcatgggcgt cgacagcacg gtcaccccgc 100680
ccgcgagggc gagagagctc tccccgctgc gcagggactg ggcggcgaga tggagcgcga 100740
cgagggagga ggagcaggcg gtgtcgacgg tgagggcggg gccctccagt ccgagcgcgt 100800
aggagacgcg gccggagatg acactggtgg cgaggcccgt actggcgtgt ccctcgacgt 100860
cctcgcggga ggtcatgacg aggttggcgt agtcctggcc ggtggtgccg acgaagatgc 100920
cggtggcgct ggagcgcagg cccgtcgggt cgatgccgga ccgctccagg gcctcccagg 100980
aggtctccag cagcaggcgc tgctgcgggt ccatcgccat cgcctcacgc ggggagatgc 101040
cgaagaaccc cgcgtcgaac ccgcccacgt cgtgcaggaa gccgccgcgt cgcgtggcgc 101100
tgacgccgcg gttgtcgccg ccaccgccga agagggcgtc caggtcccag ccgcggtcgg 101160
tggggaagcc ggtgatgcgg tcctcgccgt cggcgagcat gcgccacagg tcgtcggggg 101220
tctcgatgcc gccgggcatc cggcaggcca tgccgacgat gacgacgggg tcgtcggcga 101280
catcggcggc caccaccggc gtgccggtct cgccgtgttc gtcgaggagt tcggcgacca 101340
ggtgttcggc gaggccgtgg ggggtggggt agtcgaagac gagggtggcg gtgaggcgca 101400
ggccggtgac ggtggtgagg cggttgcgca gttcgacggc ggtcagggag tcgaagccca 101460
gctcgcggaa ctcgcgcccg ggttccacgg cccgggccga ggcgtggccc agtacggcgg 101520
cggcctcggt gcggaccagt tcgacggcgt gacggacccg gtcctcggcg ggcagcgcca 101580
ggaggcggcg ggcgaggtcg gccgcggtgc tcgcgccgcc ggcggccgtg gccgcggagc 101640
gacgcgtgcc gcggacgagg ttgcgcagca gcggcgggac caggccgagg acgcgctggt 101700
cgcccgacgg ggcgccgatc ggtacgacca ggggctcgtc ggagccggtg gcggcgtcga 101760
ggagggctag cccctgctcg acggtgagcg gggcggcccc ggaggcggtg acgcgctgca 101820
tgtcggcctc ggtgagggtg ccggtcatgc cgctggtctg ttcccaggca ccccaggcca 101880
gggagagccc ggccagaccc tcggcccggc ggtactgcgc caacgcatcc atgaacacat 101940
tggcagcggc atagttcgcc tgccccgcac tgcccatcac accggacacc gacgagaaca 102000
tcacgaaccc tgcgagaccc atgtcccgcg tcaactcgtg cagatgccac gcagcgtcca 102060
ccttcggacg caacaccccc gacaaccgct ccggcgacaa ccccgtcacc acaccgtcgt 102120
ccagcacacc cgccgtatgc accacagccg tcaacggatg ccccaccggc accgacccca 102180
acagccccgc cacggcagca cggtccgcca catcacacgc caccacatcc acgtgggcac 102240
ccagcccggc caactcctca cggaaagcgt ccacaccctc cgccgccgga ccacgccgcg 102300
acaccagcaa cagacgccgc accccacgcg ccgacaccag atgacgcgcc acctcacgcc 102360
ccagaccacc cgtcccacca gtgaccagca cggtcccctc gggattccag cgcggcggca 102420
tcgtcagcac gatcttgccc acatgcctcg cctgactcat gaaacggaac gcctcacgcg 102480
cccgacgcac atcccacgca cgcaccggaa gcggctgcaa cgccccctcc gcgaacaggc 102540
cgaggagctc ggtcagcatc tcgccgatac gctcgggggc tgcttcgccg aggtcgaagg 102600
cccggtagcg gacctcgccc gtggtctgcg ggtcgcggat gtcggtcttg cccatctcca 102660
ggaaccggcc accgggagcc gtgatccgca acgacgcgtc cacaaagtca cccgcgagcg 102720
cgttcaggac cacgtccatc cccgcgccac cggtcacctc ccggaacttc tcctcgaagc 102780
ccaggtcacg cgaggacgca atgtgagcgt cgtccagccc cagaccccgc agcgtctccc 102840

-continued

```
acttgggctc actcgccgtc gcgaagacct cggcacccat gtgccgtgcc agctggatcg 102900
ccgccatacc gacaccaccc gcaccggcgt ggatcagcac ccgctccccc gcctggaccg 102960
aggccaggtc acggaaggcg tacagggcgg tgaggaagac cagcggcacc gaggccgcgt 103020
cctcgtcgct ccactcctcg ggcacgcggg tcacgtaccg ctcgtcgacg aggacggtgt 103080
cggcgaggcc gccggggatc atgccggtca cgcggtcgcc gacggcgatc ccggtgacgt 103140
ccgggccgac ggccgtgacg aggccgaccg cctccgagcc gagcagtccg gcctcgccgg 103200
ggtacatgcc gagcgcgttc agcacgtcac ggaagttcag ccccgcagcc cgcacctcga 103260
cccggacggc gcggccctcc ggctcgtcca gtgcctcggg tgcggggacg agggagaggc 103320
cgtcgatgct gccggggacg gtggtgtcca ggcgccacgg cagccccggg accggcagta 103380
ggctcgcgcc ggtggacagc cgggccaggc gggccaccag gacggcctcg tcgcgtacgg 103440
cgaactgcgt gtcgccggcc gccaggaggg gaggaagctg cgccaggagt tcaccggagg 103500
gcgcggcggt gcccgcgtcg aggtcgagga gggcgaagcg gccggggttc tcggcctcgg 103560
cgctgcggac gagtccgtgc accgcggcgg cggcgagatc gctcacgccg gtgtcggtcc 103620
cggtggcgac ggcgccccgg gtgacgaaca cgagacgtcc ggcggcggac gtggccggct 103680
ccagccactc ctggatcagt gccagggtgc gcgcggtggc cgcgtggacg gccgtggggg 103740
tgtcgtcctc gacgccctcc agcgggacga ggaccaggtc gggggcgggc gtgacggcgg 103800
cggcgtcggc gagggaggcg agagggccgg gccaggcgcg gtcggtaccg agggtgacgg 103860
cgcgcacggg ggcggcgccg ccctcgggtg cggccaccca ctccaggcgc aggagcccgt 103920
cctgctcact gctgtgcagg gtgggggcgc gcagcgccga aggggcgcgc aggatgaggg 103980
agtcggcgga gagcaccggg gcgccctcga cgtccacggc ggcgatggac accgtgtcct 104040
caccgacccg ggcgacccgc acccgcacca cggaggcgcc gcccgcgtgc agcgagacgc 104100
cggaccagga gaacggtacg agcttcttgc cgtcaccgag accggcgaag ccgacggact 104160
ggacggcggc gtcgagcagc gcggggtgca tcccgtagta ctcggcgtcg tccacctggg 104220
gcggcagcgc gacctcgacg aaggcctcgt cgtcgcgggt ccagacggcg cgcagtccct 104280
ggaagaccgg gccgtactcg gtgcgcgcgt agaagccctc caggtcggcg gcgacggcgc 104340
cgcggggcgg ccagacggtg gagtcgaagc cggtgacgcg ctcgccacgg gtcagcagac 104400
cggaggcgtg ctcggtccag cgctgctcgg ggtcgtcgac ggcctgggag tagacggtga 104460
cgcggcgggc gccgtcggcg tcggccgcgc cgacgtggac ctggacgacg gccgccgagt 104520
tctcggtgag gatgaggggc ttggcgaggg tgaggtcctc gacgcggtcg cagccgacct 104580
ggtcaccggc gcggacggcg agttcgagga agccggtgcc ggggaaggcc accatcccgc 104640
cgaccgtgtg gtccagcagc cacgggtggg tctgcgcgga gaggcgtccg gtgaagagga 104700
ccccgtcgct gccggccagc gacacggcgg cgccgagcag cgggtgttcg gcggagacca 104760
ggcccgcggc gctgacgtcc ccggcggcgg ccatcaggac gggccagtag cgctcgtgct 104820
gccagcggta ggtgggcagt tcggtgcggc gggcaccggt gccctcgaag caggcggccc 104880
agtcgatgtc gacgccggcg acgtggagcc gggccagcgc ggtgagcagg gcgcgctcct 104940
cggcgcggtc cttgcgcagg acggggacgg cgacgacgtc gggcccgtcg aggcactgct 105000
gggcgagggc ggtgaggatg ccgtcggggc ccagttcgac gaaggtgtcg gcgccggcgc 105060
cggccagggc gcggacgccg tcggcgaagc ggaccgtgga gcggacgtgg tccacccagt 105120
actcggggtc gcacagcagg cggtcgtcgg cgagggcgcc ggtgacgttg gagacgaccg 105180
```

-continued

```
gcaggaccgg ctcgtggtag gtgaggctct cggcgacgcg gcggaactcc gcgagcatcg 105240

gctccatcag cggcgagtgg aaggcgtggc tgaccgccag gcgctgcgtc ttgcggccct 105300

cggcggcgaa ctcggcggcc agcgcgagga cctgggcctc ctcgcccgcc agggtgacgg 105360

agtcggggcc gttgacggcg gcgagggcga cgccctcggt caggcgcggg gcggcctcgg 105420

cctcggtggc ctggacggcg accatggcgc cgcccgcggg cagttcctgc atgaggcggg 105480

cgcgggcggc gaccagcgtg caggcgtcct ccagcgagaa cacaccggcg acgtgggcgg 105540

cggcgatctc gccgatggag tgcccggcca cgaagtccgg gaccacgccc caggactcga 105600

cgaggcggtg gagggcgacc tccacggcga agagcgcggg ctgggtgtag ccggtggtgt 105660

cgaggagggc cgcctcgggg gtgcggcgcc gggcgaacat cacctcccgc agcgggcggt 105720

ccaggcgcgg gtcgagcagg gcggtgatct cgtccagtgc cttcgcgaac accgggaagc 105780

gggcgtacag ttcgcggccc atctcggcgc gctgggcgcc ctggccggag aacaggacgg 105840

cgagggagcg ttcggtggcg cggccgcggg ccgcctcggc ggggacgccg tcgaggccgg 105900

agagcaggac ggcgcggtgc tcgaagaggg agcgcccggt ggccagggag tggccgatgt 105960

cgaggggcgt ggcgtcggtg agagcggtga cggcctcgat ctgcgcgtcc agggacgcct 106020

cggagcgggc gtgcacgggc cacggcacga cggtcgggac ggtctcgggc tccgccgggg 106080

actccggctc ggcggcgggt ccggcctgct cgatcacgac gtgggcgttg gtgccgctga 106140

tgccgaagga ggagacgccg gcgcggcgcg ggcggccggt ctcgggccac tcgacggcct 106200

cggagagcag ccggacggcc ccggagtccc agtcgacgtg gcgcgagggg tggtcggcgt 106260

ggagggagcg cgggacgacg ccgtgccgca tcgccatgat catcttgatg acgccggcga 106320

ctcccgcggc ggcctgcgcg tggccgatgt tcgacttgac ggagccgagc agcagcggcc 106380

ggtcctcggg gcggccctgg ccgtaggtgg cgagcagggc ctgggcctcg atggggtcgc 106440

cgagcggggt gccggtcccg tggccctcga ccgcgtcgac gtcggcggcg gtgagtccgg 106500

cggcggccag cgcctgctgg atgacgcgct gctgggaggg gccgttgggg gcggtgaagc 106560

cgttggaggc gccgtcctgg ttgacggcgg agccgcgcag cacggcgagg accgggtggc 106620

cgttgcggcg ggcgtcggag agccgctcca ggaggaggac accgaccccc tccgaccagc 106680

cggtgccgtc ggcctcgtcg gcgaacgcct tgcagcggcc gtcaccggcc aggccgccgg 106740

cgcggctgaa ctccatcagc gagccggggg cggacatgac gttgacgccg ccggcgaggg 106800

cgaggccgca ctcccccgcg cgcagggcgt gggcggcggc gtggagggcg acgagggagg 106860

aggagcaggc ggtgtcgacg gtgaccgccg gcccctccag gcccagggtg taggagaggc 106920

ggccggaggt ggcgctggcg gcgatgccgg tgccgatgtc gccggtcgcg tcggcgaggg 106980

agcgcaccag gaggtacgcg tagtcctggc cgttggtgcc gacgaagacg ccggtgcggc 107040

tgcctcgcag gctgcgcggg tcgatgccgg cgcgctccac ggcctcccag gaggtctcca 107100

gcagcagccg ctgctggggg tccatggaga cggcttcgcg cggggagacg ccgaagaagg 107160

cggcgtcgaa gtcggcgacc ccgtcgagga agccgccccg ctggctgacg gagtggccac 107220

gggcgtcgac cccggcgtcc cgcagcgcgt ccaggtccca gccccggtcg gtggggaagc 107280

cgccgacggc gtcggtgccg gaggcgacga ggtgccacag gtcctcgggg gaggtgactc 107340

ccccggggta gcggcagctc atcgcgacga cggcgacggg ctccgaggcg gcggccgcga 107400

ggtcgcggtt ctgccggcgc aggcgttcgg tctccttgag cgaggcccgg agagcttcga 107460

caactttttc gctgggcgtg gtcatgatgg ctccgtcagt cccgctcttc gtcagggtta 107520

ccgttgagtg ccgcctgcac caggccgtcg acgtccatgg cgtcgatcga cgcgtcgtag 107580
```

-continued

```
gcgtcgccgg ccccggaggg ctcggcctcc tggtccgtgc ctgttccggc cgggtcctgc 107640
ccggcgaggt ccagcagctg gtccaggagt ccgctgtcgc gcagccggtc caggggggacc 107700
tgggcgaggg cggcgcgcac ggcccgctcc tcttcgccgg ctccgtccgt ggcgggggca 107760
ccgggggtgc cggccgggag gagttgtccg aggatgtggg cggcgagtgc ggcgggcgtg 107820
gggtggtcga acacgagggt cgcggacagg gtgagtccgc tgacggcgcc gagctggttg 107880
cgcagctcga cggcgccgag ggagtcgaat ccgaggtcgc ggaaggcccg gtcggggccc 107940
acctggtcgg ttccggtgag gccgaggacc tccgcggcgc gttcgcgcac cagcgtcagg 108000
accgtctggg tacggcggct ctcgggcagc ctggccagcc ggtcgcgcag cgagggaccg 108060
gagtccgcgg cctcgccgcc ggcggatgcg gccttcttga gggcggcgta cgcgggcatc 108120
tcggccagca ggctgctggg ccggacggtg gtgaacgcgc ggacgaaccg gtcggggtcg 108180
acgtcggcga cgacggcgac cggtcgctg cccgtgacga cttgccgcag cgcgaggacc 108240
gcgaggtccg ggtcgagcgg ccggatgccg gtgcggcggg cgagcgcggc ggcgcggacg 108300
ccgtcggcca tgccctcccc gccccaggcg ccgtacgcca cggaggtggc gggcagcccc 108360
tcggccctgc gctgttcggc gagggcgtcg aggaccgcgt tggcggcggc gtaggtgccc 108420
tggcccgggt tgccgacggc ggcggacgcc gaggagaaga gggcgaacac ctccaggtcg 108480
tgggcgcggg tcagttcgtc caggagcagc gcggaggcca ccttggcccg gaacaccgtg 108540
gcgaaccgct cgggggtcag gccgtccacg acgccgtcgt ccagcactcc ggcggtgtgg 108600
atgacgccgg tgagcggcgc gtcctcgggg atcgccgcga ggacggcggc cagcgccttc 108660
cggtcggcgg tgtcgcaggc ggtgatgacg ggttcggcgc cgagcgcgcg caggtcggcg 108720
gcgagttcgc cggcgccggg cgcgtcgggt ccgctgcggc tgaggaggac caggcggcgg 108780
gctccggcac cggccaggcg gcgggcggta cgggcaccga gggcgccggt gccgccggtg 108840
atcaggacgg ttccggtggg cttccagtcg cggggcgtcc cgggccggac ggcggcgagg 108900
cggcggccga agaccgcacc gggccggacg gcgagctggt cctcgccctc ggggtcggcg 108960
aggacggcgg cgagccgttc ggcggtccgc gcgtcgacag cgagcggcag atcgacggtg 109020
ccgccccagc gctgcgggtg ctccagcgcg gcgacccggc cgagtccgtg gacggcggcc 109080
tggagcggtg cggcgacggt ctcggcgggc gagacggcgg cggcgccacg ggtgaggcac 109140
cacagcgggg cgtcggtgcg ggcgtcgccg agcgcctgga ccagggtcgc ggtcagggcc 109200
gcgccggccg ggacgccgcc ggggagggcg ccggtcccgt caccgggttc cccggcgacg 109260
gcgagcaggg agaccacacc ggtgaacggc ccggtggcgt cgagccgttc gcggatcgcg 109320
gcggcgagtc cggcgcggtc cttgccggag acctccagga cctgggcgcc cgcgccgagc 109380
gcggccagga cggcggaggt ccacggatgg tcggcgtggt cggcgggcac gacggcgagc 109440
caggtgccgg cgggggtgcc ggcggtggcc cggttcaggg gccgccaggc gatgcgctgg 109500
cgccagccgt ccacggtggt ctggtcgccg tgcttgcggc gccagtcccg cagggccggc 109560
aggacgcgca gcaacgcgtc gccgtcgacg ccgagttccc cggcgaggga gtcgaactgc 109620
tcgtcctgga ccgccgccca gaaggcggcg tccccggcgt cggccgtggt gccggtggcg 109680
gcggcgggtg cctcgtcggg ccagaaccgc agtcggcgga acgggtaggt gggcaggtcg 109740
acgcggcggg cgccggtgcc gtcgagcagt gccgcccagt cgagtccctg accggccgcg 109800
tgcagccggg ccacggcggt gatcagggcc tgctcctcgt cgcgtccggt gcgcagggcc 109860
gggacggccg tgggggccgg gcggttctcg tcggcgaggg tgtccagggt ctcctgggcg 109920
```

-continued

```
aggccgcaca ggattccgtc ggggccgagt tcgaggtagc gggtggcgcc gcgtcccgcg 109980
agggtgcgca caccgtcgcc gaagcggacc gcctcgcgga cgtgccggac ccagtacccg 110040
gggtcgcaca cctgcgcgtc ggtggccgcg tccccggtga ggttggagac caggggcagc 110100
gtcggcgggg cgtacgacac actccgggtg acccgttcga agtcctgaag catggcgtcc 110160
atgtgcagtg agtgaaacgc atggctcacc cgcaaacgcc tagtcttccg gccctgttcg 110220
gcgagggcct cggcgagcgc ggtgaccgcc ttctcgtcgc ccgagaccac cacggactcc 110280
gggccgttga cggcggcgag gcagatttgg tcggtcaggt acggggcgat ctcgtcctcg 110340
gtggcgcgca cggcgagcat ggcgccgccc gccgggagtg cctccatgag gcgggcgcgg 110400
gcggagacga cgcggcaggc gtccggcagg gagaggaccc cggccacgtg ggcggccgcg 110460
agctcgccga ccgagtgccc ggcgagcagg tcgggccgta cgccccagga ctcgaccagc 110520
cggtacaggg cgacgccgag ggcgaacagg gcgggctggg tccagccggt ccggtccagg 110580
agcgccgcct cgggggtgcc ctcgtcggcg aacatcacgt cgcgcagcgg gcgttcgagt 110640
tcctggtcga agtgggcgag gacctcgtcg agggcggtgg cgaagaccgg gaagcgggcg 110700
tagagggcgc ggcccgcccc ggggcgctgg gagccctgcc cggggaagag gaacgcggtc 110760
cggccgccgg gggccgcgcg gccgcgcagt acggcggggt gggcgcggtc ctcggcgagg 110820
gcggtgagcg cgtcgaggag gtcgtcgcgg ccggccacgg cgaggacggc ccggtgctcg 110880
aaggcggagc gggtggtgcc cagggagagc gccaggtcgg cggtggccgg cggctgcgcc 110940
gcaccggcgg tgagccggtc gcggagccgg gcggcctgct cggtcaggga gtccgcggtg 111000
gccgccgaca gcggcagggg cagcagccgt gcggcgtcgg tggcgtgcgt ggcgggctcc 111060
gtgtcccgct ccggggcggc cgggccggtg ggggcctgtt ccaggatgac gtgcgcgttg 111120
gtgccgctgg cgccgaagga ggagacagcg gcgcggcgcg ggcgtccggt ctcgggccag 111180
tcggccgcct cggtcagcag gtggaccgcg tccgggtccc aggcgacgtg gcgcgagggc 111240
ttctcggcgt gcagggtgcg cggcagcgtg ccgtgccgca tggcgaggac catcttgatg 111300
atgccggcga cgccggaggc ggcctggctg tgaccgatgt tggacttgac cgagccgagc 111360
agcagcggct gcccctcggg ccggtcctgc ccgtacgtcg ccaggagggc ctgggcctcg 111420
atggggtcac cgagggtggt cccggtcccg tgtgcctcca cggcgtcgac ctcgcgggcg 111480
gtgagtccgg cggcggccag cgccttgcgg atgacgcgct gctgggaggg gccgttgggg 111540
gcggtgagac cgttggaggc gccgtcctgg ttgatggcgg agccgcgcag gaccgcgagg 111600
acctcgtggc cgcgccggcg ggcctccgag aggcgctcga cgacgagcat gcccacgccc 111660
tcggaccagg ccgtgccgtc ggcggcgtcg gagaagggct tgcagcggcc gtccggggag 111720
agggcgccca tctcgccgaa ctcgacgaag ccgaccgggg tggacatcac ggtgacaccg 111780
ccggccaggg cgagcgagca ttcgccggag cggatcgcct gcgcggcgag gtgcagggcg 111840
gtcagggacg acgagcaggc cgtgtcgacg ctgacggagg ggccctccag gccgagggtg 111900
taggagagcc gtccggagag gaggctcgcc gactgggcgg tctcgacgtg cccggactgc 111960
ccgatggcgg gacggtagtc gccgctgccg ccgccgacga agacaccggt gtcgccgccg 112020
cgcagcacgg cggggtcgat cccggcccgc tccagcgcct cccaggcggc ctggaggacg 112080
atccgctgct gcgggtcgat gaccagggcc tcgcgcgggg agatcccgaa gaaggcgggg 112140
tcgaagtcgg cgacgtcgta gaggaatccg ccctcgcggg tgacgctgcg gccccggccg 112200
tcctcgtcgc cgtggagcag cttctccagg tcccagccac ggtcggtggg gaagccgccg 112260
atggcgtcgg taccggcccc gaccagttcc cacaggtcct cgggcgagcg gacgtcgccg 112320
```

-continued

```
gggtagcggc agctcatgcc gacgatgacg acggggtcgt ccgcgtcggc ggcggcgcgt 112380
gccacggggg cgccggtgcc gggcccggtg tcctcgccga ggagttcggt gaggaggtgg 112440
gcggcgagcg cggcgggggt cgggtagtcg aagaccaggg tcgcgggcag ggtgagcccg 112500
gtggccgtgg tgaggcggtt gcgcaggtcg accgcggtga gcgagtcgaa gccgaggtcg 112560
ttgaaggcgt tctcggccgg gacggcggcg gcgccggtgt ggcccagcac cgaggcgatc 112620
tcggtgagca cggtgtcgag gagggtgcgc ggacgctcgg aggggtcgga ctgccgcagc 112680
cgctcgcgca gcgcggaggc ggtaccggcg tccgcgccgt cgccaccggt ggtgctcagg 112740
gcctcgcggg cctcgggcac gccggtgagg agcagaccgg cgcgggtgcg ggtgaacgcc 112800
ggggcgaacc ggtcccaggc cacgtccgcg acggtcaccg aggcgggagc ggccgggttg 112860
gcggcggcct cgccgatcgc gggggcgagg gcgtcgagcg cgcgggccgg ctccatggcg 112920
ggcaggccgt tggcgcgcag gtgggcggcg agaccgtccg gcccggcgcc ctgccaggcg 112980
ccccaggaga ccgagacggc gttggtgccg tgggcgcggt gtcgctggac gagggcgtcc 113040
aggcagactc cggccgcggc gcccgcgccc tggccgccga cgccccagac ggcggagatg 113100
gagccgaaga cgacgaaggc gtccaggtca cggtcgccga cggcggtggt cagcgcctcg 113160
taggcggcgc gcgccccggt gacaccgggc gtctcctcgc cggtgtcccc ggtgtggagg 113220
acggcggtca gcggccggtc gtcggcctgc gccgccagcg cctcggtgag cggggcggcg 113280
tcggccgggt cggggtggcg gacgacggtg agggtggcgc cgagcgcctc cacctcggca 113340
cgcagggcgg tggtggcggc gtcctcgggg ccggccgggc cggcgagcag caccccggtg 113400
gcgccgtgcg cggcgagcca gcgggcgacg tgcccgccga agccctccgc ccggcccgtg 113460
accaggacgg tcccggcggg gtgccaggtg atgtccggag cgggagcggc ggcccgggac 113520
agccggcggc cgaaggcgcc ggaggcgcgc agcgccacct ggtcctcggc cgggccgtcg 113580
gtgcgggcga cggtcaggac ggcgcgcaga cggtcgacgg tgcgggcgtc ggcgacgtgg 113640
tcgacgtcga ccagtccgcc ccaccgttcg ggctcgtcca gggcgagtac ccggcccagg 113700
ccccacaggg cggcgcggtc cgggtcggcc gccgggtcgg agcggccgac ggagacggcg 113760
tcgcgggtga cgcaccacag cggggcgtcg atcccggcgg ccgccagcag gcggagcagg 113820
gtgtcggggc gggcggtgcc gtccgtcgcg gtgccggcga gcagcgagag gacaccggcg 113880
tacgcggtgc cgtcggcggc cccgtcgagc agggcggcgg tgccgtcctc gtcggcgggg 113940
acggcgaggt ggacggtgtg ctcgccgaag gtggcggcca gggcctgggt ccacgcgtcg 114000
tcgtgcccgg ccagggtcag gaccagccag ggtcggcccg ttccgtcgtc ggcggtgttc 114060
ccgaggggga cgggctgcca ggtgacgcgg tagcgccagc cgtcgagcag ggtgcgctcg 114120
gacaggccac ggcgccaggt ggagagggcg ggcagcacgt tcgacaggac cgcgtcgtcc 114180
aggtcgaggg tggcggagag cgactccagg tcctcgcgct ccacggcggc ccagaacgcg 114240
gcgtccgccg ggtcctgcgc ggtggccgtg tgcggcccgg tggccggctc gggccagtac 114300
agctcgcgct ggaaggcgta ggtcggcagg tcggtgcggc gggcgccggt gccggtgaac 114360
caggcggtcc agtcgacggc gacaccggcg gtgtggagcc gggccagggc ggtgagcagc 114420
gagtgttcct cgggtcggtc cttgcgcagc gccgggacgc tcacgccgcc gcttccgtcg 114480
gcggccgtgt cgaggacccg ggcggccatg ccggtgagga ccccgtcggg gccgatctcc 114540
aggtaggcgt cggctcccgc ctcggcgagg gcgcggacgc cgtcggcgaa gcggacggtc 114600
tcgcggacgt gccgcaccca gtactcgggg tcggtgagct gaccgggctg ggcgagggcg 114660
```

-continued

```
ccggtgacgt tggagaccac cgggacgcgc ggctcggcgt actccaggct ctccgcgacc 114720
cggcggaact cggcgagcat cggttccatc agcgccgagt ggaaggcgtg actgaccggc 114780
agaggctgcg tcttgtgccc ctcccccgcg aactcggccg ccagggccag gacttcctcc 114840
tgctcaccgg cgatgacgac ggagtcggga ccgttcacgg cggcgaggga caggccctcg 114900
gtcagccggg gcacgacctc ggcctcggtc gcccgcacgg ccaccatcgc cccgcccgtg 114960
gggagttcct gcatcaggcg ggcgcgggcg gcgaccagcg cgcaggcgtc gtcgagcgag 115020
aagactcccg ccacgtgcgc cgccgcgatc tcgccgaccg aatgacccgc cacgaactcc 115080
ggcgcgacac cccacgactc caccagccgg aacaacgcca cctccaccgc gaacagcgcc 115140
ggctgcgtgt acccggtcgc ctccagcagc gccgccgcct cggaaccctc ctcagcgaac 115200
agcacctccc gcagcgaacg ctccagcccc gtgtccagac gggccaccac cgagtccagc 115260
gcctccgcga acaccgggaa acgctcgtac aactcccggc ccatccccgc acgctgcgaa 115320
ccctggcccg agaagagcag ggcgaggcgg cgttcccagg cgcggtcgcg gacggtctcc 115380
aggggttcgc cccggcggt gaccaggtgg acggcgcggt gggcgaaggc ccctcggccg 115440
gtggccaggc tgtaggcggt gtcgagcgcg gggacctcgg gccgggcctg tgtgaaggcg 115500
gtcagccgcg cggtctgggc cgccagggcg tcctccgagc gggccgagac cagccagggc 115560
acgacggacg gctcggtgac cggttccggg gtctcggcgg tggccggttc gggctgctcc 115620
aggatgacgt gcgcgttggt gccgctcacg ccgaaggcgg agacgcccgc ccggcgcgca 115680
cggcccgtct cgggccaggc gcggtgctcg cggagcagtt ccacggtgcc gtcggaccag 115740
tcgacgtgcg aggacggcgc gtcgacgtgc agggtgcgcg gcagttcgcc gtggcccagg 115800
gcgaggacgg tcttgatgac accggcggcg cccgcggcgg cctgggtgtg gcccaggttg 115860
gacttgacgg tgccgagcag cagcggctgc tccgggtcgc ggccctcgcc gtaggcggcg 115920
atcagggcgt gggcctcgat cgggtcgccc agggtggtgc cggtgccgtg cgcctcgacg 115980
gcgtcgacct ccgccggggt gaggtgcgcg tcggccagcg cctggcggat gacgcgctgc 116040
tgggcgcggc cgttgggcgc ggtgaggccg ttggaggcgc cgtcctggtt gacggcggag 116100
ccgcgcagca cggcgaggac cgggtggccg tgacgacggg cgtcggagag ccgctccagg 116160
acgaggacgc cggcgccctc gccccaggcg gtgccgtccg cggcgtcggc gaacgccttg 116220
cagcggccgt cgccggccag gccgccctgc gcggtgaact ccacgaaggc gtccgggctc 116280
gccatcaccg agacgccgcc ggcgagggcc agggtgcact cgccggagcg cagcgccccg 116340
gcggccatgt gcagggccac cagcgccgag gagcaggcgg tgtcgacggt gaccgccggg 116400
ccctccaggc ccagggtgta ggacaggcgg ccggacatca cgctggcggt ggtgccggtc 116460
gcggcgtggc cgcgcacgtc ggtggtgccg cgccgcagca cggtggcgta gtcctggccg 116520
ttggtgccga cgaagacgcc ggtggcgctg gagcgcaggc ccgtcgggtc gatgccggcc 116580
cgctccaggg cctcccagga ggtctccagc agcaggcgct gctgcgggtc catcgcaagg 116640
gcctcgcgcg gggagatgcc gaagaacgag gcgtcgaaga gtccggcgcc ctggaggaag 116700
ccgccctcca gggtggcgga gccgccacgg gccagcgagt ccaggtccca gccgcggtcg 116760
gccgggaagc cggagacggc gtcgcggccc tcgccgagga gctgccagag ctcctcgggc 116820
gactcgacac cgccggggaa gcggcagccc atgccgacca cgacgaccgg gtcggtctcc 116880
gtggcgcggg gagcctcgcc ggccgcgttc ccgcccgccg ccggctcggg caggtcgccc 116940
aggatctcgg tcaggaggtg agcggccagg tcgcgggcgg tcgggtggtc gtagacgagg 117000
gtggcgggca gccgcaggcc ggtggtggcg cccagggtgt tgcgcagttc gacggtggtg 117060
```

-continued

```
agggagtcga agccgaggtc ggtgaaggcc tggtcggcct cgacggcgtc cgggtcgggg 117120
tgaccgagga cggcggcgac ctgggcgcgc aggaagtcca gcacgtaccg ctcgcgggcg 117180
gggccggtca gggcggcgac ctggcggcgc agcgccggtt cggtgtcgcc gtgggcggtg 117240
gccgcgccga cggtggcgcg tacctcgggc aggtcgccga cgagggcgcg gtgcggggcg 117300
aagacggtgg cgtagcgctg ccagtcgatg tcggcgacga ggagcgcggt gtcgcggtgg 117360
ccgacggcgg cgtcgagggc ggcgagggcg tcctcggggc tcatcggggt gaagccgcca 117420
cggcggaccc ggtcctcgac gccggtgccc tcgccggcca tgccggtgcc ggaccagggg 117480
ccccaggcca ccgaggtggc aggcaggccc tgttcgcgcc ggtgttcggc gagggcgtcg 117540
aggtaggcgt tggcggcggc gtagttggcc tggccggcgg cgccgagggt accggcggtc 117600
gaggagaaca ggacgaagtc ggtgaggccg aggtcgcggg tcagctcgtg caggtgggcg 117660
gcggagcggg ccttggcgtc gaggacggcg gcgaaccgct ccggggtgag ggtgtccagg 117720
aggccgtcgt cgaggacgcc cgccgcgtgc accacggtgg tgagggggcg gtcggcgggc 117780
acctcggcca ggagcgcggc gagcgcctcc cggtcggcgg tgtcgcaggc ggcgagggtg 117840
acctcggcgc ccagttcccg cagctcggcg gcgagttcgg cggcgccggg ggcgtccgcg 117900
ccgcgccggc tggtcagcag caggtgcggc gtgccgcgcc cggccaggag ccgggcgacg 117960
tgggcgccga gggcgccggt accgccggtg atcaggacgg tgccctcggg ggcgaacgga 118020
cgcgccggtt cctggggcgc cgggtggtgg gcgatccgcc gcgcgtaggt ggcggaggcg 118080
cggacggcga gctggttctc cgtgccgggc acggccagga ggtgcgccag ccggcgggcg 118140
acgcgggtgt cgaactgctc gggcaggtcg accagggcga ggcggcgtcc ggggttctcc 118200
agggcggcga cccggccgag cccccacaca cccgcctgcc cgggacgggc cagccggtcg 118260
gcgcgtccgg tgctcacggc ctgccgggtg acgatccaca ggggcgcggt gatcccggcg 118320
tcgtccaggg cgttcagggc ggcggccgtc ggcgccacgg cgcccgtccc tgccacgtcg 118380
tcggcggtgg cggcggtgtc gagggccggc agggcgagga cgccggtgaa gccgtcctcg 118440
gggcgcggca gccggcgcag ggtgtcggcg agcgcggcac ggtcgggggc cgcgaggtcg 118500
acggtgacct cggcggtgtc caggccgagg gtgtccagga gggcggcggt ctcgggcgcg 118560
gccgtaccgg tgggacgcag gaccagccag gtgccctcgg gccgtccggt gggggcgccg 118620
tcgagcggct tccacacgat ccggtggcgg cggccgtcgg cggcggcctg tgcggtgcgg 118680
cggcgccgcc acgaggacag ggccggcacc agggcggaca gcgtgtcgtc gtccaggccg 118740
aggtcggcgc cgagcgtggg caggtcggcc cgctcgacgg ccgaccagaa cgcggcgtcg 118800
gcgccggtgt cggcggggcc cgcggccgtg gccggggtga aggtggtgtc gggccagtag 118860
cggctgcgct ggaaggcgta ggtgggcagg tcgacgcggc gggcgccggt gccctcaaag 118920
gcgccggtcc agtcgacggc ggtgccgtgg acgtgcagcc gggcgagggc ggcggtgagg 118980
aacggcacct cgtcgcggtc gcggcgcagc gcggggacga cggtgacggg ccgggcgccg 119040
gtggcgtcgg ccgggtcggc gtcgaggacg tcgcgggcgg cggcggagag ggtgccgtcg 119100
ggaccgagtt ccaggcagga ggtgacgccc tggcgggcga gggtgcgcac ggcgtcggcg 119160
aaccggacgg tggcacggac ctggccgacc cagtactcgg gcgaacgcag ttcctcgggg 119220
gtggcggggg cgccggtgac ggtggagacc accggcacga gcggcgtctc gtaggtgagg 119280
ccgcgggcga cgcgggcgaa gtcgtcgagc atggcgtcca tgcgcggcga gtggaaggcg 119340
tggctgacct tcagcgcgcg ggtgcggcgg ccgtcctcgg cgaggcgggc ggcgacggcg 119400
```

-continued gcgaccggct cctcgtcacc ggcgatcacc acggcgcgcg ggccgttgac cgcggcgagg 119460
gagatccggt cctcgcctcc ctccaggagg ggcagtacct cttcctcgct cgcctcgacg 119520
gcgaccatgg cgccgcccgc cggaagggcg gccatgaggc ggccacgggc ggcgacgagg 119580
gcgcaggcgt cgtccaggga gaagaccccc gccacgtggg cggcggcgat ctcaccgacg 119640
gagtggccgg cgacctggtc ggggcgtacc ccccaggact cgacgagccg gtacagcgcc 119700
acttcgaggg cgaacagggc gggttgcgtg tacgccgtgt cgtccaggag cgcggcctcg 119760
gcggtgccct cctcggcgaa gagcacctcg cgcagcgggc ggtccagttc ctggtcgaag 119820
cgggtgagga ccgcgtccag ggcttcgccg aagaccgggt gacgctcgta caggtcccgt 119880
cccatggccg ggcgctggct gccctggccg gtgaagagga aggcgagccc tcctcgtgcg 119940
ggggcgccgg tgagcagcga ggcgtcgggg gcgccctcgc gcagcgcggt gagcgcccgc 120000
agcaggccgt cccggtcgcc ggtgaggacg gcggcgcggt gctccaggac gccacgggtg 120060
gtggccagcg agtgggccag gtccaccagc ggtacgtccg gacggccggc gaggtgtccg 120120
gcgagccgct cggcctgctc gcgcagggcg gccggggtcc gggcggagag cacgacgggg 120180
acgcccgggg gcagggtggc cgggtcgccg gcgggggccg gggacgcgga gggctcggtc 120240
gcgggctcct cgggcgcctg ctcgacgatg gtgtggacgt tggtgccgga gaggccgaag 120300
gaggagacgg cggcccggtg cgggcgtccg gtctcgggcc acggcacggt ctcggtggcc 120360
aggtcgatgg cgccggagcc ccagtcgacg tggctggagg gggtgtcgac gtgcagggtg 120420
cgcgggacgg tgccgtgccg catcgccatg accatcttca tgacaccggc gatgccggag 120480
gccatctggg tgtggccgat gttggacttc accgagccga gcagcagcgg ccggtccccg 120540
ggccggtcct ggccgtacgt cgccagcagg gcctgggcct cgatggggtc gccgagggcg 120600
gtgccggtgc cgtggccctc gaccacgtcc acctcgcccg gggtgagccg ggcgttggcg 120660
agggcctggc gtatgacgcg cgcctgggag gggccgttgg gggcggtgag gccgttggag 120720
gcgccgtcct ggttgacggc ggagccccgg atgacggcga ggacggggtg gccgttgcgg 120780
cgcgcgtcgg acagccgctc gacgaggacc aggccgacgc cctcggccag gctcatgccg 120840
tcggcgccct cggcgtacgc cttgcagcgg ccgtcggggg ccatcgcgcg ctggcggctg 120900
aagccggtga acgcctgcgg ggtggccatg acgctgacgc cgcccgccag ggcgagggtg 120960
gactcgccgt tgcgcagcga ctggcaggcc aggtggagcg cgaccaggga ggaggagcag 121020
gcggtgtcca gggtgacggc cgggccctcc aggccgaagg tgtaggcgag ccggccggac 121080
atcacgctgg agatggtgcc ggtgatcagg tggtcctcgg cgccctcgga gccggcgccg 121140
cccgcggtgt agtcctggta gctggcgccg atgaaggtgc cggtcatgct tccgcgcagg 121200
gtcgcggggt cgatgcccgc gcgctcgatc gcctcccagc cggtctccag cagcaggcgc 121260
tgctgggggt ccatcgccag tgcctcacgc ggggagatcc cgaagaagcc ggcgtcgaag 121320
tcggcgacgt cgtggaggaa tccgccctgc gtggagtagg tggtgccggg ccggtcgggg 121380
tccgggtcgt agagggcgtc ggcgtcccag ccccggtcgg cggggaagcc ggtgatggcg 121440
tcggcgccgg ccgcgatcag ctcccacagg gcctcgggcg aggtgacgcc gcccgggtag 121500
cggcagctca tcgcgacgac ggcgatcggc tcgtcgtcgg tggcggccgt ggtgcggacc 121560
gggccgtcgg ggccggcggc gggaccgccg gccaggcccc gcaggtggcc cacgagggtg 121620
agcgggtccg ggtagtcgaa cacgagggtg ctcggcaggg tgaggccggt gacggaagcc 121680
agccggttgc gcaggtcgac cgcggtgagc gagtcgaacc cgatgtcacg gaaggcgcga 121740
cgctccgaca gcacctccgg ggaggcgtgg ccgaggacgg tggccgcctc cgagcggacg 121800

-continued agttccagca ggaggcggtc ctgctcgccg gcgggcaggg agcgcaggcg gtggatgaac 121860
tctccggcct cgccggcgcg ggcctcctgc tgctcggtga ggcggcggac ctcgggcacg 121920
ttctcgaaga gttcggtggg ccgcgaggag gtgaagacgg ggtggtagcg gtcccagtcg 121980
acgtcggcga cggcgacggc gccctggtcc ccgtcgagga cctgccggag cccggcgagg 122040
gcgaggcgcg ggtccatgaa ctccaggccg ctgcggcgga tctggccggg gtcgacccgg 122100
ccgagcttca tgtcgtcggc ccagatgccc caggagacgg cggtgccgtg ggcgcctcgg 122160
gcgcaccggt gctcggcgag cgcgttgacg tgggcgttgg cggcgacgta cgcggcgtgc 122220
cggccactcc cccacatacc ggcggtggac gagtagagga cgaaggcgtc gagctggtcg 122280
tcgtcgagga gttcgtcgag gtgggcggcg cccgcggtct tggcgtggac gaccttggcg 122340
aacgcgtcga ggctggtctc ctcgatggac tggagctcga tgacggcggc ggtgtggaag 122400
acgctgcgga cggtgcggcc ctcggcggtg aggccgtcga ggagcgcggc gaccgcctcg 122460
cggtcggtga cgtcgcaggc ggcgacggtc acccggcagc cgcgttcgcc gagttcggcg 122520
gcgagttcgg cggcgccggg ggcgtccgcg ccgcggcggc tggtgaggac caggtcgcgg 122580
gcgccctggt cggcgagcca gcgggccagg tgcgggccga gcgttccggt gccgccggtg 122640
accaggacgg tgccgcgcgg gctccagcgg ccggtgccgg tgggcgccgg ggccggggag 122700
acgcggcggg ccaggacgcc ggaggcgcgg acggccagct ggtcctcgcc ggtggtgccg 122760
gccaggacgg cggcgaggcg ttcgcccgcc cggcggtcca gggtctcggg caggtcgacg 122820
gtgccgcccc accggtccgg gtgttccagg gccgcggtcc agccgaagcc ctggacgagg 122880
gcctgggcgg gccgggtgag gcggtcggcg cgcccggtgg agacggcgcc gcgggtcagc 122940
gcccacaggg gtgcctcgat cccggcgtcg ccgagggcct gcgtcagcgt gacgctgagg 123000
gcgagaccgg tggtgaggac cgggtgggcg gcgccggtgg actcgtcgtc ggccagcagg 123060
gagaccaccg cggccggttc gggcaggtcg cgcagccgct ccgtgagagc cgcccggtcg 123120
gcgtcggccc cggtcagcgc gaggggcacg gtccgcgcgc cgtgcgcggt cagctgctcc 123180
gccacggcgg cggcgtactc ggggtcggtg ccctccgcgg tgacgagcag ccaggtgccg 123240
tccagggtcg cggaggggag cgcgccgagc ggcttccagg tggcgcggta gcgccaggac 123300
ccgacggtgg aacggtcgcg cctgccacgg cgccaggtgg agagggcggg cagcagcggg 123360
gcgagcgcct cccggtcgag ttccaggcgg gaggcgaggg actccgcgtc ctcctgctcg 123420
acctcggccc agaactcggc gtcggcgggg tcgccgtcgc cggagccctg cgggcgggcg 123480
gagacggccc acaggtgctc acgctggaag gcgtaggtgg gcaggggtgt cctgcgggcg 123540
ccggtgtccg cgtagaccgc gttccagtcg gcccggccgc cgcgtaccca ctgttcggcg 123600
agggaggtga ggaagcgcgc ggtgccgccc tgttcgcggc gcagggtgcc gacggcggcg 123660
gccgggcggc cggcctcctc ggcggtggcc tggacggcca tggtcagcac ggggtgcggg 123720
ctgatctcga cgaagagcgt gtgttcggtg tcgagcaggg cgcgcacgcc gtcctcgaag 123780
cggacggtct gccgcaggtt gcggtaccag taggcggcgt ccatgccggt ggtgtcgagc 123840
gtggcgccgg tgaccgtgga gtggaacggg acccgggcgg cgcgcggtgc caccggggcg 123900
aggaggtcga ggagttcggc ctcgatccgc tccacctgtg ccgtgtggga ggcgtagtcc 123960
acggcgatcc ggcgggcacg caggtcgcgg gcggcgaact ccgcctggag ggcgtccagg 124020
gcctcgggcg taccggcgag gacgacggag cgcgggccgt tgacggcggc gacggagacc 124080
gctcccgcgt ggggggtcag gtactgctcg gcctcggcgg cggagacctg gacggacatc 124140

-continued atgccgccgg ccccggccag gacccggcgg atcgcctggg agcgcagggc gacgacgcgg 124200
gcgccgtcgt cgagggtgag ggcgccggag acgacggcgg cggcgatctc gccctgggag 124260
tggccgatca cggcgtcggg ggtgacgccg tgggcccgcc acagctccgc gagggagacc 124320
atcacggccc aggtcgcggg ctgcacgacg tcgacccggt ccagggtcgg cgcgccgtcg 124380
gcctggcgga cgacgtcgac gaggtcccag tcggtgtacg gggccagggc ggccgcgcag 124440
gcgtggagcc gctcggcgaa caccggtgac gtgtcgagga gttcggcgcc catgccggcc 124500
cactgggagc cctggccggg gaagacgaag acggtgcggc cgtcggtgtc ggcggtgccg 124560
tggaccacct ggccggtgga ctcgccggcg ccgaacgcgg cgagcgcgtc ggtgagttcg 124620
ccggcgtccg cgccgagggc gacggcgcgg tgctccagga cggagcgtgc ggtgatcagg 124680
gtgtggccga cgtcggcggg gtgcggtgcc gcgccggagg tgacgtgggc ggcgaggttg 124740
gcggcctgct cgcgcagggc ggagggggcg gcggccgaga ggatccacgg cagggtgccg 124800
cccgtgggca gggcgggtcc ggcggcgggg gcgggctcct cggcgggggc cgcctgttcc 124860
aggatggcgt gcgcgttggt gccgctgatg ccgaaggagg agacggcggc gcgcagcggg 124920
cggtcgtccc gggcccagcc ggtgttctcg gtgacgaggc ggacggtgcc gccggaccag 124980
tcgatgtggc tggagggctc cgtggcgtgc agggtgcgcg gcagggtgcc gtggcgcatc 125040
gccatgacca tcttgatgat gcccgcgacg ccggcggccg actgggtgtg gccgatgttg 125100
gacttcaccg agccgagcag cagcgggttc tcggggtcgc ggtccctgcc gtaggtggcg 125160
tgcagggcct gggcctcgat ggggtcgccg agggcggtgc cggtgccgtg tgcctcgacc 125220
gcgtcgatgt cgtcggtggt gaggccggag gcggccagcg cctggcggat gacgcggacc 125280
tgggaggggc cgttgggggc ggtcaggccg ttggaggcgc cgtcctggtt gatggcggag 125340
ccgcggacga cggcgaggac ctcgtggccg ttgcggcggg cgtcggagag ccgctccagg 125400
acgaggatgc cgacgccctc ggcgagggtc atgccgtcgg cgctctcgga gaaggccttg 125460
cagcggccgt cccgggcgag ggcccgttgc cggctgaagg cgatgaacgg catcgggttg 125520
gtcatgacgg tggcgccgcc cgccagggcg agggtggtct cgccgttgcg cagcgactgg 125580
caggccaggt ggagcgccac cagcgacgag gagcaggcgg tgtcgacggt gacggccggg 125640
ccctccaggc cgaaggagta ggcgaggcgg ccggagagca cgctggggct ggagcccgtg 125700
acggcgtggc ccgcggaccc gtcgtccatg gagacgccgt agtcctggta cgtggagccg 125760
atgaaggtgc cggtgggcgt ggagtgcacg gcggccgggt cgatgcccgc gtgctcgaac 125820
gcctcccagg tggtctccag caggaggcgc tgctgcgggt ccatggagac ggcctcgcgc 125880
ggcgagatgc cgaagaaccc ggcgtcgaac tcgcccgcgt cgtgcaggaa tccgccctgc 125940
gtggagtagg tggtgccggg ccggtcgggg tccgggtcgt acagcgcgtc gccgtcccag 126000
ccccggttga cggggaactc cgagatcgcg tcggtgttgt cggcgacgag ctgccagaag 126060
gcgtcggcgg agcgggcgcc gccggggaag cggcagctca tgccgatgat ggcgatgggc 126120
tcgtcggtga cggcggggcc ggtcgccacg gggcggtct cgaccgtgcc gaggagttcg 126180
gcacgcaggt ggcgcgcgag ggcgagcggg ttcgggtagt cgaagaccag ggtgctcggc 126240
agcgcgagtc cggtgaggtg ggcgaggcgc ttgcgcagtt cgacggcggt cagcgagtcg 126300
aacccggcgt cacggaacgc ctttttgacc ggcacccccct cggcggaggt gtggccgagc 126360
accacggcgg cctcggcccg cacgaggtcg acgagcagcc gctcctgttc ctgctcggtg 126420
aggccgccga ggcgctccgc cagcccggag acggtgccgg tgctcccggg agcagcgagg 126480
gccgcgacgg tgtcgacggt gtcgaagagg cggctggacc gggcggcggt gaagaccggg 126540

-continued tggtactgct cccagtcgac gtcggcgacg gtcacggtgg tctcgccgcg tacgacggcc 126600
cggcgcagct ccgtcatggc ggtggcgggg ttcagcagcc gcaggccggc gcgttccagg 126660
ttctccgaga cggtccggtg ggcgctggcc atgccgacct cggcccaggg gccccaggcg 126720
acggaggtgg cggcgaggcc gcgcgagcgg cggttctcgg cgagcgcgtc gaggtaggcg 126780
ttggcggcgg cgtaggcgct ctggcccgcg ctcccccaga ccccggcgac ggaggagacc 126840
aggacgagga agtcgaggtc gtggccgtcg aggagggcgt cgaggtgggc ggcgccgagg 126900
gtcttggcgg ccatggcggc ggcgacctgg tcgagcgggg tgtcggcgag cggcgcggcc 126960
tggccgacgc cggcggcgtg cacgacgccg gtgagggggg cgtcctcggg caccgcggcg 127020
aggacggcgg cgagggcgtc gcggtcggcg ctgtcgcagg cggtgagggt gacgcgggcg 127080
cccagttcct ccagttcggc gcggagttcg gcggcgccgg gggcgtcggg gccgcggcgg 127140
ccggtgagga cgaggtgggc ggcgccggag cgggcgagcc agcgcgcggc ctcggcgccg 127200
agaccgccgg tgccgccggt gaccaggacg gtgccggagg cggtgaactc gtcctcgcgg 127260
ggcagggcgt cgccggggtg ccggacgacg cggcgggcca gggtgccgcc cgcgcggacg 127320
gcgagctggt cctcgccgtc gcgggtggcg aggaggctga ccagccgctg ggtggccggg 127380
gcgtcgagga cctccggcag gtcgaccagt ccgctccact gctcggggcg ttccagggcg 127440
gcgacccggc ccaggcccca ggcggcggca cgggcggggt gggtgagcgg gtcgccgggg 127500
ccggtggaga cggcaccgcg ggtgaccgtc cacagcgggg cggtaacggc ggcgtcgccg 127560
agggcctggg cgaggaccac gccgagggcg aagccggccg ggagtccgcc ggccggtgcg 127620
tcggtgccgg tggcctcggg gcgggcggcg tcggcgagcg gcagcagcga caggatgccg 127680
cggacaccgg cggcgccttc ggccgtggcg ttctcgacgg cgtcgcgcag ggtggtggtg 127740
aggaggtcgc ggtcgaggtg ggaggcgtcg agcaccaggc gctcgacgac ggcgccgtgg 127800
ccgcgcaggg cggcgaggac ggtgtcggcc gcgccgtcgt cctcggtggt gacggccagc 127860
caggtcccgt cgagcaccgg ggcgctctca gtaccggcgg gctgccaggc gatccggtag 127920
cgggccgcgt cgaggacggc gcgttcctga cgggcgcggc gccaggagct cagcgacggc 127980
agcagcgtgt agagggaggc gtgttcctcg tcgcgcagac cgaggagccc ggcgagcccg 128040
gtggcgtcgc cgcgttcgac ggcggtccac agctcggcgt cggccgggtc gccggagccg 128100
tcaccggtgc ggcgcacggt cggcgcggtg gtgtccggcc agtaggtctc gtgctggaag 128160
gcgtacgtag gcagctcgac ggtgccggcg cctgccgggt ggaccgcgcc ccagtcgacg 128220
cggacgccgc ggacgtggag ccgggcgagg gcggtgagga cggactcgtc ctccggtcgg 128280
ccggtgcgca gcgtcgggac ggcgtcggcc tcgctgtcgt caccgagggt gtcctgggcg 128340
gcggcgcaca gggagccgcc ggggcccagt tcgaggtagg tggtggcgcc ggcctcgtgg 128400
gcggcgcgca cggcgtcggc gaagcggacg gtggagcgca cgtggcggac ccagtagtcg 128460
gcggtccgca ggtggtcgcc ctcggcgagg cggcccgtga ggtcgcaggc cacggggacg 128520
gtgggctcgt ggtacgtcag gccctcggcg acctcgcgga aggcgtccag cacggcgtcc 128580
atgcggggcg agtggaaggc gtggctgacc cgcagccggc gggtggcgcg gccgaggccg 128640
gcgaagtgcg cggcgatggc cgcggtggcc tcctcctcgc cggagacgac gacggccgac 128700
ggcccgttga cggcggcgag ggcggccacg tcctcctgcc cctggagcag gggcaggacc 128760
tcgtcctcgg acgcctggag cgaccacatg gcgccgccct cgggcagggc ctgcatcagg 128820
cgggcgcggg cggcgaccag cgcgcaggcg tcgtccaggg agaggacgcc tgcggcgtgg 128880

-continued

```
gcggcgccga tgccgccgac ggagtggccg aggagcacgc cggggcgcac gccccaggac 128940
cgcaccagcc ggtacagcgc ggtctccagg gcgaacaggg cgggctgtgt ccagccggtc 129000
tcgtacaggg cggcggcgcc cggggtgccc tcctcggcga acatgacgtc cttgagggag 129060
ccgtgcgggg tgccggcggg ggcgtcgacg aggagcgggt ccaggcgcgc gacgacctcg 129120
tccagagcct cggcgaagac cgggtggcgc tcgtacagtt cgcggccggt gccggggcgc 129180
tggctgccct ggccggtgaa gagcagggcg gtgcggccgg tgccaccggt ctcgccgagg 129240
acgagcgccg ggtcggggcg gtcggcggcg agggcggcca gggcacggcg ggcgtcgtcg 129300
gcggtgccga cgaccacggc gcgctgctcg aaggccgggc gggtggtggc cagcgagtgg 129360
gtgaggtcgg cgggggcctc gtcggggcgc gcgtcgaggt gggcgagcag ccgggcggcc 129420
tgggcgcgca gcgcgggccg ggtgcggccg gagagggtcc agggcaggac ggtggcttcg 129480
gcgggcgggg tgccggtgga cccggcgggg gcggactcgc cctgttccag gacgacgtgg 129540
gcgttggtgc cgctgatgcc gaaggaggag acaccggcgc gccgggggcg gccggtctcg 129600
ggccacgcct ccggctcctg gaggatgcgg acgtcgccgg tctcccagtc gacgtggcgg 129660
gaggggctgc cggcgtgcag ggtgcggggc agttcgccgt ggcgcatcgc catgaccatc 129720
ttgatgatgc ccgccacacc ggcggcggcc tgggtgtggc cgatgttgga cttcaccgag 129780
ccgagcagca acggccggtc cccgggccgg tcctggccgt acgtggcgag gagggcctgg 129840
gcctcgatgg ggtcgccgag ggcggtgccg gtgccgtgtg cctcgaccgc gtcgacgtcg 129900
gcggtggtga ggccggccgt gtccagggcc tggcggatga cgcgctgctg ggaggggccg 129960
ttgggggcgg tcaggccgtt ggaggcaccg tcctggttga cggcggaccc ccggaccacc 130020
gcgaggacgc ggtggccgtt gcggcgcgcg tcggagagcc gctccaggac gagcatgccg 130080
acgccctcgg accagccgac cccgtcggcc tcgtcggaga acgccttgca gcggccgtcg 130140
ggcgacaggc cgcgctggcg ggagaactcg atgagggagg tcggcgtgga catcaccgtg 130200
acgccgccgg ccagggcgag cgagcactcg cccgagcgca gggcctgcat cgcccagtgc 130260
atggcgacca gggaggagga gcaggcggtg tcgacggtga ccgccgggcc ctccaggccc 130320
agggcgtacg agacacggcc ggaggcgatg ctgggggcgg tcccgctgcc ctggtggccc 130380
tcgaaacgct cgtcggcgag ggtcgccgag tagtcgctgt acatgacgcc ggcgaagaca 130440
ccggtacggc tgccgcgcag gcccaccggg tcgataccgg cgtgctcgac ggctgtccag 130500
gacgcctcca gcagcagtcg ctgctgggag tcggtggcga gcgcctcacg gggctcatg 130560
ccgaagaagc ccgcgtcgaa ctcgcccgcg tcgtgcagga atccgccgta gcgggtgtac 130620
gaggtgccgg ggtggtccgg gtcggggtgg tagagggagt cgaggtccca gcctcggttg 130680
acgggcaggc cgccgatcgc gtcggtgccc tcggtgacca ggcgccacag gtcgtcgggc 130740
gagccgacgc cgccggggta gcggcagctc atgccgacga tgacgatcgg gtcgtcggcg 130800
gtggcggacg tccgcggggc gggggcgggg gcctcggcct cgggggcgtc ggtcagttcg 130860
gccaggaggt ggccggccag ggccgcgacg gtcgggtagt cgaagatgac ggtggcggag 130920
gtgcgcaggc cggtggcggc ggccagcccg ttccgcagct cgacggcggt cagggagtcg 130980
aacccgagct cctggaaggg gcgttcgggg tcgatgtcgg cggcggaggc gtggccgagg 131040
acggcggccg tccggtcgcg caccaggtcg acgacggcct ccgtgcgggc ctgttcgtcg 131100
agccgggcga gccgctgggc gaggccgagg gcggcctcgg aaccggtgcg caccgtgcgg 131160
cgggcgcggg tgcggaccag gccgcgcagg agcgggggca cctcgccccg gccacgcagg 131220
gcggccaggt cgaggcggac gggcaggacg gcggcgcggg gcagggcgag ggtggcgtcg 131280
```

-continued aagagggcca ggccctgttc gacggtgagc ggcggcgtgc cggagcggga catgcgctcc 131340
aggtcccgct cggagagttc gccggtcatg ccgccgtcga cgggcaccca ggggccccag 131400
ccgagggaga ggccgggcag cccggcgtcg cgacgcaggc gggcgacggc gtccaggaag 131460
gcgttgccgg ccgcgtagtt ggcctggccc ggggcgccgg tggtaccggc gagggaggag 131520
aacaccacga aggcggcgag gtcgaggtcg cgggtggccc ggtgcagatg ccagacggcg 131580
tcggccttgg gccgcaggac ggcggcgagc cgctcctcgg tgagggattc gaccagtccg 131640
tcgtcgaggg tgccggcggt gtgcacgacg gcggtgacgg ggtgggcggc cggtacggcg 131700
gcgaacagcc ggtccacggc ttccgggtcg gcgacgtcgc aggcggcgag agtgacctcg 131760
gcgcccagcg cgccgaggtc ggcggcgagt ccggcggcgc cgggggcgtc ggggccgcgc 131820
cggccggcga gcaccaggtg gcgtacgccg cgctcggtga cgaggtggcg ggcgagggcg 131880
gcgccgaggc cgccggtgcc gccggtgacg acaacggtcc cctcggggtt ccaggcggcg 131940
gcggtggtct cgccgtcggg gcggacgcgg gcgagccggg cggcgaacac ggtgtcgccc 132000
cgcagcgcgg tctgcggttc ctcggcggcg agggccgcga cgagcgcggc ggggtcggtc 132060
ccggcgacgg ggtcgaggtc gagcaggccg aagcggtggg ggtgttcggc ctgggcggag 132120
cggaccaggc cccagacggc ggcggcggcc gggtcggtga gcggcccttc gccgacggcg 132180
acggcgcccc gggtgacgaa caccaggcgc gccccggccc gggtgtcctc ggcgagccaa 132240
cgctggatgt gcccgaggac gcgggcggtg ctcgcgtgga cctcggcggg tacggcctcg 132300
gggtcgccgc cgccgacggg gacgagcacc agggccggcg tgtcgggtcc ggcggcctcg 132360
gtgagcgggc cgacggtgac ccggcggcg gtgagggcgg cgccgagccg gagggggtcg 132420
gggccgagca gaccgacggt gccgggggtt tcgggggcgt cggcgccgtg gaggcgggtc 132480
cagtcgaggt ggaagagggc gtcgcgctcc agcacgccgg cggcggcccg gcgcgcgtcg 132540
ggggcggagc gcagcacgag ggagccgacc gaggcgacgg gtgccccggt ggtgtccgcg 132600
acggtgaggg tgacggcgtc gtcgcccgcg ggggtgatgc ggacccgggc ctcggtggcg 132660
ccggccgcgt ggagggtgac gtcctgccag gcgaacggca ggccgccgcg ggcgtcctcg 132720
ccgagcgggg cgagggcggt ggcgtgcagg gccgcgtcca gcagcgccgg gtgcaggccg 132780
aacgaagagg cgtcgcccgc gggtcccgcg tcgagagcca cctcggcgaa ggtctcctcg 132840
ccccggcgcc agacggcgcg caggccgcgg aaggcggggc cgtaggcgaa gccggactcg 132900
gccagcccct cgtagaagcc gtcgaggccg acactctcgg caccggcggg cggccagacc 132960
gccgcgtcga actcctcgcc gtggtgggcg ccgttggtca gggtgccggc ggcgtgctgg 133020
gtccagggcc ggtcgtcgtc gccgtcgggg cgggagtaca gggtcagggc gcggcggccg 133080
gtctcgtcgg ggctgccgat ccagacctgg acctggacgc cgccgtcctc gggcagggcg 133140
agcggggcgg cgagggtgag ttcctcgacg cggtcgcagc cgacctcgtc gccggcgcgg 133200
acggcgagtt cgaggaaggc ggtgccggcc agcagcacgg tgccgcgcac cgtgtggtcg 133260
gcgagccagg gatgggtgcg caccgagaga cggccggtga ggagcaggcc gtcggagttg 133320
gcgagggtga cggcggcggc gagcagcggg tggtgggcgg cgccgagccc cgcggaacgc 133380
atgtcgccgg tgagccccgt gacgcccttg ggccagaagc ggcggtgctg gaaggcgtag 133440
gtcggcaggt cggtgtggcc ggcgccggtc ccctcgaacc agcggtccca gcgcaccggg 133500
acgccgcgca ggtggagtcc ggtggcggtc tcggtgaggg tggcggcctc ggggcggtcc 133560
ttgcggagcg cgggcagcac ggcggcgcgc tcgtgcccgg cggcgtccag gacggtccgg 133620

-continued

```
gtgagggcgg cgagcgtggc gtcggggccc agttcgagga agagccccgt gccgtgtccg 133680
gcgagccagg agactccgtc ggcgaagcgc acggcgtggc ggacgtgatc ggtccagtag 133740
ccggcggagg tgagctgctc gacggtggcg gggcgccgg tgaggttgga gacgaccggg 133800
acggtggggg cctgcgggga gagtccggcg acgaccgcgc ggaactcctc cagcatcggg 133860
tccatgagcg gtgagtggaa cgcgtgggag acccgcagcc tgcgggtgcg gcgcccgagg 133920
gccgcgacgc gggcggcgat ggactcgacg gcgtcctcgg ctccggagac gacgaccgcg 133980
gccgggccgt tgacggcggc gacggagacc tgtccggcgt gttcggcgac gagcggcgcg 134040
acctcgtcct cggtggcttc cagggagacc atggcgccgc cctcgtccag cgcctgcatg 134100
aggcggccac gggcggtgac cagggtgcag gcgtcggcga gggtgaacac cccggcgacg 134160
tgggcggcgg ctatctcgcc gacggagtgg ccggtgaggt ggtcgggggt gacgccccag 134220
gactcgacga gccggtacag ggccacttcg agggcgaaca gggcgggctg cgcgtactcg 134280
gtgcggtcga ggagcgcggc ctcctcgctg ccctcctcgg cgaggatcag ggcttcagc 134340
gggcggtcga gccccgcgtc gaggtgctcc aggatctcgt cgagggcgcg ggcgaagacg 134400
gggaagcggg cgtgaaggtc gcggcccatg ccgggacgct gggagccctg gcccgagaag 134460
agcacggcga gcttggtacg gccacgcagc tggtgggtgg tgagacccgg ggcgtccgca 134520
ccggcggcga gcgcggtgag cacggcgacg gcggtgtccc ggtcggcggt ggtgaaggcc 134580
gcgcggtgct ccagggcgga gcgggtggtg gcgagcgcgt gggagacgtc cagggcggac 134640
ggcgtgggcc gggcggcgag gtggtcgagc agccgggcgg cctgggcgcg cagggcctcg 134700
ggggtacggc cggagagcag ccagggcagc gccccggcgt cgacggccgg ggcggcctcg 134760
ccgtcggcgg ccggctcctg gggagcctcc tcgatgatgg tgtgcgcgtt ggtgccggag 134820
aggccgaagg aggagatgcc cgcgcgacgc ggcgcgttct cgcgggccgg ccagggggcg 134880
ggctccgtca gcaggcggac ggagccctcg ctccagtcga cgtgggtgga gggctggtcg 134940
acgtggaggg tgcgcggcag caggccgtgg cgcatcgcca tgaccatctt gatgacgccc 135000
gcgacacccg ccgcggcctg ggtgtggctg atgttggact tgaccgagcc gagcagcaac 135060
gggctgtcgg cctcgcggcc ctggccgtag gtggccagca gcgcctgggc ctcgacgggg 135120
tcgccgagga ccgtgccggt gccgtgtgcc tcgacggcgt cgacgtcggc ggcggtgagc 135180
cgggcgttga ccagggcgga ctcgatgacg cgctgctggg aggggccgtt gggggcggtc 135240
aggccgttgg aggcaccgtc ctggttgacg gcggaccccc ggaccaccgc gaggacgcgg 135300
tggccgttgc ggcgggcctc ggagagccgc tccaggacga ggacgccgac accctcggac 135360
cagccggtgc cgttggcggc gtcggcgaag gaccggcagc gcccgtcggc ggcgaggccg 135420
ccctggcggg cgaactcgac gaaggtggtg gggctggcca tgacggtgac accggcggcc 135480
agggccaggg agcactcccc cgcgcgcagc gactgggcgg ccaggtgcag ggccaccagg 135540
gaggaggagc aggcggtgtc gacggtcacg gccggtccga cggcaccgaa gaagtaggag 135600
agccgcccgg agaggatgct ggtggcgttg ccggtgagct ggaagccctg gacgtcgtcg 135660
tcggggccga cccggtagtc ctggggcatg gcgccgacga acatgccggt gcggctgccg 135720
cgtacgcccg cggggtcgat accggcccgt tcgaaggcct cccagccggt ctccaggagc 135780
aggcgctgct gcgggtccat ggacagcgcc tcgcggggcg agatgccgaa gaagtccggg 135840
tcgaaggcgg gcgcgtcgtg caggaagccg ccggcgaagt cggcggggcc ctcgccgagc 135900
gcggcctccc agccacggtc ctcgggcatg ccggtgatgc cgtcctcgcc ggcgaccagc 135960
atcttccaca ggtcctcggg gctgctcacc ccgccggggt agcggcagct catgccgacg 136020
```

-continued

```
atcgcgatgg gctcggtggc cgccgcctcc agctcggtca cccgctgccg ggagcgcttc 136080
agatcggcgc tcgcccgctt caggtagtcc cggagcttct gttccttgtc catatcaacg 136140
caacccatct ggatgaagac cggcggacgg ctggcggtcc ggcgtggaca ccgggtgccc 136200
gggacggccg gagggggccg ggccgggcgg ggtgtcccga ggaggggaaa gggcgggggg 136260
cggggcctgg gcggcctgcc gggcgcggtg tctcacgtgc ctgcgggggc ggcccgggcg 136320
ccgctccgcg gaccggagga ccagggcggc tctccggcac gcggacgggc gggcggcgcc 136380
accgccgctc cccgggagca cacgccgagc acgcgtgccg tgccctcagt tccgctgacc 136440
atggggccca gtctgcggcg ggtggggctt tggaaatccc tagtgtgtgc gcgggtgacg 136500
gggccgcagg ttcgcaggtc acgagcggcc ccgcccccggt ccccggacgg agccggccta 136560
ccagctgccg gtggccagga gctggctgta gtcccgctcc cgcgatgcct ggcgcaggtc 136620
ggactcgacc atcatgcgca tcagctgctc gaagtcgacc tcgggctccc agcccagttc 136680
gcgccgggcg ttgcccgagt cggcgcagag ggtctcgacc tcggcggggc gcaccaggcc 136740
ggggtcgacg acgacgtgct cctgccagtc gaggccgacg tgctcgaagg cgatccgggc 136800
cgcgtcgcgg acctggtgca tggctccggt ccccaccacg tagtcaccgg cctgctcctg 136860
ctggagcatc aggtgcatgg cgcggacgta gtcacccgcg aagccccagt cgcgctcggc 136920
gtcgaggttg ccgaggtgca gcttgtccat ctggcccagt ttgatctggg cgacggccag 136980
cgagatcttg cgggtgacga actcggcgcc acggcgcggc gactcgtggt tgaacaggat 137040
cccggagacc ccgtacatcc cgtacgactc gcggtagttc tgggtgatgt agtggccgaa 137100
ggccttggcc acgccgtacg ggctgcgggg gtggaaggag gtggtctccc gctgcgggct 137160
ctccgccacc ttgccgtaca tctcggagga ggacgcctgg tagaagcgga tctggccgcg 137220
gggcgagccg ccggaggact tggtgaggcc ggagacgatg cggaccgcct ccagcatgcg 137280
cagcacgccg gtgccgttga cctccgtgac cagttcgggc tgttgccagg acatcggcac 137340
gaaggagatg gcgcccaggt tgtagacctc gtcgggctgg accaggtcga ccgccgagac 137400
caggctgccc tggtccatga ggtcgccgtc cacgaaggac agctccggga tcagcttggc 137460
gatccggtcc ttgcgggggt tggcctgacc ccggcagagc cccagacct ggtacccctg 137520
gtcgaggagg tgttcggcca ggtacgaacc gtcctgtccg gtgattccgg tgatgagtgc 137580
acgcttggac atctttcctc tttccaccgc cacggtgagg accggtcggg cgggtgtccg 137640
cgccggcggg ggcggactga tggaccccca tgcgtactga cacgctccgg cggagggcag 137700
agccttgccc ccctccggag cacgagacgc acggctgcgc tcacgagccg tcctcgtcgc 137760
ggacatgcaa gcacgggcag agctaaggga tttgcgagtc ttcacggccg cgtcccgcgc 137820
acgggccgac ggaaatcacc gcataacgcg gcacacccgc cgggttcagc cggcgccgcc 137880
ggcctggcgg cgggagcgct ggtccttctc gtgggcgagc agtttcgcgt cgccctggag 137940
gcgggcggcg cccttgcgga gtgcggggag cagctgcatg agggcgtcgc ccgggcagtt 138000
ggtctcgtag gcgtcgatgt ggccgaagac ggccggcatg gtgacggtgg tgttcttggc 138060
gaaccggctg tcgctgttcc tggagagcag gtgggtgttg gcgaccgggt cggcctgggt 138120
gagggccagc ttccaggcga tgagtttctc gatggagcgg cgcatcggct cgggcacggg 138180
ggtgccggcc gtgaaggtgc cga                                         138203
```

<210> SEQ ID NO 2
<211> LENGTH: 1743
<212> TYPE: PRT

<213> ORGANISM: Streptomyces sp. FR-008

<400> SEQUENCE: 2

```
Met Val Pro Val His Ala His Asp Tyr Val Thr Asp Pro Pro Ser Thr
 1               5                  10                  15

Thr Gly Arg Thr Leu Asp Gly Leu Thr Leu Pro Arg Val Phe Ala Asp
            20                  25                  30

Ala Val His Arg Gly Gly Asp Ala Val Ala Leu Val Asp Gly Glu Tyr
        35                  40                  45

Ala Leu Thr Trp Ser Ala Trp Arg Thr Ala Val Asp Ala Leu Ala Arg
    50                  55                  60

Gly Leu Gln Glu Ser Gly Val Val Ser Gly Asp Val Val Ala Leu His
65                  70                  75                  80

Leu Pro Asn Ser Trp Glu Tyr Leu Thr Leu His Leu Ala Ala Ala Ser
                85                  90                  95

Val Gly Ala Val Thr Met Pro Val His Gln Gly Asn Ala Pro Ser Asp
            100                 105                 110

Val Arg Ala Leu Leu Glu Arg Val Arg Pro Ala Ala Val Val Leu Pro
        115                 120                 125

Ala Arg Thr Gln Glu Gly Gly Gly Pro Leu Thr Gly Thr Ala Leu Arg
    130                 135                 140

Glu Val Leu Pro Glu Leu Arg Ala Val Leu Val Thr Gly Asp Ala Ala
145                 150                 155                 160

Gly Glu Gly Thr Glu Thr Val Thr Glu Met Leu Glu Arg Trp Ser Gly
                165                 170                 175

Glu Asp Pro Leu Pro Val Glu Val Arg Pro Asp Ser Pro Phe Leu Leu
            180                 185                 190

Leu Pro Ser Ser Gly Thr Thr Ser Ala Arg Pro Lys Ile Cys Leu His
        195                 200                 205

Ser His Glu Gly Leu Leu Thr Asn Ser Arg Ala Ala Thr Glu Asp Thr
    210                 215                 220

Ala Asp Ala Tyr Ala Gly Thr Leu Ile Thr Ala Cys Pro Leu Thr His
225                 230                 235                 240

Cys Phe Gly Leu Gln Ser Ala Tyr Ser Ala Leu Phe Arg Ala Gly Arg
                245                 250                 255

Gln Val Leu Leu Ser Gly Trp Asp Val Gly Arg Phe Leu Glu Leu Ala
            260                 265                 270

Arg Arg Glu Arg Pro Ser Val Val Val Ala Val Pro Ala Gln Leu His
        275                 280                 285

Asp Leu Val Thr Arg Val Arg Glu Asp Ala Asp Gly Pro Gly Phe Arg
    290                 295                 300

Pro Gly Arg Ile Leu Thr Ala Gly Ala Ala Leu Pro Pro Ala Leu Val
305                 310                 315                 320

Arg Asp Val Arg Glu Ala Leu Asp Thr Thr Leu Val Val Val Trp Gly
                325                 330                 335

Met Ser Glu Ala Gly Asn Gly Thr Ser Ser Leu Ser Ala Asp Ala Pro
            340                 345                 350

Glu Val Val Ser Arg Ser Val Gly Arg Pro Thr Arg Asp Ala Glu Met
        355                 360                 365

Arg Val Val Asp Glu Asp Gly Ala Pro Cys Pro Pro Gly Gln Pro Gly
    370                 375                 380

Glu Leu Tyr Tyr Arg Ser Pro Ser Met Phe Arg Gly Tyr Phe Gly Glu
385                 390                 395                 400
```

-continued

```
Pro Glu Leu Thr Arg Ser Val Val Ser Glu Asp Gly Trp Leu Arg Thr
                405                 410                 415

Gly Asp Leu Ala Ser Ile Gly Glu Asp Gly Leu Val Thr Phe His Gly
            420                 425                 430

Arg Ser Ala Glu Leu Ile Asn Val Gly Gly Arg Lys Phe Asn Ala Val
        435                 440                 445

Glu Ile Gln Ala Leu Leu Ala Asp Leu Pro Asp Ile Gly Pro Leu Ala
    450                 455                 460

Val Val Ala Ala Pro Asp Pro Arg Leu Gly Glu Tyr Pro Val Leu Val
465                 470                 475                 480

Val Thr Glu Arg Pro Ala Ala Ala Pro Ala Asp Gly Thr Ala Pro Arg
                485                 490                 495

Pro Arg Gly Thr Val Gly Leu Asp Glu Val Thr Ala His Leu Arg Gly
            500                 505                 510

Leu Gly Thr Ala Glu Tyr Lys Ile Pro Leu Glu Leu Val Ala Leu Pro
        515                 520                 525

Glu Leu Pro Arg Thr Pro Ala Gly Lys Ile Asn Arg Arg Ala Leu Glu
    530                 535                 540

Gln Tyr Leu Ala Asp Ala Ala Glu Arg Thr Ala Val Thr Pro Ala Glu
545                 550                 555                 560

Ala Pro Arg Pro Gly Leu Arg Thr Ala Leu Glu Leu Val Val Thr Ala
                565                 570                 575

Val Ala Glu Val Leu Ala Ala Val Pro Gly Glu Asp Gly Ala Arg Pro
            580                 585                 590

Ala Ala Ala Gly Pro Ile Gly Pro Asp Thr Thr Phe Arg Ala His Gly
        595                 600                 605

Leu Asp Ser Val Ala Ser Val Arg Leu Arg Asn Ala Leu Ala Glu Ala
    610                 615                 620

Thr Gly Leu Thr Leu Pro Ala Gly Leu Ala Phe Asp Phe Pro Thr Pro
625                 630                 635                 640

Ala Ala Leu Ala Arg Glu Leu Ala Gly Leu Ser Ser Pro Ala Ala Glu
                645                 650                 655

Glu Ser Pro Gly Ala Ser Ala His Glu Asp Glu Pro Val Ala Ile Val
            660                 665                 670

Ser Met Ala Cys Arg Leu Pro Gly Gly Ala Thr Ser Pro Glu Ala Leu
        675                 680                 685

Trp Glu Leu Leu Arg Asp Gly Val Asp Ala Val Ser Gly Phe Pro Glu
    690                 695                 700

Asp Arg Gly Trp Asp Leu Asp Ala Leu Phe Gly Asp Asp Pro Asp Ala
705                 710                 715                 720

Pro Gly Thr Ser Val Ala Arg Glu Gly Gly Phe Leu Arg Asp Ala Ala
                725                 730                 735

His Phe Asp Ala Gly Phe Phe Gly Met Ser Ala Arg Glu Ala Leu Ala
            740                 745                 750

Thr Asp Pro Gln Gln Arg Leu Leu Leu Glu Thr Ala Trp Glu Ala Val
        755                 760                 765

Glu Arg Ala Gly Ile Ala Pro Arg Thr Leu Arg Gly Ser Arg Thr Gly
    770                 775                 780

Val Phe Thr Gly Ala Met Tyr His Asp Tyr Ala Ala Gly Ala Ser Asp
785                 790                 795                 800

Pro Ala Gly Glu Leu Glu Ser Leu Leu Pro Val Gly Thr Ala Gly Gly
                805                 810                 815

Ala Leu Ser Gly Arg Ile Ala Tyr Thr Leu Gly Leu Ser Gly Pro Ala
```

-continued

```
            820                 825                 830

Leu Thr Val Asp Thr Ala Cys Ser Ser Ser Leu Val Ala Leu His Leu
        835                 840                 845

Ala Cys Arg Ser Leu Arg Ser Gly Glu Ser Asp Leu Ala Leu Ala Gly
    850                 855                 860

Gly Val Ala Val Met Ala Thr Pro Ala Ala Phe Val Gly Phe Ser Arg
865                 870                 875                 880

Leu Arg Gly Leu Ser Pro Asp Gly Arg Cys Lys Ser Phe Gly Glu Gly
                885                 890                 895

Ala Asp Gly Ala Ala Trp Ser Glu Gly Ala Gly Leu Leu Met Leu Glu
            900                 905                 910

Arg Leu Ser Asp Ala Arg Arg Asn Gly His Pro Val Leu Ala Val Ile
        915                 920                 925

Arg Gly Ser Ala Val Asn Gln Asp Gly Ala Ser Asn Gly Leu Thr Ala
    930                 935                 940

Pro His Gly Pro Ala Gln Arg Arg Val Val Arg Gln Ala Leu Ala Asp
945                 950                 955                 960

Ala Gly Val Arg Ala Ala Glu Val Asp Val Val Glu Ala His Gly Thr
                965                 970                 975

Gly Thr Ala Leu Gly Asp Pro Ile Glu Ala Glu Ala Leu Leu Asp Thr
            980                 985                 990

Tyr Gly Arg Asp Arg Pro Glu Gly Arg Pro Leu Trp Leu Gly Ser Val
        995                 1000                1005

Lys Ser Asn Leu Gly His Thr Gln Ala Ala Ala Gly Ala Ala Ala Val
   1010                1015                1020

Ile Lys Met Val Leu Ala Leu Arg His Asp Leu Leu Pro Ala Thr Leu
1025                1030                1035                1040

His Ala Asp Thr Pro Thr Ser Arg Val Asp Trp Ser Pro Gly Thr Val
               1045                1050                1055

Gln Leu Leu Thr Arg Ala Arg Asp Trp Pro Arg Glu Glu Gly Arg Pro
           1060                1065                1070

Arg Arg Ala Gly Val Ser Ser Phe Gly Ile Ser Gly Thr Asn Ala His
       1075                1080                1085

Leu Val Leu Glu Glu Ala Pro Val Pro Ala Ala Gly Thr Glu Arg Ser
   1090                1095                1100

Ala Asp Ala Gly Ala Ala Gly Leu Arg Ala Ala Val Pro Trp Leu Val
1105                1110                1115                1120

Ser Ala Lys Asp Ala Asp Ala Leu Arg Gly Gln Ala Arg Arg Leu Ala
               1125                1130                1135

Ala His Ala Ala Ala His Pro Glu Val Ser Ala Arg Asp Leu Ala Tyr
           1140                1145                1150

Ser Leu Leu Thr Thr Arg Ala Leu His Pro Arg Thr Ala Leu Leu Thr
       1155                1160                1165

Gly Gly Asp Arg Asp Ala Leu Val Ala Ser Ala Asp Ala Phe Ala Arg
   1170                1175                1180

Gly Glu Ala Pro Gly Ser Ile Val Arg Gly Pro Leu Gly Pro Ala Pro
1185                1190                1195                1200

Gly Thr Ala Phe Val Leu Thr Gly Gln Gly Ser Gln Arg Leu Gly Met
               1205                1210                1215

Gly Arg Gly Leu Ala Ala Ala Phe Pro Val Phe Asp Asp Ala Leu Arg
           1220                1225                1230

Glu Val Cys Ala Leu Leu Asp Pro Leu Leu Glu Arg Pro Leu Thr Glu
       1235                1240                1245
```

-continued

```
Val Met Trp Ala Ala Pro Asp Ser Asp Glu Ala Gly Leu Leu Gly Gly
   1250                1255                1260

Thr Gly Tyr Ala Gln Pro Ala Leu Phe Ala Phe Glu Val Ala Leu Tyr
1265                1270                1275                1280

Arg Leu Leu Glu Ser Trp Gly Ile Val Pro Asp Arg Leu Val Gly His
               1285                1290                1295

Ser Val Gly Glu Ile Ala Ala Ala His Val Ala Gly Val Leu Ser Leu
           1300                1305                1310

Pro Asp Ala Cys Ala Leu Val Ala Ala Arg Gly Arg Leu Met Gln Ala
       1315                1320                1325

Leu Pro Pro Gly Gly Ala Met Ala Ala Val Arg Cys Ser Glu Ala Glu
   1330                1335                1340

Ile Leu Pro Leu Leu Ala Gly Arg Thr Ala Gly Ala Thr Val Ala Ala
1345                1350                1355                1360

Val Asn Gly Pro Arg Ser Val Val Leu Ser Gly Thr Glu Glu Ala Val
               1365                1370                1375

Ala Glu Val Val Thr Glu Val Ser Ala Ala Gly His Lys Thr Arg Arg
           1380                1385                1390

Leu Met Val Ser His Ala Phe His Ser Pro Leu Met Glu Pro Met Leu
       1395                1400                1405

Ala Glu Phe Arg Ala Thr Val Ala Gly Leu Ser Phe Ala Ala Pro Gln
   1410                1415                1420

Val Pro Leu Val Ser Gly Val Thr Gly Arg Pro Leu Thr Ala Glu Glu
1425                1430                1435                1440

Ala Arg Asp Pro Asp His Trp Val Arg His Ala Arg Asp Thr Val Arg
               1445                1450                1455

Phe Ala Asp Ala Ile Ser His Leu Ala Gly Glu His Thr Glu Ile Tyr
           1460                1465                1470

Val Glu Leu Gly Pro Glu Ala Ala Leu Thr Pro Met Val Glu Glu Cys
       1475                1480                1485

Leu Gly Glu Pro Glu Ser Gly Asp Gly Pro Ala Val Glu Pro Val Val
   1490                1495                1500

Arg Gly Asp Val Asp Glu Glu Arg Ala Ala Leu Ala Ala Ala Val Arg
1505                1510                1515                1520

Leu His Ala Leu Gly Leu Asp Val Gln Trp Arg Ala Val Leu Pro Glu
               1525                1530                1535

Ala Arg Ala Val Pro Leu Pro Thr Tyr Ala Phe Gln His Glu Ala Tyr
           1540                1545                1550

Trp Leu Ala Thr Ser Gly Ser Val Val Ala Gly Leu Ser Leu Pro Gly
       1555                1560                1565

Gly Arg Ala Ala Asp Thr Val Pro Asp Leu Ala Gly Arg Leu Ala Gly
   1570                1575                1580

Leu Ser Gly Gly Glu Ala Glu Ala Leu Val Thr Glu Leu Val Arg Thr
1585                1590                1595                1600

Glu Leu Ala Ala Val Thr Gly Gly Glu Ile Ser Ala Ala Gly Ala Gly
               1605                1610                1615

Thr Ala Phe Thr Glu Leu Gly Val Thr Ser Val Thr Ala Val Glu Leu
           1620                1625                1630

Arg Asn Arg Leu Thr Ala Val Thr Gly Val Arg Leu Pro Pro Thr Leu
       1635                1640                1645

Ile Phe Asp His Pro Thr Pro Thr Ala Val Ala Arg Leu Ile Gly Glu
   1650                1655                1660
```

```
Thr Val Arg Gly Ser Ser Val Pro Gly Arg Arg Asp Ala Val Ser Leu
1665                1670                1675                1680

Val Asp Glu Leu Glu Ala Leu Leu Val Ser Gly Ala Glu Val Asp Ser
                1685                1690                1695

Asp Thr Ala Ala Arg Leu Arg Ser Leu Ala Gly Arg Trp Ala Pro Ser
            1700                1705                1710

Ala Thr Gly Thr Ala Ala Asp Ala Asn Gly Pro Leu Asp Leu Asp Asp
        1715                1720                1725

Ala Ser Asp Glu Glu Leu Phe Arg Leu Met Asp Gly Gly Ala Pro
    1730                1735                1740


<210> SEQ ID NO 3
<211> LENGTH: 10625
<212> TYPE: PRT
<213> ORGANISM: Streptomyces sp. FR-008

<400> SEQUENCE: 3

Met Ala Ser Ser Glu Ala Lys Leu Arg Asp Tyr Leu Lys Lys Val Thr
1               5                   10                  15

Thr Asp Leu Arg Arg Thr Arg Gln Arg Leu Glu Thr Val Glu Ala Arg
            20                  25                  30

Glu Ser Glu Pro Ile Ala Val Ile Gly Met Ala Cys Arg Phe Pro Gly
        35                  40                  45

Gly Val Arg Ser Pro Glu Asp Leu Trp Gln Leu Val Ala Asp Gly Thr
    50                  55                  60

Asp Ala Ile Gly Pro Leu Pro Ala Asp Arg Gly Trp Asp Leu Asp Gly
65                  70                  75                  80

Leu Tyr Asp Pro Asp Pro Gly Thr Pro Gly Lys Ser Tyr Val Arg Glu
                85                  90                  95

Gly Gly Phe Leu Glu Gly Ala Ala Asp Phe Asp Ala Asp Leu Phe Gly
            100                 105                 110

Ile Ala Pro Arg Glu Ala Leu Ala Met Asp Pro Gln Gln Arg Leu Leu
        115                 120                 125

Leu Glu Thr Ala Trp Glu Ala Val Glu Arg Ala Arg Ile Ser Pro Ala
    130                 135                 140

Ser Leu Arg Asn Thr Asp Thr Gly Val Phe Val Gly Gly Ala Asp Thr
145                 150                 155                 160

Asn Tyr Gly Ser Leu Ala Arg Thr Ala Glu Glu Thr Glu Gly His Asn
                165                 170                 175

Leu Thr Gly Gly Ala Met Ser Val Leu Ser Gly Arg Ile Ser Tyr Thr
            180                 185                 190

Leu Gly Leu Glu Gly Pro Ala Val Thr Val Asp Thr Ala Cys Ser Ser
        195                 200                 205

Ser Leu Val Ala Leu His Leu Ala Val Arg Ala Leu Arg Ala Gly Glu
    210                 215                 220

Cys Ser Leu Ala Leu Ala Gly Gly Val Ala Met Met Pro Thr Thr Glu
225                 230                 235                 240

Leu Phe Thr Glu Phe Ser Arg Gln Arg Gly Leu Ala Thr Asp Gly Arg
                245                 250                 255

Cys Lys Pro Phe Ala Glu Ala Ala Asp Gly Thr Ser Trp Gly Glu Gly
            260                 265                 270

Val Gly Val Leu Leu Val Glu Arg Leu Ser Asp Ala Arg Arg Asn Gly
        275                 280                 285

His Pro Val Leu Ala Val Val Arg Gly Thr Ala Val Asn Gln Asp Gly
    290                 295                 300
```

```
Ala Ser Ser Arg Leu Thr Ala Pro Asn Gly Pro Ser Gln Arg Arg Val
305                 310                 315                 320

Ile Glu Ala Ala Leu Ala Asp Ala Arg Leu Ala Ala Asp Gln Val Asp
                325                 330                 335

Ala Val Glu Ala His Gly Thr Gly Thr Thr Leu Gly Asp Pro Ile Glu
            340                 345                 350

Ala Gln Ala Leu Leu Ala Thr Tyr Gly Gln Asn Arg Pro Glu Asp Arg
        355                 360                 365

Pro Leu Arg Leu Gly Gly Ile Lys Ser Asn Ile Gly His Ala Gln Ala
    370                 375                 380

Ala Ala Gly Val Ala Gly Val Ile Lys Met Val Met Ala Ile Arg His
385                 390                 395                 400

Gly Leu Leu Pro Ala Thr Leu His Val Asp Thr Pro Thr Pro His Val
                405                 410                 415

Asp Trp Thr Ala Gly Ala Val Glu Leu Leu Thr Glu Ala Val Asp Trp
            420                 425                 430

Pro Asp Ala Asp Arg Pro Arg Arg Ala Gly Val Ser Ala Phe Gly Ile
        435                 440                 445

Ser Gly Thr Asn Ala His Val Leu Leu Glu Gln Ala Thr Pro Glu Pro
    450                 455                 460

Ala Gly Ala Glu Asp Thr Pro Gln Asp Ala Thr Pro Ala Glu Pro Val
465                 470                 475                 480

Thr Ala Thr Asp Pro Ala Val Thr Pro Trp Leu Leu Ser Ala Arg Ser
                485                 490                 495

Gln Thr Ala Leu Arg Ala Gln Ala Ala Arg Leu Leu Ala His Leu Thr
            500                 505                 510

Asp His Thr Gly Pro Glu Ser Pro Arg Pro Ala Asp Ile Ala Leu Ser
        515                 520                 525

Leu Ala Thr Ser Arg Ala Pro Leu Pro His Arg Ala Val Val Leu Ala
    530                 535                 540

Thr Asp Pro Gly Thr Thr Glu Ala Ala Leu Thr Ser Leu Ala Ala Asp
545                 550                 555                 560

Glu Pro His Pro Ala Val Leu Glu Asp Ala Val Arg Ser Ala Ser Thr
                565                 570                 575

Ala Phe Leu Phe Ser Gly Gln Gly Ser Gln Arg Leu Gly Met Gly Arg
            580                 585                 590

Gly Leu Tyr Glu Arg Phe Pro Val Phe Ala Glu Ala Phe Asp Ala Val
        595                 600                 605

Cys Ala Gly Leu Asp Glu His Leu Glu Arg Pro Leu Arg Glu Val Val
    610                 615                 620

Trp Gly Asp Asp Thr Ser Val Leu Asp Gly Thr Ala Tyr Ala Gln Ala
625                 630                 635                 640

Gly Leu Phe Ala Val Glu Val Ala Leu Phe Arg Leu Val Glu Ser Trp
                645                 650                 655

Gly Val Arg Pro Glu Phe Val Ala Gly His Ser Ile Gly Glu Val Ala
            660                 665                 670

Ala Ala His Val Ala Gly Val Phe Ser Leu Ala Asp Ala Cys Val Leu
        675                 680                 685

Val Ala Ala Arg Gly Arg Leu Met Gln Ala Leu Pro Glu Gly Gly Ala
    690                 695                 700

Met Val Ala Val Glu Ala Ser Glu Ala Glu Val Leu Pro Arg Leu Glu
705                 710                 715                 720
```

-continued

```
Ser Val Glu Gly Val Ser Val Ala Ala Val Asn Gly Pro Ser Ser Val
                725                 730                 735

Val Val Ser Gly Ala Glu Asp Ala Val Glu Ala Val Ala Glu Val Phe
            740                 745                 750

Arg Glu Gln Gly Arg Arg Val Ser Arg Leu Arg Val Ser His Ala Phe
        755                 760                 765

His Ser Pro Leu Met Glu Pro Met Leu Gly Asp Phe Arg Glu Ala Leu
    770                 775                 780

Ala Gly Leu Ser Tyr Ala Glu Pro Ser Leu Pro Val Val Ser Asn Val
785                 790                 795                 800

Ser Gly Arg Ile Ala Glu Pro Gly Glu Leu Thr Thr Pro Asp Tyr Trp
                805                 810                 815

Val Arg His Val Arg Glu Ala Val Arg Phe Asp Asp Gly Val Gln Ala
            820                 825                 830

Leu Ala Ala Glu Gly Val Ala Arg Phe Val Glu Leu Gly Pro Asp Gly
        835                 840                 845

Val Leu Ser Gly Met Ala Arg Val Ser Ala Gly Glu Asp Ala Val Leu
    850                 855                 860

Val Pro Leu Leu Arg Lys Asp Arg Asp Glu Glu Val Thr Ala Leu Ala
865                 870                 875                 880

Ala Leu Gly Arg Leu His Ala Thr Gly Ala Pro Val Asp Trp Thr Ala
                885                 890                 895

Val Leu Ala Gly Thr Gly Ala Arg Leu Val Asp Leu Pro Thr Tyr Ala
            900                 905                 910

Phe Gln His Glu His Tyr Trp Pro Val Pro Ala Pro Ala Pro Ala Gly
        915                 920                 925

Asp Val Glu Ser Ala Gly Leu Arg Ala Ala Gly His Pro Leu Leu Ser
    930                 935                 940

Ala Ala Val Glu Leu Ser Asp Ser Gly Gly Leu Leu Leu Thr Thr Arg
945                 950                 955                 960

Leu Ser Leu Arg Thr His Pro Trp Leu Gly Glu His Val Val Met Gly
                965                 970                 975

Asn Ala Leu Leu Pro Gly Thr Ala Phe Val Glu Leu Ala Val Arg Ala
            980                 985                 990

Gly Asp Glu Val Gly Cys Asp Arg  Val Glu Glu Leu Thr  Leu Ala Ala
        995                 1000                1005

Pro Leu  Val Leu Pro Glu Gln  Gly Gly Val Gln Leu  His Leu His
    1010                1015                1020

Val Gly  Pro Ala Asp Ala Ala  Gly Arg Arg Val Leu  Ala Ala Arg
    1025                1030                1035

Ser Arg  Ala Glu Gly Ala Asp  Asp Gln Pro Trp Thr  Glu His Ala
    1040                1045                1050

Thr Gly  Val Leu Ala Pro Gly  Glu Arg Thr Val Glu  Phe Asp Thr
    1055                1060                1065

Ser Val  Trp Pro Pro Ala Asp  Ala Glu Ser Leu Asp  Leu Thr Gly
    1070                1075                1080

Leu Tyr  Glu Arg Met Ala Glu  Gly Gly Tyr Arg Tyr  Gly Pro Leu
    1085                1090                1095

Phe Gln  Gly Leu Arg Ala Ala  Trp Arg Arg Gly Asp  Asp Val Phe
    1100                1105                1110

Ala Glu  Val Ala Leu Pro Asp  Ser Ala Glu Arg Asp  Ala Thr Ala
    1115                1120                1125

Tyr Gly  Leu His Pro Ala Leu  Leu Asp Ala Ser Leu  His Val Ser
```

-continued

```
    1130                1135                1140

Ala Leu  Gly Gly Leu Ala His  Gly Val Val Pro Phe  Ser Trp Glu
    1145                1150                1155

Gly Val  Cys Leu His Ala Thr  Gly Ala Arg Glu Val  Arg Val Arg
    1160                1165                1170

Met Thr  Arg Thr Gly Asp Glu  Thr Val Thr Val Ala  Val Ala Asp
    1175                1180                1185

Pro Thr  Gly Ala Pro Val Ala  Ser Val Glu Asn Leu  Val Leu Arg
    1190                1195                1200

Arg Val  Ala Pro Asp Ala Thr  Gly Val Asp Ala Leu  Thr Arg Asp
    1205                1210                1215

Ala Leu  Phe Arg Val Asp Trp  Val Arg Thr Glu Ala  Pro Gly Asp
    1220                1225                1230

Ala Ala  Gly Thr Gly Pro Val  Gly Val Leu Gly Asp  Ser Asp Ala
    1235                1240                1245

Ser Thr  Ala Leu Ala Gly Val  Leu Arg Ala Asp Gly  Leu Ser Asp
    1250                1255                1260

Gly Gly  Phe Val Ala Phe Pro  Asp Leu Glu Asp Leu  Ala Ala Ala
    1265                1270                1275

Glu Glu  Val Pro Ala Thr Val  Leu Val Arg Val Arg  Pro Asp Ala
    1280                1285                1290

Ala Thr  Arg Pro Asp Ala Val  Val Asp Ala Val His  Ala Leu Ala
    1295                1300                1305

Ala Arg  Gly Leu Glu Leu Val  Arg Glu Trp Leu Ala  Gln Glu Arg
    1310                1315                1320

Phe Thr  Asp Ser Arg Leu Val  Phe Val Thr Ser Asp  Ala Val Asp
    1325                1330                1335

Gly Gly  Asp Leu Ala Asp Ala  Ala Leu Arg Gly Leu  Val Arg Ser
    1340                1345                1350

Ala Val  Ser Glu His Pro Gly  Arg Phe Gly Leu Met  Glu Val Gly
    1355                1360                1365

Arg Gly  Thr Asp Thr Ala Thr  Val Leu Ala Ala Val  Ala Thr Gly
    1370                1375                1380

Glu Pro  Glu Thr Ala Ala Arg  Asp Gly Glu Val Leu  Ala Pro Arg
    1385                1390                1395

Leu Ala  Arg Ile Thr Ser Gly  Thr Thr Thr Gly Pro  Arg Trp Asp
    1400                1405                1410

Ser Ile  Asp Gly Thr Val Leu  Leu Thr Gly Gly Thr  Gly Gly Leu
    1415                1420                1425

Gly Arg  Ile Val Ala Arg His  Leu Val Val Glu Arg  Gly Val Arg
    1430                1435                1440

Asp Leu  Leu Leu Val Ser Arg  Ser Gly Ala Ala Ala  Asp Gly Ala
    1445                1450                1455

Gly Gln  Leu Val Ala Glu Leu  Ser Glu Thr Gly Ala  His Val Thr
    1460                1465                1470

Val Glu  Ala Cys Asp Val Ser  Asp Pro Ala Ala Val  Ala Glu Leu
    1475                1480                1485

Val Ala  Arg His Pro Val Arg  Ala Val Val His Ser  Ala Gly Val
    1490                1495                1500

Leu Asp  Asp Gly Thr Val Glu  Ser Leu Thr Ala Glu  Arg Val Thr
    1505                1510                1515

Arg Val  Leu Arg Pro Lys Ala  Asp Ala Ala Trp Asn  Leu His Glu
    1520                1525                1530
```

-continued

```
Ala Thr  Arg Ala Leu Asp Leu  Glu Ala Phe Val Val  Phe Ser Ser
    1535                 1540                 1545

Met Ser  Gly Ile Leu Gly Gly  Pro Gly Gln Ala Asn  Tyr Ala Ala
    1550                 1555                 1560

Gly Asn  Thr Phe Leu Asp Ala  Leu Val Arg His Arg  Arg Ser Leu
    1565                 1570                 1575

Gly Leu  Pro Ala Thr Ser Leu  Ala Trp Gly Pro Trp  Thr Gln Asp
    1580                 1585                 1590

Ala Gly  Met Ile Gly Thr Leu  Ser Gly Thr Ser Arg  His Arg Val
    1595                 1600                 1605

Ala Arg  Ala Gly Met Pro Glu  Leu Thr Ala Glu Gln  Gly Thr Ala
    1610                 1615                 1620

Leu Phe  Asp Ala Ala Leu Ala  Ser Gly Glu Pro Val  Val Leu Pro
    1625                 1630                 1635

Val Arg  Leu Asp Leu Ala Ala  Leu Arg Gly Gln Gly  Asp Leu His
    1640                 1645                 1650

Pro Met  Met Leu Gly Leu Val  Arg Arg Arg Gly Arg  Arg Ala Ala
    1655                 1660                 1665

Ala Gly  Gly Ser Val Ala Ala  Ala Gly Leu Val Gln  Arg Leu Gly
    1670                 1675                 1680

Ala Leu  Gly Val Asp Glu Arg  Arg Glu Val Leu Leu  Asp Leu Val
    1685                 1690                 1695

Arg Gly  Gln Val Ala Val Val  Leu Gly His Ala Gly  Val Gln Ser
    1700                 1705                 1710

Val Asp  Pro Gly Arg Ala Phe  Gln Asp Leu Gly Phe  Asp Ser Leu
    1715                 1720                 1725

Thr Ala  Val Glu Leu Arg Asn  Arg Leu Gly Lys Ser  Thr Gly Leu
    1730                 1735                 1740

Arg Leu  Pro Ala Thr Val Val  Phe Asp Tyr Pro Thr  Val Asn Ala
    1745                 1750                 1755

Leu Val  Gly Tyr Leu Leu Glu  Glu Leu Phe Gly Gly  Val Glu Pro
    1760                 1765                 1770

Ala Ser  Val Val Pro Val Ser  Ala Leu Pro Ser Val  Ala Glu Asp
    1775                 1780                 1785

Pro Ile  Val Ile Val Gly Met  Ala Cys Arg Tyr Pro  Gly Gly Val
    1790                 1795                 1800

Ser Ser  Pro Glu Asp Leu Trp  Thr Val Val Ser Glu  Gly Val Asp
    1805                 1810                 1815

Thr Val  Ser Glu Phe Pro Val  Asn Arg Gly Trp Asp  Val Asp Ala
    1820                 1825                 1830

Leu Tyr  Asn Pro Asp Arg Asp  Ala Ser Gly Thr Thr  Tyr Thr Lys
    1835                 1840                 1845

Ala Gly  Gly Phe Leu His Asp  Ala Gly Ala Phe Asp  Ser Glu Phe
    1850                 1855                 1860

Phe Gly  Met Ser Pro Arg Glu  Ala Val Ala Thr Asp  Ser Gln Gln
    1865                 1870                 1875

Arg Leu  Leu Leu Glu Thr Thr  Trp Glu Ala Ile Glu  Arg Ser Gly
    1880                 1885                 1890

Ile Asp  Pro Ala Ser Leu Arg  Gly Ser Gln Thr Gly  Val Phe Ala
    1895                 1900                 1905

Gly Val  Met Tyr Asn Asp Tyr  Gly Asn Met Leu Ala  Asp Glu Arg
    1910                 1915                 1920
```

-continued

```
Tyr Glu  Gly Phe Arg Ser Asn  Gly Ser Ala Pro Ser  Ile Ala Ser
    1925                 1930                 1935

Gly Arg  Val Ser Tyr Thr Phe  Gly Phe Glu Gly Pro  Ala Val Thr
    1940                 1945                 1950

Val Asp  Thr Ala Cys Ser Ser  Ser Leu Val Ala Leu  His Trp Ala
    1955                 1960                 1965

Ala Gln  Ala Leu Arg Ser Gly  Glu Cys Ser Leu Ala  Val Ala Gly
    1970                 1975                 1980

Gly Val  Thr Val Met Ser Thr  Pro Thr Thr Phe Val  Glu Phe Ser
    1985                 1990                 1995

Arg Gln  Gly Gly Leu Ser Ala  Asp Gly Arg Cys Arg  Ser Phe Ala
    2000                 2005                 2010

Asp Ser  Ala Asp Gly Val Gly  Trp Ser Glu Gly Val  Gly Met Val
    2015                 2020                 2025

Val Leu  Glu Arg Leu Ser Asp  Ala Arg Arg Asn Gly  His Arg Val
    2030                 2035                 2040

Leu Ala  Val Val Arg Gly Ser  Ala Val Asn Gln Asp  Gly Ala Ser
    2045                 2050                 2055

Asn Gly  Leu Thr Ala Pro Asn  Gly Pro Ser Gln Gln  Arg Val Ile
    2060                 2065                 2070

Arg Gln  Ala Leu Ala Ser Gly  Gly Leu Ser Ala Gly  Asp Val Asp
    2075                 2080                 2085

Val Val  Glu Ala His Gly Thr  Gly Thr Thr Leu Gly  Asp Pro Ile
    2090                 2095                 2100

Glu Ala  Gln Ala Leu Leu Ala  Thr Tyr Gly Gln Glu  Arg Glu Glu
    2105                 2110                 2115

Gly Arg  Pro Leu Trp Leu Gly  Ser Val Lys Ser Asn  Leu Gly His
    2120                 2125                 2130

Thr Gln  Ala Ala Ala Gly Val  Ala Gly Val Ile Lys  Met Val Met
    2135                 2140                 2145

Ala Met  Arg His Gly Arg Leu  Pro Arg Thr Leu His  Val Asp Ala
    2150                 2155                 2160

Pro Ser  Ser His Val Asp Trp  Ser Ala Gly Ala Val  Glu Leu Leu
    2165                 2170                 2175

Thr Gly  Glu Arg Val Trp Pro  Gly Glu Glu Arg Leu  Arg Arg Ala
    2180                 2185                 2190

Gly Val  Ser Ser Phe Gly Ile  Ser Gly Thr Asn Ala  His Val Ile
    2195                 2200                 2205

Leu Glu  Gln Pro Glu Pro Val  Ala Glu Pro Glu Thr  Gly Gly Asp
    2210                 2215                 2220

Gly Ile  Ala Ala Leu Ala Pro  Gly Ile Val Pro Trp  Val Leu Ser
    2225                 2230                 2235

Gly Arg  Thr Glu Glu Ala Leu  Arg Ala Gln Ala Ala  Arg Leu Leu
    2240                 2245                 2250

Ala Gln  Val Glu Gly His Pro  Gly Leu Arg Pro Val  Asp Leu Ala
    2255                 2260                 2265

Leu Ser  Leu Ala Thr Gln Arg  Ser Leu Phe Asp His  Arg Ala Val
    2270                 2275                 2280

Val Leu  Thr Asp Asp Arg Glu  Thr Ala Val Arg Gly  Leu Ala Ala
    2285                 2290                 2295

Val Cys  Val Gly Glu Pro Asp  Pro Ala Val Val Leu  Gly Ala Val
    2300                 2305                 2310

Glu Pro  Gly Arg Thr Ala Phe  Leu Phe Ser Gly Gln  Gly Ser Gln
```

-continued

```
    2315                2320                2325

Arg Leu Gly Met Gly Arg Gly Leu Tyr Glu Arg Phe Pro Val Phe
    2330                2335                2340

Ala Glu Ala Phe Asp Ala Val Cys Ala Gly Leu Asp Ala His Leu
    2345                2350                2355

Asp Arg Pro Leu Arg Glu Val Val Trp Gly Asp Asp Thr Ser Val
    2360                2365                2370

Leu Asp Gly Thr Ala Tyr Ala Gln Ala Gly Leu Phe Ala Val Glu
    2375                2380                2385

Val Ala Leu Phe Arg Leu Val Glu Ser Trp Gly Val Arg Pro Glu
    2390                2395                2400

Phe Val Ala Gly His Ser Ile Gly Glu Val Ala Ala Ala His Val
    2405                2410                2415

Ala Gly Val Phe Ser Leu Ala Asp Ala Cys Val Leu Val Ala Ala
    2420                2425                2430

Arg Gly Arg Leu Met Gln Ala Leu Pro Glu Gly Gly Ala Met Val
    2435                2440                2445

Ala Val Glu Ala Ser Glu Ala Glu Val Leu Pro Arg Leu Glu Ser
    2450                2455                2460

Val Glu Gly Val Ser Val Ala Ala Val Asn Gly Pro Ser Ser Val
    2465                2470                2475

Val Val Ser Gly Ala Glu Glu Ala Val Glu Ala Val Ala Glu Val
    2480                2485                2490

Phe Arg Glu Leu Gly Arg Arg Val Ser Arg Leu Arg Val Ser His
    2495                2500                2505

Ala Phe His Ser Pro Leu Met Glu Pro Met Leu Asp Ala Phe His
    2510                2515                2520

Glu Val Leu Arg Asp Leu Ser Phe Ala Glu Pro Arg Leu Pro Val
    2525                2530                2535

Val Ser Asn Val Ser Gly Arg Ile Ala Glu Pro Gly Glu Leu Thr
    2540                2545                2550

Ala Pro Asp Tyr Trp Val Arg His Val Arg Glu Ala Val Arg Phe
    2555                2560                2565

Asp Asp Gly Val Arg Ala Leu Ala Glu Glu Gly Val Thr Arg Phe
    2570                2575                2580

Val Glu Leu Gly Pro Asp Gly Val Leu Ser Gly Met Ala Arg Ala
    2585                2590                2595

Ser Ala Gly Glu Asp Ala Val Leu Val Pro Leu Leu Arg Lys Asp
    2600                2605                2610

Arg Glu Glu Val Ala Val Ala Leu Ser Ala Leu Ala Glu Leu His
    2615                2620                2625

Val Arg Gly Val Ser Ala Gly Trp Gly Ala Val Leu Asp Gly Thr
    2630                2635                2640

Gly Gly Arg Ala Val Asp Leu Pro Thr Tyr Ala Phe Gln His Glu
    2645                2650                2655

His Tyr Trp Pro Thr Gly Thr Thr Thr Gly Thr Gly Asp Ile Arg
    2660                2665                2670

Leu Ala Gly Leu Gly Ala Ala Gly His Pro Leu Leu Gly Ala Ala
    2675                2680                2685

Val Glu Leu Ala Gly Ala Asp Gly Leu Ile Leu Thr Gly Arg Leu
    2690                2695                2700

Ser Thr Arg Ser His Pro Trp Leu Ala Asp His Val Val Gln Gly
    2705                2710                2715
```

-continued

```
Ala Val  Leu Val Pro Gly Thr  Ala Leu Leu Glu Met  Ala Val Arg
    2720                 2725                 2730

Ala Ala  Asp Glu Ala Gly Cys  Gly Ser Val Glu Glu  Leu Thr Leu
    2735                 2740                 2745

Ser Ala  Pro Leu Val Leu Pro  Glu Arg Gly Ala Val  Arg Val Gln
    2750                 2755                 2760

Val Gly  Val Gly Glu Pro Asp  Glu Ser Gly Arg Arg  Thr Val Ala
    2765                 2770                 2775

Ile His  Ser Arg Asp Asp Gly  Asp Glu Arg Gln Pro  Trp Ser Leu
    2780                 2785                 2790

His Ala  Gln Gly Val Leu Ala  Pro Glu Thr Ile Asp  Ala Asp Pro
    2795                 2800                 2805

Ala Ala  Glu Gly Phe Asp Ala  Ser Val Trp Pro Pro  Arg Asp Ala
    2810                 2815                 2820

Val Pro  Val Asp Val Thr Asp  Cys Tyr Glu Ser Leu  Ala Glu Ala
    2825                 2830                 2835

Gly Leu  Arg Tyr Gly Pro Val  Phe Gln Gly Leu Arg  Ala Ala Trp
    2840                 2845                 2850

Arg Arg  Asp Asp Glu Val Phe  Ala Glu Val Ala Leu  Pro Asp Gly
    2855                 2860                 2865

Val Asp  Ala Thr Ala Phe Gly  Leu His Pro Ala Leu  Phe Asp Ala
    2870                 2875                 2880

Ala Leu  His Ala Ser Phe Ala  Phe Gly Gly Asp Asp  Ala Pro Gly
    2885                 2890                 2895

Gly Val  Pro Phe Val Trp Glu  Asn Ala Thr Leu His  Ala Ser Gly
    2900                 2905                 2910

Ala Ser  Val Leu Arg Thr Arg  Leu Thr Arg Thr Gly  Asp Asp Thr
    2915                 2920                 2925

Leu Ala  Val His Val Ala Asp  Pro Thr Gly Ala Pro  Val Ala Ser
    2930                 2935                 2940

Val Gly  Ser Leu Thr Val Arg  Ala Ala Ala Gly Ala  Arg Ala Ala
    2945                 2950                 2955

Asp Thr  Ala Glu Pro Leu Tyr  Arg Val Glu Trp Val  Pro Ala Arg
    2960                 2965                 2970

Gly Thr  Arg Ala Thr Pro Ala  Ala Gly Ser Val Val  Leu Leu Gly
    2975                 2980                 2985

Glu Gly  Leu Ala Asp Leu Ala  Gly Asp Gly Ala Ala  Val Arg Ala
    2990                 2995                 3000

Asp Leu  Gln Glu Leu Ala Ala  Ala Glu Ala Val Pro  Glu Thr Val
    3005                 3010                 3015

Val Val  Ala Val Pro Pro Ala  Pro Asp Thr Glu Gly  Val Val Gly
    3020                 3025                 3030

Ser Ala  His Ala Ser Ala Ala  Trp Ala Leu Ala Leu  Val Lys Glu
    3035                 3040                 3045

Trp Leu  Ala Gln Glu Arg Phe  Ala Gly Ser Arg Leu  Val Phe Ile
    3050                 3055                 3060

Thr Arg  Gly Gly His Val Thr  Glu Pro Ala Ser Ala  Leu Thr Ser
    3065                 3070                 3075

Ala Pro  Val Arg Gly Leu Val  Arg Ser Val Ala Leu  Glu His Pro
    3080                 3085                 3090

Gly Arg  Phe Gly Leu Leu His  Leu Pro Ala Gly Thr  Asp Ala Gly
    3095                 3100                 3105
```

-continued

```
Arg Leu  Phe Ala Ala Leu Ala  Val Asp Glu Pro Glu  Thr Ala Val
    3110                 3115                 3120

Leu Asp  Ser Glu Val Cys Val  Pro Arg Leu Val Arg  Thr Thr Pro
    3125                 3130                 3135

Asp Ala  Gly Gly Glu Glu Thr  Ala Gly Ser Ser Ala  Gly Leu Gly
    3140                 3145                 3150

Ser Gly  Thr Val Leu Leu Thr  Gly Gly Thr Gly Gly  Leu Gly Arg
    3155                 3160                 3165

Ile Val  Ala Arg His Leu Val  Val Glu Arg Gly Val  Arg Asp Leu
    3170                 3175                 3180

Leu Leu  Val Ser Arg Ser Gly  Ala Ala Ala Glu Gly  Val Asp Ala
    3185                 3190                 3195

Phe Thr  Ala Glu Leu Thr Gly  Leu Gly Ala Arg Val  Ser Val Ala
    3200                 3205                 3210

Ala Cys  Asp Leu Ala Asp Arg  Thr Ala Leu Asp Ala  Leu Leu Ala
    3215                 3220                 3225

Gly Val  Pro Ala Asp Arg Pro  Val Arg Ala Val Val  His Ala Ala
    3230                 3235                 3240

Gly Val  Leu Asp Asp Gly Met  Ala Glu Ser Leu Thr  Ala Glu Arg
    3245                 3250                 3255

Val Ala  Ala Val Leu Arg Pro  Lys Val Asp Ala Ala  Trp Asn Leu
    3260                 3265                 3270

His Glu  Ala Thr Arg Gly Leu  Asp Leu Glu Ala Phe  Val Val Phe
    3275                 3280                 3285

Ser Ser  Val Ala Gly Thr Phe  Gly Ser Ala Gly Gln  Gly Ala Tyr
    3290                 3295                 3300

Ala Ala  Gly Asn Val Phe Leu  Asp Ala Leu Val Glu  Tyr Arg Arg
    3305                 3310                 3315

Ser Leu  Gly Leu Pro Gly Val  Ser Leu Val Trp Gly  Pro Trp Ala
    3320                 3325                 3330

Gln Asp  Ala Gly Met Thr Arg  Gly Leu Ser Glu Thr  Asp Arg Arg
    3335                 3340                 3345

Arg Ile  Ala Arg Ser Gly Leu  Pro Pro Val Glu Ala  Glu Gln Gly
    3350                 3355                 3360

Thr Ala  Leu Phe Asp Ala Ala  Leu Ala Ser Gly Glu  Pro Val Val
    3365                 3370                 3375

Leu Pro  Val Arg Leu Asp Leu  Ala Ala Leu Arg Gly  Glu Glu Asp
    3380                 3385                 3390

Val Pro  Ala Leu Phe Arg Gly  Leu Val Arg Arg Arg  Gly Arg Arg
    3395                 3400                 3405

Ala Ala  Ala Gly Gly Ser Val  Ala Ala Ala Gly Leu  Val Gln Arg
    3410                 3415                 3420

Leu Gly  Ala Leu Gly Val Asp  Glu Arg Arg Glu Val  Leu Leu Asp
    3425                 3430                 3435

Leu Val  Arg Gly Gln Val Ala  Val Val Leu Gly His  Ala Gly Val
    3440                 3445                 3450

Gln Ser  Val Asp Pro Gly Arg  Ala Phe Gln Asp Leu  Gly Phe Asp
    3455                 3460                 3465

Ser Leu  Thr Ala Val Glu Leu  Arg Asn Arg Leu Gly  Lys Ser Thr
    3470                 3475                 3480

Gly Leu  Arg Leu Pro Ala Thr  Val Val Phe Asp Tyr  Pro Thr Val
    3485                 3490                 3495

Asn Ala  Leu Val Gly Tyr Leu  Leu Glu Glu Leu Phe  Gly Gly Val
```

-continued

```
    3500                3505                3510

Glu Pro  Ala Ala Val Val Pro  Val Ser Ala Leu Pro  Ser Val Ala
    3515                3520                3525

Glu Asp  Pro Ile Val Ile Val  Gly Met Ala Cys Arg  Tyr Pro Gly
    3530                3535                3540

Gly Val  Ser Ser Pro Glu Asp  Leu Trp Arg Val Val  Ser Glu Gly
    3545                3550                3555

Val Asp  Thr Val Ser Asp Phe  Pro Ser Asp Arg Gly  Trp Asp Val
    3560                3565                3570

Asp Ala  Leu Tyr Asn Pro Asp  Arg Ala Val Pro Gly  Thr Ser Tyr
    3575                3580                3585

Thr Arg  Ser Gly Gly Phe Leu  His Asp Ala Pro Glu  Phe Asp Pro
    3590                3595                3600

Glu Phe  Phe Gly Met Ser Pro  Arg Glu Ala Val Ser  Thr Asp Ala
    3605                3610                3615

Gln Gln  Arg Leu Leu Leu Glu  Thr Thr Trp Glu Ala  Ile Glu Arg
    3620                3625                3630

Ser Gly  Ile Asp Pro Val Ser  Leu Arg Gly Ser Gln  Thr Gly Val
    3635                3640                3645

Phe Ala  Gly Val Met Tyr His  Asp Tyr Ala Asn Leu  Leu Ala Ser
    3650                3655                3660

Pro Glu  Tyr Glu Gly Tyr Gln  Gly Ser Gly Ser Ala  Gly Ser Val
    3665                3670                3675

Ala Ser  Gly Arg Val Ser Tyr  Thr Phe Gly Phe Glu  Gly Pro Ala
    3680                3685                3690

Val Thr  Val Asp Thr Ala Cys  Ser Ser Ser Leu Val  Ala Leu His
    3695                3700                3705

Trp Ala  Ala Gln Ala Leu Arg  Ser Gly Glu Cys Ser  Leu Ala Val
    3710                3715                3720

Ala Gly  Gly Val Thr Val Met  Ser Thr Pro Ser Thr  Phe Val Glu
    3725                3730                3735

Phe Ser  Arg Gln Gly Gly Leu  Ser Ala Asp Gly Arg  Cys Arg Ser
    3740                3745                3750

Phe Ala  Asp Ser Ala Asp Gly  Val Gly Trp Ser Glu  Gly Val Gly
    3755                3760                3765

Met Val  Val Leu Glu Arg Leu  Ser Asp Ala Arg Arg  Asn Gly His
    3770                3775                3780

Arg Val  Leu Ala Val Val Arg  Gly Ser Ala Val Asn  Gln Asp Gly
    3785                3790                3795

Ala Ser  Asn Gly Leu Thr Ala  Pro Asn Gly Pro Ser  Gln Gln Arg
    3800                3805                3810

Val Ile  Arg Gln Ala Leu Ala  Ser Gly Gly Leu Ser  Ala Gly Asp
    3815                3820                3825

Val Asp  Val Val Glu Ala His  Gly Thr Gly Thr Thr  Leu Gly Asp
    3830                3835                3840

Pro Ile  Glu Ala Gln Ala Leu  Leu Ala Thr Tyr Gly  Gln Gly Arg
    3845                3850                3855

Asp Glu  Glu Arg Pro Leu Leu  Leu Gly Ser Val Lys  Ser Asn Ile
    3860                3865                3870

Gly His  Thr Gln Ala Ala Ala  Gly Val Ala Gly Val  Ile Lys Met
    3875                3880                3885

Val Met  Ala Met Arg His Gly  Arg Leu Pro Arg Thr  Leu His Val
    3890                3895                3900
```

-continued

```
Asp Ala  Pro Ser Ser His Val  Asp Trp Ser Ala Gly  Ala Val Glu
    3905                 3910                 3915

Leu Leu  Thr Gly Glu Arg Val  Trp Pro Gly Glu Glu  Arg Ala Arg
    3920                 3925                 3930

Arg Ala  Gly Val Ser Ser Phe  Gly Ile Ser Gly Thr  Asn Ala His
    3935                 3940                 3945

Val Ile  Leu Glu Gln Pro Glu  Pro Val Thr Gly Ser  Gly Pro Gly
    3950                 3955                 3960

Glu Ala  Asp Gly Thr Glu Ala  Ser Ser Gly Val Gln  Pro Trp Val
    3965                 3970                 3975

Leu Ser  Ala Arg Thr Glu Glu  Ala Leu Arg Ala Gln  Ala Ala Arg
    3980                 3985                 3990

Leu Ala  Asp Phe Leu Thr Asp  Ala Pro Ala Asp Val  Arg Asp Val
    3995                 4000                 4005

Ala Leu  Ser Leu Ala Thr Gln  Arg Thr Leu Phe Asp  His Arg Ala
    4010                 4015                 4020

Val Val  Leu Gly Ala Asp Leu  Glu Thr Ala Leu Thr  Ser Leu Arg
    4025                 4030                 4035

Ala Leu  Ala Ala Gly Ala Pro  Asp Ala Ala Val Ala  Glu Gly Val
    4040                 4045                 4050

Ala Gly  Asn Gly Arg Thr Ala  Phe Leu Phe Pro Gly  Gln Gly Ser
    4055                 4060                 4065

Gln Arg  Leu Gly Met Gly Arg  Asp Leu Tyr Glu Arg  Phe Pro Val
    4070                 4075                 4080

Leu Ala  Glu Ala Phe Asp Ala  Val Cys Ala Glu Leu  Asp Glu His
    4085                 4090                 4095

Leu Asp  Arg Pro Leu Arg Glu  Val Val Trp Gly Asp  Asp Ala Glu
    4100                 4105                 4110

Leu Leu  Asn Arg Thr Ala Tyr  Ala Gln Pro Gly Leu  Phe Ala Val
    4115                 4120                 4125

Glu Val  Ala Leu Phe Arg Leu  Val Glu Ser Trp Gly  Val Arg Pro
    4130                 4135                 4140

Glu Phe  Val Ala Gly His Ser  Ile Gly Glu Val Ala  Ala Ala His
    4145                 4150                 4155

Val Ala  Gly Val Phe Thr Leu  Ala Asp Ala Ala Ala  Leu Val Ala
    4160                 4165                 4170

Ala Arg  Gly Arg Leu Met Gln  Ala Leu Pro Glu Gly  Gly Ala Met
    4175                 4180                 4185

Ala Ala  Val Glu Ala Thr Cys  Ala Glu Val Leu Pro  His Leu Thr
    4190                 4195                 4200

Gly Asn  Leu Ser Ile Ala Ala  Val Asn Gly Pro Ser  Ser Val Val
    4205                 4210                 4215

Val Ser  Gly Ser Glu Ala Ser  Val Glu Ser Val Ala  Glu Val Phe
    4220                 4225                 4230

Arg Glu  Leu Gly Arg Arg Val  Ser Arg Leu Arg Val  Ser His Ala
    4235                 4240                 4245

Phe His  Ser Pro Leu Met Glu  Pro Met Leu His Ala  Phe Arg Glu
    4250                 4255                 4260

Val Val  Glu Gly Leu Ser Phe  Ala Ala Pro Arg Ile  Pro Leu Val
    4265                 4270                 4275

Ser Asn  Ile Thr Gly Thr Leu  Ala Glu Pro Gly Gln  Val Asp Glu
    4280                 4285                 4290
```

-continued

```
Pro Glu  Tyr Trp Val Thr His  Val Arg Glu Ala Val  Arg Phe Asp
    4295                 4300                 4305

Asp Gly  Val Arg Ala Leu Ala  Glu Glu Gly Val Thr  Arg Phe Val
    4310                 4315                 4320

Glu Val  Gly Pro Asp Gly Val  Leu Ser Gly Met Ala  Arg Glu Ser
    4325                 4330                 4335

Ala Gly  Glu Asp Ala Val Leu  Val Pro Leu Leu Arg  Lys Asp Arg
    4340                 4345                 4350

Glu Glu  Thr Gly Ser Ala Leu  Ser Ala Leu Gly Arg  Leu His Thr
    4355                 4360                 4365

Val Gly  Val Asp Val Asp Trp  Ser Gly Phe Leu Val  Gly Ala Arg
    4370                 4375                 4380

Pro Val  Asp Leu Pro Thr Tyr  Ala Phe Gln Lys Gln  Arg Tyr Trp
    4385                 4390                 4395

Pro Glu  Ala Thr Leu Pro Arg  Ala Gly Asp Val Arg  Phe Ala Gly
    4400                 4405                 4410

Leu Gly  Ser Ala Gly His Pro  Leu Leu Gly Ala Ala  Val Glu Leu
    4415                 4420                 4425

Ala Gly  Ala Asp Gly Ala Asp  Gly Val Val Leu Thr  Gly Arg Leu
    4430                 4435                 4440

Ser Thr  Arg Ser His Pro Trp  Leu Ala Asp His Val  Val Gln Gly
    4445                 4450                 4455

Thr Val  Leu Val Pro Gly Thr  Ala Leu Leu Glu Met  Ala Val Arg
    4460                 4465                 4470

Ala Ala  Asp Glu Ala Gly Cys  Gly Ser Val Glu Glu  Leu Thr Leu
    4475                 4480                 4485

Ser Ala  Pro Leu Val Leu Pro  Glu Arg Gly Ala Leu  Gln Ile Gln
    4490                 4495                 4500

Ile Arg  Val Ala Ala Pro Asp  Glu Asp Gly Arg Arg  Ala Leu Gly
    4505                 4510                 4515

Val His  Ala Arg Thr Glu Asp  Asp Asp Gly Ala Pro  Trp Thr Val
    4520                 4525                 4530

His Ala  Thr Gly Thr Leu Ala  Pro Glu Thr Leu Ala  Pro Asp Pro
    4535                 4540                 4545

Phe Asp  Ala Thr Val Trp Pro  Pro Arg Asp Ala Ala  Gln Val Asp
    4550                 4555                 4560

Val Thr  Asp Cys Tyr Glu Arg  Leu Ala Glu Ala Gly  Phe Ala Tyr
    4565                 4570                 4575

Gly Pro  Ala Phe Arg Gly Leu  Arg Ala Ala Trp Arg  His Gly Asp
    4580                 4585                 4590

Ala Leu  Tyr Ala Glu Val Ala  Leu Asp Gly Gly Thr  Asp Gly Asp
    4595                 4600                 4605

Ala Phe  Gly Leu His Pro Ala  Leu Phe Asp Ala Ala  Leu His Ala
    4610                 4615                 4620

Phe Ala  Leu Ala Asp Asp Gly  Arg Gly Gly Val Pro  Phe Ser Trp
    4625                 4630                 4635

Gly Gly  Val Ser Leu His Ala  Ser Gly Ala Thr Ala  Leu Arg Val
    4640                 4645                 4650

Arg Leu  Thr Arg Asp Ala Asp  Gly Thr Met Ala Leu  Ala Leu Ala
    4655                 4660                 4665

Asp Pro  Ala Gly Ser Pro Val  Ala Thr Val His Ser  Leu Thr Val
    4670                 4675                 4680

Arg Pro  Leu Ala Thr Gly Gln  Leu Thr Thr Pro Ala  Arg Asp Ser
```

-continued

```
    4685                4690                4695

Leu Tyr Gln Val Glu Trp Val Pro Ala Arg Pro Leu Asp Gly Pro
    4700                4705                4710

Ala Asp Thr Gly Ala Val Ala Val Leu Gly Glu Ala Arg Ser Ala
    4715                4720                4725

Val Pro Ala Ala Asp Asp Phe Val Thr Tyr Ala Thr Leu Glu Glu
    4730                4735                4740

Leu Ala Ala Ala Glu Glu Met Pro Ser Thr Val Leu Val Ala Ala
    4745                4750                4755

Ser Asp Asp Ala Asp Gly Thr Asp Pro Ala Gln Ala Ala His Thr
    4760                4765                4770

Ala Ala Ala Arg Ala Leu Ala Leu Val Arg Ser Trp Leu Ala Glu
    4775                4780                4785

Asp Arg Phe Ala Gly Ser Arg Leu Val Phe Val Thr Ala Ser Thr
    4790                4795                4800

Asp Arg Thr Thr Gly Leu Ala Asp Ala Ala Ala Arg Gly Leu Val
    4805                4810                4815

Arg Ser Ala Ile Ser Glu His Pro Gly Arg Phe Gly Leu Leu Glu
    4820                4825                4830

Leu Pro Ala Asp Ala Asp Thr Ala Ser Leu Arg Ser Ala Leu Ala
    4835                4840                4845

Ser Gly Glu Ala Glu Ser Val Val Arg Asp Gly Glu Val Arg Val
    4850                4855                4860

Pro Arg Leu Ala Arg Val Thr Pro Glu Ala Thr Glu Gly Leu Arg
    4865                4870                4875

Trp Asp Ala Leu Thr Gly Pro Val Leu Ile Thr Gly Gly Thr Gly
    4880                4885                4890

Gly Leu Gly Arg Val Leu Ala Arg His Leu Val Met Thr His Gly
    4895                4900                4905

Val Arg Asp Leu Leu Leu Val Ser Arg Ser Gly Ala Asn Ala Glu
    4910                4915                4920

Gly Ala Gly Glu Leu Val Thr Glu Leu Thr Glu Ala Gly Ala His
    4925                4930                4935

Val Ala Val Glu Ala Cys Asp Ala Ala Asp Ala Asp Ala Val Ala
    4940                4945                4950

Gly Leu Val Thr Arg His Gly Val Arg Ala Val Val His Ala Ala
    4955                4960                4965

Gly Val Ile Asp Asp Ala Thr Leu Ala Ser Leu Thr Ala Glu Arg
    4970                4975                4980

Val Ala Ala Val Leu Arg Pro Lys Val Asp Ala Ala Trp Asn Leu
    4985                4990                4995

His Glu Ala Thr Arg Asp Leu Gly Leu Glu Ala Phe Val Val Phe
    5000                5005                5010

Ser Ser Val Ala Gly Thr Phe Gly Ser Ala Gly Gln Gly Ala Tyr
    5015                5020                5025

Ala Ala Gly Asn Val Phe Leu Asp Ala Leu Val Glu Tyr Arg Arg
    5030                5035                5040

Ala Leu Gly Leu Pro Gly Val Ser Leu Val Trp Gly Pro Trp Ala
    5045                5050                5055

Gln Asp Ala Gly Met Thr Arg Glu Leu Ser Glu Thr Asp Arg Arg
    5060                5065                5070

Arg Ile Ala Arg Ser Gly Leu Pro Pro Val Glu Ala Glu Gln Gly
    5075                5080                5085
```

```
Thr Ala  Leu Phe Asp Ala Ala  Leu Ala Ser Gly Glu  Pro Val Val
    5090                 5095                 5100

Leu Pro  Val Arg Leu Asp Leu  Pro Ala Leu Arg Ala  Gln Gly Glu
    5105                 5110                 5115

Val Pro  Pro Leu Leu Ser Gly  Leu Ile Arg Thr Ser  Val Arg Arg
    5120                 5125                 5130

Thr Ala  Ala Ala Ala Gly Ala  Ala Ala Thr Gly Leu  Ala Ala Arg
    5135                 5140                 5145

Leu Ala  Gly Leu Ala Glu Ala  Glu Arg Arg Glu Val  Leu Leu Asp
    5150                 5155                 5160

Leu Val  Arg Gly Gln Ile Ala  Val Val Leu Gly His  Ser Gly Ala
    5165                 5170                 5175

Gln Thr  Val Asn Pro His Arg  Ala Phe Gln Asp Leu  Gly Phe Asp
    5180                 5185                 5190

Ser Leu  Thr Ala Val Glu Leu  Arg Asn Arg Leu Gly  Lys Val Thr
    5195                 5200                 5205

Gly Leu  Arg Leu Pro Ala Thr  Val Val Phe Asp Tyr  Pro Thr Ala
    5210                 5215                 5220

Asp Leu  Leu Ala Gly His Leu  Leu Asp Gly Val Leu  Gly Thr Glu
    5225                 5230                 5235

Pro Ala  Val Ala Val Pro Val  Ala Ala Leu Pro Ser  Val Ala Asp
    5240                 5245                 5250

Asp Pro  Val Val Ile Val Gly  Met Ala Cys Arg Tyr  Pro Gly Gly
    5255                 5260                 5265

Val Thr  Ser Pro Glu Asp Leu  Trp Ser Val Val Ser  Asp Gly Val
    5270                 5275                 5280

Asp Ala  Val Gly Asp Phe Pro  Ser Asp Arg Gly Trp  Asp Val Glu
    5285                 5290                 5295

Ser Leu  Tyr Ser Glu Asp Arg  Gly Val Pro Gly Thr  Thr Tyr Thr
    5300                 5305                 5310

Arg Ser  Gly Gly Phe Leu His  Asp Ala Pro Glu Phe  Asp Pro Glu
    5315                 5320                 5325

Phe Phe  Gly Met Ser Pro Arg  Glu Ala Val Ser Thr  Asp Ala Gln
    5330                 5335                 5340

Gln Arg  Leu Leu Leu Glu Thr  Thr Trp Glu Ala Ile  Glu Arg Ser
    5345                 5350                 5355

Gly Ile  Asp Pro Val Ser Leu  Arg Gly Ser Gln Thr  Gly Val Phe
    5360                 5365                 5370

Ala Gly  Val Met Tyr Asn Asp  Tyr Gly Ser Ile Leu  Thr Asp Asp
    5375                 5380                 5385

Gln Tyr  Glu Gly Tyr Arg Gly  Asn Gly Ser Ala Gly  Ser Ile Ala
    5390                 5395                 5400

Ser Gly  Arg Val Ser Tyr Thr  Phe Gly Phe Glu Gly  Pro Ala Val
    5405                 5410                 5415

Thr Val  Asp Thr Ala Cys Ser  Ser Ser Leu Val Ala  Met His Trp
    5420                 5425                 5430

Ala Ala  Gln Ala Leu Arg Ser  Gly Glu Cys Ser Leu  Ala Val Ala
    5435                 5440                 5445

Gly Gly  Val Thr Val Met Ala  Thr Pro Thr Ala Phe  Val Glu Phe
    5450                 5455                 5460

Ser Arg  Gln Gly Ala Leu Ser  Pro Asp Ser Arg Cys  Lys Ala Phe
    5465                 5470                 5475
```

-continued

```
Ser Asp  Ala Ala Asp Gly Ala  Gly Trp Ser Glu Gly  Val Gly Met
    5480                 5485                 5490

Val Val  Leu Glu Arg Leu Ser  Asp Ala Arg Arg Asn  Gly His Arg
    5495                 5500                 5505

Val Leu  Ala Val Val Arg Gly  Ser Ala Val Asn Gln  Asp Gly Ala
    5510                 5515                 5520

Ser Asn  Gly Leu Thr Ala Pro  Asn Gly Pro Ser Gln  Gln Arg Val
    5525                 5530                 5535

Ile Arg  Gln Ala Leu Ala Ser  Gly Gly Leu Ser Ala  Gly Asp Val
    5540                 5545                 5550

Asp Val  Val Glu Ala His Gly  Thr Gly Thr Thr Leu  Gly Asp Pro
    5555                 5560                 5565

Ile Glu  Ala Gln Ala Leu Leu  Ala Thr Tyr Gly Gln  Gly Arg Asp
    5570                 5575                 5580

Glu Glu  Arg Pro Leu Leu Leu  Gly Ser Val Lys Ser  Asn Ile Gly
    5585                 5590                 5595

His Thr  Gln Ala Ala Ala Gly  Val Ala Gly Val Ile  Lys Met Val
    5600                 5605                 5610

Met Ala  Met Arg His Gly Arg  Leu Pro Arg Thr Leu  His Val Asp
    5615                 5620                 5625

Ala Pro  Ser Ser His Val Asp  Trp Ser Ala Gly Ala  Val Glu Leu
    5630                 5635                 5640

Leu Thr  Gly Glu Arg Val Trp  Pro Gly Glu Glu Arg  Leu Arg Arg
    5645                 5650                 5655

Ala Gly  Val Ser Ser Phe Gly  Ile Ser Gly Thr Asn  Ala His Val
    5660                 5665                 5670

Ile Leu  Glu Gln Pro Glu Glu  Ala Gln Glu Pro Ala  Pro Thr Val
    5675                 5680                 5685

Ala Pro  Ala Val Asp Val Pro  Trp Val Leu Ser Ala  Arg Ser Ala
    5690                 5695                 5700

Pro Ala  Leu Arg Ala Gln Ala  Glu Arg Leu Arg Val  His Val Ala
    5705                 5710                 5715

Ala Glu  Pro Val Ser Ala Pro  Asp Val Ala Phe Ser  Leu Val Ser
    5720                 5725                 5730

Gly Arg  Ala Thr Phe Asp His  Arg Ala Val Val Leu  Gly Thr Asp
    5735                 5740                 5745

Arg Glu  Ala Ala Leu Glu Ala  Leu Ala Ser Gly Leu  Pro Asp Ala
    5750                 5755                 5760

Gly Val  Val Glu Gly Val Ala  Thr Gly Gly Arg Thr  Ala Phe Leu
    5765                 5770                 5775

Phe Ser  Gly Gln Gly Ser Gln  Arg Leu Gly Met Gly  Arg Gly Leu
    5780                 5785                 5790

Tyr Glu  Arg Phe Pro Val Phe  Ala Glu Ala Phe Asp  Ala Val Cys
    5795                 5800                 5805

Ala Gly  Leu Asp Glu His Leu  Glu Arg Pro Leu Arg  Glu Val Val
    5810                 5815                 5820

Trp Gly  Asp Asp Thr Ser Val  Leu Asp Gly Thr Ala  Tyr Ala Gln
    5825                 5830                 5835

Ala Gly  Leu Phe Ala Val Glu  Val Ala Leu Phe Arg  Leu Val Glu
    5840                 5845                 5850

Ser Trp  Gly Val Arg Pro Glu  Phe Val Ala Gly His  Ser Ile Gly
    5855                 5860                 5865

Glu Val  Ala Ala Ala His Val  Ala Gly Val Phe Thr  Leu Ala Asp
```

-continued

```
    5870                5875                5880

Ala Ala  Ala Leu Val Ala Ala  Arg Gly Arg Leu Met  Gln Ala Leu
    5885                5890                5895

Pro Glu  Gly Gly Ala Met Val  Ala Leu Glu Ala Ser  Glu Ala Glu
    5900                5905                5910

Val Leu  Pro Arg Leu Glu Ser  Val Glu Gly Val Ser  Val Ala Ala
    5915                5920                5925

Val Asn  Gly Ser Ser Ser Val  Val Val Ser Gly Ala  Glu Asp Ala
    5930                5935                5940

Val Glu  Ala Val Ala Glu Val  Phe Arg Glu Gln Gly  Arg Arg Val
    5945                5950                5955

Ser Arg  Leu Arg Val Ser His  Ala Phe His Ser Pro  Leu Met Glu
    5960                5965                5970

Pro Met  Leu Gly Asp Phe Arg  Glu Val Leu Ser Gly  Leu Ser Tyr
    5975                5980                5985

Ala Glu  Pro Ser Leu Pro Val  Val Ser Asn Val Ser  Gly Arg Ile
    5990                5995                6000

Ala Glu  Pro Gly Glu Leu Thr  Thr Pro Asp Tyr Trp  Val Thr His
    6005                6010                6015

Val Arg  Glu Ala Val Arg Phe  Asp Asp Gly Val Arg  Ala Leu Ala
    6020                6025                6030

Glu Glu  Gly Val Thr Arg Phe  Val Glu Leu Gly Pro  Asp Gly Val
    6035                6040                6045

Leu Ser  Gly Met Ala Arg Glu  Gly Ala Gly Glu Asp  Ala Val Leu
    6050                6055                6060

Val Pro  Leu Leu Arg Lys Asp  Arg Glu Glu Thr Ser  Thr Ala Leu
    6065                6070                6075

Ala Ala  Leu Ala Arg Leu His  Thr Val Gly Ala Glu  Val Lys Trp
    6080                6085                6090

Thr Gly  Phe Phe Ala Gly Thr  Ala Ala Arg Thr Val  Asp Leu Pro
    6095                6100                6105

Thr Tyr  Ala Phe Gln Lys Arg  Arg Phe Trp Pro Glu  Thr Thr Val
    6110                6115                6120

Arg Ala  Ala Ala Asp Pro Arg  Ser Ala Gly Val Asp  Ala Ala Asp
    6125                6130                6135

His Pro  Leu Leu Gly Ala Val  Val Ser Leu Pro Asp  Ser Gly Gly
    6140                6145                6150

Val Val  Leu Thr Gly Arg Leu  Ser Val Glu Ala Gln  Pro Trp Leu
    6155                6160                6165

Ala Asp  His Val Val Leu Gly  Arg Val Leu Leu Pro  Gly Thr Gly
    6170                6175                6180

Leu Val  Glu Leu Ala Leu Ala  Ala Gly Asp Ala Ala  Gly Ser Thr
    6185                6190                6195

Ala Leu  Glu Glu Leu Thr Leu  Ala Ala Pro Leu Val  Leu Pro Glu
    6200                6205                6210

Asp Thr  Gly Leu Gln Leu Arg  Val Val Ala Gly Pro  Lys Thr Asp
    6215                6220                6225

Gly Arg  Arg Thr Val Ala Val  His Ser Arg Pro Glu  Gly Ala Glu
    6230                6235                6240

Asp Ala  Pro Trp Thr Ala His  Ala His Gly Phe Leu  Thr Asp Ala
    6245                6250                6255

Pro Ala  Gly Ser Gly Glu Ala  Leu Thr Glu Trp Pro  Pro Pro Gly
    6260                6265                6270
```

-continued

```
Ala Asp Pro Val Pro Val Glu His Ala Tyr Glu Glu Phe Arg His
    6275                6280                6285

Arg Gly Tyr Gly Tyr Gly Pro Val Phe Gln Gly Leu Arg Ala Ala
    6290                6295                6300

Trp Arg Arg Asp Asp Ala Met Phe Ala Glu Val Ala Leu Pro Glu
    6305                6310                6315

Asp Ala Ala Gly Glu Ala Gly Arg Phe Gly Leu His Pro Ala Val
    6320                6325                6330

Leu Asp Ala Ala Met His Ala Gly Ile Leu Asn Glu Glu Glu Gly
    6335                6340                6345

Gln Ala Val Val Pro Phe Ala Trp Asn Asp Val Thr Leu His Ala
    6350                6355                6360

Val Gly Ala Ser Ala Val Arg Val Arg Val Ser Arg Val Asp Ala
    6365                6370                6375

His Thr Val Ser Leu Thr Leu Ala Asp Ser Thr Gly Ala Pro Val
    6380                6385                6390

Leu Thr Val Gly Ser Leu Ala Ser Arg Pro Val Ser Ala Glu Gln
    6395                6400                6405

Leu Gly Ser Ala Ser Ala Gly Ala Gly Ala Leu Tyr Gly Ile Glu
    6410                6415                6420

Trp Thr Pro Val Thr Val Asp Thr Ser Thr Ala Pro Ala His Val
    6425                6430                6435

Ser Trp Ala Glu Ala Leu Glu Ala Asp Thr Thr Ala Pro Gly Ala
    6440                6445                6450

Val Val Leu Glu Val Arg Glu Pro Ala Gly Pro Asp Val Pro Ala
    6455                6460                6465

Ala Val Arg Ala Val Leu Asp Gln Val Leu Pro Ala Ile Gln Gln
    6470                6475                6480

Trp Leu Arg Asp Glu Arg Phe Thr Ser Ser Arg Leu Val Val Val
    6485                6490                6495

Thr Arg Gly Ala Ala Pro Ala Gly Ser Ser Ala Asp Val Val Gln
    6500                6505                6510

Ala Pro Val Trp Gly Leu Val Arg Ala Ala Leu Ala Glu Asn Pro
    6515                6520                6525

Gly Arg Phe Ala Leu Ala Asp Val Ser Val Asp Ala Asp Asp Ala
    6530                6535                6540

Ala Val Asp Arg Ala Val Ala Ala Ala Leu Ser Gly Glu Ala Glu
    6545                6550                6555

Val Ala Val Arg Asp Gly Val Val Leu Val Pro Arg Leu Ser Arg
    6560                6565                6570

Leu Ala Glu Pro Glu Leu Pro Leu Ser Val Pro Ser Leu Asp Gly
    6575                6580                6585

Glu Gly Ala Val Leu Val Thr Gly Gly Thr Gly Gly Leu Gly Ala
    6590                6595                6600

Val Met Ala Arg Tyr Leu Val Ala Glu Arg Gly Val Arg Asp Leu
    6605                6610                6615

Val Leu Val Ser Arg Arg Gly Gly Asp Ala Pro Gly Ala Ala Glu
    6620                6625                6630

Leu Ala Gly Glu Leu Arg Glu Ala Gly Ala Ala Val Glu Val Val
    6635                6640                6645

Ala Cys Asp Leu Ser Asp Arg Glu Ser Val Val Gly Leu Val Glu
    6650                6655                6660
```

-continued

```
Ser Leu Val Ala Gly Arg Gly Leu Arg Ala Val Val His Ala Ala
    6665                6670                6675

Gly Val Gly Gly Gly Gly Leu Val Gly Thr Leu Ser Ser Asp Arg
    6680                6685                6690

Phe Asp Ala Val Leu Gly Ala Lys Ala Asp Ala Ala Trp Trp Leu
    6695                6700                6705

His Glu Ala Thr Ala Gly Val Glu Leu Ala Ala Phe Val Leu Val
    6710                6715                6720

Ser Ser Ala Gly Gly Leu Val Leu Thr Ala Gly Gln Gly Asn Tyr
    6725                6730                6735

Ala Ala Ala Asn Val Phe Leu Asp Ala Leu Ala Ser Arg Arg Arg
    6740                6745                6750

Ala Glu Gly Leu Val Ala Thr Ser Met Ala Phe Gly Phe Trp Asp
    6755                6760                6765

Val Gly Ala Gly Leu Gly Glu Tyr Leu Ser Glu Val Asp Arg Arg
    6770                6775                6780

Arg Met Ala Ser Gln Gly Leu Pro Leu Leu Ser His Glu Ala Gly
    6785                6790                6795

Leu Glu Leu Phe Ala Ala Gly Leu Asp Arg Gly Glu Ala Thr Val
    6800                6805                6810

Val Pro Leu Arg Val Asp Thr Ala Ala Leu Arg Thr Arg Thr Asp
    6815                6820                6825

Glu Ile Pro Ala Leu Leu Lys Ser Leu Ala Pro Val Arg Arg Ser
    6830                6835                6840

Ala Ala Val Val Pro Pro Ala Thr Val Glu Gly Ser Pro Ala His
    6845                6850                6855

Arg Leu Ala Ser Leu Pro Glu Ala Glu Arg His Arg Thr Leu Leu
    6860                6865                6870

His Leu Val Arg Ser Gln Val Ala Ala Val Leu Gly His Gly Ser
    6875                6880                6885

Ala Glu Ala Ile Gly Ala Asp Arg Ala Phe Gln Glu Leu Gly Phe
    6890                6895                6900

Asp Ser Leu Ala Ala Thr Glu Leu Arg Asn Gln Leu Asn Thr Leu
    6905                6910                6915

Thr Gly Leu Arg Leu Pro Ala Thr Leu Val Phe Asp His Pro Asn
    6920                6925                6930

Ala Leu Ala Val Thr Asp His Leu Ser Ala Arg Leu Ala Gly Glu
    6935                6940                6945

Ser Ala Arg Ala Glu Thr Pro Val Arg Thr Gly Thr Ala Ala Pro
    6950                6955                6960

Ala Asp Asp Glu Pro Ile Ala Ile Val Gly Met Ala Cys Arg Tyr
    6965                6970                6975

Pro Gly Gly Val Thr Thr Pro Glu Glu Leu Trp Arg Leu Val Thr
    6980                6985                6990

Asp Gly Val Asp Thr Val Ser Asp Leu Pro Gly Asp Arg Gly Trp
    6995                7000                7005

Asp Ile Glu Gly Leu Tyr Asp Pro Glu Pro Gly Lys Glu Gly Lys
    7010                7015                7020

Ser Tyr Thr Arg Arg Gly Ser Phe Leu His Asp Ala Ala Gln Phe
    7025                7030                7035

Asp Pro Gly Phe Phe Gly Ile Ser Pro Arg Glu Ala Leu Tyr Met
    7040                7045                7050

Asp Pro Gln Gln Arg Leu Leu Leu Glu Thr Ser Trp Glu Ala Leu
```

```
    7055                7060                7065

Glu Arg  Ala Gly Ile Asp Pro  Ala Thr Leu Arg Gly  Ser Arg Thr
    7070                7075                7080

Gly Val  Phe Ala Gly Val Met  Tyr His Asp Tyr Ala  Leu Asn Val
    7085                7090                7095

Ser Pro  Ser Gly Thr Ala Gly  Gly Ser Val Val Ser  Gly Arg Leu
    7100                7105                7110

Ser Tyr  Thr Phe Gly Trp Glu  Gly Pro Ala Val Thr  Val Asp Thr
    7115                7120                7125

Ala Cys  Ser Ser Ser Leu Val  Ala Leu His Leu Ala  Val Gln Ala
    7130                7135                7140

Leu Arg  Ser Gly Glu Cys Ser  Leu Ala Val Ala Gly  Gly Ala Thr
    7145                7150                7155

Val Met  Ser Thr Pro Gly Met  Phe Val Glu Phe Ser  Arg Gln Arg
    7160                7165                7170

Gly Leu  Ser Val Asp Gly Arg  Cys Lys Ala Phe Ala  Gly Ala Ala
    7175                7180                7185

Asp Gly  Val Gly Trp Ser Glu  Gly Val Gly Val Leu  Leu Val Glu
    7190                7195                7200

Arg Leu  Ser Asp Ala Val Arg  Asn Gly His Arg Val  Leu Ala Val
    7205                7210                7215

Val Lys  Gly Thr Ala Val Asn  Gln Asp Gly Ala Ser  Asn Gly Phe
    7220                7225                7230

Thr Ala  Pro Asn Gly Pro Ser  Gln Gln Arg Val Ile  Arg Gln Ala
    7235                7240                7245

Leu His  Gly Ala Gly Val Pro  Ala Ser Glu Val Asp  Val Val Glu
    7250                7255                7260

Ala His  Gly Thr Gly Thr Thr  Leu Gly Asp Pro Ile  Glu Ala Gln
    7265                7270                7275

Ala Leu  Leu Ala Thr Tyr Gly  Gln Asp Arg Pro Glu  Asp Arg Pro
    7280                7285                7290

Leu Leu  Leu Gly Ser Val Lys  Ser Asn Ile Gly His  Ala Gln Ala
    7295                7300                7305

Ala Ala  Gly Val Ala Gly Val  Ile Lys Met Val Met  Ala Met Glu
    7310                7315                7320

His Gly  Thr Val Pro Arg Thr  Leu His Val Asp Arg  Pro Ser Pro
    7325                7330                7335

His Val  Asp Trp Thr Glu Gly  Arg Ala Glu Leu Val  Thr Glu Asp
    7340                7345                7350

Arg Pro  Trp Pro Val Thr Gly  Arg Pro Arg Arg Ala  Ser Val Ser
    7355                7360                7365

Ala Phe  Gly Leu Ser Gly Thr  Asn Ala His Val Val  Leu Glu Gln
    7370                7375                7380

Gly Pro  Asp Ala Ala Ala Asp  Ala Pro Ser Thr Ala  Glu Glu Gly
    7385                7390                7395

Arg Ala  Pro Ala Val Leu Pro  Trp Thr Val Ser Ala  Ala Thr Pro
    7400                7405                7410

Asp Ala  Leu Arg Ala Gln Ala  Thr Arg Leu Leu Asp  His Leu Ala
    7415                7420                7425

Asp Arg  Pro Gly Thr Arg Pro  Leu Asp Val Ala His  Ala Leu Ala
    7430                7435                7440

Thr Ser  Arg Thr Pro Leu Glu  Ala Arg Ala Val Val  Leu Gly Thr
    7445                7450                7455
```

-continued

```
Gly Arg Asp Asp Leu Leu Thr Gly Leu Arg Ala Leu Ala Ala Gly
    7460                7465                7470

Glu His Ala Pro Gly Val Ile Thr Gly Thr Ala Arg Ser Val Gly
    7475                7480                7485

Thr Thr Ala Phe Leu Phe Ser Gly Gln Gly Ala Gln Arg Leu Glu
    7490                7495                7500

Met Gly Arg Gly Leu His Glu Ala Phe Pro Val Phe Ala Glu Ala
    7505                7510                7515

Phe Asp Ala Val Cys Ala Gly Leu Asp Glu His Leu Asp Arg Pro
    7520                7525                7530

Leu Arg Glu Val Ala Trp Gly Glu Asn Ala Pro Asp Leu Asp Gly
    7535                7540                7545

Thr Ala Tyr Ala Gln Ser Ala Leu Phe Ala Tyr Glu Val Ala Leu
    7550                7555                7560

Phe Arg Leu Leu Ala Ser Trp Gly Val Thr Pro Asp Leu Val Ala
    7565                7570                7575

Gly His Ser Ile Gly Glu Val Ala Ala Ala His Val Ala Gly Val
    7580                7585                7590

Phe Ser Leu Ala Asp Ala Cys Ala Leu Val Ala Ala Arg Gly Arg
    7595                7600                7605

Leu Met Gln Ala Leu Pro Glu Gly Gly Ala Met Val Ala Val Glu
    7610                7615                7620

Ala Ser Glu Thr Glu Val Leu Pro His Leu Glu Ser Val Glu Gly
    7625                7630                7635

Val Ser Val Ala Ala Val Asn Gly Pro Ser Ser Val Val Val Ser
    7640                7645                7650

Gly Ala Gly Glu Ala Val Glu Ala Val Ala Glu Val Phe Arg Glu
    7655                7660                7665

Gln Gly Arg Arg Val Ser Gln Leu Arg Val Ser His Ala Phe His
    7670                7675                7680

Ser Pro Leu Met Glu Pro Met Leu Ala Asp Phe Arg Glu Val Leu
    7685                7690                7695

Ser Gly Val Ser Tyr Ala Glu Pro Ser Leu Pro Val Val Ser Asn
    7700                7705                7710

Val Ser Gly Arg Ile Ala Glu Ser Gly Glu Leu Ala Thr Pro Asp
    7715                7720                7725

Tyr Trp Val Thr His Val Arg Glu Ala Val Arg Phe Gly Asp Gly
    7730                7735                7740

Val Arg Ala Leu Arg Ala Ala Gly Val Asp Arg Cys Val Glu Ile
    7745                7750                7755

Gly Pro Asp Ala Val Leu Thr Gly Met Ala Arg Thr Cys Leu Asp
    7760                7765                7770

Gly Asp Glu Asp Thr Ala Val Leu Leu Val Pro Ser Ala Arg Lys
    7775                7780                7785

Gly Arg Glu Glu Pro Asp Ala Leu Leu Thr Ala Leu Ala Gln Leu
    7790                7795                7800

His Thr Ala Gly Thr Ala Val Asp Trp Ala Gly Phe Phe Ala Gly
    7805                7810                7815

Ser Gly Ala Gly Pro Val Asp Leu Pro Thr Tyr Ala Phe Gln Arg
    7820                7825                7830

Gln Arg Tyr Trp Leu Thr Ala Thr Asp Gly Ala Pro Ala Ala Ala
    7835                7840                7845
```

-continued

```
Gly Ala Gly Leu Asp Ala Ala Asp His Pro Leu Leu Gly Ala Val
    7850                7855                7860

Val Ser Leu Pro Asp Ser Gly Gly Ala Val Leu Thr Gly Leu Leu
    7865                7870                7875

Ser Val Glu Ala Gln Pro Trp Leu Ala Asp His Val Val Leu Gly
    7880                7885                7890

Arg Val Met Leu Pro Gly Ala Val Leu Val Glu Leu Ala Leu Ala
    7895                7900                7905

Ala Gly Glu Ser Val Asp Cys Ala Val Leu Asp Glu Leu Thr Leu
    7910                7915                7920

Ala Thr Pro Leu Val Leu Pro Glu His Gly Gly Ala Gln Val Arg
    7925                7930                7935

Val Val Val Gly Pro Arg Thr Ala Glu Arg Arg Thr Val Ala Val
    7940                7945                7950

Tyr Ser Arg Pro Glu Gly Thr Gly Gln Glu Trp Ala Thr His Ala
    7955                7960                7965

Thr Gly Phe Leu Thr Asp Asn Ala Leu Val Ala Gly Ala Glu Ala
    7970                7975                7980

Ala Leu Glu Gln Trp Pro Pro Thr Gly Ala Ala Ser Val Pro Val
    7985                7990                7995

Asp Ser Ala Tyr Gln Ile Phe Arg Glu Arg Gly Tyr Gly Tyr Gly
    8000                8005                8010

Pro Val Phe Gln Gly Leu Arg Ala Ala Trp Arg Arg Gly Gly Glu
    8015                8020                8025

Leu Phe Ala Glu Val Ala Leu Pro Glu Glu Ala Ala Ser Glu Ala
    8030                8035                8040

Gly Arg Phe Gly Leu His Pro Ala Leu Leu Asp Ala Ala Met His
    8045                8050                8055

Val Ala Ile Leu Asn Asp Ser Asn Asp Ser Asn Asp Ser Asn Asp
    8060                8065                8070

Asn Ala Glu Gly Gly Ser Gly Gly Thr Val Ile Pro Phe Ala Trp
    8075                8080                8085

Asn Arg Val Ala Leu His Ala Val Gly Ala Ala Ala Val Arg Val
    8090                8095                8100

Arg Ile Ala Thr Ala Ala Asp Gly Gly Met Asp Ile Arg Val Thr
    8105                8110                8115

Asp Val Thr Gly Ala Pro Val Leu Thr Val Gly Ser Met Val Ser
    8120                8125                8130

Arg Thr Val Ser Ala Gly Gln Leu Gly Ala Ala Pro Arg Asp Ala
    8135                8140                8145

Gly Ala Leu Tyr Ala Pro Glu Trp Val Pro Val Thr Arg Leu Asp
    8150                8155                8160

Asp Thr Asp Thr Ala Trp Ala Thr Trp Ser Arg Val Glu Glu Ala
    8165                8170                8175

Gly Thr Glu Val Pro Ala Val Val Val Leu Asp Ala Ser Ala Pro
    8180                8185                8190

Ala Gly Ala Asp Val Pro Gly Ser Val Arg Ser Ala Leu Asp Gly
    8195                8200                8205

Val Leu Thr Val Ala Gln Arg Trp Leu Thr Glu Glu Arg Phe Ala
    8210                8215                8220

Ala Ser Arg Leu Val Val Val Thr Arg Gly Ala Met Pro Val Gly
    8225                8230                8235

Ser Gly Gly Ala Pro Ala Glu Gly Asp Val Val Gln Ala Pro Val
```

-continued 8240 8245 8250

Trp Gly Leu Val Arg Ala Ala Leu Ala Glu Asn Pro Gly Arg Phe
8255 8260 8265

Ala Leu Ala Asp Val Ala Val Asp Ala Asp Asp Ala Ala Val Asp
8270 8275 8280

Cys Ala Val Ala Ala Val Leu Ser Gly Glu Ala Glu Val Ala Val
8285 8290 8295

Arg Asp Gly Val Val Leu Val Pro Arg Leu Thr Arg Leu Thr Ala
8300 8305 8310

Asp Ala Pro Ala Ala Glu Leu Pro Leu Ser Val Pro Ser Leu Asp
8315 8320 8325

Gly Glu Gly Ala Val Leu Val Thr Gly Gly Thr Gly Gly Leu Gly
8330 8335 8340

Ala Val Met Ala Arg Tyr Leu Val Ala Glu Arg Gly Val Arg Asp
8345 8350 8355

Leu Val Leu Val Ser Arg Arg Gly Gly Asp Ala Pro Gly Ala Ala
8360 8365 8370

Glu Leu Ala Gly Glu Leu Arg Glu Ala Gly Ala Ala Val Glu Val
8375 8380 8385

Val Ala Cys Asp Leu Ser Asp Arg Glu Ser Val Val Asp Leu Val
8390 8395 8400

Gly Ser Leu Val Ser Gly Arg Gly Leu Leu Ala Val Val His Ala
8405 8410 8415

Ala Gly Val Gly Asp Asn Gly Leu Leu Gly Ser Leu Thr Pro Asp
8420 8425 8430

Arg Phe Asp Ala Val Leu Gly Ala Lys Ala Asp Ala Ala Trp Trp
8435 8440 8445

Leu His Glu Ala Thr Ala Gly Val Glu Leu Ala Ala Phe Val Leu
8450 8455 8460

Val Ser Ser Ala Gly Gly Leu Val Leu Thr Ala Gly Gln Gly Asn
8465 8470 8475

Tyr Ala Ala Ala Asn Val Phe Leu Asp Ala Leu Ala Ser Arg Arg
8480 8485 8490

Arg Ala Glu Gly Leu Val Ala Thr Ser Met Ala Phe Gly Phe Trp
8495 8500 8505

Asp Val Gly Ala Gly Leu Gly Glu Tyr Leu Ser Glu Val Asp Arg
8510 8515 8520

Arg Arg Met Ala Ser Gln Gly Leu Pro Leu Leu Ser His Glu Ala
8525 8530 8535

Gly Leu Glu Leu Phe Ala Ala Gly Leu Asp Arg Ser Glu Ala Thr
8540 8545 8550

Val Val Pro Leu Arg Val Asp Thr Ala Ala Leu Arg Thr Arg Thr
8555 8560 8565

Asp Glu Ile Pro Ala Leu Leu Arg Ala Leu Ala Pro Ala Arg Arg
8570 8575 8580

Ala Thr Ala Ala Ser Gly Ser Ala Ala Ala Pro Gly Pro Asp Asp
8585 8590 8595

Ser Pro Ser Arg Arg Leu Ala Glu Leu Pro Ala Pro Glu Arg His
8600 8605 8610

Arg Ala Val Leu His Leu Val Arg Ser Gln Val Ala Ala Val Leu
8615 8620 8625

Gly His Gly Ser Ala Glu Ala Ile Gly Ala Asp Arg Ala Phe Gln
8630 8635 8640

-continued

```
Glu Leu Gly Phe Asp Ser Leu Ala Ala Thr Glu Leu Arg Asn Gln
    8645                8650                8655

Leu Asn Thr Leu Thr Gly Leu Arg Leu Pro Ala Thr Leu Val Phe
    8660                8665                8670

Asp His Pro Asn Ala Leu Ala Val Thr Glu Val Val Glu Glu Glu
    8675                8680                8685

Leu Ala Ala Ala His Pro Ala Ser Gly Ala Gly Gly Ala Thr Gly
    8690                8695                8700

Asp Asp Asp Gly Val Arg Arg Ala Leu Ser Ala Ile Pro Ala Arg
    8705                8710                8715

Arg Leu Arg Asp Ala Gly Leu Ala Glu Thr Leu Leu Glu Leu Ala
    8720                8725                8730

Ala Asp Ser Asp Glu Met Ser Asp Thr Asp Arg Asp Ala Leu Leu
    8735                8740                8745

Ala Ala Phe Asp Gly Asp Asp Glu Asp Asp Ala Ser Gly Pro Tyr
    8750                8755                8760

Asp Glu Ser Asp Gly Ala Ala Glu Thr Ala Gly Thr Gly Thr Ala
    8765                8770                8775

Thr Glu Pro Gly Ala Asp Ala Leu Arg Ala Ala Arg Ala Glu Thr
    8780                8785                8790

Ala Arg Leu Arg Arg Asp Asn Arg Arg Leu Thr Ser Ala Gln His
    8795                8800                8805

Glu Pro Ile Ala Ile Val Gly Met Ala Cys Arg Tyr Pro Gly Gly
    8810                8815                8820

Val Ser Ser Pro Glu Asp Leu Trp Arg Leu Val Thr Ser Gly Asp
    8825                8830                8835

Asp Ala Ile Val Pro Phe Pro Gln Asp Arg Gly Trp Asp Leu Ser
    8840                8845                8850

Ile Leu Arg Asp Pro Asp Gly Asp His Pro Asp Gly Leu Tyr Ala
    8855                8860                8865

Arg Glu Gly Gly Phe Leu Asp Gly Ala Ala Asp Phe Asp Pro Ala
    8870                8875                8880

Phe Phe Gly Ile Ser Pro Arg Glu Ala Leu Gly Met Asp Pro Gln
    8885                8890                8895

Gln Arg Leu Ala Leu Glu Met Ser Trp Glu Ala Leu Glu Arg Ala
    8900                8905                8910

Gly Ile Asp Pro Ala Ser Leu Lys Gly Ser Arg Thr Gly Val Phe
    8915                8920                8925

Thr Gly Val Met Tyr His Asp Tyr Pro Gly Ser Asp Gly Asn Gly
    8930                8935                8940

Ser Val Val Thr Gly Arg Val Ala Tyr Lys Leu Gly Leu Glu Gly
    8945                8950                8955

Pro Ala Val Ser Val Asp Thr Ala Cys Ser Ser Ser Leu Val Ala
    8960                8965                8970

Leu His Leu Ala Val Gln Ala Leu Arg Gln Gly Glu Cys Ser Leu
    8975                8980                8985

Ala Val Thr Gly Gly Val Thr Val Leu Ser Thr Pro Ala Val Phe
    8990                8995                9000

Ala Glu Phe Gly Arg Gln Gly Gly Leu Ala Pro Asp Gly Arg Cys
    9005                9010                9015

Lys Ser Phe Ala Ser Ala Ala Asp Gly Thr Gly Phe Ser Glu Gly
    9020                9025                9030
```

-continued

```
Ala Gly Phe Leu Val Val Glu Arg Leu Ser Asp Ala Val Arg Asn
    9035                9040                9045

Gly His Glu Val Leu Ala Val Val Arg Gly Ser Ala Val Asn Gln
    9050                9055                9060

Asp Gly Ala Ser Asn Gly Leu Thr Ala Pro Asn Gly Pro Ser Gln
    9065                9070                9075

Arg Arg Val Ile Arg Gln Ala Leu Ala Asn Ala Arg Leu Ala Ala
    9080                9085                9090

Asp Gln Val Asp Ala Val Glu Ala His Gly Thr Gly Thr Thr Leu
    9095                9100                9105

Gly Asp Pro Ile Glu Ala Gln Ala Leu Leu Ala Thr Tyr Gly Gln
    9110                9115                9120

Asp Arg Pro Glu Asp Arg Pro Leu Leu Leu Gly Ser Val Lys Ser
    9125                9130                9135

Asn Ile Gly His Ala Gln Ala Ala Ala Gly Val Ala Gly Val Ile
    9140                9145                9150

Lys Met Val Leu Ala Leu Arg Asn Gly Leu Leu Pro Ala Thr Leu
    9155                9160                9165

Asn Val Asp Ala Pro Ser Asp Gln Val Asp Trp Thr Thr Gly Ser
    9170                9175                9180

Val Glu Leu Leu Thr Glu Ala Arg Gln Trp Thr Gly Ser Gly Arg
    9185                9190                9195

Pro Arg Arg Ala Gly Ile Ser Ser Phe Gly Ile Ser Gly Thr Asn
    9200                9205                9210

Ala His Val Ile Val Glu Gln Ala Pro Ala Ala Val Pro Ser Asp
    9215                9220                9225

Glu Pro Ala Thr Gly Ala Asp Asp Asp Gly Val Ala Pro Val Val
    9230                9235                9240

Pro Trp Leu Leu Ser Ala Arg Asp Arg Asp Ala Leu Arg Ala Gln
    9245                9250                9255

Ala Glu Arg Leu Leu His His Leu Thr Gly Asp His Pro Ala Ala
    9260                9265                9270

Gly Gly Thr Glu Ala Arg Pro Leu Asp Val Ala Tyr Ser Leu Ala
    9275                9280                9285

Thr Ala Arg Thr Ala Phe Glu His Arg Val Ala Val Thr Gly Ala
    9290                9295                9300

Gly Arg Asp Gly Leu Leu Ala Ala Leu Gly Ser Val Ala Arg Gly
    9305                9310                9315

Glu Glu Pro Ala Thr Thr Thr Gly Glu Gly Leu Leu Ala Leu Leu
    9320                9325                9330

Phe Pro Gly Gln Gly Ser Gln Arg Leu Gly Met Gly Arg Asp Leu
    9335                9340                9345

Tyr Glu Arg Phe Pro Val Phe Ala Glu Ala Phe Asp Ala Val Cys
    9350                9355                9360

Ala Gly Leu Asp Ala His Leu Asp Arg Pro Leu Arg Glu Val Val
    9365                9370                9375

Trp Gly Asp Asp Glu Asp Ala Leu Asn Ala Thr Ala Tyr Ala Gln
    9380                9385                9390

Ala Ala Leu Phe Ala Leu Gly Val Gly Leu His Arg Leu Val Ala
    9395                9400                9405

Ser Trp Gly Val Thr Pro Asp Leu Val Ala Gly His Ser Ile Gly
    9410                9415                9420

Glu Ile Ala Ala Ala His Val Ala Gly Val Phe Ser Leu Ala Asp
```

-continued

```
    9425                9430                9435

Ala Cys  Ala Leu Val Ala Ala  Arg Gly Arg Leu Met  Gln Ala Leu
    9440                9445                9450

Pro Glu  Gly Gly Ala Met Ala  Ala Val Gln Ala Thr  Glu Asp Glu
    9455                9460                9465

Val Leu  Ala His Leu Thr Asp  Gly Val Ser Val Ala  Ala Val Asn
    9470                9475                9480

Gly Pro  Thr Ser Val Val Val  Ser Gly Thr Ala Glu  Gly Val Glu
    9485                9490                9495

Lys Val  Thr Glu Ala Leu Arg  Glu Arg Gly Arg Arg  Thr Thr Ala
    9500                9505                9510

Leu Arg  Val Ser His Ala Phe  His Ser Pro Leu Met  Glu Pro Met
    9515                9520                9525

Leu Ala  Glu Phe Arg Ala Val  Val Ala Gly Leu Ser  Pro Gln Ala
    9530                9535                9540

Pro Val  Ile Pro Val Val Ser  Asn Leu Thr Gly Thr  Thr Ala Arg
    9545                9550                9555

Ala Glu  Glu Leu Cys Ser Ala  Glu Tyr Trp Val Arg  His Val Arg
    9560                9565                9570

Glu Ala  Val Arg Phe Ala Asp  Gly Val Arg Ala Leu  His Glu Ala
    9575                9580                9585

Gly Ala  Thr Arg Tyr Leu Glu  Leu Gly Pro Asp Gly  Val Ala Cys
    9590                9595                9600

Ala Met  Ala Arg Glu Ser Leu  Pro Glu Ser Ala Val  Thr Val Ala
    9605                9610                9615

Ala Gln  Arg Arg Thr Val Pro  Gly Glu Gln Ala Leu  Val Glu Ala
    9620                9625                9630

Val Ala  Arg Leu His Gly His  Gly Val Arg Val Asp  Trp Pro Ala
    9635                9640                9645

Phe Phe  Ala Gly Arg Gly Ala  Arg Arg Val Glu Leu  Pro Thr Tyr
    9650                9655                9660

Ala Phe  Gln Arg Arg Arg Phe  Trp Pro Ala Gly Met  Met Pro Leu
    9665                9670                9675

Gly Ala  Gly Ala Glu Ala Ala  Gly Leu Ala Pro Ala  Gly His Pro
    9680                9685                9690

Leu Leu  Gly Gly Ala Val Glu  Leu Ala Gly Thr Asp  Gly His Leu
    9695                9700                9705

Phe Thr  Gly Arg Leu Ser Gln  Gly Thr His Gly Trp  Ile Ser Asp
    9710                9715                9720

His Arg  Val Met Gly Ala Val  Leu Val Pro Gly Thr  Ala Leu Leu
    9725                9730                9735

Glu Leu  Ala Val His Ala Gly  Gly Val Leu Gly Cys  Asp Val Val
    9740                9745                9750

Glu Glu  Leu Thr Leu Ala Ala  Pro Leu Val Leu Pro  Glu Gln Gly
    9755                9760                9765

Thr Val  Gln Val Gln Val Gly  Val Gly Ala Pro Asp  Glu Glu Gly
    9770                9775                9780

Arg Arg  Gly Ile Thr Ile His  Ser Arg Pro Ala Asp  Asp Ser Gly
    9785                9790                9795

Ala Pro  Trp Thr Ser His Ala  Glu Gly Thr Leu Ala  Ala Gly Pro
    9800                9805                9810

Ala Gln  Ala Pro Ala Thr Asp  Phe Asp Ala Thr Val  Trp Pro Pro
    9815                9820                9825
```

-continued

```
Glu Lys Ala Glu Pro Leu Asp Thr Thr Gly Leu Tyr Glu Arg Phe
    9830                9835                9840

Glu Asp Ala Gly Phe Ala Tyr Gly Pro Val Phe Gln Gly Leu Arg
    9845                9850                9855

Ala Ala Trp Ser Arg Asp Gly Glu Val Phe Ala Glu Ala Ser Leu
    9860                9865                9870

Pro Asp Gly Thr Asp Gly Asp Ala Phe Thr Leu His Pro Ala Leu
    9875                9880                9885

Phe Asp Ala Gly Leu His Ala Thr Ala Leu Ala Gly Asp Gly Gly
    9890                9895                9900

Glu Ser Glu Gly Thr Gly Gly Val Pro Phe Ser Trp Asn Gly Val
    9905                9910                9915

Ser Val His Ala Val Gly Ala Ser Ser Val Arg Leu Arg Leu Ser
    9920                9925                9930

Arg Thr Asp Asp Gly Thr Leu Ala Ile Ala Val Thr Asp Thr Ala
    9935                9940                9945

Gly Thr Pro Val Ala Ser Val Gly Ser Leu Val Thr Arg Pro Leu
    9950                9955                9960

Ser Ala Gly Gln Phe Gly Gly Ala Gly Gly Ala Gly Arg Asp Ser
    9965                9970                9975

Leu Phe Gln Leu Asp Trp Ala Ala Ala Gly Asp Pro Ala Thr Arg
    9980                9985                9990

Asp Ala Glu Thr Pro Gly Pro Val Ala Val Leu Gly Pro Asp Thr
    9995                10000               10005

Ala Leu Leu Gly Gly Gly Asp Leu Leu Ala Glu Ala Gly Thr Glu
    10010               10015               10020

Gly Val Thr Gly Leu Ala Asp Leu Val Thr Gly Thr Gly Pro Gly
    10025               10030               10035

Glu Asp Val Pro Ser Val Val Leu Leu Pro Val Ala Thr Ala Pro
    10040               10045               10050

Glu Ala Gly Ser Gly Thr Gly Asp Val Ala Ala Ala Ala His Ala
    10055               10060               10065

Ala Thr Ala Arg Val Leu Glu Thr Leu Arg Asp Trp Ser Ala Gln
    10070               10075               10080

Glu Arg Phe Ala Ala Ser Arg Leu Val Val Val Thr Arg Gly Ala
    10085               10090               10095

Ser Asp Gly Ala Asp Pro Ala Ala Ala Ala Val Trp Gly Leu Val
    10100               10105               10110

Arg Ala Ala Gln Ala Glu Asn Pro Gly Arg Phe Ile Leu Leu Asp
    10115               10120               10125

Leu Glu Pro Ser Ala Thr Ser Pro Leu Gly Met Ser Ala Leu Arg
    10130               10135               10140

Ala Ala Leu Ala Ser Gly Glu Pro Gln Leu Ala Leu Arg Glu Asp
    10145               10150               10155

Arg Leu Leu Ala Pro Arg Leu Val Arg Ala Val Thr Pro Ala Glu
    10160               10165               10170

Ser Asp Ala Ala Gly Trp Asp Pro Glu Gly Thr Val Leu Ile Thr
    10175               10180               10185

Gly Gly Thr Gly Gly Leu Gly Ala Thr Val Ala Arg His Leu Val
    10190               10195               10200

Ala Glu His Gly Val Arg Ser Leu Leu Leu Val Ser Arg Arg Gly
    10205               10210               10215
```

-continued

```
Pro Ala Ala Glu Gly Ala Gly Glu Leu Ala Ala Ala Leu Glu Glu
    10220                   10225                   10230

Ser Gly Ala His Val Thr Val Ala Ala Cys Asp Val Gly Asp Arg
    10235                   10240                   10245

Thr Ala Val Asp Ala Leu Leu Ala Glu Ile Pro Ala Asp Arg Pro
    10250                   10255                   10260

Leu Arg Ala Val Ile His Ala Ala Gly Val Leu Asp Asp Gly Val
    10265                   10270                   10275

Leu Asp Ser Leu Thr Pro Glu Arg Leu Ala Ala Val Leu Arg Pro
    10280                   10285                   10290

Lys Ala Asp Ala Ala Trp His Leu His Glu Ala Thr Glu Gly Leu
    10295                   10300                   10305

Thr Leu Asp Ala Phe Val Leu Phe Ser Ser Val Ala Gly Thr Leu
    10310                   10315                   10320

Gly Ser Ala Gly Gln Ala Asn Tyr Ala Ala Gly Asn Ala Phe Leu
    10325                   10330                   10335

Asp Ala Leu Ala Arg His Arg Arg Asp Arg Gly Leu Pro Ala Val
    10340                   10345                   10350

Ser Met Ala Trp Gly Pro Trp Thr Arg Gly Ser Gly Met Thr Gly
    10355                   10360                   10365

Glu Leu Thr Glu Ala Asp Thr Ala Arg Met Ala Arg Ala Gly Met
    10370                   10375                   10380

Pro Pro Ile Asp Pro Glu Gln Gly Leu Ala Leu Phe Asp Ala Val
    10385                   10390                   10395

Thr Gly Ala Ala Glu Gln Ala Pro Ala Val Leu Pro Val Arg Leu
    10400                   10405                   10410

Asp Leu Gly Ala Leu Arg Ser Leu Gly Glu Val Pro Pro Leu Phe
    10415                   10420                   10425

Arg Ser Leu Ile Arg Thr Gln Ala Arg Arg Ala Ala Ser Asp Gly
    10430                   10435                   10440

Gly Ala Ala Ala Ala Ala Asp Leu Thr Arg Arg Leu Thr Gly Leu
    10445                   10450                   10455

Thr Arg Thr Glu Gly Glu Glu Val Leu Leu Asp Leu Val Arg Gly
    10460                   10465                   10470

Gln Ile Ala Thr Val Leu Gly His Ala Gly Gln Ala Asp Ile Glu
    10475                   10480                   10485

Pro Ala Arg Ala Phe Gln Asp Leu Gly Phe Asp Ser Leu Thr Ser
    10490                   10495                   10500

Val Glu Leu Arg Asn Arg Leu Gly Ala Leu Thr Gly Val Arg Leu
    10505                   10510                   10515

Pro Ala Thr Leu Leu Phe Asp Tyr Pro Thr Pro Gly Glu Leu Val
    10520                   10525                   10530

Ala His Leu Tyr Thr Arg Val Ala Pro Ala Pro Ala Asp Gly Ser
    10535                   10540                   10545

Ala Val Val Leu Ala Glu Leu Asp Lys Leu Glu Arg Ala Phe Ala
    10550                   10555                   10560

Gly Ala Glu Val Gly Ala Glu Leu Phe Asp Gln Val Ala Gly Arg
    10565                   10570                   10575

Leu Glu Val Leu Arg Gly Lys Trp Gln Glu Met Arg Ala Glu Ala
    10580                   10585                   10590

Leu Lys Gly Gly Glu Lys Ala Glu Glu Ser Phe Asp Phe Ala Ser
    10595                   10600                   10605

Ala Ser Asp Glu Asp Met Phe Asp Met Leu Asp Asn Glu Leu Gly
```

-continued

```
    10610               10615               10620

Leu Ser
    10625


<210> SEQ ID NO 4
<211> LENGTH: 5541
<212> TYPE: PRT
<213> ORGANISM: Streptomyces sp. FR-008

<400> SEQUENCE: 4

Met Ser Asn Glu Asp Arg Leu Arg Ala Tyr Leu Lys Arg Ala Val Thr
 1               5                  10                  15

Asp Leu Gln Glu Ala Arg Gln Gln Leu Ser Asp Ala Glu Asn Arg Asp
            20                  25                  30

Arg Glu Pro Val Ala Val Val Ala Met Ala Cys Arg Tyr Pro Gly Gly
        35                  40                  45

Val Arg Thr Pro Gln Asp Leu Trp Glu Leu Ala Arg Asp Gly Val Asp
    50                  55                  60

Ala Ile Ser Ala Phe Pro Ala Asn Arg Gly Trp Asp Leu Asp His Leu
65                  70                  75                  80

Phe His Pro Asp Pro Ala His His Gly Thr Thr Tyr Thr Arg Glu Gly
                85                  90                  95

Gly Phe Leu His Asp Ala Gly Glu Phe Asp Pro Ala Phe Phe Gly Ile
            100                 105                 110

Ser Pro Arg Glu Ala Leu Ala Met Asp Pro Gln Gln Arg Leu Leu Leu
        115                 120                 125

Glu Thr Ser Trp Glu Ala Leu Glu Arg Ala Gly Ile Leu Pro Asp Thr
    130                 135                 140

Leu Ala Gly Ser Thr Thr Gly Val Phe Val Gly Thr Gly His Gly Asp
145                 150                 155                 160

Tyr Asp Gly Ala Ser Arg Gly Arg Gln Lys Glu Val Ala Gly His Leu
                165                 170                 175

Leu Thr Gly Asn Thr Val Ala Val Ala Ser Gly Arg Leu Ser Tyr Thr
            180                 185                 190

Tyr Gly Phe Glu Gly Pro Ala Val Thr Val Asp Thr Ala Cys Ser Ser
        195                 200                 205

Ser Leu Val Ala Leu His Leu Ala Val Arg Ser Leu Arg Gln Gly Glu
    210                 215                 220

Cys Ser Leu Ala Leu Ala Gly Gly Ala Thr Val Met Ser Thr Pro Lys
225                 230                 235                 240

Met Phe Thr Glu Phe Ser Arg Gln Gln Gly Leu Ala Ala Asp Gly Arg
                245                 250                 255

Cys Lys Pro Phe Ala Ala Gly Ala Asp Gly Thr Ala Trp Ser Glu Gly
            260                 265                 270

Val Gly Leu Ile Leu Leu Glu Arg Leu Ser Asp Ala Gln Arg Asn Gly
        275                 280                 285

His Glu Ile Leu Ala Val Ile Arg Gly Ser Ala Ile Asn Gln Asp Gly
    290                 295                 300

Ala Ser Asn Gly Leu Thr Ala Pro Asn Gly Pro Ser Gln Gln Arg Leu
305                 310                 315                 320

Ile Arg Gln Ala Leu Ile Asp Ala Gly Leu Thr Ser Gly Glu Val Asp
                325                 330                 335

Val Val Glu Ala His Gly Thr Gly Thr Thr Leu Gly Asp Pro Ile Glu
            340                 345                 350
```

-continued

```
Ala Gln Ala Leu Leu Asn Thr Tyr Gly Gln Asp Arg Gly Asp Ala His
        355                 360                 365

Pro Leu Leu Leu Gly Ser Leu Lys Ser Asn Thr Gly His Thr Gln Ala
    370                 375                 380

Ala Ser Gly Val Ala Gly Val Ile Lys Met Val Gln Ala Met Arg His
385                 390                 395                 400

Gly Thr Leu Pro Lys Ser Leu His Val Asp Ala Pro Thr Pro His Ala
                405                 410                 415

Asp Trp Ala Thr Gly Gly Val Glu Leu Leu Thr Glu Ser Thr Thr Trp
            420                 425                 430

Pro Glu Thr Gly Arg Pro Arg Arg Ala Ala Val Ser Ser Phe Gly Val
        435                 440                 445

Ser Gly Thr Asn Ala His Leu Ile Leu Glu Gln Ala Pro Glu Asp Gln
    450                 455                 460

Thr Pro Arg Ala Glu Glu Pro Gly Thr Glu Pro Ser Ala Asp Asp Ser
465                 470                 475                 480

Ala Asp Thr Val Arg Ser Trp Met Val Ser Gly Lys Ser Arg Ala Ala
                485                 490                 495

Val Gly Glu Gln Ala Ala Arg Leu Ala Ala Ser Val Arg Ala Ser Asp
            500                 505                 510

Ala Ser Val Leu Asp Val Ala His Ala Leu Val Ser Ser Arg Val Ala
        515                 520                 525

Met Asp Arg Arg Ala Val Val Val Gly Ser Asp Arg Glu Glu Leu Leu
    530                 535                 540

Ala Gly Leu Asp Ala Leu Ala Ala Gly Glu Pro Ser Val Arg Val Val
545                 550                 555                 560

Glu Gly Thr Ala Gly Glu Gly Ala Gly Asp Val Ala Phe Val Phe Pro
                565                 570                 575

Gly Gln Gly Ser Gln Trp Val Gly Met Ala Val Glu Leu Leu Gly Ser
            580                 585                 590

Ser Pro Val Phe Ala Gly Arg Val Ala Glu Cys Ala Ala Ala Leu Glu
        595                 600                 605

Pro Phe Thr Glu Trp Ser Leu Leu Asp Val Leu Asn Gly Val Glu Gly
    610                 615                 620

Ala Ala Ser Leu Glu Arg Val Asp Val Val Gln Pro Val Leu Trp Ala
625                 630                 635                 640

Val Met Val Ser Leu Ala Glu Val Trp Arg Ala Gln Gly Val Glu Pro
                645                 650                 655

Gly Ala Val Ile Gly His Ser Gln Gly Glu Ile Ala Ala Ala Val Val
            660                 665                 670

Ala Gly Gly Leu Ser Leu Glu Asp Gly Ala Arg Val Val Ala Leu Arg
        675                 680                 685

Ser Arg Ala Leu Arg Ala Leu Ser Gly Leu Gly Gly Met Val Ser Val
    690                 695                 700

Ala Arg Asn Val Asp Glu Val Arg Gly Leu Leu Ala Gly Trp Glu Gly
705                 710                 715                 720

Arg Ile Ser Val Ala Ala Val Asn Gly Pro Ser Ser Val Val Val Ser
                725                 730                 735

Gly Asp Ala Glu Ala Leu Asp Glu Phe Val Ala Ala Cys Asp Ala Ser
            740                 745                 750

Gly Val Arg Ala Arg Arg Val Ala Val Asp Tyr Ala Ser His Ser Ala
        755                 760                 765

His Val Glu Arg Ile Glu Glu Glu Leu Ala Gly Leu Leu Ala Pro Val
```

-continued

```
    770                 775                 780

Ala Pro Arg Ser Cys Asp Val Pro Phe Tyr Ser Thr Leu Ser Gly Gly
785                 790                 795                 800

Val Ile Asp Thr Ala Gly Leu Asp Ala Gly Tyr Trp Tyr Arg Asn Leu
                805                 810                 815

Arg Gly Thr Val Glu Phe Glu Ala Gly Thr Arg Ala Leu Leu Ala Asp
            820                 825                 830

Gly Phe Arg Val Phe Val Glu Val Ser Ala His Pro Val Val Ala Thr
        835                 840                 845

Gly Val Gln Glu Thr Ile Glu Asp Ala Ser Val Gln Ala Gly Val Val
    850                 855                 860

Gly Thr Leu Arg Arg Asp Glu Gly Gly Leu Glu Arg Phe Ala Leu Ser
865                 870                 875                 880

Leu Gly Glu Ala Trp Ala Leu Gly Ala Glu Val Asp Trp Glu Thr His
                885                 890                 895

Tyr Ala Gly Thr Arg Pro Arg His Val Asp Leu Pro Thr Tyr Pro Phe
            900                 905                 910

Arg Arg Asp Trp Tyr Trp Leu Thr Pro Ala Glu Ser Ala Ala Ala Ala
        915                 920                 925

Ala Thr Gly Asp Pro Ala Asp Gly Asp Phe Trp Ser Ala Val Glu Ser
    930                 935                 940

Gly Asp Leu Thr Arg Leu Ser Ser Val Leu Glu Val Thr Gly Asp Asp
945                 950                 955                 960

Val Glu Ala Phe Gly Thr Leu Leu Pro Ala Leu Ala Ser Trp Arg Arg
                965                 970                 975

Arg Arg Thr Leu Arg Ser Thr Leu Asp Thr Trp Arg His Arg Val Thr
            980                 985                 990

Trp Thr Ala Leu Thr Gly Ala Asp Asp Ala Val Pro Ala Gly Arg Trp
        995                 1000                1005

Pro Ala Leu Val Pro Ala Gly His Ala Asp Asp Pro Trp Val His Ala
   1010                1015                1020

Val Leu Gly Ala Leu Thr Gly Arg Gly Leu Arg Val Glu Arg His Asp
1025               1030                1035                1040

Leu Thr Gly Asp Glu Asp Thr Ala Ala Leu Thr Ala Leu Leu Thr Gly
               1045                1050                1055

Thr Gly Asp Thr Glu Pro Asp Gly Ala Glu Gly Ile Ala Gly Val Leu
           1060                1065                1070

Ser Leu Leu Ala Leu Asp Glu Arg Pro His Pro Asp His Pro Ala Val
       1075                1080                1085

Pro Arg Gly Leu Ala Thr Ala Lys Glu Leu Leu His Ala Leu Ser Gly
   1090                1095                1100

Thr Glu Ala Ser Val Trp Ala Leu Thr Arg Gly Ala Val Ala Val Asp
1105               1110                1115                1120

Ser Arg Asp Arg Leu Thr Ser Pro Val Gln Ala Glu Thr Trp Gly Phe
               1125                1130                1135

Gly Arg Ala Val Ala Leu Glu Leu Pro Asp Ala Trp Gly Gly Leu Ala
           1140                1145                1150

Asp Leu Pro Ala Asp Pro Asp Ala Arg Ser Leu Ala Arg Leu Ala Thr
       1155                1160                1165

Leu Leu Gly Gly Pro Glu Asp Gln Ile Ala Val Arg Ser Ser Gly Ala
   1170                1175                1180

Tyr Ala Arg Arg Leu Ala Arg Met Pro Leu Pro Glu Pro Ala Arg Val
1185               1190                1195                1200
```

-continued

```
Thr Asp Val Asp Ala Glu Leu Ala Val Arg Ala Ala Asp Asp Gly
                1205                1210                1215

Ile Gly Gly Trp Gly Asp His Asp Thr Val Leu Ile Thr Gly Gly Thr
            1220                1225                1230

Gly Ala Leu Gly Ala His Val Ala Arg Ser Leu Ala Ala Ser Gly Ala
        1235                1240                1245

Arg His Leu Val Leu Thr Ser Arg Arg Gly Pro Gly Ser Pro Gly Ala
    1250                1255                1260

Val Gly Leu Val Ala Glu Leu Glu Glu Leu Gly Ala Arg Val Thr Val
1265                1270                1275                1280

Ala Asp Cys Asp Val Ala Asp Arg Asp Gln Leu Ala Arg Leu Leu Asp
                1285                1290                1295

Ser Leu Pro Ala Gly Leu Pro Leu Thr Gly Val Val His Ala Ala Gly
            1300                1305                1310

Val Leu Asp Asp Gly Val Leu Asp Ala Leu Thr Leu Asp Arg Phe Glu
        1315                1320                1325

Ala Val Leu Arg Pro Lys Thr Leu Gly Thr Ala His Leu His Glu Leu
    1330                1335                1340

Thr Arg Asp His Asp Val Thr Leu Phe Val Leu Phe Ser Ser Ile Val
1345                1350                1355                1360

Gly Val Leu Gly Asn Ala Gly Gln Ala Asn Tyr Ala Ala Ala Asn Ala
                1365                1370                1375

Tyr Leu Asp Ala Val Ala Glu Gln Arg Arg Ala Glu Gly Leu Pro Val
            1380                1385                1390

Thr Ser Val Ala Trp Gly Pro Trp Ala Asp Ala Gly Met Ala Thr Ala
        1395                1400                1405

Asp Val Leu Ala Asp Arg Met Ser His Asp Gly Leu Ala Pro Met Asp
    1410                1415                1420

Pro Val Thr Ala Val Ala Ala Leu Arg Ala Ala Val Ala Glu Gly Val
1425                1430                1435                1440

Pro His Ala Thr Val Leu Asp Val Asp Trp Arg Ala Tyr Gly Thr Ala
                1445                1450                1455

Met Thr Ala Ala Arg Pro Ser Pro Leu Val Gly Asp Leu Pro Glu Val
            1460                1465                1470

Arg Arg Ala Leu Glu Ala Ala Ala Ala Thr Ala Pro Asp Thr His Ala
        1475                1480                1485

Leu Arg Asp Arg Leu Arg Gly Leu Ala Pro Ala Glu Gln Asp Arg Leu
    1490                1495                1500

Leu Thr Asp Leu Val Arg Ala Glu Val Ala Thr Ala Leu Arg His Ser
1505                1510                1515                1520

Ser Pro Glu Ala Val Asp Val Asn Arg Ala Phe Lys Asp Leu Gly Phe
                1525                1530                1535

Asp Ser Leu Thr Ala Val Glu Val Arg Asn Arg Ile Thr Ala Ala Thr
            1540                1545                1550

Asp Val Lys Leu Pro Thr Thr Leu Leu Phe Asp Tyr Pro Asn Thr Thr
        1555                1560                1565

Ala Val Val Ala His Leu Arg Thr Leu Leu Leu Gly Asp Glu Arg Pro
    1570                1575                1580

Val Ala Ala Pro Val Val Val Ser Ala Gly Val Thr Asp Glu Pro Met
1585                1590                1595                1600

Ala Val Val Ala Met Ala Cys Arg Phe Pro Gly Gly Val Thr Thr Pro
                1605                1610                1615
```

-continued

```
Glu Glu Leu Trp His Leu Met Ala Ala Glu Val Asp Ala Val Ser Thr
            1620                1625                1630

Pro Pro Glu Asp Arg Gly Trp Asp Leu Asp Ala Leu Tyr Asp Pro Asp
        1635                1640                1645

Pro Glu Arg His Gly Thr Thr Tyr Ser Arg Glu Gly Gly Phe Ile Gln
    1650                1655                1660

Asp Val Ala Gly Phe Asp Pro Val Phe Phe Gly Ile Ser Pro Arg Glu
1665                1670                1675                1680

Ala Leu Ala Met Asp Pro Gln Gln Arg Leu Leu Leu Glu Thr Ser Trp
                1685                1690                1695

Glu Thr Phe Glu Arg Ala Gly Ile Asp Pro Gly Thr Leu Arg Asn Ser
            1700                1705                1710

Ala Thr Gly Val Phe Val Gly Ser Ile Thr Thr Asp Tyr Gln Val Arg
        1715                1720                1725

Leu Gly Gly Ala Ala Ala Gln Glu Gln Leu Ala Gly His Leu Met Thr
    1730                1735                1740

Gly Asn Ala Ser Ser Ile Ala Ser Gly Arg Leu Ser Tyr Thr Tyr Gly
1745                1750                1755                1760

Phe Glu Gly Pro Ala Val Thr Met Asp Thr Gly Cys Ser Ser Ser Met
                1765                1770                1775

Val Ala Leu His Leu Ala Leu Gln Ser Leu Arg Thr Gly Glu Cys Thr
            1780                1785                1790

Met Ala Leu Ala Gly Gly Val Thr Val Met Ser Thr Pro Glu Pro Tyr
        1795                1800                1805

Val Glu Phe Ser Arg Gln Arg Gly Leu Ala Ala Asp Gly Arg Cys Lys
    1810                1815                1820

Ala Phe Ala Glu Gly Ala Asp Gly Met Gly Phe Ala Glu Gly Val Gly
1825                1830                1835                1840

Leu Val Leu Leu Glu Arg Leu Ser Asp Ala Arg Arg Asn Gly His Pro
                1845                1850                1855

Val Leu Ala Val Val Arg Gly Ser Ala Leu Asn Gln Asp Gly Ala Ser
            1860                1865                1870

Asn Gly Leu Thr Ala Pro Asn Gly Pro Ser Gln Gln Arg Val Ile Arg
        1875                1880                1885

Gln Ala Leu Ala Asn Ala Gly Leu Ala Pro Gly Glu Val Asp Val Val
    1890                1895                1900

Glu Ala His Gly Thr Gly Thr Pro Leu Gly Asp Pro Ile Glu Ala Gln
1905                1910                1915                1920

Ala Ile Leu Ala Thr Tyr Gly Gln Asp Arg Asp Pro Ala Arg Pro Leu
                1925                1930                1935

Leu Leu Gly Ser Leu Lys Ser Asn Ile Gly His Thr Gln Ala Ala Ala
            1940                1945                1950

Gly Val Ala Gly Met Met Lys Met Ile Leu Ala Met Arg Gln Gly Thr
        1955                1960                1965

Leu Pro Lys Ser Leu His Ile Thr Arg Pro Thr Ser Val Val Asp Trp
    1970                1975                1980

Ser Ser Gly Ala Val Arg Leu Val Thr Glu Ser Thr Pro Trp Pro Glu
1985                1990                1995                2000

Thr Gly Arg Pro Arg Arg Ala Gly Val Ser Ser Phe Gly Ile Ser Gly
                2005                2010                2015

Thr Asn Gly His Leu Ile Leu Glu Glu Ala Pro Ala Pro Glu Pro Ala
            2020                2025                2030

Glu Asp Glu Pro Ala Asp Pro Phe Thr Glu Pro Ser Ala Asp Asp Ser
```

-continued

```
        2035                2040                2045

Ala Asp Thr Val Arg Ser Trp Met Val Ser Gly Lys Ser Arg Ala Ala
    2050                2055                2060

Val Gly Glu Gln Ala Ala Arg Leu Ala Ala Ser Val Arg Thr Ser Asp
2065                2070                2075                2080

Ala Ser Val Leu Asp Val Ala His Ala Leu Val Ser Ser Arg Val Ala
                2085                2090                2095

Met Asp Arg Arg Ala Val Val Val Gly Arg Asp Gly Glu Glu Leu Leu
            2100                2105                2110

Ala Gly Leu Asp Ala Leu Ala Ala Gly Glu Pro Ser Pro Arg Leu Val
        2115                2120                2125

Glu Gly Ser Val Gly Asp Gly Ser Gly Lys Val Ala Phe Val Phe Pro
    2130                2135                2140

Gly Gln Gly Ser Gln Trp Val Gly Met Ala Val Glu Leu Leu Gly Ser
2145                2150                2155                2160

Ser Pro Val Phe Ala Gly Arg Val Ala Glu Cys Ala Ala Ala Leu Glu
                2165                2170                2175

Pro Phe Thr Glu Trp Ser Leu Leu Asp Val Leu Asn Gly Val Glu Gly
            2180                2185                2190

Ala Ala Ser Leu Glu Arg Val Asp Val Val Gln Pro Val Leu Trp Ala
        2195                2200                2205

Val Met Val Ser Leu Ala Glu Val Trp Arg Ala Gln Gly Val Glu Pro
    2210                2215                2220

Gly Ala Val Ile Gly His Ser Gln Gly Glu Ile Ala Ala Ala Val Val
2225                2230                2235                2240

Ala Gly Gly Leu Ser Leu Glu Asp Gly Ala Arg Val Val Ala Leu Arg
                2245                2250                2255

Ser Arg Ala Leu Arg Ala Leu Ser Gly Leu Gly Gly Met Val Ser Val
            2260                2265                2270

Ala Arg Asn Val Asp Glu Val Arg Gly Leu Leu Ala Gly Trp Glu Gly
        2275                2280                2285

Arg Ile Ser Val Ala Ala Val Asn Gly Pro Ser Ser Val Val Val Ser
    2290                2295                2300

Gly Asp Ala Glu Ala Leu Asp Glu Phe Val Ala Ala Cys Asp Ala Ser
2305                2310                2315                2320

Gly Val Arg Ala Arg Arg Val Ala Val Asp Tyr Ala Ser His Ser Ala
                2325                2330                2335

His Val Glu Arg Ile Glu Glu Glu Leu Ala Gly Leu Leu Ala Pro Val
            2340                2345                2350

Ala Pro Arg Ser Cys Asp Val Pro Phe Tyr Ser Thr Leu Ser Gly Gly
        2355                2360                2365

Val Ile Asp Thr Ala Gly Leu Asp Ala Gly Tyr Trp Tyr Arg Asn Leu
    2370                2375                2380

Arg Gly Thr Val Glu Phe Glu Ala Gly Thr Arg Ala Leu Leu Ala Asp
2385                2390                2395                2400

Gly Phe Arg Val Phe Val Glu Val Ser Ala His Pro Val Val Ala Thr
                2405                2410                2415

Gly Val Gln Glu Thr Ile Glu Asp Ala Ser Val Gln Ala Gly Val Val
            2420                2425                2430

Gly Thr Leu Arg Arg Asp Glu Gly Gly Leu Glu Arg Phe Ala Leu Ser
        2435                2440                2445

Leu Gly Glu Ala Trp Ala Leu Gly Ala Glu Val Asp Trp Glu Thr His
    2450                2455                2460
```

-continued

```
Tyr Ala Gly Thr Arg Pro Arg His Val Asp Leu Pro Thr Tyr Ala Phe
2465                2470                2475                2480

Gln Arg Gln His Tyr Trp Pro Arg Phe Ala Glu Leu Gly Gly Asp Val
                2485                2490                2495

Ser Ser Ala Gly Leu Asp Ser Pro Asp His Pro Leu Leu Gly Ala Ser
            2500                2505                2510

Val Glu Leu Ala Gly Gly Asp Gly Leu Val Ala Thr Ala Arg Trp Ser
        2515                2520                2525

Leu Arg Thr His Pro Trp Leu Ala Asp His Ala Val Ser Gly Thr Val
    2530                2535                2540

Ile Val Pro Gly Thr Ala Leu Val Glu Ser Val Ile Arg Ala Gly Asp
2545                2550                2555                2560

Val Leu Gly Cys Gly Arg Ile Glu Glu Leu Ala Leu Gln Ala Pro Val
                2565                2570                2575

Val Leu Gln Glu Arg Gly Glu Ala Gln Val Gln Ile Gly Val Gly Glu
            2580                2585                2590

Pro Asp Ala Ser Gly Arg Arg Pro Val Thr Val His Thr Arg Thr Thr
        2595                2600                2605

Gly Pro Asp Gly Ala Thr Glu Asp Leu Trp Thr Leu Arg Ala Gln Gly
    2610                2615                2620

Thr Leu Thr Glu Pro Gly Ala Pro Ala Val Asp Arg Pro Glu Glu Phe
2625                2630                2635                2640

Thr Ser Trp Pro Pro Pro Gly Ala Thr Ala Val Ala Ala Glu Gly Phe
                2645                2650                2655

Tyr Glu Leu Leu Ala Gly Arg Gly Tyr Glu Phe Gly Pro Val Phe Gln
            2660                2665                2670

Gly Val Arg Ala Thr Trp Ser Arg Gly Glu Asp Leu Tyr Ala Glu Val
        2675                2680                2685

Val Leu Pro Glu Gln Val Arg Gly Asp Ala Gly Arg Phe Gly Ile His
    2690                2695                2700

Pro Ala Leu Leu Asp Ala Ala Leu His Ala Ala His Leu Ala Pro Gly
2705                2710                2715                2720

Ser Ala Gly Arg Thr Val Val Pro Phe Thr Trp Ser Gly Val Cys Leu
                2725                2730                2735

His Ala Ala Gly Ala Thr Ala Leu Arg Val Arg Val Ser Pro Ala Gly
            2740                2745                2750

Gln Asp Ala Ile Ser Val Gln Leu Thr Asp Pro Thr Gly Ala Pro Val
        2755                2760                2765

Ala Thr Ile Asp Ala Leu Ala Val Arg Glu Ile Ala Pro Asp Thr Leu
    2770                2775                2780

Asp Pro Ser Ala Arg Ala Ala Arg Asp Trp Leu Phe Arg Leu Asp Trp
2785                2790                2795                2800

Thr Pro Val Thr Pro Pro Ala Ala Val Pro Ala Ala Thr Gly Trp Ala
                2805                2810                2815

Val Leu Gly Thr Pro Ala Asp Pro Val Thr Ala Pro Asp Gly Ser Gly
            2820                2825                2830

Thr Thr Leu Pro Ala Phe Ala Thr Pro Gly Ala Leu Ala Glu His Thr
        2835                2840                2845

Glu Ala Asn Gly His Arg Pro Asp Ala Val Leu Leu Phe Ala Gly Ala
    2850                2855                2860

Ala Ala Ser Gly Thr Ala Ala Ala Pro Asp Ala Glu Pro Gly Val Pro
2865                2870                2875                2880
```

-continued

```
Asp Ala Val Leu Asp Asp Val Leu Ala Thr Val Gln Ser Trp Leu Ala
                2885                2890                2895

Asp Glu Thr Thr Glu Gly Val Pro Leu Val Val Val Thr Arg Gly Ala
            2900                2905                2910

Val Pro Thr Gly Pro Ala Asp Pro Ala His Asp Leu Pro Gly Ala Ala
        2915                2920                2925

Val Trp Gly Leu Val Arg Ser Ala Gln Ser Gln His Pro Gly Arg Leu
    2930                2935                2940

Val Leu Val Asp Leu Asp Ile His Asp Asp Ser Trp Leu Ala Leu Pro
2945                2950                2955                2960

Ala Ala Leu Ala Ala Gly Glu Pro Gln Leu Ala Leu Arg Gln Gly Ala
                2965                2970                2975

Ala Tyr Ala Pro Arg Leu Val Arg Pro Arg Thr Ser Asp Ala Leu Thr
            2980                2985                2990

Val Pro Glu Gly Thr Gly Asn Trp Arg Leu Asp Ile Pro Glu Lys Gly
        2995                3000                3005

Ser Val Asp Arg Leu Asp Leu Val Ala Ala Pro Gly Thr Ala Glu Glu
    3010                3015                3020

Pro Ala Ala Gly Glu Val Val Ile Glu Val Arg Ala Ala Gly Leu Asn
3025                3030                3035                3040

Phe Arg Asp Val Leu Asn Thr Leu Gly Met Tyr Pro Gly Pro Ala Val
                3045                3050                3055

Leu Leu Gly Ala Glu Ala Ala Gly Val Val Thr Ala Val Gly Glu Gly
            3060                3065                3070

Val Thr Gly Phe Ala Pro Gly Asp Arg Val Met Gly Leu Val Ser Gly
        3075                3080                3085

Gly Phe Ala Pro Arg Ala Val Ala Asp Ala Arg Met Leu Ala Pro Val
    3090                3095                3100

Pro Asp Gly Trp Thr Trp Ala Gln Ala Ala Ser Val Pro Val Ala Phe
3105                3110                3115                3120

Leu Thr Ala Tyr Tyr Gly Leu Arg Asp Leu Ala His Leu Asp Ala Gly
                3125                3130                3135

Glu Ser Val Leu Val His Ala Ala Ala Gly Gly Val Gly Met Ala Ala
            3140                3145                3150

Ala Gln Leu Ala Arg His Trp Gly Ala Glu Val Tyr Gly Thr Ala Gly
        3155                3160                3165

Asp His Lys Arg Thr Leu Leu Arg Ala Asp Gly Trp Asp Asp Ala His
    3170                3175                3180

Leu Ala Ser Ser Arg Thr Leu Ala Phe Glu Asp Arg Phe Arg Thr Thr
3185                3190                3195                3200

Ser Gly Gly Arg Gly Val Asp Val Val Leu Asn Ser Leu Ala Gly Asp
                3205                3210                3215

Tyr Ile Asp Ala Ser Leu Arg Leu Leu Ala Pro Gly Gly Arg Leu Val
            3220                3225                3230

Asp Met Gly Lys Thr Asp Val Arg Asp Pro Gly Gln Val Leu Arg Asp
        3235                3240                3245

His Pro Ala Ala Ala Leu Tyr Gln Ala Tyr Glu Leu Arg Glu Ala Gly
    3250                3255                3260

Glu Asp Arg Ile Gln Glu Met Phe Arg Asp Leu Ser Glu Leu Phe Ala
3265                3270                3275                3280

Ser Gly Ala Leu Arg Pro Leu Pro Thr Val Thr Trp Asp Val Arg His
                3285                3290                3295

Ala Arg Glu Ala Phe Arg His Met Ala Gln Ala Lys His Tyr Gly Lys
```

-continued

```
        3300                3305                3310

Ile Val Leu Thr Leu Pro Arg Ala Trp Asp Pro Glu Gly Thr Val Leu
    3315                3320                3325

Val Thr Gly Gly Ala Gly Val Leu Gly Gly Ile Leu Ala Arg His Leu
  3330                3335                3340

Val Thr Arg His Gly Met Arg His Leu Val Leu Thr Gly Arg Arg Gly
3345                3350                3355                3360

Pro Asp Thr Pro Gly Ala Gly Glu Leu Ala Ala Glu Leu Arg Glu Leu
            3365                3370                3375

Gly Ala Glu Val Thr Leu Ala Ala Cys Asp Ala Ala Asp Ala Asp Ala
        3380                3385                3390

Leu Ala Ala Val Leu Ala Ala Val Pro Ala Glu His Pro Leu Thr Ala
    3395                3400                3405

Val Val His Ala Ala Gly Val Leu Asp Asp Gly Val Leu Glu Ser Leu
  3410                3415                3420

Thr Pro Asp Arg Leu Arg Thr Val Leu Ala Pro Lys Ala Asp Ala Ala
3425                3430                3435                3440

Arg His Leu His Arg Leu Thr Arg Asp Leu Asp Leu Thr Asp Leu Val
            3445                3450                3455

Leu Phe Ser Ala Gly Ala Gly Val Phe Gly Asn Ala Gly Gln Ala Asn
        3460                3465                3470

Tyr Ala Ala Ala Asn Thr Tyr Leu Asp Ala Leu Ala His Arg Arg Arg
    3475                3480                3485

Ala Asp Gly Leu Pro Thr Thr Ser Leu Ser Trp Gly Leu Trp Ala Asp
  3490                3495                3500

Thr Ser Ala Leu Thr Gly Gln Leu Asp Asp Thr Asp Leu Ala Arg Val
3505                3510                3515                3520

Arg Arg Ser Gly Val Leu Pro Leu Ser Ala Ala Asp Gly Met Val Leu
            3525                3530                3535

Phe Asp Ala Ala Leu Thr Glu Gln Arg Pro His Leu Val Pro Val Arg
        3540                3545                3550

Leu Glu Thr Gly Gln Leu Arg Ala Ser Gly Asp Glu Val Pro Pro Leu
    3555                3560                3565

Leu Arg Ser Leu Tyr Arg Gly Pro Val Arg Arg Thr Ala Glu Ala Gly
  3570                3575                3580

Ala Ala Thr Gly Thr Asp Gly Leu Arg Ala Arg Leu Ala Gly Arg Ser
3585                3590                3595                3600

Ala Glu Asp Arg Leu Ser Thr Leu Arg Asp Leu Val Gly Ala His Ala
            3605                3610                3615

Ala Ala Val Leu Gly His Asp Asp Thr Glu Pro Phe His Ala Gly Arg
        3620                3625                3630

Ala Phe Arg Asp Leu Gly Phe Asp Ser Leu Thr Ala Val Glu Leu Arg
    3635                3640                3645

Asn Arg Leu Ser Ala Ala Thr Gly Leu Arg Leu Pro Ala Thr Leu Val
  3650                3655                3660

Phe Asp His Pro Thr Val Ala Ala Leu Ala Ala His Leu Asp Gly Glu
3665                3670                3675                3680

Leu Ser Asp Gly Thr Pro Ala Ala Leu Pro Ala Ala Pro Ala Pro Ala
            3685                3690                3695

Pro Ala Ala Pro Gly Asp Asp Asp Pro Phe Ala Ile Val Gly Met Ala
        3700                3705                3710

Cys Arg Leu Pro Gly Asp Ile His Ser Pro Glu Asp Leu Trp Arg Leu
    3715                3720                3725
```

```
Leu Ala Asp Gly Ala Asp Ala Val Ala Pro Phe Pro Asp Asp Arg Gly
   3730                3735                3740

Trp Asp Leu Ala Arg Leu Tyr Asp Ser Val Pro Glu Gly Gln Gly Ser
3745                3750                3755                3760

Ser Arg Thr Arg Glu Gly Gly Phe Leu His Asp Ala Ala Asp Phe Asp
                3765                3770                3775

Ala Asp Phe Phe Gly Ile Ser Pro Arg Glu Ala Leu Ala Met Asp Pro
            3780                3785                3790

Gln Gln Arg Leu Leu Leu Glu Thr Ala Trp Glu Thr Phe Glu Arg Ala
       3795                3800                3805

Gly Ile Asp Pro Arg Ser Val Arg Gly Ser Arg Thr Gly Val Phe Ala
   3810                3815                3820

Gly Leu Ser Ser Ser Asp Tyr Leu Lys Arg Val Thr His Val Pro Asp
3825                3830                3835                3840

Glu Ile Ala Gly Tyr Val Asn Asn Gly Asn Ala Asn Ser Ile Val Ser
                3845                3850                3855

Gly Arg Val Ser Tyr Thr Leu Gly Leu Glu Gly Pro Ala Val Thr Val
            3860                3865                3870

Asp Thr Ala Cys Ser Ser Ser Leu Val Ala Leu His Met Ala Leu Gln
       3875                3880                3885

Ala Leu Arg Arg Gly Glu Cys Thr Met Ala Leu Ala Gly Gly Val Thr
   3890                3895                3900

Val Met Ser Ser Pro Glu Ile Ile Val Asp Phe Ser Arg Gln Arg Gly
3905                3910                3915                3920

Leu Ala Ala Asp Gly Arg Cys Lys Pro Phe Ala Glu Ala Ala Asp Gly
                3925                3930                3935

Thr Gly Phe Ser Glu Gly Val Gly Leu Ile Leu Val Glu Arg Leu Ser
            3940                3945                3950

Asp Ala Arg Arg Asn Gly His Gln Val Leu Ala Val Val Arg Gly Ser
       3955                3960                3965

Ala Val Asn Gln Asp Gly Ala Ser Asn Gly Leu Ser Ala Pro Asn Gly
   3970                3975                3980

Pro Ala Gln Gln Arg Val Ile Arg Gln Ala Leu Ala Asp Ala Gly Val
3985                3990                3995                4000

Gly Ala Ala Glu Val Asp Val Val Glu Ala His Gly Thr Gly Thr Arg
                4005                4010                4015

Leu Gly Asp Pro Ile Glu Ala Gln Ala Leu Leu Ala Thr Tyr Gly Arg
            4020                4025                4030

Asp Arg Asp Gly Gly His Pro Leu Phe Leu Gly Ser Val Lys Ser Asn
       4035                4040                4045

Leu Gly His Thr Gln Ala Ala Ala Gly Val Ala Gly Val Met Lys Met
   4050                4055                4060

Val Leu Ala Leu Arg His Arg Leu Leu Pro Glu Ser Leu His Ile Asp
4065                4070                4075                4080

Ala Pro Thr Pro His Val Asp Trp Ala Asp Ser Gly Val Arg Leu Leu
                4085                4090                4095

Thr Glu Ala Thr Ala Trp Pro Glu Ala Gly Ala Ser Arg Pro Arg Arg
            4100                4105                4110

Ala Ala Val Ser Ser Phe Gly Ile Ser Gly His Gln Arg Pro Arg His
       4115                4120                4125

Pro Gly Gly Gly Pro Pro Pro Pro Pro Ala Arg Thr Ala Ala Ser Arg
   4130                4135                4140
```

-continued

Ser Pro Pro Ala Pro Asp Ala Ala Glu Thr Arg Pro Ala Pro Leu Pro
4145 4150 4155 4160

Trp Val Leu Ser Ala Arg Ser Glu Ala Ala Leu Arg Gly Gln Ala Lys
4165 4170 4175

Ala Leu Leu Thr His Leu Asp Ala His Pro Gly Thr Asp Pro Ala Asp
4180 4185 4190

Ile Ala His Thr Leu Val Thr Arg Arg Ala Gln Leu Glu Lys Arg Ala
4195 4200 4205

Val Val Val Gly Ser Ala Thr Gly Asp Phe Arg Ala Gly Leu Ala Ala
4210 4215 4220

Leu Ala Glu Gly Ser Pro Ala Ala His Val Val Thr Gly Gly Arg Gly
4225 4230 4235 4240

Ala Gly Arg Asp Arg Arg Thr Val Leu Val Phe Pro Gly Gln Gly Ser
4245 4250 4255

Gln Trp Ala Gly Met Gly Ala Glu Leu Leu Asp Ala Ser Pro Ala Phe
4260 4265 4270

Ala Asp Arg Val Ala Ala Cys Glu Glu Ala Leu Ala Pro Tyr Val Asp
4275 4280 4285

Trp Ser Leu Thr Ala Val Leu Arg Gln Glu Glu Gly Ala Pro Ala Leu
4290 4295 4300

Asp Arg Val Asp Val Val Gln Pro Val Thr Trp Ala Val Met Val Ala
4305 4310 4315 4320

Leu Ala Glu Val Trp Arg Ala His Gly Leu Arg Pro Ala Ala Val Leu
4325 4330 4335

Gly His Ser Gln Gly Glu Ile Ala Ala Ala Ala Val Ala Gly Ala Leu
4340 4345 4350

Ser Leu Ala Asp Ala Ala Arg Ile Val Ala Val Arg Ser Arg Ala Ile
4355 4360 4365

Ala Arg Glu Leu Ser Gly His Gly Gly Met Val Ala Val Thr Ala Pro
4370 4375 4380

His Asp Glu Val Thr Ala Leu Leu Ala Asp Leu Pro Gly Val Cys Val
4385 4390 4395 4400

Ala Ala Val Asn Gly Pro Ser Ser Val Val Val Ser Gly Asp Thr Gly
4405 4410 4415

Gly Leu Asp Thr Leu Leu Ala Ala Cys Glu Glu Gln Gly Val Arg Ala
4420 4425 4430

Arg Arg Val Pro Val Asp Tyr Ala Ser His Ser Ala His Val Asp Arg
4435 4440 4445

Leu Ala Glu Ser Leu Pro Ala Ala Leu Asp Gly Ile Glu Pro Arg Asp
4450 4455 4460

Gly Asp Ile Pro Phe Phe Ser Thr Val Thr Ala Asp Trp His Pro Gly
4465 4470 4475 4480

Thr Gly Leu Gly Ala Ala Tyr Trp His Arg Asn Leu Arg Gly Thr Val
4485 4490 4495

Arg Leu Glu Glu Ser Leu Arg Ala Leu Val Glu Gln Gly His Asp Val
4500 4505 4510

Phe Val Glu Cys Gly Pro His Pro Val Leu Thr Val Gly Ile Glu Asp
4515 4520 4525

Thr Val Ala Ala Leu Gly Ala Asp Ala Val Ala Leu Gly Ser Leu Arg
4530 4535 4540

Arg Asp Asp Gly Gly Pro Ala Arg Val Leu Thr Ala Leu Ala Ala Ala
4545 4550 4555 4560

His Val Glu Gly Val Pro Val Asp Trp Arg Pro Ala Val Ser His Gly

-continued 4565 4570 4575

Thr Ala Val Asp Leu Pro Thr Tyr Ala Phe Gln Arg Arg Arg Tyr Trp
4580 4585 4590

Leu Asp Ala Gly Thr Pro Gln Gly Asp Pro Ala Gly Leu Asp Ser Val
4595 4600 4605

Val Arg Leu Ala Asp Gly Gly Ala Val Leu Ser Gly Ser Leu Ser Leu
4610 4615 4620

Thr Thr Gln Pro Trp Leu Asp Ala His Arg Thr His Gly Ala Ala Val
4625 4630 4635 4640

Val Pro Thr Thr Ala Leu Leu Asp Trp Ala Val Arg Ala Gly Asp Glu
4645 4650 4655

Thr Gly Leu Pro Val Val Ala Ala Leu Asp Glu His Ser Pro Leu Val
4660 4665 4670

Val Pro Glu Glu Gly His Val Glu Ile Gln Leu Thr Val Ser Ala Ala
4675 4680 4685

Asp Thr Asp Ser Arg Pro Phe Ser Val His Ser Arg Leu His Ala Ala
4690 4695 4700

Asp Ala Gly Glu Pro Ala Thr Pro Trp Thr Arg Asn Ala Thr Gly Asp
4705 4710 4715 4720

Leu Thr Asp Arg Pro Thr Thr Thr Pro Gln Ala Ser Gly Thr Trp Pro
4725 4730 4735

Pro Ala Asp Ala Val Ala Ala Asp Pro Ala Pro Val Arg Ala Leu Ala
4740 4745 4750

Glu Asp Arg Gly Leu Asp Leu Ala Ala Pro Phe Asp Thr Val Arg Ser
4755 4760 4765

Leu Trp Arg Ala Gly Thr Asp Val Leu Ala Glu Val Ala Leu Pro Asp
4770 4775 4780

Ala Ala His Ala Asp Ala Ala Arg Phe Arg Leu His Pro Ala Leu Leu
4785 4790 4795 4800

Gln Thr Pro Leu Ala Leu Ala Ala Thr Thr Glu Glu Ala Thr Ala Pro
4805 4810 4815

Val Leu Pro Ala Ala Trp Arg Asp Val Thr Val His Ala Thr Gly Ala
4820 4825 4830

Ser Arg Leu Arg Val Arg Leu Thr Pro Gly Asp Asp Ala Thr Trp Ser
4835 4840 4845

Val Glu Ala Arg Asp Ala Ala Gly Asp Leu Val Leu Thr Gly Thr Ala
4850 4855 4860

Val Thr Arg Ser Ala Gly Pro Asp Arg Leu Pro Ala Thr Ala Gly Pro
4865 4870 4875 4880

Asp Ala Pro His Arg Val Ala Trp Leu Pro Trp Thr Asp Thr Thr Ser
4885 4890 4895

Ser Ala Thr Pro Glu Pro His Gly Pro Trp Ala Val Ile Gly Ala Pro
4900 4905 4910

Gly Arg Leu Thr Ala Ala Leu Glu Arg Ser Gly Ala Thr Val Gln Leu
4915 4920 4925

His Pro Asp Leu Ala Ala Leu Thr Thr Ala Leu Asp Asn Asp Glu Ala
4930 4935 4940

Ala Pro Pro Ala Leu Val Val Ala Phe His Gly His Asp Ser Gly Glu
4945 4950 4955 4960

Asp Pro Thr Lys Ala Ala His Thr Ser Ala Ala Arg Ala Leu Thr Leu
4965 4970 4975

Ser Thr Ala Trp Leu Arg Glu Pro Arg Leu Ala Asp Ala Arg Leu Leu
4980 4985 4990

-continued

```
Leu Val Thr Glu Gly Ala Val Ala Thr Gly Pro Asp Asp Thr Val Pro
       4995                5000                5005

Gly Leu Ala Asp Ala Thr Ala Trp Gly Leu Leu Arg Ser Ala Gln Thr
   5010                5015                5020

Glu His Pro Gly Arg Phe Leu Leu Ala Asp Leu Asp Pro Ala Pro Gly
5025                5030                5035                5040

Asp Thr Asp Glu Asp Ser Ala Ala Asp Ala Leu Ile Ala Ala Ala Ala
               5045                5050                5055

Ala Ala Ala Arg Thr Gly Glu His Gln Phe Ala Val Arg Ala Gly Thr
           5060                5065                5070

Val Thr Val Pro Arg Leu Val Pro Ala Gly His Pro Glu Gly Ala Pro
       5075                5080                5085

Ala Pro Ala Ala Thr Ala Pro Trp Gly Glu Gly Thr Gly Ala Gly Thr
   5090                5095                5100

Val Leu Ile Thr Gly Gly Thr Gly Thr Leu Gly Ala Leu Val Ala Arg
5105                5110                5115                5120

His Leu Val Thr Arg His Gly Val Arg His Leu Leu Leu Thr Ser Arg
               5125                5130                5135

Arg Gly Pro Gly Ala Pro Gly Ala Ala Ala Leu Arg Glu Glu Leu Ala
           5140                5145                5150

Ala Leu Gly Ala Glu Ala Glu Ile Val Ala Cys Asp Val Ala Asp Arg
       5155                5160                5165

Glu Gln Leu Ala Gly Val Leu Asp Ala Val Pro Ala Glu His Pro Leu
   5170                5175                5180

Thr Ala Val Val His Thr Ala Gly Val Leu Asp Asp Gly Thr Leu Asp
5185                5190                5195                5200

Gly Leu Thr Ala Asp Arg Val Ala His Val Leu Arg Pro Lys Ala Asp
               5205                5210                5215

Ala Ala Trp His Leu His Glu Leu Thr Arg Asp Thr Lys Leu Thr Ala
           5220                5225                5230

Phe Val Met Phe Ser Ser Tyr Ala Gly Val Ala Gly Gly Pro Gly Gln
       5235                5240                5245

Ala Asn Tyr Ala Ala Ala Asn Ala Phe Leu Asp Ala Leu Ala Gln His
   5250                5255                5260

Arg Arg Ala Ser Gly Leu Pro Ala His Ser Leu Ala Trp Gly Leu Trp
5265                5270                5275                5280

Glu Asp Arg Ser Asp Leu Thr Gly Ala Leu Asp Thr Thr Gly Leu Ala
               5285                5290                5295

Arg Leu Glu Arg Ser Gly Ile Arg Pro Leu Thr Ala Gly Gln Gly Leu
           5300                5305                5310

Ala Leu Leu Asp Ala Ser Thr Ala Leu Asp Thr Ala His Leu Val Pro
       5315                5320                5325

Val Arg Leu Asp Thr Arg Thr Leu Arg Ala Asp Glu Val Pro Pro Leu
   5330                5335                5340

Leu Arg Ala Leu Ala Arg Pro Ala Val Arg Arg Ala Ala Asp Ser Gly
5345                5350                5355                5360

Pro Gly Ala Ala Thr Gly Ala Pro Ala Asp Leu Arg Glu Arg Leu Ala
               5365                5370                5375

Gly Leu Ser Gly Pro Gln Gln Arg Ala Leu Leu His Arg Thr Val Leu
           5380                5385                5390

Gly His Leu Ala Ala Val Leu Gly His Ala Ser Ala Ala Ser Leu Asp
       5395                5400                5405
```

-continued

```
Ala Asp Arg Gly Phe Leu Asp Leu Gly Met Ser Ser Leu Thr Ala Val
   5410                5415                5420

Glu Leu Arg Asn Arg Leu Asn Ala Asp Thr Gly Leu Ser Leu Pro Thr
5425                5430                5435                5440

Thr Leu Ile Phe Asp His Pro Asp Pro Ala Ala Leu Val Arg His Leu
               5445                5450                5455

Gln Thr Glu Leu Gly Thr Gly Ala Gly Glu Pro Asp Gln Ala Val Phe
           5460                5465                5470

Ala Glu Leu Ala Ala Leu Glu Ala Ala Val Gly Gly Ala Ala Leu Asp
       5475                5480                5485

Asp Gln Asp Arg Ala Arg Leu Ala Gln Arg Leu Lys Ala Leu Gly Trp
   5490                5495                5500

Lys Leu Asp Ala Thr Ser Gln Asp Ala Asp Glu Pro Asp Asp Asp Ser
5505                5510                5515                5520

Asp Leu Asp Thr Thr Thr Asp Asp Glu Met Phe Asp Leu Ile Asp Asn
               5525                5530                5535

Glu Leu Gly Leu Ala
           5540


<210> SEQ ID NO 5
<211> LENGTH: 2049
<212> TYPE: PRT
<213> ORGANISM: Streptomyces sp. FR-008

<400> SEQUENCE: 5

Met Pro Asp Asp Lys Lys Leu Val Asp Tyr Leu Lys Trp Val Thr Ala
 1               5                  10                  15

Asp Leu His Lys Thr Arg Arg Arg Leu Glu Glu Ala Glu Ala His Arg
            20                  25                  30

Arg Glu Pro Ile Ala Val Val Gly Met Ala Cys Arg Leu Pro Gly Gly
        35                  40                  45

Val Ala Thr Pro Glu Glu Tyr Trp Arg Leu Leu Glu Glu Gly Arg Asp
    50                  55                  60

Gly Ile Ala Pro Phe Pro Ala Asp Arg Gly Trp Asp Leu Asp Ala Leu
65                  70                  75                  80

Asn Gly Glu Gly Ala Gly Ser Ser Ala Ala Gly Glu Gly Gly Phe Val
                85                  90                  95

Asp Ala Ala Ala Phe Asp Ala Gly Phe Phe Gly Ile Ser Pro Arg Glu
            100                 105                 110

Ala Val Ala Met Asp Pro Gln Gln Arg Ile Leu Leu Glu Thr Thr Trp
        115                 120                 125

Glu Ala Val Glu Arg Ala Gly Ile Asp Pro Val Ser Leu Arg Gly Ser
    130                 135                 140

Arg Thr Gly Val Tyr Val Gly Thr Ala Gly Val Asp Tyr Val Gly Val
145                 150                 155                 160

Val Met Asn Ser Arg Glu Asp Ala Glu Gly His Ala Thr Thr Gly Leu
                165                 170                 175

Thr Ala Ser Val Val Ser Gly Arg Leu Ser Tyr Ala Phe Asp Leu Ala
            180                 185                 190

Gly Pro Ala Val Thr Val Asp Thr Ala Cys Ser Ala Ser Leu Val Ala
        195                 200                 205

Ile His Leu Ala Ala Gln Ala Leu Arg Asn Gly Glu Cys Gly Leu Ala
    210                 215                 220

Leu Ala Gly Gly Val Thr Val Met Ser Thr Pro Met Gly Phe Ser Gly
225                 230                 235                 240
```

-continued

```
Phe Thr Arg Gln Gly Gly Ile Ser Thr Ser Gly Arg Cys Lys Ala Phe
                245                 250                 255

Ala Asp Ser Ala Asp Gly Thr Gly Trp Ala Glu Gly Ala Gly Val Leu
            260                 265                 270

Val Leu Glu Arg Leu Ser Asp Ala Arg Arg Asn Gly His Gln Val Leu
        275                 280                 285

Ala Val Val Arg Gly Ser Ala Val Asn Gln Asp Gly Ala Ser Asn Gly
    290                 295                 300

Leu Thr Ala Pro Asn Gly Pro Ser Gln Gln Arg Val Ile Arg Gln Ala
305                 310                 315                 320

Leu Ala Gly Ala Gly Leu Ser Ala Ala Asp Val Asp Ala Val Glu Ala
                325                 330                 335

His Gly Thr Gly Thr Pro Leu Gly Asp Pro Ile Glu Ala Gln Ala Leu
            340                 345                 350

Leu Ala Thr Tyr Gly Gln Asp Arg Pro Glu Asp Arg Pro Leu Leu Leu
        355                 360                 365

Gly Ser Val Lys Ser Asn Ile Gly His Ser Gln Ala Ala Ala Gly Val
    370                 375                 380

Ala Gly Val Ile Lys Thr Val Leu Ala Ile Gln His Gly Val Leu Pro
385                 390                 395                 400

Arg Ser Leu His Ile Asp Glu Ala Ser Ser His Val Asp Trp Gly Ala
                405                 410                 415

Gly Asn Val Arg Leu Leu Thr Glu Asn Thr Ala Trp Pro Glu Thr Gly
            420                 425                 430

Arg Pro Arg Arg Ala Gly Val Ser Ser Phe Gly Ile Ser Gly Thr Asn
        435                 440                 445

Ala His Val Val Ile Glu Gln Ala Pro Glu Pro Glu Glu Pro Ala Thr
    450                 455                 460

Pro Glu Asp Gly Thr Pro Thr Ala Arg Pro Thr Leu Val Pro Trp Pro
465                 470                 475                 480

Val Ser Ala Lys Thr Arg Glu Ala Leu Asp Ala Gln Leu Ala Arg Val
                485                 490                 495

Thr Ser Val Thr Gly Ala Ala Pro Leu Asp Ile Gly His Ser Leu Ala
            500                 505                 510

Thr Gly Arg Ser Thr Phe Glu His Arg Ala Val Leu Leu Ala Gly Pro
        515                 520                 525

Glu Gly Glu Pro Ala Glu Ala Ala Arg Gly Arg Ala Thr Glu Arg Thr
    530                 535                 540

Leu Ala Leu Leu Phe Ser Gly Gln Gly Ser Gln Arg Ala Gly Met Gly
545                 550                 555                 560

Arg Glu Leu Tyr Glu Arg Phe Pro Val Phe Ala Glu Ala Leu Asp Ala
                565                 570                 575

Val Val Ala Arg Leu Asp Thr Gly Leu Glu Arg Ser Leu Arg Glu Val
            580                 585                 590

Leu Phe Val Glu Glu Gly Ser Glu Ala Ala Ala Leu Leu Asp Val Thr
        595                 600                 605

Gly Tyr Thr Gln Pro Ala Leu Phe Ala Val Glu Val Ala Leu Phe Arg
    610                 615                 620

Leu Val Glu Ser Trp Gly Val Ser Pro Glu Phe Val Ala Gly His Ser
625                 630                 635                 640

Val Gly Glu Ile Ala Ala Ala His Val Ala Gly Val Phe Ser Leu Asp
                645                 650                 655
```

-continued

```
Asp Ala Cys Arg Leu Val Ala Ala Arg Ala Arg Leu Met Gln Glu Leu
            660                 665                 670

Pro Thr Gly Gly Ala Met Val Ala Val Arg Ala Thr Glu Ala Glu Val
        675                 680                 685

Thr Pro Arg Leu Thr Glu Gly Leu Ser Leu Ala Ala Val Asn Gly Pro
    690                 695                 700

Asp Ser Val Val Val Ser Gly Pro Glu Gly Glu Val Thr Ala Leu Ala
705                 710                 715                 720

Ala Glu Phe Glu Thr Glu Gly Arg Lys Ile Gln Arg Leu Ser Val Ser
                725                 730                 735

His Ala Phe His Ser Ala Leu Met Glu Pro Met Leu Asp Ala Phe Arg
            740                 745                 750

Glu Val Ala Arg Ser Leu Glu Tyr Ala Glu Pro Arg Val Pro Val Val
        755                 760                 765

Ser Asn Val Thr Gly Ala Leu Ala Ala Pro Gly Gln Leu Thr Asp Pro
    770                 775                 780

Glu Tyr Trp Val Arg His Val Arg Glu Thr Val Arg Phe Ala Asp Gly
785                 790                 795                 800

Val Arg Thr Leu Ala Glu Ala Gly Ala Asp Ala Phe Leu Glu Ile Gly
                805                 810                 815

Pro Gly Gly Val Leu Thr Ala Leu Ala Arg Gln Ser Leu Asp Thr Leu
            820                 825                 830

Asp Gly Gly Thr Gly Ala Val Ala Ala Pro Ala Leu Arg Ser Arg Arg
        835                 840                 845

Pro Glu Gln Glu Ala Leu Leu Thr Gly Leu Ala Gln Leu His Val Ala
    850                 855                 860

Gly Val Arg Val Asp Trp Ala Ala Trp Phe Thr Gly Thr Gly Ala Arg
865                 870                 875                 880

Arg Thr Asp Leu Pro Thr Tyr Ala Trp Gln His Arg Arg Tyr Trp Pro
                885                 890                 895

Arg Pro Leu Ala His Ala Ala Asp Ile Pro Gly Ala Gly Leu Thr Pro
            900                 905                 910

Ala Glu His Pro Leu Leu Gly Ala Ala Val Ser Leu Ala Gly Ser Glu
        915                 920                 925

Gly Val Leu Leu Thr Gly Arg Val Gly Leu Arg Thr His Pro Trp Leu
    930                 935                 940

Ala Asp His Val Met Gly Gly Leu Val Leu Phe Pro Ala Thr Ala Phe
945                 950                 955                 960

Leu Glu Leu Ala Val Arg Ala Gly Asp Gln Ala Gly Cys Gly Arg Val
                965                 970                 975

Gln Glu Leu Thr Leu Thr Thr Pro Leu Ala Leu Asp Pro Arg Gly Ala
            980                 985                 990

Ala Ser Val Gln Val Gly Val Gly Pro Pro Asp Ala Ala Gly Cys Arg
        995                 1000                1005

Pro Leu Ala Ile His Ser Arg Pro Glu Asp Ala Ala Asp Asp Glu Pro
    1010                1015                1020

Trp Thr Gln His Ala Thr Gly Val Leu Val Ala Gly Ala Arg Gln Val
1025                1030                1035                1040

Ala Phe Gly Gln Ser Ala Trp Pro Pro Ala Asp Ala Thr Pro Val Asp
                1045                1050                1055

Leu Asp Gly Phe Tyr Glu Arg Thr Glu Tyr Gly Pro Leu Phe Gln Gly
            1060                1065                1070

Leu Arg Ala Val Trp Thr Arg Gly Asp Glu Val Leu Ala Glu Leu Glu
```

```
        1075                1080                1085

Leu Pro Ala Arg Ala Asp Asp Ala Ala Leu Phe Gly Leu His Pro Ala
    1090                1095                1100

Leu Leu Thr Ala Ala Leu His Ala Val Glu Tyr Val Glu Leu Lys Asp
1105                1110                1115                1120

Ala Asp Gln Gly Leu Leu Pro Phe Ser Trp Ser Gly Val Thr Leu His
                1125                1130                1135

Ala Ser Gly Ala Ala Arg Leu Arg Val Arg Ile Thr Lys Ala Gly Glu
            1140                1145                1150

Asp Thr Val Ser Ile Ala Ala Val Asp Thr Ala Gly Arg Pro Val Leu
        1155                1160                1165

Ser Val Glu Ser Leu Ala Leu Arg Pro Ser Gly Ala Ala Arg Leu Leu
    1170                1175                1180

Lys Pro Gly Thr Asp Arg Ser Thr Leu Leu Gly Leu Asp Trp Val Pro
1185                1190                1195                1200

Ala Glu Pro Thr Gly Pro Ala Ala Gly Gly Pro Arg Val Ala Leu Gly
                1205                1210                1215

Thr Asp Pro Phe Gly Thr Gly Thr Val Leu Ala Gly Leu Asp Glu Val
            1220                1225                1230

Thr Glu Thr Gly Thr Gln Val Leu Val Pro Val Pro Asp Gly Gly Glu
        1235                1240                1245

Asp Pro Val Thr Ala Thr His Glu Ala Thr Arg Ala Thr Leu Ala Leu
    1250                1255                1260

Leu Gln Glu Trp Leu Asp Gly Pro Arg Pro Ala Gly Ala Arg Leu Val
1265                1270                1275                1280

Phe Val Ala Arg Gly Val Val Ala Ala Arg Pro Gly Asp Pro Ala Ala
                1285                1290                1295

Asn Leu Ala Gly Ala Ala Val Trp Gly Met Val Arg Thr Ala Gln Ala
            1300                1305                1310

Glu His Pro Ala Asp Phe Thr Leu Val Asp Val Glu Pro Gly Ala Pro
        1315                1320                1325

Phe Pro Leu Glu Ala Val Leu Ala Val Asp Glu Pro Gln Ala Ala Val
    1330                1335                1340

Arg Asp Gly Gln Val Leu Val Gly Arg Leu Thr Gln Leu Pro Pro Pro
1345                1350                1355                1360

Thr Pro Gln Asp Gly Pro Glu Asn Thr Asp Pro Phe Gly Val Thr Arg
                1365                1370                1375

Asp Gly Thr Val Leu Val Thr Gly Gly Thr Gly Thr Leu Gly Ala Arg
            1380                1385                1390

Thr Ala Arg His Leu Val Thr Arg His Gly Val Thr Arg Leu Leu Leu
        1395                1400                1405

Ala Gly Arg Arg Gly Pro Asp Ala Pro Gly Ala Ala Ala Leu Arg Glu
    1410                1415                1420

Glu Leu Thr Ala Leu Gly Ala His Val Thr Val Ala Ala Cys Asp Val
1425                1430                1435                1440

Ser Asp Arg Asp Ala Leu Ala Ala Leu Leu Gly Gly Ile Pro Ala Glu
                1445                1450                1455

His Pro Leu Thr Ala Val Val His Ala Ala Gly Val Leu Asp Asp Ala
            1460                1465                1470

Val Val Thr Ser Leu Thr Pro Asp Arg Leu Ala Thr Val Leu Arg Ser
        1475                1480                1485

Lys Ala Asp Ala Ala Trp His Leu His Asp Leu Thr Arg Gly Leu Gly
    1490                1495                1500
```

```
Leu Asp Ala Phe Val Leu Tyr Ser Ser Ile Ser Gly Val Thr Ala Arg
1505                1510                1515                1520

Ala Gly Gln Ala Asn Tyr Val Ala Ala Asn Leu Phe Leu Asp Thr Leu
                1525                1530                1535

Ala Gln His Arg Ala Ala Gln Gly Leu Pro Ala Leu Ser Val Ala Trp
            1540                1545                1550

Gly Ala Trp Asp Leu Asp Glu Gly Met Ala Gly Asp Leu Leu Thr Asp
        1555                1560                1565

Thr Gly Arg Arg Arg Ile Arg Ser Gly Gly Ile Asp Thr Leu Pro Gly
    1570                1575                1580

Asp Arg Ala Leu Asp Leu Leu Asp Thr Ala Leu Thr Leu Gly Glu Pro
1585                1590                1595                1600

Leu Val Val Ala Thr Asn Leu Ala Ala Pro Pro Ala Thr Ala His Leu
                1605                1610                1615

Asp Glu Val Pro Pro Leu Met Arg Gly Leu Val Arg Pro Pro Arg Arg
            1620                1625                1630

Thr Ala Ala Ala Thr Thr Asp Ala Pro Ala Arg Val Leu Asp Ala Ala
        1635                1640                1645

Ser Phe Arg Glu Asn Phe Ala Asn Leu Gly Ala Gly Glu Gln Glu Thr
    1650                1655                1660

Thr Leu Arg Glu Thr Val Val Ala Cys Ala Ala Ala Leu Leu Gly His
1665                1670                1675                1680

Thr Asp Thr Ser Glu Ile Asp Pro Asp Arg Asp Phe Leu Glu Leu Gly
                1685                1690                1695

Phe Asp Ser Leu Ile Gly Ile Glu Leu Arg Arg Lys Leu Ser Glu Ile
            1700                1705                1710

Thr Gly Leu Gln Leu Pro Ala Ser Ile Val Tyr Asp Ser Gly Ser Pro
        1715                1720                1725

Asn Gly Leu Thr Ala Trp Leu Arg Thr Glu Leu Gly Ala Gln Gly Ser
    1730                1735                1740

Gly Ala Pro Gln Thr Gly Ala Ala Gly Gly Pro Thr Glu Asn Asp Ser
1745                1750                1755                1760

Met Glu Arg Leu Phe Leu Asp Gly Leu Ala Gln Gly Lys Val Arg Glu
                1765                1770                1775

Ala Gln Arg Met Leu Ala Thr Val Ala Ala Leu Arg Pro Ser Phe Glu
            1780                1785                1790

Val Thr Ala Glu Leu Glu Asp Leu Pro Trp Pro Val Thr Leu Ala Glu
        1795                1800                1805

Gly Pro Ala Pro Thr Arg Leu Val Cys Val Ser Ala Pro Thr Ala Asn
    1810                1815                1820

Gly Gly Val His Gln Tyr Ala Thr Leu Ser Gly His Phe Arg Gly Arg
1825                1830                1835                1840

Arg Asp Val Thr Ala Leu Pro Leu Ile Gly Phe Asn Thr Gly Glu Ala
                1845                1850                1855

Leu Pro Ala His Ala Glu Ala Ala Ala Arg Ile Ile Ala Asp Cys Thr
            1860                1865                1870

Leu Gln Ala Ala Asp Gly Lys Pro Phe Val Leu Val Gly His Ser Ser
        1875                1880                1885

Gly Gly Ser Leu Ala Tyr Ala Ala Ala Gly Val Leu Glu His Thr Trp
    1890                1895                1900

Gly Ile Arg Pro Glu Ala Val Val Leu Leu Asp Thr Leu Ser Ile Gln
1905                1910                1915                1920
```

```
His Lys Ser Asp Glu Gly Val Asp Tyr Asn Gly Met Met Lys Phe Asn
               1925                1930                1935

Phe Thr Ala Val Asp Asp Ser Pro Val Arg Leu Thr Asn Ser Arg Leu
           1940                1945                1950

Ser Ala Met Gly Arg Trp Met Val Leu Leu Asn Ala Leu Asp Val His
       1955                1960                1965

Pro Thr Thr Val Pro Val Leu Glu Ile Lys Cys Thr Arg Ala Leu Ile
   1970                1975                1980

Glu Gly Val Pro Ala Pro Asp Pro Glu Arg Leu His Leu Pro Val Val
1985                1990                1995                2000

Pro Asp Ala Glu Val Arg Pro Leu Asp Ser Asp His Leu Ser Leu Ile
               2005                2010                2015

Arg Glu Asp Ser Gly Pro Ala Ala Asp Leu Met Asp Ala Trp Leu Thr
           2020                2025                2030

Ala Leu Glu Thr Thr Ala Thr Thr Asp Ala Pro Glu Thr Ala Pro Ala
       2035                2040                2045

Gly


<210> SEQ ID NO 6
<211> LENGTH: 7771
<212> TYPE: PRT
<213> ORGANISM: Streptomyces sp. FR-008

<400> SEQUENCE: 6

Met Thr Thr Pro Ser Glu Lys Val Val Glu Ala Leu Arg Ala Ser Leu
 1               5                  10                  15

Lys Glu Thr Glu Arg Leu Arg Arg Gln Asn Arg Asp Leu Ala Ala Ala
            20                  25                  30

Ala Ser Glu Pro Val Ala Val Val Ala Met Ser Cys Arg Tyr Pro Gly
        35                  40                  45

Gly Val Thr Ser Pro Glu Asp Leu Trp His Leu Val Ala Ser Gly Thr
    50                  55                  60

Asp Ala Val Gly Gly Phe Pro Thr Asp Arg Gly Trp Asp Leu Asp Ala
65                  70                  75                  80

Leu Arg Asp Ala Gly Val Asp Ala Arg Gly His Ser Val Ser Gln Arg
                85                  90                  95

Gly Gly Phe Leu Asp Gly Val Ala Asp Phe Asp Ala Ala Phe Phe Gly
            100                 105                 110

Val Ser Pro Arg Glu Ala Val Ser Met Asp Pro Gln Gln Arg Leu Leu
        115                 120                 125

Leu Glu Thr Ser Trp Glu Ala Val Glu Arg Ala Gly Ile Asp Pro Arg
    130                 135                 140

Ser Leu Arg Gly Ser Arg Thr Gly Val Phe Val Gly Thr Asn Gly Gln
145                 150                 155                 160

Asp Tyr Ala Tyr Leu Leu Val Arg Ser Leu Ala Asp Ala Thr Gly Asp
                165                 170                 175

Ile Gly Thr Gly Ile Ala Ala Ser Ala Thr Ser Gly Arg Leu Ser Tyr
            180                 185                 190

Thr Leu Gly Leu Glu Gly Pro Ala Val Thr Val Asp Thr Ala Cys Ser
        195                 200                 205

Ser Ser Leu Val Ala Leu His Ala Ala Ala His Ala Leu Arg Ala Gly
    210                 215                 220

Glu Cys Gly Leu Ala Leu Ala Gly Gly Val Asn Val Met Ser Ala Pro
225                 230                 235                 240
```

-continued

```
Gly Ser Leu Met Glu Phe Ser Arg Ala Gly Gly Leu Ala Gly Asp Gly
                245                 250                 255

Arg Cys Lys Ala Phe Ala Asp Glu Ala Asp Gly Thr Gly Trp Ser Glu
            260                 265                 270

Gly Val Gly Val Leu Leu Leu Glu Arg Leu Ser Asp Ala Arg Arg Asn
        275                 280                 285

Gly His Pro Val Leu Ala Val Leu Arg Gly Ser Ala Val Asn Gln Asp
    290                 295                 300

Gly Ala Ser Asn Gly Phe Thr Ala Pro Asn Gly Pro Ser Gln Gln Arg
305                 310                 315                 320

Val Ile Gln Gln Ala Leu Ala Ala Ala Gly Leu Thr Ala Ala Asp Val
                325                 330                 335

Asp Ala Val Glu Gly His Gly Thr Gly Thr Pro Leu Gly Asp Pro Ile
            340                 345                 350

Glu Ala Gln Ala Leu Leu Ala Thr Tyr Gly Gln Gly Arg Pro Glu Asp
        355                 360                 365

Arg Pro Leu Leu Leu Gly Ser Val Lys Ser Asn Ile Gly His Ala Gln
    370                 375                 380

Ala Ala Ala Gly Val Ala Gly Val Ile Lys Met Ile Met Ala Met Arg
385                 390                 395                 400

His Gly Val Val Pro Arg Ser Leu His Ala Asp His Pro Ser Arg His
                405                 410                 415

Val Asp Trp Asp Ser Gly Ala Val Arg Leu Leu Ser Glu Ala Val Glu
            420                 425                 430

Trp Pro Glu Thr Gly Arg Pro Arg Arg Ala Gly Val Ser Ser Phe Gly
        435                 440                 445

Ile Ser Gly Thr Asn Ala His Val Val Ile Glu Gln Ala Gly Pro Ala
    450                 455                 460

Ala Glu Pro Glu Ser Pro Ala Glu Pro Glu Thr Val Pro Thr Val Val
465                 470                 475                 480

Pro Trp Pro Val His Ala Arg Ser Glu Ala Ser Leu Asp Ala Gln Ile
                485                 490                 495

Glu Ala Val Thr Ala Leu Thr Asp Ala Thr Pro Leu Asp Ile Gly His
            500                 505                 510

Ser Leu Ala Thr Gly Arg Ser Leu Phe Glu His Arg Ala Val Leu Leu
        515                 520                 525

Ser Gly Leu Asp Gly Val Pro Ala Glu Ala Ala Arg Gly Arg Ala Thr
    530                 535                 540

Glu Arg Ser Leu Ala Val Leu Phe Ser Gly Gln Gly Ala Gln Arg Ala
545                 550                 555                 560

Glu Met Gly Arg Glu Leu Tyr Ala Arg Phe Pro Val Phe Ala Lys Ala
                565                 570                 575

Leu Asp Glu Ile Thr Ala Leu Leu Asp Pro Arg Leu Asp Arg Pro Leu
            580                 585                 590

Arg Glu Val Met Phe Ala Arg Arg Arg Thr Pro Glu Ala Ala Leu Leu
        595                 600                 605

Asp Thr Thr Gly Tyr Thr Gln Pro Ala Leu Phe Ala Val Glu Val Ala
    610                 615                 620

Leu His Arg Leu Val Glu Ser Trp Gly Val Val Pro Asp Phe Val Ala
625                 630                 635                 640

Gly His Ser Ile Gly Glu Ile Ala Ala Ala His Val Ala Gly Val Phe
                645                 650                 655

Ser Leu Glu Asp Ala Cys Thr Leu Val Ala Ala Arg Ala Arg Leu Met
```

-continued

```
            660                 665                 670

Gln Glu Leu Pro Ala Gly Gly Ala Met Val Ala Val Gln Ala Thr Glu
        675                 680                 685

Ala Glu Ala Ala Pro Arg Leu Thr Glu Gly Val Ala Leu Ala Ala Val
    690                 695                 700

Asn Gly Pro Asp Ser Val Thr Leu Ala Gly Glu Glu Ala Gln Val Leu
705                 710                 715                 720

Ala Leu Ala Ala Glu Phe Ala Ala Glu Gly Arg Lys Thr Gln Arg Leu
                725                 730                 735

Ala Val Ser His Ala Phe His Ser Pro Leu Met Glu Pro Met Leu Ala
            740                 745                 750

Glu Phe Arg Arg Val Ala Glu Ser Leu Thr Tyr His Glu Pro Val Leu
        755                 760                 765

Pro Val Val Ser Asn Val Thr Gly Ala Leu Ala Asp Asp Arg Leu Leu
    770                 775                 780

Cys Asp Pro Glu Tyr Trp Val Asp His Val Arg Ser Thr Val Arg Phe
785                 790                 795                 800

Ala Asp Gly Val Arg Ala Leu Ala Gly Ala Gly Ala Asp Thr Phe Val
                805                 810                 815

Glu Leu Gly Pro Asp Gly Ile Leu Thr Ala Leu Ala Gln Gln Cys Leu
            820                 825                 830

Asp Gly Pro Asp Val Val Ala Val Pro Val Leu Arg Lys Asp Arg Ala
        835                 840                 845

Glu Glu Arg Ala Leu Leu Thr Ala Leu Ala Arg Leu His Val Ala Gly
    850                 855                 860

Val Asp Ile Asp Trp Ala Ala Cys Phe Glu Gly Thr Gly Ala Arg Arg
865                 870                 875                 880

Thr Glu Leu Pro Thr Tyr Arg Trp Gln His Glu Arg Tyr Trp Pro Val
                885                 890                 895

Leu Met Ala Ala Ala Gly Asp Val Ser Ala Ala Gly Leu Val Ser Ala
            900                 905                 910

Glu His Pro Leu Leu Gly Ala Ala Val Ser Leu Ala Gly Ser Asp Gly
        915                 920                 925

Val Leu Phe Thr Gly Arg Leu Ser Ala Gln Thr His Pro Trp Leu Leu
    930                 935                 940

Asp His Thr Val Gly Gly Met Val Ala Phe Pro Gly Thr Gly Phe Leu
945                 950                 955                 960

Glu Leu Ala Val Arg Ala Gly Asp Gln Val Gly Cys Asp Arg Val Glu
                965                 970                 975

Asp Leu Thr Leu Ala Lys Pro Leu Ile Leu Thr Glu Asn Ser Ala Ala
            980                 985                 990

Val Val Gln Val His Val Gly Ala Ala Asp Ala Asp Gly Ala Arg Arg
        995                1000                1005

Val Thr Val Tyr Ser Gln Ala Val Asp Asp Pro Glu Gln Arg Trp Thr
   1010                1015                1020

Glu His Ala Ser Gly Leu Leu Thr Arg Gly Glu Arg Val Thr Gly Phe
1025                1030                1035                1040

Asp Ser Thr Val Trp Pro Pro Arg Gly Ala Val Ala Ala Asp Leu Glu
               1045                1050                1055

Gly Phe Tyr Ala Arg Thr Glu Tyr Gly Pro Val Phe Gln Gly Leu Arg
           1060                1065                1070

Ala Val Trp Thr Arg Asp Asp Glu Ala Phe Val Glu Val Ala Leu Pro
       1075                1080                1085
```

-continued

```
Pro Gln Val Asp Asp Ala Glu Tyr Tyr Gly Met His Pro Ala Leu Leu
    1090                1095                1100

Asp Ala Ala Val Gln Ser Val Gly Phe Ala Gly Leu Gly Asp Gly Lys
1105                1110                1115                1120

Lys Leu Val Pro Phe Ser Trp Ser Gly Val Ser Leu His Ala Gly Gly
                1125                1130                1135

Ala Ser Val Val Arg Val Arg Val Ala Arg Val Gly Glu Asp Thr Val
            1140                1145                1150

Ser Ile Ala Ala Val Asp Val Glu Gly Ala Pro Val Leu Ser Ala Asp
        1155                1160                1165

Ser Leu Ile Leu Arg Ala Pro Ser Ala Leu Arg Ala Pro Thr Leu His
    1170                1175                1180

Ser Ser Glu Gln Asp Gly Leu Leu Arg Leu Glu Trp Val Ala Ala Pro
1185                1190                1195                1200

Glu Gly Gly Ala Ala Pro Val Arg Ala Val Thr Leu Gly Thr Asp Arg
                1205                1210                1215

Ala Trp Pro Gly Pro Leu Ala Ser Leu Ala Asp Ala Ala Ala Val Thr
            1220                1225                1230

Pro Ala Pro Asp Leu Val Leu Val Pro Leu Glu Gly Val Glu Asp Asp
        1235                1240                1245

Thr Pro Thr Ala Val His Ala Ala Thr Ala Arg Thr Leu Ala Leu Ile
    1250                1255                1260

Gln Glu Trp Leu Glu Pro Ala Thr Ser Ala Ala Gly Arg Leu Val Phe
1265                1270                1275                1280

Val Thr Arg Gly Ala Val Ala Thr Gly Thr Asp Thr Gly Val Ser Asp
                1285                1290                1295

Leu Ala Ala Ala Ala Val His Gly Leu Val Arg Ser Ala Glu Ala Glu
            1300                1305                1310

Asn Pro Gly Arg Phe Ala Leu Leu Asp Leu Asp Ala Gly Thr Ala Ala
        1315                1320                1325

Pro Ser Gly Glu Leu Leu Ala Gln Leu Pro Pro Leu Leu Ala Ala Gly
    1330                1335                1340

Asp Thr Gln Phe Ala Val Arg Asp Glu Ala Val Leu Val Ala Arg Leu
1345                1350                1355                1360

Ala Arg Leu Ser Thr Gly Ala Ser Leu Leu Pro Val Pro Gly Leu Pro
                1365                1370                1375

Trp Arg Leu Asp Thr Thr Val Pro Gly Ser Ile Asp Gly Leu Ser Leu
            1380                1385                1390

Val Pro Ala Pro Glu Ala Leu Asp Glu Pro Glu Gly Arg Ala Val Arg
        1395                1400                1405

Val Glu Val Arg Ala Ala Gly Leu Asn Phe Arg Asp Val Leu Asn Ala
    1410                1415                1420

Leu Gly Met Tyr Pro Gly Glu Ala Gly Leu Leu Gly Ser Glu Ala Val
1425                1430                1435                1440

Gly Leu Val Thr Ala Val Gly Pro Asp Val Thr Gly Ile Ala Val Gly
                1445                1450                1455

Asp Arg Val Thr Gly Met Ile Pro Gly Gly Leu Ala Asp Thr Val Leu
            1460                1465                1470

Val Asp Glu Arg Tyr Val Thr Arg Val Pro Glu Glu Trp Ser Asp Glu
        1475                1480                1485

Asp Ala Ala Ser Val Pro Leu Val Phe Leu Thr Ala Leu Tyr Ala Phe
    1490                1495                1500
```

-continued

```
Arg Asp Leu Ala Ser Val Gln Ala Gly Glu Arg Val Leu Ile His Ala
1505                1510                1515                1520

Gly Ala Gly Gly Val Gly Met Ala Ala Ile Gln Leu Ala Arg His Met
                1525                1530                1535

Gly Ala Glu Val Phe Ala Thr Ala Ser Glu Pro Lys Trp Glu Thr Leu
            1540                1545                1550

Arg Gly Leu Gly Leu Asp Asp Ala His Ile Ala Ser Ser Arg Asp Leu
        1555                1560                1565

Gly Phe Glu Glu Lys Phe Arg Glu Val Thr Gly Gly Ala Gly Met Asp
    1570                1575                1580

Val Val Leu Asn Ala Leu Ala Gly Asp Phe Val Asp Ala Ser Leu Arg
1585                1590                1595                1600

Ile Thr Ala Pro Gly Gly Arg Phe Leu Glu Met Gly Lys Thr Asp Ile
                1605                1610                1615

Arg Asp Pro Gln Thr Thr Gly Glu Val Arg Tyr Arg Ala Phe Asp Leu
            1620                1625                1630

Gly Glu Ala Ala Pro Glu Arg Ile Gly Glu Met Leu Thr Glu Leu Leu
        1635                1640                1645

Gly Leu Phe Ala Glu Gly Ala Leu Gln Pro Leu Pro Val Arg Ala Trp
    1650                1655                1660

Asp Val Arg Arg Ala Arg Glu Ala Phe Arg Phe Met Ser Gln Ala Arg
1665                1670                1675                1680

His Val Gly Lys Ile Val Leu Thr Met Pro Pro Arg Trp Asn Pro Glu
                1685                1690                1695

Gly Thr Val Leu Val Thr Gly Gly Thr Gly Gly Leu Gly Arg Glu Val
            1700                1705                1710

Ala Arg His Leu Val Ser Ala Arg Gly Val Arg Arg Leu Leu Leu Val
        1715                1720                1725

Ser Arg Arg Gly Pro Ala Ala Glu Gly Val Asp Ala Phe Arg Glu Glu
    1730                1735                1740

Leu Ala Gly Leu Gly Ala His Val Asp Val Val Ala Cys Asp Val Ala
1745                1750                1755                1760

Asp Arg Ala Ala Val Ala Gly Leu Leu Gly Ser Val Pro Val Gly His
                1765                1770                1775

Pro Leu Thr Ala Val Val His Thr Ala Gly Val Leu Asp Asp Gly Val
            1780                1785                1790

Val Thr Gly Leu Ser Pro Glu Arg Leu Ser Gly Val Leu Arg Pro Lys
        1795                1800                1805

Val Asp Ala Ala Trp His Leu His Glu Leu Thr Arg Asp Met Gly Leu
    1810                1815                1820

Ala Gly Phe Val Met Phe Ser Ser Val Ser Gly Val Met Gly Ser Ala
1825                1830                1835                1840

Gly Gln Ala Asn Tyr Ala Ala Ala Asn Val Phe Met Asp Ala Leu Ala
                1845                1850                1855

Gln Tyr Arg Arg Ala Glu Gly Leu Ala Gly Leu Ser Leu Ala Trp Gly
            1860                1865                1870

Ala Trp Glu Gln Thr Ser Gly Met Thr Gly Thr Leu Thr Glu Ala Asp
        1875                1880                1885

Met Gln Arg Val Thr Ala Ser Gly Ala Ala Pro Leu Thr Val Glu Gln
    1890                1895                1900

Gly Leu Ala Leu Leu Asp Ala Ala Thr Gly Ser Asp Glu Pro Leu Val
1905                1910                1915                1920

Val Pro Ile Gly Ala Pro Ser Gly Asp Gln Arg Val Leu Gly Leu Val
```

-continued

```
                1925                1930                1935

Pro Pro Leu Leu Arg Asn Leu Val Arg Gly Thr Arg Arg Ser Ala Ala
            1940                1945                1950

Thr Ala Ala Gly Gly Ala Ser Thr Ala Ala Asp Leu Ala Arg Arg Leu
        1955                1960                1965

Leu Ala Leu Pro Ala Glu Asp Arg Val Arg His Ala Val Glu Leu Val
    1970                1975                1980

Arg Thr Glu Ala Ala Ala Val Leu Gly His Ala Ser Ala Arg Ala Val
1985                1990                1995                2000

Glu Pro Gly Arg Glu Phe Arg Glu Leu Gly Phe Asp Ser Leu Thr Ala
                2005                2010                2015

Val Glu Leu Arg Asn Arg Leu Thr Thr Val Thr Gly Leu Arg Leu Thr
            2020                2025                2030

Ala Thr Leu Val Phe Asp Tyr Pro Thr Pro His Gly Leu Ala Glu His
        2035                2040                2045

Leu Val Ala Glu Leu Leu Asp Glu His Gly Glu Thr Gly Thr Pro Val
    2050                2055                2060

Val Ala Ala Asp Val Ala Asp Asp Pro Val Val Ile Val Gly Met Ala
2065                2070                2075                2080

Cys Arg Met Pro Gly Gly Ile Glu Thr Pro Asp Asp Leu Trp Arg Met
                2085                2090                2095

Leu Ala Asp Gly Glu Asp Arg Ile Thr Gly Phe Pro Thr Asp Arg Gly
            2100                2105                2110

Trp Asp Leu Asp Ala Leu Phe Gly Gly Gly Gly Asp Asn Arg Gly Val
        2115                2120                2125

Ser Ala Thr Arg Arg Gly Gly Phe Leu His Asp Val Gly Gly Phe Asp
    2130                2135                2140

Ala Gly Phe Phe Gly Ile Ser Pro Arg Glu Ala Met Ala Met Asp Pro
2145                2150                2155                2160

Gln Gln Arg Leu Leu Leu Glu Thr Ser Trp Glu Ala Leu Glu Arg Ser
                2165                2170                2175

Gly Ile Asp Pro Thr Gly Leu Arg Ser Ser Ala Thr Gly Ile Phe Val
            2180                2185                2190

Gly Thr Thr Gly Gln Asp Tyr Ala Asn Leu Val Met Thr Ser Arg Glu
        2195                2200                2205

Asp Val Glu Gly His Ala Ser Thr Gly Leu Ala Thr Ser Val Ile Ser
    2210                2215                2220

Gly Arg Val Ser Tyr Ala Leu Gly Leu Glu Gly Pro Ala Leu Thr Val
2225                2230                2235                2240

Asp Thr Ala Cys Ser Ser Ser Leu Val Ala Leu His Leu Ala Ala Gln
                2245                2250                2255

Ser Leu Arg Ser Gly Glu Ser Ser Leu Ala Leu Ala Gly Gly Val Thr
            2260                2265                2270

Val Leu Ser Thr Pro Met Asn Phe Phe Gly Phe Thr Arg Gln Gly Gly
        2275                2280                2285

Leu Ala Gly Asp Gly Leu Cys Lys Ala Phe Ala Asp Ala Ala Asp Gly
    2290                2295                2300

Thr Gly Trp Ser Glu Gly Val Gly Met Leu Val Leu Glu Arg Leu Ser
2305                2310                2315                2320

Asp Ala Arg Arg Asn Gly His Asp Val Leu Ala Val Val Arg Gly Ser
                2325                2330                2335

Ala Ile Asn Gln Asp Gly Ala Ser Asn Gly Leu Thr Ala Pro Asn Gly
            2340                2345                2350
```

-continued

```
Pro Ser Gln Gln Arg Val Ile Arg Gln Ala Leu Ala Thr Ala Gly Leu
       2355                2360                2365

Ser Ala Asp Glu Val Asp Ala Val Glu Ala His Gly Thr Gly Thr Thr
   2370                2375                2380

Leu Gly Asp Pro Ile Glu Ala Gln Ala Leu Leu Ala Thr Tyr Gly Gln
2385                2390                2395                2400

Asp Arg Pro Glu Asp Arg Pro Leu Leu Leu Gly Ser Ile Lys Ser Asn
               2405                2410                2415

Ile Gly His Thr Gln Ala Ala Ala Gly Val Ala Gly Val Ile Lys Met
           2420                2425                2430

Val Leu Ala Met Arg His Gly Ala Leu Pro Arg Ser Leu His Ile Asp
       2435                2440                2445

Gln Pro Ser Thr His Val Asp Trp Glu Ala Gly Ala Val Arg Leu Leu
   2450                2455                2460

Thr Glu Thr Thr Gly Trp Pro Glu Thr Gly Arg Pro Trp Arg Ala Gly
2465                2470                2475                2480

Val Ser Ser Phe Gly Leu Ser Gly Thr Asn Ala His Val Ile Leu Glu
               2485                2490                2495

Gln Pro Glu Pro Glu Thr Ala Asp Thr Glu Ser Pro Glu Pro Gln Ala
           2500                2505                2510

Glu Pro Glu Ala Leu Ala Arg Val Val Pro Trp Pro Val Ser Ala Arg
       2515                2520                2525

Thr Glu Glu Ala Leu Pro Gly Gln Leu Ala Arg Ile Thr Ala Leu Asp
   2530                2535                2540

Ala Ala Pro Leu Asp Ile Gly His Ser Leu Ala Thr Gly Arg Ala Ser
2545                2550                2555                2560

Phe Asp His Arg Val Val Leu Leu Ala Gly Ala Asp Gly Glu Asp Glu
               2565                2570                2575

Pro Val Glu Val Ala Arg Gly Arg Ala Val Glu Arg Arg Leu Ala Val
           2580                2585                2590

Leu Phe Ser Gly Gln Gly Ser Gln Arg Ala Gly Met Gly Arg Glu Leu
       2595                2600                2605

Tyr Gly Arg Phe Pro Val Phe Thr Lys Ala Leu Asp Glu Val Leu Ala
   2610                2615                2620

Leu Leu Asp Pro Lys Leu Asp Arg Pro Leu Arg Glu Val Leu Phe Ala
2625                2630                2635                2640

Glu Glu Gly Ser Glu Thr Ala Ala Leu Leu Asp Thr Thr Gly Tyr Thr
               2645                2650                2655

Gln Pro Ala Leu Phe Ala Val Glu Val Ala Leu Tyr Arg Leu Val Glu
           2660                2665                2670

Ser Phe Gly Val Val Pro Glu Phe Val Ala Gly His Ser Val Gly Glu
       2675                2680                2685

Ile Ser Ala Ala His Ile Ala Gly Val Leu Ser Leu Glu Asp Ala Cys
   2690                2695                2700

Thr Leu Val Ala Ala Arg Ala Arg Leu Met Gln Glu Leu Pro Ala Gly
2705                2710                2715                2720

Gly Ala Met Val Ala Val Gln Ala Thr Glu Ala Glu Thr Ala Gly Arg
               2725                2730                2735

Leu Thr Gly Gly Leu Ser Leu Ala Ala Val Asn Gly Pro Asp Ser Val
           2740                2745                2750

Val Ile Ala Gly Pro Asp His Glu Val Asp Ala Leu Ala Ser Glu Phe
       2755                2760                2765
```

-continued

```
Ala Ala Glu Gly Arg Lys Val Gln Arg Leu Ala Val Ser His Ala Phe
    2770                2775                2780

His Ser Ala Leu Met Glu Pro Met Leu Asp Ala Phe His Asp Val Ala
2785                2790                2795                2800

Lys Gly Leu Gly Tyr Gly Glu Pro Arg Ile Pro Val Val Ser Asp Val
                2805                2810                2815

Thr Gly Thr Leu Ala Glu Pro Gly Gln Leu Ser Arg Pro Glu Tyr Trp
            2820                2825                2830

Val Glu His Val Arg Ser Thr Val Arg Phe Ala Asp Ala Val His Ala
        2835                2840                2845

Leu Asp Gln Ala Gly Ala Asn Ala Tyr Leu Glu Ile Gly Pro Gly Gly
    2850                2855                2860

Val Leu Thr Val Leu Ala Gln Gln Thr Leu Asp Ala Ala Gly Thr Ala
2865                2870                2875                2880

Ser Asp Ser Val Thr Ala Pro Ala Leu Arg Lys Asp Arg Ala Glu Glu
                2885                2890                2895

Pro Ala Leu Leu Thr Ala Leu Ala Thr Leu His Val Thr Gly Val Pro
            2900                2905                2910

Val Asp Trp Ala Gly Cys Phe Glu Gly Thr Gly Ala Arg Arg Val Glu
        2915                2920                2925

Leu Pro Thr Tyr Ala Phe Gln His Glu Arg Tyr Trp Pro Arg Pro Ser
    2930                2935                2940

Ala His Gly Gly Asp Val Thr Gly Ala Gly Leu Ser Pro Ala Ala His
2945                2950                2955                2960

Pro Leu Leu Gly Ala Ala Thr Gly Leu Ala Ala Ser Glu Gly Val Leu
                2965                2970                2975

Phe Thr Gly Arg Leu Ser Leu Thr Thr His Pro Trp Leu Ala Asp His
            2980                2985                2990

Thr Val Gly Gly Gly Met Val Leu Phe Pro Ala Thr Gly Phe Leu Glu
        2995                3000                3005

Leu Ala Val Arg Ala Ala Asp Glu Val Gly Cys Asp Arg Val Glu Glu
    3010                3015                3020

Phe Thr Leu Ala Thr Pro Leu Leu Leu Pro Ala Asp Thr Ala Val Val
3025                3030                3035                3040

Val Gln Val Trp Ala Gly Ala Pro Asp Glu Ser Gly Ala Arg Thr Val
                3045                3050                3055

Ser Leu Tyr Ser Arg Ser Ala Asp Val Pro Asp Ala Thr Trp Thr Gln
            3060                3065                3070

His Ala Thr Gly Val Leu Thr Ser Gly Ala Val Thr Leu Pro Ala Val
        3075                3080                3085

Ala Glu Ile Trp Pro Pro Lys Gly Ala Val Ala Val Gly Leu Glu Asp
    3090                3095                3100

Phe Tyr Asp Arg Thr Glu Tyr Gly Pro Val Phe Arg Thr Ile Arg Ala
3105                3110                3115                3120

Val Trp Lys Arg Gly Asp Glu Ala Phe Val Glu Ala Ala Leu Pro Pro
                3125                3130                3135

Gln Ala Asp Asp Ala Glu Tyr Tyr Gly Met His Pro Ala Leu Leu Asp
            3140                3145                3150

Ala Ala Val Gln Ser Val Gly Phe Ala Gly Leu Asp Asp Glu His Gln
        3155                3160                3165

Leu Leu Pro Phe Leu Trp Ala Gly Val Ser Leu His Ala Gly Gly Ala
    3170                3175                3180

Ser Val Val Arg Phe Arg Val Ala Arg Thr Gly Glu Asp Ser Val Ser
```

-continued

```
3185                3190                3195                3200

Ile Ala Ala Val Asp Val Glu Gly Ala Pro Val Leu Ser Ala Glu Ser
                3205                3210                3215

Leu Val Leu Arg Val Pro Ala Gly Asp His Ala Pro Ala Ala Arg Arg
            3220                3225                3230

Thr Glu Leu Asp Ser Leu Leu Arg Leu Glu Trp Thr Ala Gly Pro Glu
        3235                3240                3245

Thr Gly Asp Ala Pro Ala Ala Arg His Thr Thr Ala Gly Ala Leu Gly
    3250                3255                3260

Thr Gly Gly Ala Ala Ala Thr Leu Ala Pro Leu Thr Gly Glu Glu Asp
3265                3270                3275                3280

Leu Val Leu Val Glu Val Pro Ala Pro Ala Glu Gly Ala Asp Val Pro
                3285                3290                3295

Ala Ala Thr His Glu Arg Ala Ala Gln Ala Leu Ala Leu Ala Gln Glu
            3300                3305                3310

Trp Leu Ala Asp Glu Arg Phe Ala Asp Thr Arg Leu Val Phe Val Thr
        3315                3320                3325

Arg Gly Ala Val Cys Ala Arg Pro Gly Glu Arg Val Asp Asp Leu Pro
    3330                3335                3340

Ala Ala Ala Val Trp Gly Leu Val Arg Ala Ala Gln Ser Glu Asn Pro
3345                3350                3355                3360

Thr Arg Phe Ala Leu Leu Asp Leu Asp Asp Thr Thr Pro Val Glu Thr
                3365                3370                3375

Ala Leu Pro Gln Leu Leu Gly Pro Leu Ser Gly Gly Asp Ala Gln Phe
            3380                3385                3390

Val Val Arg Glu Gly Ala Val Leu Val Gly Arg Leu Asp Arg Ala Val
        3395                3400                3405

Thr Ala Pro Ser Leu Leu Pro Pro Ala Asp Gly Pro Trp Arg Leu Asp
    3410                3415                3420

Ser Pro Ser Arg Gly Ser Leu Asp Ala Leu Thr Leu Arg Pro Cys Pro
3425                3430                3435                3440

Glu Glu Leu Ala Glu Pro Gln Glu Arg Gln Val Arg Val Glu Val Arg
                3445                3450                3455

Ala Ala Gly Leu Asn Phe Arg Asp Val Leu Asn Ala Leu Gly Met Tyr
            3460                3465                3470

Pro Gly Glu Ala Gly Leu Leu Gly Ala Glu Ala Ala Gly Phe Val Thr
        3475                3480                3485

Ala Val Gly Pro Glu Val Thr Gly Leu Ser Val Gly Asp Arg Val Met
    3490                3495                3500

Gly Met Val Pro Gly Gly Leu Ala Thr Glu Thr Leu Ile Asp Glu Arg
3505                3510                3515                3520

Phe Leu Thr Arg Val Pro Glu Glu Trp Ser Asp Glu Asp Ala Ala Ser
                3525                3530                3535

Val Pro Leu Val Phe Leu Thr Ala Tyr Tyr Ala Leu Thr Glu Leu Ala
            3540                3545                3550

Gly Leu Ser Ala Gly Glu Arg Val Leu Ile His Ala Gly Ala Gly Gly
        3555                3560                3565

Val Gly Met Ala Ala Ile Gln Leu Ala Arg His Met Gly Ala Glu Val
    3570                3575                3580

Phe Ala Thr Ala Ser Glu Pro Lys Trp Glu Thr Leu Arg Gly Leu Gly
3585                3590                3595                3600

Leu Asp Asp Ala His Ile Ala Ser Ser Arg Asp Leu Gly Phe Glu Glu
                3605                3610                3615
```

Lys Phe Arg Glu Glu Thr Gly Gly Ala Gly Met Asp Val Val Leu Asn
3620 3625 3630

Ala Leu Ala Gly Asp Phe Val Asp Ala Ser Leu Arg Ile Thr Ala Ser
3635 3640 3645

Gly Gly Arg Phe Leu Glu Met Gly Lys Thr Asp Ile Arg Asp Pro His
3650 3655 3660

Ala Val Gly Asp Val Arg Tyr Arg Ala Phe Asp Leu Gly Glu Ala Gly
3665 3670 3675 3680

Pro Asp Arg Thr Gly Glu Met Leu Ser Glu Leu Leu Gly Leu Phe Ala
3685 3690 3695

Glu Gly Ala Leu Arg Pro Leu Pro Val Arg Ala Trp Asp Val Arg Arg
3700 3705 3710

Ala Arg Glu Ala Phe Arg Phe Met Ser Gln Ala Arg His Val Gly Lys
3715 3720 3725

Ile Val Leu Thr Met Pro Pro Arg Trp Asn Pro Glu Gly Thr Val Leu
3730 3735 3740

Val Thr Gly Gly Thr Gly Gly Leu Gly Arg Glu Val Ala Arg His Leu
3745 3750 3755 3760

Val Ser Ala Arg Gly Val Arg Arg Leu Leu Leu Val Ser Arg Arg Gly
3765 3770 3775

Pro Ala Ala Glu Gly Val Asp Ala Phe Arg Glu Glu Leu Ala Gly Leu
3780 3785 3790

Gly Ala His Val Asp Val Val Ala Cys Asp Val Ala Asp Arg Ala Ala
3795 3800 3805

Val Ala Gly Leu Leu Ala Ser Val Pro Val Gly His Pro Leu Thr Ala
3810 3815 3820

Val Val His Thr Ala Gly Val Leu Asp Asp Gly Val Val Thr Gly Leu
3825 3830 3835 3840

Ser Pro Glu Arg Leu Ser Gly Val Leu Arg Pro Lys Val Asp Ala Ala
3845 3850 3855

Trp His Leu His Glu Leu Thr Arg Asp Met Gly Leu Ala Gly Phe Val
3860 3865 3870

Met Phe Ser Ser Val Ser Gly Val Met Gly Ser Ala Gly Gln Gly Asn
3875 3880 3885

Tyr Ala Ala Ala Asn Val Phe Met Asp Ala Leu Ala Gln Tyr Arg Arg
3890 3895 3900

Ala Glu Gly Leu Ala Gly Leu Ser Leu Ala Trp Gly Ala Trp Glu Gln
3905 3910 3915 3920

Thr Ser Gly Met Thr Gly Thr Leu Thr Asp Ala Gly Val Arg Arg Met
3925 3930 3935

Ser Ala Ser Ala Ala Pro Ala Leu Thr Val Glu Gln Gly Leu Ala Leu
3940 3945 3950

Leu Asp Ala Ala Val Val Ser Asp Glu Pro His Leu Val Pro Leu Gly
3955 3960 3965

Ala Ser Gly Ser Thr Arg Met Pro Gly Glu Val Pro Pro Leu Leu Arg
3970 3975 3980

Asn Leu Val Arg Gly Thr Arg Arg Ala Ala Ala Thr Ala Val Gly Gly
3985 3990 3995 4000

Ala Gly Thr Ala Asp Glu Leu Thr Arg Arg Leu Leu Asp Leu Arg Glu
4005 4010 4015

Asp Glu Arg Leu Arg Phe Ala Val Asn Leu Ile Arg Ala Glu Ala Ala
4020 4025 4030

-continued

```
Ser Val Leu Gly His Ser Ser Ala Gln Ala Ile Asp Ala Glu Arg Asp
        4035                4040                4045

Phe His Asp Leu Gly Phe Asp Ser Leu Thr Ala Val Glu Leu Arg Asn
    4050                4055                4060

Arg Leu Thr Gly Ala Thr Gly Leu Arg Leu Pro Ala Thr Leu Val Phe
4065                4070                4075                4080

Asp His Pro Thr Pro Gly Val Leu Ala Glu His Leu Ile Ala Ala Leu
                4085                4090                4095

Leu Asp Glu Gln Arg Ala Thr Gly Ala Thr Ala Pro Thr Pro Val Ala
            4100                4105                4110

Ala Ala Leu Ala Glu Asp Pro Val Val Ile Val Gly Met Ala Cys Arg
        4115                4120                4125

Met Pro Gly Gly Val Ser Ser Pro Glu Glu Leu Trp Gln Leu Val Leu
    4130                4135                4140

Asp Gly Gln Glu Gly Ile Ser Ala Phe Pro Thr Asp Arg Gly Trp Asp
4145                4150                4155                4160

Leu Asp Thr Leu Gln Arg Gly Gly Glu Ser Gly His Gly Arg Ser Ala
                4165                4170                4175

Thr Ser Glu Gly Gly Phe Leu Tyr Asp Val Ala Asp Phe Asp Ala Gly
            4180                4185                4190

Phe Phe Gly Ile Ser Pro Arg Glu Ala Leu Ala Met Asp Pro Gln Gln
        4195                4200                4205

Arg Leu Leu Leu Glu Thr Thr Trp Glu Ala Phe Glu Arg Ala Gly Ile
    4210                4215                4220

Thr Pro Thr Glu Val Arg Gly Ser Arg Thr Gly Val Phe Val Gly Thr
4225                4230                4235                4240

Ser Gly Gln Asp Tyr Thr Thr Leu Val Met Asn Ser Arg Gln Asp Ala
                4245                4250                4255

Glu Gly His Ala Pro Thr Gly Leu Ala Thr Ser Val Ile Ser Gly Arg
            4260                4265                4270

Leu Ser Tyr Thr Phe Gly Leu Glu Gly Pro Ala Val Thr Ile Asp Thr
        4275                4280                4285

Ala Cys Ser Ser Ser Leu Val Ala Leu His Trp Ala Ala His Ala Leu
    4290                4295                4300

Arg Ser Gly Glu Ala Asp Leu Ala Leu Ala Gly Gly Val Thr Val Met
4305                4310                4315                4320

Ser Thr Ala Met Gly Tyr Ala Gly Phe Thr Arg Gln Gly Gly Leu Ala
                4325                4330                4335

Thr Asp Gly Arg Cys Lys Ala Phe Ala Asp Ala Ala Asp Gly Thr Gly
            4340                4345                4350

Trp Ser Glu Gly Val Gly Met Leu Val Val Glu Arg Leu Ser Asp Ala
        4355                4360                4365

Arg Arg Asn Gly His Pro Val Leu Ala Val Leu Arg Gly Ser Ala Val
    4370                4375                4380

Asn Gln Asp Gly Ala Ser Asn Gly Leu Thr Ala Pro Asn Gly Pro Ser
4385                4390                4395                4400

Gln Gln Arg Val Ile Arg Gln Ala Leu Ala Ser Ala Gly Leu Ser Thr
                4405                4410                4415

Asp Glu Val Asp Ala Val Glu Ala His Gly Thr Gly Thr Thr Leu Gly
            4420                4425                4430

Asp Pro Ile Glu Ala Gln Ala Leu Leu Ala Thr Tyr Gly Gln Asp Arg
        4435                4440                4445

Pro Gly Asp Arg Pro Leu Leu Leu Gly Ser Ile Lys Ser Asn Ile Gly
```

-continued

```
    4450                4455                4460

His Ala Gln Ala Ala Ala Gly Val Ala Gly Val Ile Lys Thr Val Met
4465                4470                4475                4480

Ala Ile Arg His Gly Val Leu Pro Arg Ser Leu His Ile Asp Arg Pro
                4485                4490                4495

Ser Thr His Val Asp Trp Thr Glu Gly Asp Val Arg Leu Leu Thr Glu
            4500                4505                4510

Thr Thr Glu Trp Pro Glu Thr Gly Arg Pro Arg Arg Ala Ala Val Ser
        4515                4520                4525

Ser Phe Gly Ile Ser Gly Thr Asn Ala His Thr Ile Ile Glu Gln Ala
    4530                4535                4540

Pro Glu Ile Val Glu Ala Thr Pro Ala Ala Ala Ser Ala Pro Ala Pro
4545                4550                4555                4560

Ala Ala Val Pro Trp Pro Val Ser Ala Lys Ser Pro Glu Ala Leu Asp
                4565                4570                4575

Ala Gln Leu Ala Arg Ile Ala Thr Val Thr Gly Ala Thr Pro Leu Asp
            4580                4585                4590

Ile Gly His Ser Leu Ala Thr Gly Arg Ala Ser Phe Glu Tyr Arg Ala
        4595                4600                4605

Val Leu Leu Ala Gly Thr Gly Ala Glu Asp Glu Pro Val Glu Val Ala
    4610                4615                4620

Arg Gly Arg Ala Val Glu Arg Arg Leu Ala Val Leu Phe Pro Gly Gln
4625                4630                4635                4640

Gly Ser Gln Arg Ala Gly Met Gly Arg Glu Leu Tyr Glu Arg Tyr Pro
                4645                4650                4655

Val Phe Ala Lys Ala Leu Asp Glu Ile Thr Ala Leu Leu Asp Pro Glu
            4660                4665                4670

Leu Asp Arg Pro Leu Arg Glu Val Leu Phe Ala Glu Glu Gly Ser Glu
        4675                4680                4685

Thr Ala Ala Leu Leu Asp Thr Thr Gly Tyr Thr Gln Pro Ala Leu Phe
    4690                4695                4700

Ala Val Glu Val Ala Leu His Arg Leu Leu Glu Ser Gln Gly Val Ser
4705                4710                4715                4720

Pro Glu Tyr Val Ala Gly His Ser Val Gly Glu Ile Ala Ala Ala His
                4725                4730                4735

Val Ala Gly Val Phe Ser Leu Glu Asp Ala Cys Arg Leu Val Ala Ala
            4740                4745                4750

Arg Ala Arg Leu Met Gln Glu Leu Pro Ala Gly Gly Ala Met Ala Ala
        4755                4760                4765

Val Gln Ala Thr Glu Ala Glu Ile Ala Pro Arg Leu Thr Glu Gly Leu
    4770                4775                4780

Ser Leu Ala Ala Val Asn Gly Pro Asp Ser Val Val Val Ser Gly Pro
4785                4790                4795                4800

Glu Ser Glu Val Thr Ala Leu Ala Ala Glu Phe Val Ala Glu Gly Arg
                4805                4810                4815

Lys Thr Gln Arg Leu Gln Val Ser His Ala Phe His Ser Ala Leu Thr
            4820                4825                4830

Glu Pro Met Leu Asp Ala Phe Arg Glu Val Ala Arg Ser Leu Ala Tyr
        4835                4840                4845

Ala Glu Pro Arg Leu Pro Val Val Ser Asn Val Thr Gly Ala Leu Ala
    4850                4855                4860

Ala Pro Gly Gln Leu Thr Asp Pro Glu Tyr Trp Val Arg His Val Arg
4865                4870                4875                4880
```

```
Glu Thr Val Arg Phe Ala Asp Gly Val Arg Ala Leu Ala Glu Ala Gly
                4885                4890                4895

Ala Asp Ala Tyr Leu Glu Ala Gly Pro Gly Gly Val Leu Thr Ala Leu
            4900                4905                4910

Ala Arg Gln Thr Leu Gly Thr Asp Ser Glu Ala Val Thr Ala Pro Ala
        4915                4920                4925

Leu Arg Lys Asp Arg Ala Glu Glu Pro Ala Leu Leu Thr Ala Leu Ala
    4930                4935                4940

Thr Leu His Val Thr Gly Val Pro Val Asp Trp Ala Ala Cys Phe Glu
4945                4950                4955                4960

Gly Thr Gly Ala Arg Arg Val Asp Leu Pro Thr Tyr Ala Phe Gln Arg
                4965                4970                4975

Val Arg His Trp Pro Asp Thr Arg Arg Pro Gly Thr Gly Gly Gly Ser
            4980                4985                4990

Ser Asp Pro Leu Asp Gly Ala Phe Trp Thr Ala Val Glu Gly Glu Asp
        4995                5000                5005

Leu Thr Arg Leu Ala Thr Asp Leu Ala Val Asp Thr Glu Ala Leu Gly
    5010                5015                5020

Ala Val Leu Pro Ala Leu Ser Thr Trp Arg Arg Arg Arg Asp Gln
5025                5030                5035                5040

Ala Met Val Asp Ser Asn Arg His His Glu Thr Trp Lys Pro Leu Ser
                5045                5050                5055

Leu Pro Pro Gly Ala Pro Ala Pro Ala Gly Thr Trp Leu Ala Val Val
            5060                5065                5070

Pro Ala Ala Tyr Gly Glu Asp Pro Trp Thr Ala Ala Val Leu Asp Ala
        5075                5080                5085

Val Gly Thr Asp Val Val Arg Leu Thr Val Asp Thr Val Glu Arg His
    5090                5095                5100

Ala Leu Ala Asp Arg Leu Arg Ala Leu Ser Ala Asp Gly Ala Ala Leu
5105                5110                5115                5120

Ala Gly Val Val Ser Leu Leu Ala Leu Ala Asp Thr Pro Glu Ala Ala
                5125                5130                5135

Val Ser Gly Asp Pro Ala Gly Ala Pro Ala Ala Pro Thr Ala Val Leu
            5140                5145                5150

Phe Gln Ala Leu Leu Asp Ala Gly Val Asp Ala Pro Leu Trp Cys Leu
        5155                5160                5165

Thr Arg Gly Ala Val Ala Val Ala Gly Ser Glu Ala Val Thr Ala Pro
    5170                5175                5180

Ala Gln Ala Ala Val Trp Gly Leu Gly Arg Val Ala Ala Leu Glu His
5185                5190                5195                5200

Pro Ala Val Trp Gly Gly Leu Val Asp Leu Pro Ser Ala Trp Asp Glu
                5205                5210                5215

Arg Ala Ala Arg Arg Phe Ala Ala Val Leu Ala Gly His Asp Gly Glu
            5220                5225                5230

Asp Gln Val Ala Val Arg Ser Ser Ala Ala Phe Ala Arg Arg Leu Val
        5235                5240                5245

Pro Ala Pro Ala Ala Glu Pro Gly Asp Gly Trp Gln Pro Arg Gly Thr
    5250                5255                5260

Val Leu Val Thr Gly Gly Thr Gly Gly Arg Gly Ala His Val Ala Arg
5265                5270                5275                5280

Trp Leu Ala Gly Ala Gly Ala Ala His Leu Val Leu Leu Gly Arg Arg
                5285                5290                5295
```

-continued

```
Gly Pro Asp Ala Pro Gly Ala Asp Ala Leu Arg Ala Glu Leu Glu Ala
            5300                5305                5310

Ala Gly Ala Arg Val Thr Leu Val Ala Cys Asp Ala Ala Asp Arg Asp
        5315                5320                5325

Ala Leu Ala Ala Val Leu Asp Gly Ile Pro Ala Asp Thr Pro Leu Ser
    5330                5335                5340

Ala Val Val His Ala Ala Ala Val Val Asp Asp Gly Val Leu Asp Asp
5345                5350                5355                5360

Leu Thr Pro Glu Arg Phe Ala Ala Pro His His Ala Arg Thr Ala Pro
                5365                5370                5375

Ala Leu His Leu Asp Glu Leu Thr Arg Gly Leu Asp Leu Asp Val Phe
            5380                5385                5390

Ala Leu Cys Ser Ser Val Ala Gly Thr Val Gly Thr Ala Gly Arg Ala
        5395                5400                5405

Asn Leu Ala Ala Ala Thr Ala Val Leu Asp Ala Leu Ala Arg Ser Arg
    5410                5415                5420

Arg Ser Glu Gly Leu Pro Ala Thr Ser Met Ala Trp Gly Ala Trp Ile
5425                5430                5435                5440

Gly Asp Ala Asp Glu Thr Gly Gly Asp Asp Ala Pro Ala Ala Pro Arg
                5445                5450                5455

Ala Gly Ala Gly His Pro Ala Val His Pro Asp Leu Ala Leu Ala Ala
            5460                5465                5470

Leu Arg Gln Ala Val Thr Arg Pro Glu Ala Ala Pro Val Leu Phe Asp
        5475                5480                5485

Pro Arg Gln Pro Gln Val Leu Asp Gly Leu Ile Gly Met Arg Gly Asn
    5490                5495                5500

Ala Leu Leu Arg Asp Leu Pro Asp Ala Arg Gln Ala Leu Ala Asp Ala
5505                5510                5515                5520

Glu Thr Thr Arg Asp Arg Ala Arg Thr Ala Ala Ser Gly Leu Ala Glu
                5525                5530                5535

Arg Leu Arg Gly Leu Pro Ala Asp Glu Arg Thr Asp Ser Val Thr Glu
            5540                5545                5550

Leu Val Arg Thr His Ala Ala Ala Val Leu Gly His Pro Gly Pro Glu
        5555                5560                5565

Ala Val Ala Ala Asp Arg Asn Phe Arg Asp Leu Gly Phe Asp Ser Leu
    5570                5575                5580

Thr Ala Ile Glu Leu Pro Asn Arg Ile Ala Leu Ala Thr Gly Leu Arg
5585                5590                5595                5600

Leu Pro Ala Thr Thr Val Tyr Asp Tyr Pro Thr Ala Gln Ala Leu Ala
                5605                5610                5615

Glu His Leu Leu Ala Glu Leu Leu Gly Glu Gln Asp Thr Pro Gly Ser
            5620                5625                5630

Gly Arg Ala Thr Pro Ala Ala Leu Ala Glu Asp Pro Val Val Ile Val
        5635                5640                5645

Gly Met Ala Cys Arg Leu Pro Gly Gly Val Arg Ser Pro Gln Asp Leu
    5650                5655                5660

Trp Ala Met Val Ser Glu Gly Arg Asp Gly Ile Glu Ala Phe Pro Glu
5665                5670                5675                5680

Asp Arg Gly Trp Asp Leu Ala Thr Leu Thr Thr Gly Gly Ala Asp Gly
                5685                5690                5695

Arg Gly Arg Ser Ala Thr Leu Arg Gly Gly Phe Leu Ser Gly Ala Ala
            5700                5705                5710

Asp Phe Asp Ala Ala Phe Phe Gly Ile Ser Pro Arg Glu Ala Leu Ala
```

```
        5715                5720                5725

Met Asp Pro Gln Gln Arg Leu Leu Leu Glu Thr Thr Trp Glu Ala Phe
    5730                5735                5740

Glu Arg Ser Gly Ile Asp Ala Asp Gln Leu Arg Gly Ser Arg Thr Gly
5745                5750                5755                5760

Val Phe Val Gly Thr Asn Gly Gln Asp Tyr Ser Thr Leu Val Met Asn
                5765                5770                5775

Ser Arg Glu Asp Leu Glu Gly His Ala Gly Thr Gly Leu Ala Ala Ser
            5780                5785                5790

Val Val Ser Gly Arg Leu Ala Tyr Thr Phe Gly Leu Glu Gly Pro Ala
        5795                5800                5805

Val Thr Val Asp Thr Ala Cys Ser Ser Ser Leu Val Ala Leu His Trp
    5810                5815                5820

Ala Met Gln Ala Leu Arg Ala Gly Glu Cys Asp Leu Ala Val Ala Gly
5825                5830                5835                5840

Gly Ile Thr Met Met Ser Thr Pro Ser Ala Phe Ser Gly Phe Thr Leu
                5845                5850                5855

Gln Asn Gly Leu Ala Val Asp Gly Arg Cys Lys Ala Tyr Ala Asp Ala
            5860                5865                5870

Ala Asp Gly Thr Gly Trp Ser Glu Gly Val Gly Leu Ile Val Val Glu
        5875                5880                5885

Arg Leu Ser Asp Ala Arg Arg Asn Gly His Glu Val Leu Ala Val Val
    5890                5895                5900

Arg Gly Ser Ala Ile Asn Gln Asp Gly Ala Ser Asn Gly Leu Thr Ala
5905                5910                5915                5920

Pro Asn Gly Pro Ser Gln Gln Arg Val Ile Arg Gln Ala Leu Ala Gly
                5925                5930                5935

Gly Gly Leu Thr Pro Ser Asp Ile Asp Ala Val Glu Gly His Gly Thr
            5940                5945                5950

Gly Thr Pro Leu Gly Asp Pro Ile Glu Ala Gln Ala Leu Leu Ala Thr
        5955                5960                5965

Tyr Gly Gln Asp Arg Pro Ala Asp Arg Pro Leu Leu Leu Gly Ser Ile
    5970                5975                5980

Lys Ser Asn Ile Gly His Thr Gln Ala Ala Ala Gly Val Ala Gly Ile
5985                5990                5995                6000

Ile Lys Thr Val Met Ala Met Arg His Gly Val Leu Pro Arg Thr Leu
                6005                6010                6015

His Val Asp Arg Pro Ser Thr His Val Asp Trp Glu Ser Gly Ala Ile
            6020                6025                6030

Arg Leu Leu Thr Glu Glu Ser Ala Trp Pro Asp Ser Gly Arg Pro Trp
        6035                6040                6045

Arg Ala Gly Ile Ser Ser Phe Gly Ile Ser Gly Thr Asn Ala His Thr
    6050                6055                6060

Ile Ile Glu Gln Ala Pro Ala Pro Glu Pro Ala Glu Pro Gly Ala Ala
6065                6070                6075                6080

Leu Leu Pro Gly Pro Thr Pro Thr Val Val Pro Trp Pro Val Ser Ala
                6085                6090                6095

Lys Ser Glu Glu Ala Leu Asp Gly Gln Ile Ala Ala Val Thr Ala Leu
            6100                6105                6110

Asp Gly Ala Ala Pro Leu Asp Val Gly His Ser Leu Ala Thr Gly Arg
        6115                6120                6125

Ala Arg Phe Asp His Arg Ala Val Leu Leu Ala Arg Pro Gly Thr Thr
    6130                6135                6140
```

-continued

```
Pro Trp Glu Ala Ala Arg Gly Arg Ala Ala Val Arg Ser Leu Ala Leu
6145                6150                6155                6160

Leu Phe Ser Gly Gln Gly Ser Gln Arg Ala Gly Met Gly Arg Glu Leu
                6165                6170                6175

Tyr Asp Arg Phe Pro Val Phe Ala Glu Ala Leu Asp Ala Val Leu Ala
            6180                6185                6190

Arg Leu Asp Thr Gly Leu Thr Pro Ser Leu Arg Glu Val Leu Phe Ala
        6195                6200                6205

Glu Glu Gly Ser Gly Thr Ala Ala Leu Leu Asp Thr Thr Gly Tyr Thr
    6210                6215                6220

Gln Pro Ala Leu Phe Ala Val Glu Val Ala Leu Tyr Arg Leu Val Glu
6225                6230                6235                6240

Ser Trp Gly Val Arg Pro Gly His Val Ala Gly His Ser Val Gly Glu
                6245                6250                6255

Ile Ala Ala Ala His Val Ala Gly Val Phe Ser Leu Glu Asp Ala Cys
            6260                6265                6270

Arg Leu Val Ala Ala Arg Ala Arg Leu Met Gln Glu Leu Pro Ser Gly
        6275                6280                6285

Gly Ala Met Val Ala Val Arg Ala Thr Glu Ala Glu Val Val Pro Arg
    6290                6295                6300

Leu Thr Glu Gly Leu Ser Leu Ala Ala Val Asn Gly Pro Asp Ser Val
6305                6310                6315                6320

Val Ile Ala Gly Thr Glu Asp Glu Ala Leu Ala Leu Ala Glu Ala Phe
                6325                6330                6335

Ala Ala Glu Gly Arg Lys Thr Gln Arg Leu Pro Val Ser His Ala Phe
            6340                6345                6350

His Ser Pro Leu Met Glu Pro Met Leu Asp Ala Phe Arg Gln Val Ala
        6355                6360                6365

Glu Ser Leu Glu Tyr Ala Glu Pro Arg Ile Pro Val Val Ser Asp Val
    6370                6375                6380

Thr Gly Ala Leu Ala Glu Pro Gly Gln Leu Thr Arg Ala Ala Tyr Trp
6385                6390                6395                6400

Val Glu His Val Arg Ala Thr Val Arg Phe Ala Asp Gly Val Arg Ala
                6405                6410                6415

Leu Ala Gly Ala Gly Ala Asn Ala Phe Leu Glu Ile Gly Pro Gly Gly
            6420                6425                6430

Val Leu Thr Ala Leu Ala Gln Ser Val Leu Glu Ala Asp Asp Arg Asp
        6435                6440                6445

Glu Ala Val Val Leu Pro Ala Leu Arg Lys Asp Arg Asp Glu Glu Thr
    6450                6455                6460

Ala Leu Leu Thr Ala Val Ala Gly Leu His Val Ser Gly Val Arg Val
6465                6470                6475                6480

Asp Trp Ser Ala Trp Phe Thr Gly Thr Gly Ala Arg Arg Thr Glu Leu
                6485                6490                6495

Pro Thr Tyr Ala Phe Gln Arg Glu Arg Tyr Trp Pro Arg Pro Ala Ala
            6500                6505                6510

Leu Thr Gly Asp Ile Ser Thr Ala Gly Leu Ile Ser Ala Glu His Pro
        6515                6520                6525

Leu Leu Gly Ala Ala Val Pro Leu Ala Asp Ser Glu Gly Val Leu Phe
    6530                6535                6540

Thr Ser Gln Ile Ser Met Gln Val His Pro Trp Leu Leu Asp His Arg
6545                6550                6555                6560
```

-continued

```
Val Gly Gly Thr Val Ile Met Pro Gly Thr Gly Tyr Leu Glu Met Ala
                6565                6570                6575

Ile Arg Ala Ala Asp Gln Val Gly Cys Ala Arg Val Glu Glu Leu Val
            6580                6585                6590

Leu Ala Ala Pro Met Val Leu Asp Glu Lys His Pro Val Ser Val Gln
        6595                6600                6605

Val Val Val Gly Ala Pro Asp Asp Thr Gly Thr Arg Pro Val Thr Phe
    6610                6615                6620

Tyr Ser Arg Pro Ser Asp Ala Val Asp Ala Pro Trp Ser Arg His Ala
6625                6630                6635                6640

Asp Gly Phe Leu Ala Val Gln Glu Arg Thr Asp Ser Phe Glu Ala Pro
                6645                6650                6655

Val Trp Pro Pro Ala Asp Ala Val Ser Val Glu Phe Asp Gly Asp Tyr
            6660                6665                6670

Ser Arg Thr Gly Tyr Gly Pro Ser Phe Gln Gly Leu Arg Gln Val Trp
        6675                6680                6685

Leu Arg Gly Glu Glu Ala Phe Val Glu Val Ala Leu Pro Glu Glu Val
    6690                6695                6700

Ala Gly Asp Ala Gln Tyr Phe Gly Met His Pro Ala Leu Leu Asp Ala
6705                6710                6715                6720

Val Gln His Ala Asn Gly Tyr Leu Gly Val Gly Ser Glu Glu Asn Pro
                6725                6730                6735

Leu Leu Pro Phe Ala Trp Asn Gly Val Ser Leu His Ala Arg Gly Ala
            6740                6745                6750

Thr Thr Leu Arg Val Arg Ile Thr Arg Leu Gly Asp Glu Ser Val Arg
        6755                6760                6765

Leu Thr Ala Val Asp Ala Glu Gly Val Pro Val Leu Cys Ala Glu Ser
    6770                6775                6780

Leu Val Leu Arg Ala Pro Thr Val Pro Ser Ala Pro Val Ala Thr Gly
6785                6790                6795                6800

Gly Gln Glu Pro Val Phe Arg Leu Asp Trp Thr Ala Ala Pro Ala Val
                6805                6810                6815

Lys Pro Thr Glu Gly Leu Thr Ala Ala Thr Leu Gly Glu Asp Val Phe
            6820                6825                6830

Gly Val Gly Thr Ala Leu Ala Ser Leu Thr Glu Leu Thr Gly Pro Asp
        6835                6840                6845

Ala Asp Pro Ser Ala Ala Pro Asp Phe Val Leu Val Pro Leu Ala Gly
    6850                6855                6860

Ala Gly Asp Ala Ala Gly Ala Gly Asp Pro Asp Ala His Gly Ala Asp
6865                6870                6875                6880

Val Pro Ala Ala Val His Ala Leu Thr Thr Arg Thr Leu Asp Leu Leu
                6885                6890                6895

Gln Gln Trp Gln Ala Ala Glu Arg Leu Gly His Ser Arg Leu Val Phe
            6900                6905                6910

Val Thr Thr Gly Ala Val Ala Ala His Asp Thr Glu Thr Val Arg Asp
        6915                6920                6925

Leu Ala Ala Gly Ala Ala Trp Gly Leu Val Arg Ser Ala Gln Ser Glu
    6930                6935                6940

Asn Pro Asp Arg Phe Val Leu Leu Asp Leu Asp Gly Ala Asp Ala Pro
6945                6950                6955                6960

Asp Thr Leu Arg Ala Leu Leu Pro Asp Leu Pro Gly Leu Leu Gly Ser
                6965                6970                6975

Gly Asp Ala Gln Phe Ala Val Arg Glu Gly Thr Ala Leu Val Gly Arg
```

-continued

```
            6980                6985                6990

Leu Glu Arg Leu Thr Thr Ala Pro Gly Leu Leu Ala Pro Thr Gly Thr
        6995                7000                7005

Pro Trp Arg Leu Asp Thr Thr Gly Lys Gly Ser Leu Asp Asn Leu Val
    7010                7015                7020

Leu Ala Pro Cys Pro Glu Val Leu Gln Pro Leu Gly Ala His Glu Val
7025                7030                7035                7040

Arg Ile Asp Val Glu Ala Ala Gly Leu Asn Phe Arg Asp Val Leu Asn
                7045                7050                7055

Ala Leu Gly Met Tyr Pro Gly Glu Ser Gly Pro Met Gly Thr Glu Ala
            7060                7065                7070

Ala Gly Val Val Thr Ala Val Gly Glu Ala Val Thr Gly Leu Ala Pro
        7075                7080                7085

Gly Asp Arg Val Leu Gly Thr Val Pro Gly Gly Phe Gly Pro Val Val
    7090                7095                7100

Val Ala Asp Gln His Tyr Val Thr Gln Val Pro Glu Gly Trp Thr Met
7105                7110                7115                7120

Arg Asp Ala Ala Ser Val Pro Leu Val Phe Leu Thr Ala Leu Tyr Ala
                7125                7130                7135

Phe Arg Asp Leu Ala Ser Val Gln Ala Gly Glu Arg Val Leu Ile His
            7140                7145                7150

Ala Gly Ala Gly Gly Val Gly Met Ala Ala Ile Gln Leu Ala Arg His
        7155                7160                7165

Val Gly Ala Glu Val Phe Ala Thr Ala Ser Glu Pro Lys Trp Glu Thr
    7170                7175                7180

Leu Arg Ser Leu Gly Leu Asp Asp Ala His Ile Ala Ser Ser Arg Asp
7185                7190                7195                7200

Leu Gly Phe Glu Glu Lys Phe Arg Glu Val Thr Gly Gly Ala Gly Met
                7205                7210                7215

Asp Val Val Leu Asn Ala Leu Ala Gly Asp Phe Val Asp Ala Ser Leu
            7220                7225                7230

Arg Ile Thr Ala Pro Gly Gly Arg Phe Leu Glu Met Gly Lys Thr Asp
        7235                7240                7245

Ile Arg Asp Pro Gln Thr Thr Gly Glu Val Arg Tyr Gln Ala Phe Asp
    7250                7255                7260

Leu Gly Glu Ala Gly Pro Glu Arg Asn Lys Ala Leu Leu Gly Glu Leu
7265                7270                7275                7280

Leu Asp Leu Phe Ala Glu Gly Ala Leu Arg Pro Leu Pro Val Arg Thr
                7285                7290                7295

Trp Asp Val Arg Arg Ala Arg Glu Ala Phe Arg Phe Met Ser Gln Ala
            7300                7305                7310

Lys His Thr Gly Lys Ile Val Leu Thr Met Pro Pro Arg Trp Asn Pro
        7315                7320                7325

Glu Gly Thr Val Leu Ile Thr Gly Gly Thr Gly Ala Leu Gly Gly His
    7330                7335                7340

Leu Ala Arg Arg Phe Ala Arg Ala Gly Met Arg His Leu Leu Leu Thr
7345                7350                7355                7360

Ser Arg Arg Gly Ala Asp Ala Pro Gly Ala Ala Glu Leu Ala Ala Glu
                7365                7370                7375

Leu Arg Glu Leu Gly Ala Glu Val Thr Val Ala Ala Cys Asp Thr Ala
            7380                7385                7390

Asp Arg Glu Ala Thr Ala Ala Leu Leu Asp Ala Val Pro Ala Ala His
        7395                7400                7405
```

```
Pro Leu Thr Ala Val Val His Thr Ala Gly Ile Leu Asp Asp Gly Val
   7410                7415                7420

Ile Ala Ser Leu Thr Pro Glu Arg Leu Ala Ala Val Leu Arg Pro Lys
7425                7430                7435                7440

Val Asp Ala Ala Trp His Leu His Glu Leu Thr Arg Asp Leu Asp Leu
               7445                7450                7455

Ala Ala Phe Leu Pro Phe Ser Ser Val Ala Gly Val Met Gly Ser Pro
           7460                7465                7470

Gly Gln Gly Asn Tyr Ala Ala Ala Asn Ser Phe Leu Asp Ala Leu Thr
       7475                7480                7485

Arg His Arg Arg His Leu Gly Leu Ala Gly Thr Ser Leu Ala Trp Gly
   7490                7495                7500

Pro Trp Ala His Asp Gly Gly Met Thr Ser Thr Leu Ser Asp Thr Asp
7505                7510                7515                7520

Met Arg Arg Met Gln Ser Gly Gly Leu Pro Pro Leu Ala Val Asp Gln
               7525                7530                7535

Gly Leu Glu Leu Phe Asp Ile Ala Arg Gly Ser Asp Glu Ser Phe Leu
           7540                7545                7550

Val Leu Val Gly Leu Ala Ala Gly Ala Met Arg Gly Ala Ala Pro Glu
       7555                7560                7565

Asp Leu Pro Pro Leu Phe Arg Ser Met Val Arg Ser Gly Arg Arg Thr
   7570                7575                7580

Ala Ala Ser Thr Asp Ala Ala Gly Ala Ser Ala Ala Leu Gly Ala Lys
7585                7590                7595                7600

Leu Ala Gly Leu Gly Ala Ala Glu Arg Val Arg Tyr Val Thr Asp Leu
               7605                7610                7615

Val Arg Glu Gln Ala Ala Arg Val Leu Gly His Ala Ser Pro Lys Ser
           7620                7625                7630

Val Asp Val Ser Gln Glu Phe Arg Glu Leu Gly Val Asp Ser Leu Thr
       7635                7640                7645

Ala Leu Glu Leu Arg Asn His Leu Ala Thr Ala Thr Gly Leu Arg Leu
   7650                7655                7660

Pro Ala Thr Leu Val Phe Asp Tyr Pro Thr Pro Thr Ala Leu Ala Glu
7665                7670                7675                7680

His Phe Val Ala Glu Leu Ala Gly Asp Asp Ala Val Pro Gln Gly Pro
               7685                7690                7695

Ser Leu Leu Ala Glu Leu Asp Arg Phe Glu Thr Leu Leu Ser Ala Gly
           7700                7705                7710

Asp Pro Asp Glu Ile Thr Arg Ala Gly Leu Ala Leu Arg Leu Gly Gln
       7715                7720                7725

Met Leu Asp Gln Val Arg Gly Asn Ala Pro Glu Gln Ala Gly Ser Ser
   7730                7735                7740

Leu Asp Asp Asp Phe Glu Ser Ala Ser Thr Asp Glu Val Phe Ala Phe
7745                7750                7755                7760

Ile Asp Asn Glu Leu Gly Arg Leu Gly Asp Leu
               7765                7770
```

```
<210> SEQ ID NO 7
<211> LENGTH: 9548
<212> TYPE: PRT
<213> ORGANISM: Streptomyces sp. FR-008

<400> SEQUENCE: 7

Met Gly Cys Val Asp Met Asp Lys Glu Gln Lys Leu Arg Asp Tyr Leu
```

-continued

```
1               5                   10                  15

Lys Arg Ala Ser Ala Asp Leu Lys Arg Ser Arg Gln Arg Val Thr Glu
            20                  25                  30

Leu Glu Ala Ala Ala Thr Glu Pro Ile Ala Ile Val Gly Met Ser Cys
        35                  40                  45

Arg Tyr Pro Gly Gly Val Ser Ser Pro Glu Asp Leu Trp Lys Met Leu
    50                  55                  60

Val Ala Gly Glu Asp Gly Ile Thr Gly Met Pro Glu Asp Arg Gly Trp
65                  70                  75                  80

Glu Ala Ala Leu Gly Glu Gly Pro Ala Asp Phe Ala Gly Gly Phe Leu
                85                  90                  95

His Asp Ala Pro Ala Phe Asp Pro Asp Phe Phe Gly Ile Ser Pro Arg
            100                 105                 110

Glu Ala Leu Ser Met Asp Pro Gln Gln Arg Leu Leu Leu Glu Thr Gly
        115                 120                 125

Trp Glu Ala Phe Glu Arg Ala Gly Ile Asp Pro Ala Gly Val Arg Gly
    130                 135                 140

Ser Arg Thr Gly Met Phe Val Gly Ala Met Pro Gln Asp Tyr Arg Val
145                 150                 155                 160

Gly Pro Asp Asp Asp Val Gln Gly Phe Gln Leu Thr Gly Asn Ala Thr
                165                 170                 175

Ser Ile Leu Ser Gly Arg Leu Ser Tyr Phe Phe Gly Ala Val Gly Pro
            180                 185                 190

Ala Val Thr Val Asp Thr Ala Cys Ser Ser Ser Leu Val Ala Leu His
        195                 200                 205

Leu Ala Ala Gln Ser Leu Arg Ala Gly Glu Cys Ser Leu Ala Leu Ala
    210                 215                 220

Ala Gly Val Thr Val Met Ala Ser Pro Thr Thr Phe Val Glu Phe Ala
225                 230                 235                 240

Arg Gln Gly Gly Leu Ala Ala Asp Gly Arg Cys Arg Ser Phe Ala Asp
                245                 250                 255

Ala Ala Asn Gly Thr Gly Trp Ser Glu Gly Val Gly Val Leu Val Leu
            260                 265                 270

Glu Arg Leu Ser Glu Ala Arg Arg Asn Gly His Arg Val Leu Ala Val
        275                 280                 285

Val Arg Gly Ser Ala Val Asn Gln Asp Gly Ala Ser Asn Gly Leu Thr
    290                 295                 300

Ala Pro Asn Gly Pro Ser Gln Gln Arg Val Ile Glu Ser Ala Leu Val
305                 310                 315                 320

Asn Ala Arg Leu Thr Ala Ala Asp Val Asp Ala Val Glu Ala His Gly
                325                 330                 335

Thr Gly Thr Val Leu Gly Asp Pro Val Glu Ala Gln Ala Leu Leu Ala
            340                 345                 350

Thr Tyr Gly Gln Gly Arg Glu Ala Asp Ser Pro Leu Leu Leu Gly Ser
        355                 360                 365

Val Lys Ser Asn Ile Ser His Thr Gln Ala Ala Ala Gly Val Ala Gly
    370                 375                 380

Val Ile Lys Met Val Met Ala Met Arg His Gly Leu Leu Pro Arg Thr
385                 390                 395                 400

Leu His Val Asp Gln Pro Ser Thr His Val Asp Trp Ser Glu Gly Ser
                405                 410                 415

Leu Leu Thr Glu Pro Ala Pro Trp Pro Ala Arg Glu Asn Ala Pro Arg
            420                 425                 430
```

-continued

```
Arg Ala Gly Ile Ser Ser Phe Gly Leu Ser Gly Thr Asn Ala His Thr
        435                 440                 445

Ile Ile Glu Glu Ala Pro Gln Glu Pro Ala Ala Asp Gly Glu Ala Ala
    450                 455                 460

Pro Ala Val Asp Ala Gly Ala Leu Pro Trp Leu Leu Ser Gly Arg Thr
465                 470                 475                 480

Pro Glu Ala Leu Arg Ala Gln Ala Ala Arg Leu Leu Asp His Leu Ala
                485                 490                 495

Ala Arg Pro Thr Pro Ser Ala Leu Asp Val Ser His Ala Leu Ala Thr
            500                 505                 510

Thr Arg Ser Ala Leu Glu His Arg Ala Ala Phe Thr Thr Ala Asp Arg
        515                 520                 525

Asp Thr Ala Val Ala Val Leu Thr Ala Leu Ala Ala Gly Ala Asp Ala
    530                 535                 540

Pro Gly Leu Thr Thr His Gln Leu Arg Gly Arg Thr Lys Leu Ala Val
545                 550                 555                 560

Leu Phe Ser Gly Gln Gly Ser Gln Arg Pro Gly Met Gly Arg Asp Leu
                565                 570                 575

His Ala Arg Phe Pro Val Phe Ala Arg Ala Leu Asp Glu Ile Leu Glu
            580                 585                 590

His Leu Asp Ala Gly Leu Asp Arg Pro Leu Lys Pro Leu Ile Leu Ala
        595                 600                 605

Glu Glu Gly Ser Glu Glu Ala Ala Leu Leu Asp Arg Thr Glu Tyr Ala
    610                 615                 620

Gln Pro Ala Leu Phe Ala Leu Glu Val Ala Leu Tyr Arg Leu Val Glu
625                 630                 635                 640

Ser Trp Gly Val Thr Pro Asp His Leu Thr Gly His Ser Val Gly Glu
                645                 650                 655

Ile Ala Ala Ala His Val Ala Gly Val Phe Thr Leu Ala Asp Ala Cys
            660                 665                 670

Thr Leu Val Thr Ala Arg Gly Arg Leu Met Gln Ala Leu Asp Glu Gly
        675                 680                 685

Gly Ala Met Val Ser Leu Glu Ala Thr Glu Asp Glu Val Ala Pro Leu
    690                 695                 700

Val Ala Glu His Ala Gly Gln Val Ser Val Ala Ala Val Asn Gly Pro
705                 710                 715                 720

Ala Ala Val Val Val Ser Gly Ala Glu Asp Ala Val Glu Ser Ile Ala
                725                 730                 735

Ala Arg Val Ala Ala Leu Gly Arg Arg Thr Arg Arg Leu Arg Val Ser
            740                 745                 750

His Ala Phe His Ser Pro Leu Met Asp Pro Met Leu Glu Glu Phe Arg
        755                 760                 765

Ala Val Val Ala Gly Leu Ser Pro Gln Ala Pro Thr Val Pro Val Val
    770                 775                 780

Ser Asn Leu Thr Gly Ala Pro Ala Thr Val Glu Gln Leu Thr Ser Ala
785                 790                 795                 800

Gly Tyr Trp Thr Asp His Val Arg His Ala Val Arg Phe Ala Asp Gly
                805                 810                 815

Val Ser Trp Leu Ala Gly His Gly Thr Gly Leu Phe Leu Glu Leu Gly
            820                 825                 830

Pro Asp Ala Thr Leu Ala Ala Leu Thr Arg Thr Val Leu Asp Ala Ala
        835                 840                 845
```

-continued

```
Gly His Glu Arg Ala Ala Val Leu Pro Ala Leu Arg Lys Asp Arg Pro
    850                 855                 860

Glu Ala Ala Thr Leu Thr Glu Thr Ala Thr Gly Leu His Leu Arg Gly
865                 870                 875                 880

Val Pro Val Arg Trp Asp Arg Trp Phe Glu Gly Thr Gly Ala Gly His
                885                 890                 895

Thr Asp Leu Pro Thr Tyr Ala Phe Gln His Arg Arg Phe Trp Pro Lys
            900                 905                 910

Gly Val Thr Gly Leu Thr Gly Asp Met Arg Ser Ala Gly Leu Gly Ala
        915                 920                 925

Ala His His Pro Leu Leu Ala Ala Ala Val Thr Leu Ala Asn Ser Asp
    930                 935                 940

Gly Leu Leu Leu Thr Gly Arg Leu Ser Val Arg Thr His Pro Trp Leu
945                 950                 955                 960

Ala Asp His Thr Val Arg Gly Thr Val Leu Leu Ala Gly Thr Ala Phe
                965                 970                 975

Leu Glu Leu Ala Val Arg Ala Gly Asp Glu Val Gly Cys Asp Arg Val
            980                 985                 990

Glu Glu Leu Thr Leu Ala Ala Pro Leu Ala Leu Pro Glu Asp Gly Gly
        995                 1000                1005

Val Gln Val Gln Val Trp Ile Gly Ser Pro Asp Glu Thr Gly Arg Arg
   1010                 1015                1020

Ala Leu Thr Leu Tyr Ser Arg Pro Asp Gly Asp Asp Asp Arg Pro Trp
1025                1030                1035                1040

Thr Gln His Ala Ala Gly Thr Leu Thr Asn Gly Ala His His Gly Glu
               1045                1050                1055

Glu Phe Asp Ala Ala Val Trp Pro Pro Ala Gly Ala Glu Ser Val Gly
           1060                1065                1070

Leu Asp Gly Phe Tyr Glu Gly Leu Ala Glu Ser Gly Phe Ala Tyr Gly
       1075                1080                1085

Pro Ala Phe Arg Gly Leu Arg Ala Val Trp Arg Arg Gly Glu Glu Thr
   1090                1095                1100

Phe Ala Glu Val Ala Leu Asp Ala Gly Pro Ala Gly Asp Ala Ser Ser
1105                1110                1115                1120

Phe Gly Leu His Pro Ala Leu Leu Asp Ala Ala Leu His Ala Thr Ala
               1125                1130                1135

Leu Ala Pro Leu Gly Glu Asp Ala Arg Gly Gly Leu Pro Phe Ala Trp
           1140                1145                1150

Gln Asp Val Thr Leu His Ala Ala Gly Ala Thr Glu Ala Arg Val Arg
       1155                1160                1165

Ile Thr Pro Ala Gly Asp Asp Ala Val Thr Leu Thr Val Ala Asp Thr
   1170                1175                1180

Thr Gly Ala Pro Val Ala Ser Val Gly Ser Leu Val Leu Arg Ser Ala
1185                1190                1195                1200

Pro Asp Ala Arg Arg Ala Ala Ala Gly Val Leu Glu Arg Asp Ala Leu
               1205                1210                1215

Phe His Leu Asp Trp Thr Arg Leu His Gly Ala Asp Ala Pro Glu Thr
           1220                1225                1230

Pro Gly Thr Val Gly Leu Leu Gly Pro Asp Pro Leu Arg Leu Gly Ala
       1235                1240                1245

Ala Leu Thr Ala Ala Gly Val Thr Val Gly Pro Leu Thr Glu Ala Ala
   1250                1255                1260

Gly Pro Asp Thr Pro Ala Leu Val Leu Val Pro Val Gly Gly Gly Asp
```

-continued

```
1265                1270                1275                1280

Pro Glu Ala Val Pro Ala Glu Val His Ala Ser Thr Ala Arg Val Leu
                1285                1290                1295

Gly His Ile Gln Arg Trp Leu Ala Glu Asp Thr Arg Ala Gly Ala Arg
            1300                1305                1310

Leu Val Phe Val Thr Arg Gly Ala Val Ala Val Gly Glu Gly Pro Leu
        1315                1320                1325

Thr Asp Pro Ala Ala Ala Ala Val Trp Gly Leu Val Arg Ser Ala Gln
    1330                1335                1340

Ala Glu His Pro His Arg Phe Gly Leu Leu Asp Leu Asp Pro Val Ala
1345                1350                1355                1360

Gly Thr Asp Pro Ala Ala Leu Val Ala Ala Leu Ala Ala Glu Glu Pro
                1365                1370                1375

Gln Thr Ala Leu Arg Gly Asp Thr Val Phe Ala Ala Arg Leu Ala Arg
            1380                1385                1390

Val Arg Pro Asp Gly Glu Thr Thr Ala Ala Ala Trp Asn Pro Glu Gly
        1395                1400                1405

Thr Val Val Val Thr Gly Gly Thr Gly Gly Leu Gly Ala Ala Leu Ala
    1410                1415                1420

Arg His Leu Val Thr Glu Arg Gly Val Arg His Leu Val Leu Ala Gly
1425                1430                1435                1440

Arg Arg Gly Pro Asp Ala Pro Gly Ala Ala Gly Leu Ala Ala Asp Leu
                1445                1450                1455

Gly Ala Leu Gly Ala Glu Val Thr Leu Ala Ala Cys Asp Val Ala Asp
            1460                1465                1470

Pro Glu Ala Val Asp Arg Leu Phe Ala Ala Val Pro Ala Ala His Pro
        1475                1480                1485

Val Thr Ala Val Val His Thr Ala Gly Thr Leu Asp Asp Gly Leu Val
    1490                1495                1500

Glu Ser Leu Thr Glu Glu Arg Leu Ala Ala Val Leu Arg Pro Lys Ala
1505                1510                1515                1520

Asp Ala Val Trp His Leu His Arg Ala Thr Arg Asp Leu Asp Leu Ala
                1525                1530                1535

Ala Phe Val Val Phe Ser Ser Leu Ala Gly Thr Thr Gly Ala Pro Gly
            1540                1545                1550

Gln Ala Asn Tyr Ala Ala Gly Asn Ala Phe Leu Asp Ala Val Ala Arg
        1555                1560                1565

Leu Arg Arg Asp Ala Gly Leu Pro Gly Leu Ser Leu Gly Trp Gly Pro
    1570                1575                1580

Trp Val Pro Val Asp Gly Gly Met Thr Gly Glu Leu Ser Glu Arg Asp
1585                1590                1595                1600

Leu Glu Arg Met Ser Arg Ser Gly Thr Pro Pro Leu Thr Val Glu Gln
                1605                1610                1615

Gly Leu Ala Leu Phe Asp Ala Thr Leu Ala Leu Pro Arg Ala Ala Val
            1620                1625                1630

Leu Pro Val Arg Leu Asp Leu Ala Ala Leu Arg Gly Arg Gly Glu Val
        1635                1640                1645

Pro Pro Leu Leu Arg Gly Leu Val Arg Thr Arg Ala Arg Arg Thr Val
    1650                1655                1660

Arg Thr Gly Ser Glu Ala Ala Leu Gly Leu Ala Gln Arg Leu Ala Arg
1665                1670                1675                1680

Leu Asp Glu Gln Ala Arg Thr Glu Ala Val Val Asp Leu Val Arg Asp
                1685                1690                1695
```

```
Arg Thr Ala Ala Val Leu Gly His Ala Ser Ala Ala Asp Ile Asp Pro
            1700                1705                1710

Glu Arg Pro Phe Gln Glu Leu Gly Phe Asp Ser Leu Thr Ala Val Glu
        1715                1720                1725

Leu Arg Asn Gly Leu Ala Ala Ala Thr Gly Leu Arg Thr Ser Ala Thr
    1730                1735                1740

Val Ile Phe Asp Tyr Pro Thr Val Ala Ala Leu Ala Gly His Leu Leu
1745                1750                1755                1760

Ala Glu Leu Thr Asp Ala Pro Glu Ala Glu Ala Pro Ala Pro Ala Pro
                1765                1770                1775

Arg Thr Ser Ala Thr Ala Asp Asp Pro Ile Val Ile Val Gly Met Ser
            1780                1785                1790

Cys Arg Tyr Pro Gly Gly Val Gly Ser Pro Asp Asp Leu Trp Arg Leu
        1795                1800                1805

Val Thr Glu Gly Thr Asp Ala Ile Gly Gly Leu Pro Val Asn Arg Gly
    1810                1815                1820

Trp Asp Leu Asp Ser Leu Tyr His Pro Asp Pro Asp His Pro Gly Thr
1825                1830                1835                1840

Ser Tyr Thr Arg Tyr Gly Gly Phe Leu His Asp Ala Gly Glu Phe Asp
                1845                1850                1855

Ala Gly Phe Phe Gly Met Ser Pro Arg Glu Ala Leu Ala Thr Asp Ser
            1860                1865                1870

Gln Gln Arg Leu Leu Leu Glu Ala Ser Trp Thr Ala Val Glu His Ala
        1875                1880                1885

Gly Ile Asp Pro Val Gly Leu Arg Gly Ser Arg Thr Gly Val Phe Ala
    1890                1895                1900

Gly Val Met Tyr Ser Asp Tyr Ser Ala Thr Leu Ala Asp Glu Arg Phe
1905                1910                1915                1920

Glu Gly His Gln Gly Ser Gly Thr Ala Pro Ser Ile Ala Ser Gly Arg
                1925                1930                1935

Val Ser Tyr Ala Leu Gly Leu Glu Gly Pro Ala Val Thr Val Asp Thr
            1940                1945                1950

Ala Cys Ser Ser Ser Leu Val Ala Met His Trp Ala Met Gln Ala Leu
        1955                1960                1965

Arg Ser Gly Glu Cys Ser Leu Ala Leu Ala Gly Gly Val Thr Val Met
    1970                1975                1980

Ser Thr Pro Thr Ser Leu Ile Glu Phe Ser Arg Gln Arg Gly Leu Ser
1985                1990                1995                2000

Pro Asp Gly Arg Cys Lys Ala Phe Ser Asp Glu Ala Asp Gly Val Gly
                2005                2010                2015

Trp Ser Glu Gly Val Gly Met Leu Val Leu Glu Arg Leu Ser Asp Ala
            2020                2025                2030

Arg Arg Asn Gly His Arg Val Leu Ala Val Val Arg Gly Ser Ala Val
        2035                2040                2045

Asn Gln Asp Gly Ala Ser Asn Gly Leu Thr Ala Pro Asn Gly Pro Ser
    2050                2055                2060

Gln Gln Arg Val Ile Arg Gln Ala Leu Asp Thr Ala Gly Leu Thr Thr
2065                2070                2075                2080

Ala Asp Val Asp Ala Val Glu Ala His Gly Thr Gly Thr Ala Leu Gly
                2085                2090                2095

Asp Pro Ile Glu Ala Gln Ala Leu Leu Ala Thr Tyr Gly Gln Asp Arg
            2100                2105                2110
```

-continued

```
Pro Gly Asp Arg Pro Leu Leu Leu Gly Ser Val Lys Ser Asn Ile Gly
        2115                2120                2125

His Thr Gln Ala Ala Ala Gly Val Ala Gly Ile Ile Lys Met Val Met
    2130                2135                2140

Ala Met Arg His Gly Glu Leu Pro Arg Thr Leu His Ala Gly Ser Pro
2145                2150                2155                2160

Ser Arg His Val Asp Trp Glu Thr Gly Asp Val Arg Ile Leu Gln Glu
                2165                2170                2175

Pro Glu Ala Trp Pro Glu Thr Gly Arg Pro Arg Arg Ala Gly Val Ser
            2180                2185                2190

Ser Phe Gly Ile Ser Gly Thr Asn Ala His Val Val Leu Glu Gln Gly
        2195                2200                2205

Glu Ser Ala Pro Ala Gly Ser Thr Gly Thr Pro Pro Ala Glu Ala Thr
    2210                2215                2220

Val Leu Pro Trp Thr Leu Ser Gly Arg Thr Arg Pro Ala Leu Arg Ala
2225                2230                2235                2240

Gln Ala Ala Arg Leu Leu Ala His Leu Asp Ala Arg Pro Asp Glu Ala
                2245                2250                2255

Pro Ala Asp Leu Thr His Ser Leu Ala Thr Thr Arg Pro Ala Phe Glu
            2260                2265                2270

Gln Arg Ala Val Val Val Gly Thr Ala Asp Asp Ala Arg Arg Ala Leu
        2275                2280                2285

Ala Ala Leu Ala Ala Asp Arg Pro Asp Pro Ala Leu Val Leu Gly Glu
    2290                2295                2300

Thr Gly Gly Thr Gly Arg Thr Ala Leu Leu Phe Thr Gly Gln Gly Ser
2305                2310                2315                2320

Gln Arg Pro Gly Thr Gly Arg Glu Leu Tyr Glu Arg His Pro Val Phe
                2325                2330                2335

Ala Glu Ala Leu Asp Glu Val Val Ala Arg Leu Asp Pro Leu Leu Val
            2340                2345                2350

Asp Ala Pro Ala Gly Thr Pro His Gly Ser Leu Lys Asp Val Met Phe
        2355                2360                2365

Ala Glu Glu Gly Thr Pro Gly Ala Ala Ala Leu Tyr Glu Thr Gly Trp
    2370                2375                2380

Thr Gln Pro Ala Leu Phe Ala Leu Glu Thr Ala Leu Tyr Arg Leu Val
2385                2390                2395                2400

Arg Ser Trp Gly Val Arg Pro Gly Val Leu Leu Gly His Ser Val Gly
                2405                2410                2415

Gly Ile Gly Ala Ala His Ala Ala Gly Val Leu Ser Leu Asp Asp Ala
            2420                2425                2430

Cys Ala Leu Val Ala Ala Arg Ala Arg Leu Met Gln Ala Leu Pro Glu
        2435                2440                2445

Gly Gly Ala Met Trp Ser Leu Gln Ala Ser Glu Asp Glu Val Leu Pro
    2450                2455                2460

Leu Leu Gln Gly Gln Glu Asp Val Ala Ala Leu Ala Ala Val Asn Gly
2465                2470                2475                2480

Pro Ser Ala Val Val Val Ser Gly Glu Glu Glu Ala Thr Ala Ala Ile
                2485                2490                2495

Ala Ala His Phe Ala Gly Leu Gly Arg Ala Thr Arg Arg Leu Arg Val
            2500                2505                2510

Ser His Ala Phe His Ser Pro Arg Met Asp Ala Val Leu Asp Ala Phe
        2515                2520                2525

Arg Glu Val Ala Glu Gly Leu Thr Tyr His Glu Pro Thr Val Pro Val
```

-continued

```
    2530                2535                2540

Ala Cys Asp Leu Thr Gly Arg Leu Ala Glu Gly Asp His Leu Arg Thr
2545                2550                2555                2560

Ala Asp Tyr Trp Val Arg His Val Arg Ser Thr Val Arg Phe Ala Asp
                2565                2570                2575

Ala Val Arg Ala Ala His Glu Ala Gly Ala Thr Thr Tyr Leu Glu Leu
            2580                2585                2590

Gly Pro Gly Gly Ser Leu Cys Ala Ala Ala Gln Asp Thr Leu Gly Asp
        2595                2600                2605

Asp Ser Glu Ala Asp Ala Val Pro Thr Leu Arg Thr Gly Arg Pro Glu
    2610                2615                2620

Asp Glu Ser Val Leu Thr Ala Leu Ala Arg Leu His Val Arg Gly Val
2625                2630                2635                2640

Arg Val Asp Trp Gly Ala Val His Pro Ala Gly Ala Gly Thr Val Glu
                2645                2650                2655

Leu Pro Thr Tyr Ala Phe Gln His Glu Thr Tyr Trp Pro Asp Thr Thr
            2660                2665                2670

Ala Pro Thr Val Arg Arg Thr Gly Asp Gly Ser Gly Asp Pro Ala Asp
        2675                2680                2685

Ala Glu Leu Trp Thr Ala Val Glu Arg Gly Asp Ala Thr Gly Leu Ala
    2690                2695                2700

Gly Leu Leu Gly Leu Arg Asp Glu Glu His Ala Ser Leu Tyr Thr Leu
2705                2710                2715                2720

Leu Pro Ser Leu Ser Ser Trp Arg Arg Ala Arg Gln Glu Arg Ala Val
                2725                2730                2735

Leu Asp Ala Ala Arg Tyr Arg Ile Ala Trp Gln Pro Ala Gly Thr Glu
            2740                2745                2750

Ser Ala Pro Val Leu Asp Gly Thr Trp Leu Ala Val Thr Thr Glu Asp
        2755                2760                2765

Asp Gly Ala Ala Asp Thr Val Leu Ala Ala Leu Arg Gly His Gly Ala
    2770                2775                2780

Val Val Glu Arg Leu Val Leu Asp Ala Ser His Leu Asp Arg Asp Leu
2785                2790                2795                2800

Leu Thr Thr Thr Leu Arg Asp Ala Val Glu Asn Ala Thr Ala Glu Gly
                2805                2810                2815

Ala Ala Gly Val Arg Gly Ile Leu Ser Leu Leu Pro Leu Ala Asp Ala
            2820                2825                2830

Ala Arg Pro Glu Ala Thr Gly Thr Asp Ala Pro Ala Gly Gly Leu Pro
        2835                2840                2845

Ala Gly Phe Ala Leu Gly Val Val Leu Ala Gln Ala Leu Gly Asp Ala
    2850                2855                2860

Ala Val Thr Ala Pro Leu Trp Thr Val Thr Arg Gly Ala Val Ser Thr
2865                2870                2875                2880

Gly Pro Gly Asp Pro Leu Thr His Pro Ala Arg Ala Ala Ala Trp Gly
                2885                2890                2895

Leu Gly Arg Val Ala Ala Leu Glu Arg Pro Glu Gln Trp Ser Gly Leu
            2900                2905                2910

Val Asp Leu Pro Glu Val Leu Asp Ala Pro Ala Thr Gln Arg Leu Val
        2915                2920                2925

Ser Leu Leu Ala Thr Arg Asp Gly Glu Asp Gln Leu Ala Val Arg Ala
    2930                2935                2940

Gly Gly Thr Leu Ala Arg Arg Val Val Arg His Pro Gly Asp Ala Leu
2945                2950                2955                2960
```

```
Pro Arg Glu Asp Glu Phe Thr Ala Ser Gly Thr Val Leu Val Thr Gly
                2965                2970                2975

Gly Thr Gly Gly Leu Gly Ala Glu Ala Ala Arg Trp Leu Ala Arg Ser
            2980                2985                2990

Gly Ala Ala His Leu Val Leu Thr Gly Arg Arg Gly Pro Asp Ala Pro
        2995                3000                3005

Gly Ala Ala Glu Leu Arg Ala Glu Leu Glu Glu Leu Gly Ala Arg Val
    3010                3015                3020

Thr Leu Thr Ala Cys Asp Ser Ala Asp Arg Asp Ala Leu Ala Ala Val
3025                3030                3035                3040

Leu Ala Ala Val Pro Glu Asp Ala Pro Leu Thr Gly Val Val His Ala
                3045                3050                3055

Ala Gly Val Gly Gln Ala Ala Pro Leu Ala Asp Thr Pro Leu Asp Gln
            3060                3065                3070

Val Ala Ala Ala Met Ala Ala Lys Thr Leu Gly Ala Ala His Leu Asp
        3075                3080                3085

Ala Leu Leu Asp Gly His Asp Leu Asp Phe Leu Val Leu Val Ser Ser
    3090                3095                3100

Val Ala Gly Val Trp Gly Ser Ala Gly Gln Ser Ala Tyr Ala Ala Ala
3105                3110                3115                3120

Asn Ala Tyr Leu Asp Ala Leu Ala Glu Asn Arg Arg Ser Arg Gly Leu
                3125                3130                3135

Ala Ala Thr Ser Val Ala Trp Gly Pro Trp Ala Glu Val Gly Met Ala
            3140                3145                3150

Ser Ala His Arg Thr Val Ser Glu Asn Leu Glu Arg Ala Gly Leu Arg
        3155                3160                3165

Leu Leu Asn Pro Ala Thr Ala Met Thr Glu Leu Arg Arg Ala Val Val
    3170                3175                3180

Arg Gly Glu Thr Thr Val Thr Val Ala Asp Val Asp Trp Glu Gln Tyr
3185                3190                3195                3200

His Pro Val Phe Thr Ala Ala Arg Ser Ser Arg Leu Phe Asp Thr Val
                3205                3210                3215

Asp Thr Val Ala Ala Leu Ala Ala Pro Gly Ser Thr Gly Thr Val Ser
            3220                3225                3230

Gly Leu Ala Glu Arg Leu Gly Gly Leu Thr Glu Gln Glu Gln Glu Arg
        3235                3240                3245

Leu Leu Val Asp Leu Val Arg Ala Glu Ala Ala Val Val Leu Gly His
    3250                3255                3260

Thr Ser Ala Glu Gly Val Pro Val Lys Lys Ala Phe Arg Asp Ala Gly
3265                3270                3275                3280

Phe Asp Ser Leu Thr Ala Val Glu Leu Arg Lys Arg Leu Ala His Leu
                3285                3290                3295

Thr Gly Leu Ala Leu Pro Ser Thr Leu Val Phe Asp Tyr Pro Asn Pro
            3300                3305                3310

Leu Ala Leu Ala Arg His Leu Arg Ala Glu Leu Leu Gly Thr Val Glu
        3315                3320                3325

Thr Ala Pro Val Ala Thr Gly Pro Ala Val Thr Asp Glu Pro Ile Ala
    3330                3335                3340

Ile Ile Gly Met Ser Cys Arg Phe Pro Gly Gly Ala Arg Ser Ala Asp
3345                3350                3355                3360

Ala Phe Trp Gln Leu Val Ala Asp Asn Thr Asp Ala Ile Ser Glu Phe
                3365                3370                3375
```

-continued

```
Pro Val Asn Arg Gly Trp Asp Gly Asp Ala Leu Tyr Asp Pro Asp Pro
            3380                3385                3390

Asp Arg Pro Gly Thr Thr Tyr Ser Thr Gln Gly Gly Phe Leu His Asp
        3395                3400                3405

Ala Gly Glu Phe Asp Ala Gly Phe Phe Gly Ile Ser Pro Arg Glu Ala
    3410                3415                3420

Val Ser Met Asp Pro Gln Gln Arg Leu Leu Leu Glu Thr Thr Trp Glu
3425                3430                3435                3440

Ala Phe Glu His Ala Gly Ile Asp Pro Ala Ala Val His Ser Thr Pro
                3445                3450                3455

Thr Gly Thr Phe Ile Gly Ser Thr Tyr Gln Asp Tyr Gly Val Ser Met
            3460                3465                3470

Asp Asp Gly Ser Ala Gly His Ala Val Thr Gly Ser Ser Pro Ser Val
        3475                3480                3485

Leu Ser Gly Arg Leu Ala Tyr Ser Phe Gly Leu Glu Gly Pro Ala Val
    3490                3495                3500

Thr Val Asp Thr Ala Cys Ser Ser Ser Leu Val Ala Leu His Leu Ala
3505                3510                3515                3520

Cys Gln Ser Leu Arg Asn Gly Glu Thr Thr Leu Ala Leu Ala Gly Gly
                3525                3530                3535

Ala Thr Val Met Thr Asn Pro Met Pro Phe Ile Ala Phe Ser Arg Gln
            3540                3545                3550

Arg Ala Leu Ala Arg Asp Gly Arg Cys Lys Ala Phe Ser Glu Ser Ala
        3555                3560                3565

Asp Gly Met Thr Leu Ala Glu Gly Val Gly Ile Leu Val Leu Glu Arg
    3570                3575                3580

Leu Ser Asp Ala Arg Arg Asn Gly His Glu Val Leu Ala Val Val Arg
3585                3590                3595                3600

Gly Ser Ala Ile Asn Gln Asp Gly Ala Ser Asn Gly Leu Thr Ala Pro
                3605                3610                3615

Asn Gly Pro Ser Gln Val Arg Val Ile Arg Gln Ala Leu Ala Ala Ser
            3620                3625                3630

Gly Leu Thr Thr Asp Asp Ile Asp Ala Val Glu Ala His Gly Thr Gly
        3635                3640                3645

Thr Ala Leu Gly Asp Pro Ile Glu Ala Gln Ala Leu His Ala Thr Tyr
    3650                3655                3660

Gly Arg Asp Arg Asp Pro Glu Asn Pro Leu Leu Leu Gly Ser Val Lys
3665                3670                3675                3680

Ser Asn Ile Gly His Thr Gln Ser Ala Ala Gly Val Ala Gly Ile Ile
                3685                3690                3695

Lys Met Val Met Ala Met Arg His Gly Thr Leu Pro Arg Thr Leu His
            3700                3705                3710

Ala Thr Glu Pro Ser Ser His Ile Asp Trp Ser Gly Gly Thr Val Arg
        3715                3720                3725

Leu Val Thr Glu Asn Thr Gly Trp Ala Arg Asp Asp Arg Pro Leu Arg
    3730                3735                3740

Ala Ala Val Ser Ser Phe Gly Ile Ser Gly Thr Asn Ala His Ala Ile
3745                3750                3755                3760

Leu Glu Gln Ala Ala Pro Ala Glu Glu Pro Ala Pro Ala Ala Gly Pro
                3765                3770                3775

Ala Leu Pro Thr Gly Gly Thr Leu Pro Trp Ile Leu Ser Ala Ala Ala
            3780                3785                3790

Pro Ser Ala Leu Arg Glu Gln Ala Ala Asn Leu Ala Ala His Val Thr
```

```
        3795                3800                3805

Ser Gly Ala Ala Pro His Pro Ala Asp Val Gly His Thr Leu Ile Thr
    3810                3815                3820

Ala Arg Ser Val Leu Glu His Arg Ala Val Ala Leu Gly Ala Asp Ala
3825                3830                3835                3840

Gly Glu Leu Thr Asp Ala Leu Ala Ala Phe Gly Ala Gly Glu Ser Thr
                3845                3850                3855

Gly Gln Val Val His Gly Thr Ala Asp Thr Asp Gly Arg Thr Val Phe
            3860                3865                3870

Val Phe Pro Gly Gln Gly Ser Gln Trp Ala Gly Met Gly Ala Glu Leu
        3875                3880                3885

Leu Asp Thr Ser Pro Val Phe Ala Glu Arg Leu His Ala Cys Ala Ala
    3890                3895                3900

Ala Leu Ala Pro Tyr Thr Asp Trp Asp Leu Val Asp Val Val Arg Gln
3905                3910                3915                3920

Ala Asp Gly Ala Pro Thr Leu Asp Arg Val Asp Val Val Gln Pro Ala
                3925                3930                3935

Thr Trp Ala Val Met Val Ser Leu Ala Glu Leu Trp Arg Ala His Gly
            3940                3945                3950

Val Thr Pro Asp Ala Val Ile Gly His Ser Gln Gly Glu Ile Ala Ala
        3955                3960                3965

Ala Val Val Ser Gly Ala Leu Thr Leu Asp Asp Gly Ala Arg Val Val
    3970                3975                3980

Ala Leu Arg Ser Gln Ala Ile Arg Arg Val Leu Ala Gly Ala Gly Gly
3985                3990                3995                4000

Met Met Ser Val Gln Val Ser Ala Ala Glu Ala Glu Gln Tyr Leu Thr
                4005                4010                4015

Pro His Ala Gly Ala Val Ser Val Ala Ala Val Asn Gly Pro Arg Ser
            4020                4025                4030

Val Val Leu Ala Gly Thr Pro Glu Ala Leu Asp Ala Leu Gln Ala Glu
        4035                4040                4045

Phe Ala Ala Arg Asp Leu Arg Ala Arg Arg Ile Ala Val Asp Tyr Ala
    4050                4055                4060

Ser His Thr Ala Gln Val Glu Arg Ile Glu Ala Glu Leu Leu Asp Leu
4065                4070                4075                4080

Leu Ala Pro Val Ala Pro Arg Ala Ala Arg Val Pro Phe His Ser Thr
                4085                4090                4095

Val Thr Gly Ala Thr Leu Asp Thr Thr Gly Met Asp Ala Ala Tyr Trp
            4100                4105                4110

Tyr Arg Asn Leu Arg Gln Thr Val Arg Phe Glu Asp Gly Val Arg Ala
        4115                4120                4125

Leu Leu Asp Thr Glu His Thr Leu Phe Val Glu Ile Ser Pro His Pro
    4130                4135                4140

Val Leu Thr Met Ala Val Gln Ala Thr Ala Glu Glu Ala Gly Arg Pro
4145                4150                4155                4160

Ala Ala Ala Val Gly Thr Leu Arg Arg Glu Gln Gly Gly Thr Ala Arg
                4165                4170                4175

Phe Leu Thr Ser Leu Ala Glu Gln Trp Val Arg Gly Gly Arg Ala Asp
            4180                4185                4190

Trp Asn Ala Val Tyr Ala Asp Thr Gly Ala Arg Arg Thr Pro Leu Pro
        4195                4200                4205

Thr Tyr Ala Phe Gln Arg Glu His Leu Trp Ala Val Ser Ala Arg Pro
    4210                4215                4220
```

-continued

Gln Gly Ser Gly Asp Gly Asp Pro Ala Asp Ala Glu Phe Trp Ala Glu
4225 4230 4235 4240

Val Glu Gln Glu Asp Ala Glu Ser Leu Ala Ser Arg Leu Glu Leu Asp
4245 4250 4255

Arg Glu Ala Leu Ala Pro Leu Leu Pro Ala Leu Ser Thr Trp Arg Arg
4260 4265 4270

Gly Arg Arg Asp Arg Ser Thr Val Gly Ser Trp Arg Tyr Arg Ala Thr
4275 4280 4285

Trp Lys Pro Leu Gly Ala Leu Pro Ser Ala Thr Leu Asp Gly Thr Trp
4290 4295 4300

Leu Leu Val Thr Ala Glu Gly Thr Asp Pro Glu Tyr Ala Ala Ala Val
4305 4310 4315 4320

Ala Glu Gln Leu Thr Ala His Gly Ala Arg Thr Val Pro Leu Ala Leu
4325 4330 4335

Thr Gly Ala Asp Ala Asp Arg Ala Ala Leu Thr Glu Arg Leu Arg Asp
4340 4345 4350

Leu Pro Glu Pro Ala Ala Val Val Ser Leu Leu Ala Asp Asp Glu Ser
4355 4360 4365

Thr Gly Ala Ala His Pro Val Leu Thr Thr Gly Leu Ala Leu Ser Val
4370 4375 4380

Thr Leu Thr Gln Ala Leu Gly Asp Ala Gly Ile Glu Ala Pro Leu Trp
4385 4390 4395 4400

Ala Leu Thr Arg Gly Ala Val Ser Thr Gly Arg Ala Asp Arg Leu Thr
4405 4410 4415

Arg Pro Ala Gln Ala Leu Val Gln Gly Phe Gly Trp Thr Ala Ala Leu
4420 4425 4430

Glu His Pro Asp Arg Trp Gly Gly Thr Val Asp Leu Pro Glu Thr Leu
4435 4440 4445

Asp Arg Arg Ala Gly Glu Arg Leu Ala Ala Val Leu Ala Gly Thr Thr
4450 4455 4460

Gly Glu Asp Gln Leu Ala Val Arg Ala Ser Gly Val Leu Ala Arg Arg
4465 4470 4475 4480

Val Ser Pro Ala Pro Ala Pro Thr Gly Thr Gly Arg Trp Ser Pro Arg
4485 4490 4495

Gly Thr Val Leu Val Thr Gly Gly Thr Gly Thr Leu Gly Pro His Leu
4500 4505 4510

Ala Arg Trp Leu Ala Asp Gln Gly Ala Arg Asp Leu Val Leu Thr Ser
4515 4520 4525

Arg Arg Gly Ala Asp Ala Pro Gly Ala Ala Glu Leu Ala Ala Glu Leu
4530 4535 4540

Gly Glu Arg Gly Cys Arg Val Thr Val Ala Ala Cys Asp Val Thr Asp
4545 4550 4555 4560

Arg Glu Ala Val Ala Ala Leu Leu Asp Gly Leu Thr Ala Glu Gly Arg
4565 4570 4575

Thr Val Arg Ser Val Phe His Thr Ala Ala Val Ile Glu Leu Gln Ser
4580 4585 4590

Ile Glu Glu Thr Ser Leu Asp Ala Phe Ala Lys Val Val His Ala Lys
4595 4600 4605

Thr Ala Gly Ala Ala His Leu Asp Glu Leu Leu Asp Asp Asp Gln Leu
4610 4615 4620

Asp Ala Phe Val Leu Tyr Ser Ser Thr Ala Gly Met Trp Gly Ser Gly
4625 4630 4635 4640

-continued

```
Arg His Ala Ala Tyr Val Ala Ala Asn Ala His Val Asn Ala Leu Ala
                4645                4650                4655

Glu His Arg Cys Ala Arg Gly Ala His Gly Thr Ala Val Ser Trp Gly
            4660                4665                4670

Ile Trp Ala Asp Asp Met Lys Leu Gly Arg Val Asp Pro Gly Gln Ile
        4675                4680                4685

Arg Arg Ser Gly Leu Glu Phe Met Asp Pro Arg Leu Ala Leu Ala Gly
    4690                4695                4700

Leu Arg Gln Val Leu Asp Gly Asp Gln Gly Ala Val Ala Val Ala Asp
4705                4710                4715                4720

Val Asp Trp Asp Arg Tyr His Pro Val Phe Thr Ser Ser Arg Pro Thr
                4725                4730                4735

Glu Leu Phe Glu Asn Val Pro Glu Val Arg Arg Leu Thr Glu Gln Gln
            4740                4745                4750

Glu Ala Arg Ala Gly Glu Ala Gly Glu Phe Ile His Arg Leu Arg Ser
        4755                4760                4765

Leu Pro Ala Gly Glu Gln Asp Arg Leu Leu Leu Glu Leu Val Arg Ser
    4770                4775                4780

Glu Ala Ala Thr Val Leu Gly His Ala Ser Pro Glu Val Leu Ser Glu
4785                4790                4795                4800

Arg Arg Ala Phe Arg Asp Ile Gly Phe Asp Ser Leu Thr Ala Val Asp
                4805                4810                4815

Leu Arg Asn Arg Leu Ala Ser Val Thr Gly Leu Thr Leu Pro Ser Thr
            4820                4825                4830

Leu Val Phe Asp Tyr Pro Asp Pro Leu Thr Leu Val Gly His Leu Arg
        4835                4840                4845

Gly Leu Ala Gly Gly Pro Ala Ala Gly Pro Asp Gly Pro Val Arg Thr
    4850                4855                4860

Thr Ala Ala Thr Asp Asp Glu Pro Ile Ala Val Val Ala Met Ser Cys
4865                4870                4875                4880

Arg Tyr Pro Gly Gly Val Thr Ser Pro Glu Ala Leu Trp Glu Leu Ile
                4885                4890                4895

Ala Ala Gly Ala Asp Ala Ile Thr Gly Phe Pro Ala Asp Arg Gly Trp
            4900                4905                4910

Asp Ala Asp Ala Leu Tyr Asp Pro Asp Pro Asp Arg Pro Gly Thr Thr
        4915                4920                4925

Tyr Ser Thr Gln Gly Gly Phe Leu His Asp Val Ala Asp Phe Asp Ala
    4930                4935                4940

Gly Phe Phe Gly Ile Ser Pro Arg Glu Ala Leu Ala Met Asp Pro Gln
4945                4950                4955                4960

Gln Arg Leu Leu Leu Glu Thr Gly Trp Glu Ala Ile Glu Arg Ala Gly
                4965                4970                4975

Ile Asp Pro Ala Thr Leu Arg Gly Ser Met Thr Gly Thr Phe Ile Gly
            4980                4985                4990

Ala Ser Tyr Gln Asp Tyr Thr Ala Gly Gly Ala Gly Ser Glu Gly Ala
        4995                5000                5005

Glu Asp His Leu Ile Thr Gly Thr Ile Ser Ser Val Met Ser Gly Arg
    5010                5015                5020

Leu Ala Tyr Thr Phe Gly Leu Glu Gly Pro Ala Val Thr Leu Asp Thr
5025                5030                5035                5040

Ala Cys Ser Ser Ser Leu Val Ala Leu His Leu Ala Cys Gln Ser Leu
                5045                5050                5055

Arg Asn Gly Glu Ser Thr Leu Ala Leu Ala Gly Gly Val Ser Val Met
```

-continued

```
        5060                5065                5070

Ala Thr Pro Gln Ala Phe Thr Gly Phe Ser Arg Gln Arg Ala Met Ala
    5075                5080                5085

Pro Asp Gly Arg Cys Lys Ala Tyr Ala Glu Gly Ala Asp Gly Met Ser
  5090                5095                5100

Leu Ala Glu Gly Val Gly Leu Val Leu Val Glu Arg Leu Ser Asp Ala
5105                5110                5115                5120

Arg Arg Asn Gly His Pro Val Leu Ala Val Ile Arg Gly Ser Ala Val
            5125                5130                5135

Asn Gln Asp Gly Ala Ser Asn Gly Leu Thr Ala Pro Asn Gly Pro Ser
        5140                5145                5150

Gln Ala Arg Val Ile Arg Gln Ala Leu Ala Asn Ala Arg Leu Thr Pro
    5155                5160                5165

Gly Glu Val Asp Val Val Glu Gly His Gly Thr Gly Thr Ala Leu Gly
  5170                5175                5180

Asp Pro Ile Glu Ala Gln Ala Leu Leu Ala Thr Tyr Gly Gln Asp Arg
5185                5190                5195                5200

Pro Gly Asp Arg Pro Leu Leu Leu Gly Ser Val Lys Ser Asn Ile Gly
            5205                5210                5215

His Thr Gln Met Ala Ser Gly Ile Ala Gly Val Met Lys Met Val Met
        5220                5225                5230

Ala Met Arg His Gly Thr Val Pro Arg Thr Leu His Val Asp Thr Pro
    5235                5240                5245

Ser Ser His Val Asp Trp Gly Ser Gly Ala Ile Asp Leu Ala Thr Glu
  5250                5255                5260

Thr Val Pro Trp Pro Glu Thr Gly Arg Pro His Arg Ala Ala Val Ser
5265                5270                5275                5280

Ser Phe Gly Leu Ser Gly Thr Asn Val His Thr Ile Val Glu Gln Ala
            5285                5290                5295

Pro Glu Glu Pro Ala Thr Glu Pro Ser Ala Ser Pro Ala Pro Ala Gly
        5300                5305                5310

Asp Pro Ala Thr Leu Pro Pro Gly Val Pro Val Val Leu Ser Ala Arg
    5315                5320                5325

Thr Pro Ala Ala Leu Arg Glu Gln Ala Glu Arg Leu Ala Gly His Leu
  5330                5335                5340

Ala Gly Arg Pro Asp Val Pro Leu Val Asp Leu Ala His Ser Leu Ala
5345                5350                5355                5360

Thr Thr Arg Gly Val Leu Glu His Arg Ala Ala Val Leu Thr Gly Asp
            5365                5370                5375

Arg Asp Gly Leu Leu Arg Ala Leu Thr Ala Leu Arg Glu Gly Ala Pro
        5380                5385                5390

Asp Ala Ser Leu Leu Thr Gly Ala Pro Ala Arg Gly Gly Leu Ala Phe
    5395                5400                5405

Leu Phe Thr Gly Gln Gly Ser Gln Arg Pro Ala Met Gly Arg Asp Leu
  5410                5415                5420

Tyr Glu Arg His Pro Val Phe Gly Glu Ala Leu Asp Ala Val Leu Thr
5425                5430                5435                5440

Arg Phe Asp Gln Glu Leu Asp Arg Pro Leu Arg Glu Val Leu Phe Ala
            5445                5450                5455

Glu Glu Gly Thr Ala Glu Ala Ala Leu Leu Asp Asp Thr Ala Tyr Thr
        5460                5465                5470

Gln Pro Ala Leu Phe Ala Leu Glu Val Ala Leu Tyr Arg Leu Val Glu
    5475                5480                5485
```

```
Ser Trp Gly Val Arg Pro Asp Gln Val Ala Gly His Ser Val Gly Glu
    5490                5495                5500

Ile Ala Ala Ala His Val Ala Gly Val Phe Ser Leu Asp Asp Ala Cys
5505                5510                5515                5520

Ala Leu Val Ala Ala Arg Gly Arg Leu Met Ala Ala Leu Pro Ala Gly
                5525                5530                5535

Gly Ala Met Val Ala Val Glu Ala Ser Glu Glu Glu Val Leu Pro Leu
            5540                5545                5550

Leu Glu Gly Gly Glu Asp Arg Ile Ser Leu Ala Ala Val Asn Gly Pro
        5555                5560                5565

Arg Ala Val Val Ile Ala Gly Asp Glu Glu Pro Val Ala Ala Val Ala
    5570                5575                5580

Ala Arg Leu Ala Glu Asp Gly Arg Arg Thr Arg Ala Leu Lys Val Ser
5585                5590                5595                5600

His Ala Phe His Ser Pro Arg Met Asp Ala Met Leu Asp Asp Phe Ala
                5605                5610                5615

Arg Val Ala Arg Gly Leu Thr Tyr Glu Thr Pro Leu Val Pro Val Val
            5620                5625                5630

Ser Thr Val Thr Gly Ala Pro Ala Thr Pro Glu Glu Leu Arg Ser Pro
        5635                5640                5645

Glu Tyr Trp Val Gly Gln Val Arg Ala Thr Val Arg Phe Ala Asp Ala
    5650                5655                5660

Val Arg Thr Leu Ala Arg Gln Gly Val Thr Ser Cys Leu Glu Leu Gly
5665                5670                5675                5680

Pro Asp Gly Thr Leu Ser Ala Ala Ala Arg Asp Val Leu Asp Ala Asp
                5685                5690                5695

Pro Ala Asp Ala Thr Gly Ala Arg Pro Val Thr Val Val Pro Ala Leu
            5700                5705                5710

Arg Arg Asp Arg Asp Glu Val Pro Phe Leu Thr Ala Ala Leu Ala Arg
        5715                5720                5725

Leu His Val His Gly Thr Ala Val Asp Trp Thr Gly Ala Phe Glu Gly
    5730                5735                5740

Thr Gly Ala Arg Arg Val Asp Leu Pro Thr Tyr Ala Phe Gln Arg Ser
5745                5750                5755                5760

Arg Tyr Trp Pro Asp Thr Thr Phe Thr Pro Ala Thr Ala Ala Gly Pro
                5765                5770                5775

Ala Asp Thr Gly Ala Asp Ala Ala Phe Trp Ser Ala Val Glu Arg Ala
            5780                5785                5790

Asp Leu Pro Thr Leu Gly Ala Asp Leu Gly Leu Asp Asp Asp Thr Leu
        5795                5800                5805

Ser Ala Leu Val Pro Ala Leu Ser Ser Trp Arg Arg Arg Arg Thr Ala
    5810                5815                5820

Gln Ala Ala Ala Asp Gly Arg Arg His Arg Ile Val Trp Lys Pro Leu
5825                5830                5835                5840

Asp Gly Ala Pro Thr Gly Arg Pro Glu Gly Thr Trp Leu Val Leu Arg
                5845                5850                5855

Pro Thr Gly Thr Ala Ala Pro Glu Thr Ala Ala Leu Leu Asp Thr Leu
            5860                5865                5870

Gly Leu Asp Thr Ala Glu Val Thr Val Asp Leu Ala Ala Pro Asp Arg
        5875                5880                5885

Ala Ala Leu Ala Asp Thr Leu Arg Arg Leu Pro Arg Pro Glu Asp Gly
    5890                5895                5900
```

-continued

```
Phe Thr Gly Val Leu Ala Leu Pro Ala Leu Asp Thr Ala Ala Thr Ala
5905                5910                5915                5920

Asp Asp Val Ala Gly Thr Gly Ala Val Ala Pro Thr Ala Ala Ala Leu
                5925                5930                5935

Asn Ala Leu Asp Asp Ala Gly Ile Thr Ala Pro Leu Trp Ile Val Thr
            5940                5945                5950

Arg Gln Ala Val Ser Thr Gly Arg Ala Asp Arg Leu Ala Arg Pro Gly
        5955                5960                5965

Gln Ala Gly Val Trp Gly Leu Gly Arg Val Ala Ala Leu Glu Asn Pro
    5970                5975                5980

Gly Arg Arg Leu Ala Leu Val Asp Leu Pro Glu Gln Phe Asp Thr Arg
5985                5990                5995                6000

Val Ala Arg Arg Leu Ala His Leu Leu Ala Val Pro Gly Thr Glu Asn
                6005                6010                6015

Gln Leu Ala Val Arg Ala Ser Ala Thr Tyr Ala Arg Arg Ile Ala His
            6020                6025                6030

His Pro Ala Pro Gln Glu Pro Ala Arg Pro Phe Ala Pro Glu Gly Thr
        6035                6040                6045

Val Leu Ile Thr Gly Gly Thr Gly Ala Leu Gly Ala His Val Ala Arg
    6050                6055                6060

Leu Leu Ala Gly Arg Gly Thr Pro His Leu Leu Leu Thr Ser Arg Arg
6065                6070                6075                6080

Gly Ala Asp Ala Pro Gly Ala Ala Glu Leu Ala Ala Glu Leu Arg Glu
                6085                6090                6095

Leu Gly Ala Glu Val Thr Leu Ala Ala Cys Asp Thr Ala Asp Arg Glu
            6100                6105                6110

Ala Leu Ala Ala Leu Leu Ala Glu Val Pro Ala Asp Arg Pro Leu Thr
        6115                6120                6125

Thr Val Val His Ala Ala Gly Val Leu Asp Asp Gly Leu Leu Asp Thr
    6130                6135                6140

Leu Thr Pro Glu Arg Phe Ala Ala Val Leu Asp Ala Lys Ala Arg Ser
6145                6150                6155                6160

Ala Ala His Leu His Glu Leu Thr Arg Asp Leu Gly Leu Thr Asp Phe
                6165                6170                6175

Val Leu Phe Ser Ser Thr Ala Gly Thr Leu Gly Ala Ala Gly Gln Ala
            6180                6185                6190

Asn Tyr Ala Ala Ala Asn Ala Tyr Leu Asp Ala Leu Ala Glu His Arg
        6195                6200                6205

Arg Glu Gln Gly Leu Pro Ala Thr Ser Val Ala Trp Gly Pro Trp Ser
    6210                6215                6220

Gly Thr Gly Met Ala Gly Glu Gly Thr Gly Val Glu Asp Arg Val Arg
6225                6230                6235                6240

Arg Gly Gly Phe Thr Pro Met Ser Pro Glu Asp Ala Leu Ala Ala Leu
                6245                6250                6255

Asp Ala Ala Val Gly His Arg Asp Thr Ala Leu Leu Val Ala Asp Ile
            6260                6265                6270

Asp Trp Gln Arg Tyr Ala Thr Val Phe Ala Pro His Arg Ala Leu Val
        6275                6280                6285

Gly Asp Leu Pro Glu Val Arg Ala Thr Val Gly Ala Ala Thr Ala His
    6290                6295                6300

Gly Asp Thr Glu Pro Ala Leu Arg Arg Gln Val Ala Ala Leu Thr Gly
6305                6310                6315                6320

Pro Ala Arg Glu Arg Tyr Val Leu Asp Phe Leu Arg Ala Gln Val Ala
```

-continued

```
                6325                6330                6335

Ala Val Leu Gly His Pro Asp Pro Asp Ala Val Glu Ala Asp Gln Ala
            6340                6345                6350

Phe Thr Asp Leu Gly Phe Asp Ser Leu Thr Thr Val Glu Leu Arg Asn
        6355                6360                6365

Thr Leu Gly Ala Thr Thr Gly Leu Arg Leu Pro Ala Thr Leu Val Tyr
    6370                6375                6380

Asp His Pro Thr Ala Arg Asp Leu Ala Ala His Leu Leu Thr Glu Ile
6385                6390                6395                6400

Leu Gly Asp Leu Pro Glu Pro Ala Ala Gly Gly Asn Ala Ala Gly Glu
                6405                6410                6415

Ala Pro Arg Ala Thr Glu Thr Asp Pro Val Val Val Val Gly Met Gly
            6420                6425                6430

Cys Arg Phe Pro Gly Gly Val Glu Ser Pro Glu Glu Leu Trp Gln Leu
        6435                6440                6445

Leu Gly Glu Gly Arg Asp Ala Val Ser Gly Phe Pro Ala Asp Arg Gly
    6450                6455                6460

Trp Asp Leu Asp Ser Leu Ala Arg Gly Gly Ser Ala Thr Leu Glu Gly
6465                6470                6475                6480

Gly Phe Leu Gln Gly Ala Gly Leu Phe Asp Ala Ser Phe Phe Gly Ile
                6485                6490                6495

Ser Pro Arg Glu Ala Leu Ala Met Asp Pro Gln Gln Arg Leu Leu Leu
            6500                6505                6510

Glu Thr Ser Trp Glu Ala Leu Glu Arg Ala Gly Ile Asp Pro Thr Gly
        6515                6520                6525

Leu Arg Ser Ser Ala Thr Gly Val Phe Val Gly Thr Asn Gly Gln Asp
    6530                6535                6540

Tyr Ala Thr Val Leu Arg Arg Gly Thr Thr Asp Val Arg Gly His Ala
6545                6550                6555                6560

Ala Thr Gly Thr Thr Ala Ser Val Met Ser Gly Arg Leu Ser Tyr Thr
                6565                6570                6575

Leu Gly Leu Glu Gly Pro Ala Val Thr Val Asp Thr Ala Cys Ser Ser
            6580                6585                6590

Ala Leu Val Ala Leu His Met Ala Ala Gly Ala Leu Arg Ser Gly Glu
        6595                6600                6605

Cys Thr Leu Ala Leu Ala Gly Gly Val Ser Val Met Ala Ser Pro Asp
    6610                6615                6620

Ala Phe Val Glu Phe Thr Ala Gln Gly Gly Leu Ala Gly Asp Gly Arg
6625                6630                6635                6640

Cys Lys Ala Phe Ala Asp Ala Ala Asp Gly Thr Ala Trp Gly Glu Gly
                6645                6650                6655

Ala Gly Val Leu Val Leu Glu Arg Leu Ser Asp Ala Arg Arg His Gly
            6660                6665                6670

His Pro Val Leu Ala Val Leu Arg Gly Ser Ala Val Asn Gln Asp Gly
        6675                6680                6685

Ala Ser Asn Gly Leu Thr Ala Pro Asn Gly Arg Ala Gln Gln Arg Val
    6690                6695                6700

Ile Arg Gln Ala Leu Ala Asp Ala His Leu Thr Pro Ala Glu Val Asp
6705                6710                6715                6720

Ala Val Glu Ala His Gly Thr Gly Thr Thr Leu Gly Asp Pro Ile Glu
                6725                6730                6735

Ala His Ala Leu Ile Ala Ala Tyr Gly Glu Gly Arg Asp Pro Glu Gln
            6740                6745                6750
```

-continued

```
Pro Leu Leu Leu Gly Thr Val Lys Ser Asn Leu Gly His Thr Gln Ala
        6755                6760                6765

Ala Ala Gly Ala Ala Gly Val Ile Lys Thr Val Leu Ala Leu Gly His
    6770                6775                6780

Gly Glu Leu Pro Arg Thr Leu His Val Asp Ala Pro Ser Ser His Val
6785                6790                6795                6800

Asp Trp Ser Asp Gly Thr Val Glu Leu Leu Arg Glu His Arg Ala Trp
                6805                6810                6815

Pro Glu Thr Gly Arg Ala Arg Arg Ala Gly Val Ser Ala Phe Gly Val
            6820                6825                6830

Ser Gly Thr Asn Ala His Val Ile Leu Glu Gln Pro Glu Pro Ala Thr
        6835                6840                6845

Ala Glu Thr Pro Glu Pro Val Thr Glu Pro Ser Val Val Pro Trp Leu
    6850                6855                6860

Val Ser Ala Arg Ser Glu Asp Ala Leu Ala Ala Gln Thr Ala Arg Leu
6865                6870                6875                6880

Thr Ala Phe Thr Gln Ala Arg Pro Glu Val Pro Ala Leu Asp Thr Ala
                6885                6890                6895

Tyr Ser Leu Ala Thr Gly Arg Gly Ala Phe Ala His Arg Ala Val His
            6900                6905                6910

Leu Val Thr Ala Gly Gly Glu Pro Leu Glu Thr Val Arg Asp Arg Ala
        6915                6920                6925

Trp Glu Arg Arg Leu Ala Leu Leu Phe Ser Gly Gln Gly Ser Gln Arg
    6930                6935                6940

Ala Gly Met Gly Arg Glu Leu Tyr Glu Arg Phe Pro Val Phe Ala Glu
6945                6950                6955                6960

Ala Leu Asp Ser Val Val Ala Arg Leu Asp Thr Gly Leu Glu Arg Ser
                6965                6970                6975

Leu Arg Glu Val Leu Phe Ala Glu Glu Gly Ser Glu Ala Ala Ala Leu
            6980                6985                6990

Leu Glu Ala Thr Gly Tyr Thr Gln Pro Ala Leu Phe Ala Val Glu Val
        6995                7000                7005

Ala Leu Phe Arg Leu Val Glu Ser Trp Gly Val Ala Pro Glu Phe Val
    7010                7015                7020

Ala Gly His Ser Val Gly Glu Ile Ala Ala Ala His Val Ala Gly Val
7025                7030                7035                7040

Phe Ser Leu Asp Asp Ala Cys Ala Leu Val Ala Ala Arg Ala Arg Leu
                7045                7050                7055

Met Gln Glu Leu Pro Thr Gly Gly Ala Met Val Ala Val Arg Ala Thr
            7060                7065                7070

Glu Ala Glu Val Val Pro Arg Leu Thr Glu Gly Leu Ser Leu Ala Ala
        7075                7080                7085

Val Asn Gly Pro Asp Ser Val Val Ile Ala Gly Glu Gln Glu Glu Val
    7090                7095                7100

Leu Ala Leu Ala Ala Glu Phe Ala Gly Glu Gly His Lys Thr Gln Pro
7105                7110                7115                7120

Leu Pro Val Ser His Ala Phe His Ser Ala Leu Met Glu Pro Met Leu
                7125                7130                7135

Ala Glu Phe Arg Arg Val Ala Glu Ser Leu Glu Tyr Ala Glu Pro Arg
            7140                7145                7150

Val Pro Val Val Ser Asn Val Thr Gly Ala Leu Ala Gln Pro Gly Gln
        7155                7160                7165
```

```
Leu Thr Asp Pro Glu Tyr Trp Val Arg His Val Arg Glu Thr Val Arg
    7170                7175                7180

Phe Ala Asp Gly Val Arg Ala Leu Ala Glu Ala Gly Ala Asp Ala Tyr
7185                7190                7195                7200

Leu Glu Ile Gly Pro Asp Gly Val Leu Thr Gly Met Ala Ala Arg Val
                7205                7210                7215

Leu Asp Thr Ala Ala Asp Gly Ser Gly Gly Val Ser Val Pro Ala Leu
            7220                7225                7230

Arg Lys Asp Arg Pro Glu Glu His Ser Leu Leu Thr Ala Leu Ala Arg
        7235                7240                7245

Leu His Thr Ala Gly Val Ala Val Asp Trp Thr Ala Trp Phe Thr Gly
    7250                7255                7260

Thr Gly Ala Arg Arg Thr Asp Leu Pro Thr Tyr Ala Phe Gln Arg Glu
7265                7270                7275                7280

Leu Tyr Trp Pro Glu Pro Ala Thr Gly Pro His Thr Ala Thr Ala Gln
                7285                7290                7295

Asp Pro Ala Asp Ala Ala Phe Trp Ala Ala Val Glu Arg Glu Asp Leu
            7300                7305                7310

Glu Ser Leu Ser Ala Thr Leu Asp Leu Asp Asp Ala Val Leu Ser Asn
        7315                7320                7325

Val Leu Pro Ala Leu Ser Thr Trp Arg Arg Gly Leu Ser Glu Arg Thr
    7330                7335                7340

Leu Leu Asp Gly Trp Arg Tyr Arg Val Thr Trp Gln Pro Val Pro Leu
7345                7350                7355                7360

Gly Asn Thr Ala Asp Asp Gly Thr Gly Arg Pro Trp Leu Val Leu Thr
                7365                7370                7375

Leu Ala Gly His Asp Asp Ala Trp Thr Gln Ala Leu Ala Ala Thr Phe
            7380                7385                7390

Gly Glu His Thr Val His Leu Ala Val Pro Ala Asp Glu Asp Gly Thr
        7395                7400                7405

Ala Ala Leu Leu Asp Gly Ala Ala Asp Gly Thr Ala Tyr Ala Gly Val
    7410                7415                7420

Leu Ser Leu Leu Ala Gly Thr Ala Thr Asp Gly Thr Ala Arg Pro Asp
7425                7430                7435                7440

Thr Leu Leu Arg Leu Leu Ala Ala Ala Gly Ile Asp Ala Pro Leu Trp
                7445                7450                7455

Cys Val Thr Arg Asp Ala Val Ser Val Gly Arg Ser Asp Pro Ala Ala
            7460                7465                7470

Asp Pro Asp Arg Ala Ala Leu Trp Gly Leu Gly Arg Val Leu Ala Leu
        7475                7480                7485

Asp Glu Pro Glu Arg Trp Gly Gly Leu Val Asp Val Asp His Val Ala
    7490                7495                7500

Asp Ala Arg Thr Val Asp Arg Leu Arg Ala Val Leu Thr Val Ala Arg
7505                7510                7515                7520

Thr Asp Gly Pro Ala Glu Asp Gln Val Ala Leu Arg Ala Ser Gly Ala
                7525                7530                7535

Phe Gly Arg Arg Leu Ser Arg Ala Ala Ala Pro Ala Pro Asp Ile Thr
            7540                7545                7550

Trp His Pro Ala Gly Thr Val Leu Val Thr Gly Arg Ala Glu Gly Phe
        7555                7560                7565

Gly Gly His Val Ala Arg Trp Leu Ala Ala His Gly Ala Thr Gly Val
    7570                7575                7580

Leu Leu Ala Gly Pro Ala Gly Pro Glu Asp Ala Ala Thr Thr Ala Leu
```

-continued 7585 7590 7595 7600

Arg Ala Glu Val Glu Ala Leu Gly Ala Thr Leu Thr Val Val Arg His
7605 7610 7615

Pro Asp Pro Ala Asp Ala Ala Pro Leu Thr Glu Ala Leu Ala Ala Gln
7620 7625 7630

Ala Asp Asp Arg Pro Leu Thr Ala Val Leu His Thr Gly Asp Thr Gly
7635 7640 7645

Glu Glu Thr Pro Gly Val Thr Gly Ala Arg Ala Ala Tyr Glu Ala Leu
7650 7655 7660

Thr Thr Ala Val Gly Asp Arg Asp Leu Asp Ala Phe Val Val Phe Gly
7665 7670 7675 7680

Ser Ile Ser Ala Val Trp Gly Val Gly Gly Gln Gly Ala Gly Ala Ala
7685 7690 7695

Ala Gly Val Cys Leu Asp Ala Leu Val Gln Arg His Arg Ala His Gly
7700 7705 7710

Thr Asn Ala Val Ser Val Ser Trp Gly Ala Trp Gln Gly Ala Gly Pro
7715 7720 7725

Asp Gly Leu Ala Ala His Leu Arg Ala Asn Gly Leu Pro Ala Met Glu
7730 7735 7740

Pro Ala Arg Ala Leu Asp Ala Leu Ala Pro Ala Ile Gly Glu Ala Ala
7745 7750 7755 7760

Ala Asn Pro Ala Ala Pro Ala Ser Val Thr Val Ala Asp Val Ala Trp
7765 7770 7775

Asp Arg Phe Ala Pro Ala Phe Thr Arg Thr Arg Ala Gly Leu Leu Leu
7780 7785 7790

Thr Gly Val Pro Glu Ala Arg Glu Ala Leu Ser Thr Thr Gly Gly Asp
7795 7800 7805

Gly Ala Asp Ala Gly Thr Ala Ser Ala Leu Arg Glu Arg Leu Arg Gln
7810 7815 7820

Ser Asp Pro Ser Glu Arg Pro Arg Thr Leu Leu Asp Thr Val Leu Thr
7825 7830 7835 7840

Glu Ile Ala Ser Val Leu Gly His Thr Gly Ala Ala Ala Val Pro Ala
7845 7850 7855

Glu Asn Ala Phe Asn Asp Leu Gly Phe Asp Ser Leu Thr Ala Val Asp
7860 7865 7870

Leu Arg Asn Arg Leu Thr Thr Ala Thr Gly Leu Thr Leu Pro Ala Thr
7875 7880 7885

Leu Val Phe Asp Tyr Pro Thr Pro Ala Ala Leu Ala Ala His Leu Leu
7890 7895 7900

Thr Glu Leu Leu Gly Glu Asp Thr Gly Pro Gly Thr Gly Ala Pro Val
7905 7910 7915 7920

Ala Arg Ala Ala Ala Asp Ala Asp Asp Pro Val Val Ile Val Gly Met
7925 7930 7935

Ser Cys Arg Tyr Pro Gly Asp Val Arg Ser Pro Glu Asp Leu Trp Glu
7940 7945 7950

Leu Val Gly Ala Gly Thr Asp Ala Ile Gly Gly Phe Pro Thr Asp Arg
7955 7960 7965

Gly Trp Asp Leu Glu Lys Leu Leu His Gly Asp Glu Asp Gly Arg Gly
7970 7975 7980

Arg Ser Val Thr Arg Glu Gly Gly Phe Leu Tyr Asp Val Ala Asp Phe
7985 7990 7995 8000

Asp Pro Ala Phe Phe Gly Ile Ser Pro Arg Glu Ala Leu Val Ile Asp
8005 8010 8015

-continued

Pro Gln Gln Arg Ile Val Leu Gln Ala Ala Trp Glu Ala Leu Glu Arg
8020 8025 8030

Ala Gly Ile Asp Pro Ala Val Leu Arg Gly Gly Asp Thr Gly Val Phe
8035 8040 8045

Val Gly Gly Gly Ser Gly Asp Tyr Arg Pro Ala Ile Gly Gln Ser Gly
8050 8055 8060

His Val Glu Thr Ala Gln Ser Ala Ser Leu Leu Ser Gly Arg Leu Ser
8065 8070 8075 8080

Tyr Thr Leu Gly Leu Glu Gly Pro Ser Val Ser Val Asp Thr Ala Cys
8085 8090 8095

Ser Ser Ser Leu Thr Ala Leu His Leu Ala Ala Gln Ala Ile Arg Ser
8100 8105 8110

Gly Glu Cys Ser Leu Ala Leu Ala Gly Gly Val Thr Val Met Ser Thr
8115 8120 8125

Pro Val Gly Phe Val Glu Phe Gly Glu Met Gly Ala Leu Ser Pro Asp
8130 8135 8140

Gly Arg Cys Lys Pro Phe Ser Asp Ala Ala Asp Gly Thr Ala Trp Ser
8145 8150 8155 8160

Glu Gly Val Gly Met Leu Val Val Glu Arg Leu Ser Glu Ala Arg Arg
8165 8170 8175

Arg Gly His Glu Val Leu Ala Val Leu Arg Gly Ser Ala Ile Asn Gln
8180 8185 8190

Asp Gly Ala Ser Asn Gly Leu Thr Ala Pro Asn Gly Pro Ser Gln Gln
8195 8200 8205

Arg Val Ile Arg Lys Ala Leu Ala Ala Ala Gly Leu Thr Ala Arg Glu
8210 8215 8220

Val Asp Ala Val Glu Ala His Gly Thr Gly Thr Thr Leu Gly Asp Pro
8225 8230 8235 8240

Ile Glu Ala Gln Ala Leu Leu Ala Thr Tyr Gly Gln Asp Arg Pro Glu
8245 8250 8255

Gly Gln Pro Leu Leu Leu Gly Ser Val Lys Ser Asn Ile Gly His Ser
8260 8265 8270

Gln Ala Ala Ser Gly Val Ala Gly Ile Ile Lys Met Val Leu Ala Met
8275 8280 8285

Arg His Gly Thr Leu Pro Arg Thr Leu His Ala Glu Lys Pro Ser Arg
8290 8295 8300

His Val Ala Trp Asp Pro Asp Ala Val His Leu Leu Thr Glu Ala Ala
8305 8310 8315 8320

Asp Trp Pro Glu Thr Gly Arg Pro Arg Arg Ala Ala Val Ser Ser Phe
8325 8330 8335

Gly Ala Ser Gly Thr Asn Ala His Val Ile Leu Glu Gln Ala Pro Thr
8340 8345 8350

Gly Pro Ala Ala Pro Glu Arg Asp Thr Glu Pro Ala Thr His Ala Thr
8355 8360 8365

Asp Ala Ala Arg Leu Leu Pro Leu Pro Leu Ser Ala Ala Thr Ala Asp
8370 8375 8380

Ser Leu Thr Glu Gln Ala Ala Arg Leu Arg Asp Arg Leu Thr Ala Gly
8385 8390 8395 8400

Ala Ala Gln Pro Pro Ala Thr Ala Asp Leu Ala Leu Ser Leu Gly Thr
8405 8410 8415

Thr Arg Ser Ala Phe Glu His Arg Ala Val Leu Ala Val Ala Gly Arg
8420 8425 8430

```
Asp Asp Leu Leu Asp Ala Leu Thr Ala Leu Ala Glu Asp Arg Ala His
        8435                8440                8445

Pro Ala Val Leu Arg Gly Arg Ala Ala Pro Gly Gly Arg Thr Ala Phe
    8450                8455                8460

Leu Phe Pro Gly Gln Gly Ser Gln Arg Pro Gly Ala Gly Arg Ala Leu
8465                8470                8475                8480

Tyr Ala Arg Phe Pro Val Phe Ala Thr Ala Leu Asp Glu Val Leu Ala
                8485                8490                8495

His Phe Asp Gln Glu Leu Glu Arg Pro Leu Arg Asp Val Met Phe Ala
            8500                8505                8510

Asp Glu Gly Thr Pro Glu Ala Ala Leu Leu Asp Arg Thr Gly Trp Thr
        8515                8520                8525

Gln Pro Ala Leu Phe Ala Leu Gly Val Ala Leu Tyr Arg Leu Val Glu
    8530                8535                8540

Ser Trp Gly Val Arg Pro Asp Leu Leu Ala Gly His Ser Val Gly Glu
8545                8550                8555                8560

Leu Ala Ala Ala His Val Ala Gly Val Leu Ser Leu Pro Asp Ala Cys
                8565                8570                8575

Arg Val Val Ser Ala Arg Ala Arg Leu Met Glu Ala Leu Pro Ala Gly
            8580                8585                8590

Gly Ala Met Leu Ala Val Arg Ala Thr Glu Asp Glu Ile Ala Pro Tyr
        8595                8600                8605

Leu Thr Asp Gln Ile Cys Leu Ala Ala Val Asn Gly Pro Glu Ser Val
    8610                8615                8620

Val Val Ser Gly Asp Glu Lys Ala Val Thr Ala Leu Ala Glu Ala Leu
8625                8630                8635                8640

Ala Glu Gln Gly Arg Lys Thr Arg Arg Leu Arg Val Ser His Ala Phe
                8645                8650                8655

His Ser Leu His Met Asp Ala Met Leu Gln Asp Phe Glu Arg Val Thr
            8660                8665                8670

Arg Ser Val Ser Tyr Ala Pro Pro Thr Leu Pro Leu Val Ser Asn Leu
        8675                8680                8685

Thr Gly Asp Ala Ala Thr Asp Ala Gln Val Cys Asp Pro Gly Tyr Trp
    8690                8695                8700

Val Arg His Val Arg Glu Ala Val Arg Phe Gly Asp Gly Val Arg Thr
8705                8710                8715                8720

Leu Ala Gly Arg Gly Ala Thr Arg Tyr Leu Glu Leu Gly Pro Asp Gly
                8725                8730                8735

Ile Leu Cys Gly Leu Ala Gln Glu Thr Leu Asp Thr Leu Ala Asp Glu
            8740                8745                8750

Asn Arg Pro Ala Pro Thr Ala Val Pro Ala Leu Arg Thr Gly Arg Asp
        8755                8760                8765

Glu Glu Gln Ala Leu Ile Thr Ala Val Ala Arg Leu His Ala Ala Gly
    8770                8775                8780

Gln Gly Leu Asp Trp Ala Ala Leu Leu Asp Gly Thr Gly Ala Arg Arg
8785                8790                8795                8800

Val Asp Leu Pro Thr Tyr Pro Phe Arg Arg Leu Arg Phe Trp Pro Asp
                8805                8810                8815

Glu Ala Pro Ala Ala Ala Thr Gly Thr Thr Ala Asp Ala Gly Asp Ala
            8820                8825                8830

Ala Phe Trp Ala Ala Val Gln Asp Glu Gln Phe Asp Ser Leu Ala Gly
        8835                8840                8845

Glu Leu Gly Val Asp Gly Asp Ala Leu Leu Arg Val Leu Pro Ala Leu
```

-continued

```
8850                8855                8860

Arg Asp Trp Arg Arg Lys His Gly Asp Gln Thr Thr Val Asp Gly Trp
8865                8870                8875                8880

Arg Gln Arg Ile Ala Trp Arg Pro Leu Asn Arg Ala Thr Ala Gly Thr
                8885                8890                8895

Pro Ala Gly Thr Trp Leu Ala Val Val Pro Ala Asp His Ala Asp His
            8900                8905                8910

Pro Trp Thr Ser Ala Val Leu Ala Ala Leu Gly Ala Gly Ala Gln Val
        8915                8920                8925

Leu Glu Val Ser Gly Lys Asp Arg Ala Gly Leu Ala Ala Ala Ile Arg
    8930                8935                8940

Glu Arg Leu Asp Ala Thr Gly Pro Phe Thr Gly Val Val Ser Leu Leu
8945                8950                8955                8960

Ala Val Ala Gly Glu Pro Gly Asp Gly Thr Gly Ala Leu Pro Gly Gly
                8965                8970                8975

Val Pro Ala Gly Ala Ala Leu Thr Ala Thr Leu Val Gln Ala Leu Gly
            8980                8985                8990

Asp Ala Arg Thr Asp Ala Pro Leu Trp Cys Leu Thr Arg Gly Ala Ala
        8995                9000                9005

Ala Val Ser Pro Ala Glu Thr Val Ala Ala Pro Leu Gln Ala Ala Val
    9010                9015                9020

His Gly Leu Gly Arg Val Ala Ala Leu Glu His Pro Gln Arg Trp Gly
9025                9030                9035                9040

Gly Thr Val Asp Leu Pro Leu Ala Val Asp Ala Arg Thr Ala Glu Arg
                9045                9050                9055

Leu Ala Ala Val Leu Ala Asp Pro Glu Gly Glu Asp Gln Leu Ala Val
            9060                9065                9070

Arg Pro Gly Ala Val Phe Gly Arg Arg Leu Ala Ala Val Arg Pro Gly
        9075                9080                9085

Thr Pro Arg Asp Trp Lys Pro Thr Gly Thr Val Leu Ile Thr Gly Gly
    9090                9095                9100

Thr Gly Ala Leu Gly Ala Arg Thr Ala Arg Arg Leu Ala Gly Ala Gly
9105                9110                9115                9120

Ala Arg Arg Leu Val Leu Leu Ser Arg Ser Gly Pro Asp Ala Pro Gly
                9125                9130                9135

Ala Gly Glu Leu Ala Ala Asp Leu Arg Ala Leu Gly Ala Glu Pro Val
            9140                9145                9150

Ile Thr Ala Cys Asp Thr Ala Asp Arg Lys Ala Leu Ala Ala Val Leu
        9155                9160                9165

Ala Ala Ile Pro Glu Asp Ala Pro Leu Thr Gly Val Ile His Thr Ala
    9170                9175                9180

Gly Val Leu Asp Asp Gly Val Val Asp Gly Leu Thr Pro Glu Arg Phe
9185                9190                9195                9200

Ala Thr Val Phe Arg Ala Lys Val Ala Ser Ala Leu Leu Leu Asp Glu
                9205                9210                9215

Leu Thr Arg Ala His Asp Leu Glu Val Phe Ala Leu Phe Ser Ser Ala
            9220                9225                9230

Ser Ala Ala Val Gly Asn Pro Gly Gln Gly Thr Tyr Ala Ala Ala Asn
        9235                9240                9245

Ala Val Leu Asp Ala Leu Ala Glu Gln Arg Arg Ala Glu Gly Leu Pro
    9250                9255                9260

Ala Thr Ser Val Ala Tyr Gly Ala Trp Gly Gly Glu Gly Met Ala Asp
9265                9270                9275                9280
```

```
Gly Val Arg Ala Ala Ala Leu Ala Arg Arg Thr Gly Ile Arg Pro Leu
                9285                9290                9295

Asp Pro Asp Leu Ala Val Leu Ala Leu Arg Gln Val Val Thr Gly Ser
            9300                9305                9310

Asp Pro Val Ala Val Val Ala Asp Val Asp Pro Asp Arg Phe Val Arg
        9315                9320                9325

Ala Phe Thr Thr Val Arg Pro Ser Ser Leu Leu Ala Glu Met Pro Ala
    9330                9335                9340

Tyr Ala Ala Leu Lys Lys Ala Ala Ser Ala Gly Gly Glu Ala Ala Asp
9345                9350                9355                9360

Ser Gly Pro Ser Leu Arg Asp Arg Leu Ala Arg Leu Pro Glu Ser Arg
                9365                9370                9375

Arg Thr Gln Thr Val Leu Thr Leu Val Arg Glu Arg Ala Ala Glu Val
            9380                9385                9390

Leu Gly Leu Thr Gly Thr Asp Gln Val Gly Pro Asp Arg Ala Phe Arg
        9395                9400                9405

Asp Leu Gly Phe Asp Ser Leu Gly Ala Val Glu Leu Arg Asn Gln Leu
    9410                9415                9420

Gly Ala Val Ser Gly Leu Thr Leu Ser Ala Thr Leu Val Phe Asp His
9425                9430                9435                9440

Pro Thr Pro Ala Ala Leu Ala Ala His Ile Leu Gly Gln Leu Leu Pro
                9445                9450                9455

Ala Gly Thr Pro Gly Ala Pro Ala Thr Asp Gly Ala Gly Glu Glu Glu
            9460                9465                9470

Arg Ala Val Arg Ala Ala Leu Ala Gln Val Pro Leu Asp Arg Leu Arg
        9475                9480                9485

Asp Ser Gly Leu Leu Asp Gln Leu Leu Asp Leu Ala Gly Gln Asp Pro
    9490                9495                9500

Ala Gly Thr Gly Thr Asp Gln Glu Ala Glu Pro Ser Gly Ala Gly Asp
9505                9510                9515                9520

Ala Tyr Asp Ala Ser Ile Asp Ala Met Asp Val Asp Gly Leu Val Gln
                9525                9530                9535

Ala Ala Leu Asn Gly Asn Pro Asp Glu Glu Arg Asp
            9540                9545
```

<210> SEQ ID NO 8
<211> LENGTH: 335
<212> TYPE: PRT
<213> ORGANISM: Streptomyces sp. FR-008

<400> SEQUENCE: 8

```
Met Asn Gly Leu His Leu Pro Pro Ala Pro Leu Pro Ala Pro Gly Val
 1               5                  10                  15

Ser Ala Ala Gly Ser Gly Asp Leu Met Ile Glu Ala Glu Gly Val Ser
            20                  25                  30

Lys Ala Tyr Gly Thr Val His Ala Leu Asp Ser Val Ser Leu Ala Val
        35                  40                  45

Pro Arg Gly Thr Val Leu Gly Leu Leu Gly His Asn Gly Ala Gly Lys
    50                  55                  60

Thr Thr Leu Val Asp Ile Leu Thr Thr Ala Leu Pro Pro Thr Ser Gly
65                  70                  75                  80

Arg Ala Arg Val Ala Gly Tyr Asp Val Ala Asp Lys Pro Val Glu Ile
                85                  90                  95

Arg Arg Arg Ile Gly Leu Thr Gly Gln Phe Ala Ser Val Asp Ala Gln
```

```
            100                 105                 110

Leu Ser Gly Tyr Asp Asn Leu Val Leu Ile Ala Arg Leu Leu Gly Ala
        115                 120                 125

Gly Arg Arg Ala Ala Arg Val Arg Ala Arg Glu Leu Leu Glu Leu Phe
    130                 135                 140

Arg Leu Thr Glu Val Ala Asp Arg Arg Ala Ser Ser Tyr Ser Gly Gly
145                 150                 155                 160

Leu Arg Arg Arg Leu Asp Leu Ala Val Ser Leu Val Gly Ala Pro Glu
                165                 170                 175

Val Leu Phe Leu Asp Glu Pro Thr Thr Gly Leu Asp Pro Ser Ser Arg
            180                 185                 190

Ile Asn Leu Trp Glu Ile Val Glu Gly Leu Val Glu Gln Gly Thr Thr
        195                 200                 205

Val Leu Leu Thr Thr Gln Tyr Leu Glu Glu Ala Asp Arg Leu Ala Asp
    210                 215                 220

Arg Ile Ala Val Leu Ser Ala Gly Arg Val Val Ala Ala Gly Thr Ala
225                 230                 235                 240

Pro Glu Leu Lys Ala Thr Val Gly Arg Arg Thr Val Thr Leu Thr Leu
                245                 250                 255

Glu Thr Gly Glu Asp Val Ser Ala Ala Arg Thr Ala Leu Arg Gly Ala
            260                 265                 270

Gly Phe Ala Pro Val Asp Gly Glu Ala Arg Thr Val Val Val Pro Ile
        275                 280                 285

Asp Ala Thr Arg Glu Ile Ala Asp Ile Ile Arg Ser Leu Asp Gln Ala
    290                 295                 300

Gly Val Glu Ala Ser Glu Leu Asn Phe Gly Glu Pro Thr Leu Asp Asp
305                 310                 315                 320

Val Tyr Leu Thr Leu Ala Glu Gln Ala Ala Gly Arg Thr Arg Ala
                325                 330                 335


<210> SEQ ID NO 9
<211> LENGTH: 239
<212> TYPE: PRT
<213> ORGANISM: Streptomyces sp. FR-008

<400> SEQUENCE: 9

Met Val Thr Asp Pro Gly Ile Val Leu Phe Gly Leu Ile Gln Pro Val
 1               5                  10                  15

Val Ile Leu Phe Val Leu Thr Gln Val Phe Ser Lys Met Gly Met Pro
            20                  25                  30

Pro His Phe Pro Asp Gly Val Ser Tyr Leu Asp Tyr Val Leu Pro Ala
        35                  40                  45

Val Leu Val Asp Asn Ala Ala Gln Ser Ala Met Gln Ser Gly Val Gly
    50                  55                  60

Leu Val Glu Asp Gln Lys Asn Gly Ile Val Ala Arg Leu Arg Ser Leu
65                  70                  75                  80

Pro Val His Pro Gly Ala Leu Leu Ala Ala Arg Ser Leu Val Gly Leu
                85                  90                  95

Val Arg Ser Ala Val Gln Val Ala Val Ile Met Ala Leu Ala Met Thr
            100                 105                 110

Val Leu Gly Tyr Ser Pro Asn Gly Gly Ala Ala Glu Leu Ala Leu Ser
        115                 120                 125

Ala Gly Leu Thr Leu Phe Ile Ser Phe Ser Leu Gly Trp Ala Phe Ile
    130                 135                 140
```

-continued

```
Ala Ala Gly Ala Trp Leu Arg Arg Ala Glu Pro Leu Gln Asn Leu Ala
145                 150                 155                 160

Leu Ile Val Ile Phe Pro Leu Met Phe Ala Ser Ser Ala Tyr Val Pro
                165                 170                 175

Val Ala Asp Leu Pro Ser Trp Leu Gly Ala Val Ala Ser Val Asn Pro
            180                 185                 190

Leu Thr Tyr Ala Ile Asp Ala Thr Arg Ala Leu Ala Leu Asp Val Pro
        195                 200                 205

Gly Leu Asp His Ala Ile Pro Ala Val Val Ile Cys Ala Val Ile Ala
    210                 215                 220

Val Val Gly Met Ile Ala Ala Val Arg Gly Phe Arg Arg Pro Leu
225                 230                 235


<210> SEQ ID NO 10
<211> LENGTH: 222
<212> TYPE: PRT
<213> ORGANISM: Streptomyces sp. FR-008

<400> SEQUENCE: 10

Met Asp Pro Ala Pro Ala Ala Asp Pro Ala Gly Ser Pro Glu Arg Ala
 1               5                  10                  15

Ala Val Leu Ala Asp Gly Phe Asp Arg Ala Gly Ala Tyr Val Ala Cys
            20                  25                  30

Leu Asp Pro Ser Leu Thr Ile Gln Gln Val Asn Gln Glu Phe Glu Arg
        35                  40                  45

Arg Phe Gly Gly Ser Ser Ser Glu Leu Cys Gly Ser Arg Phe Cys Asp
    50                  55                  60

Leu Val His Pro Ser Val Gln Gln Pro Leu Met His Gln Phe Ala Arg
65                  70                  75                  80

Met Leu Asp Gly Lys Arg His Arg Phe Ala Thr Glu Val Ile Ala Val
                85                  90                  95

Asp Gln Glu Arg Thr Ala Ser Thr Leu Pro Leu Asn Ala Leu Ala Val
            100                 105                 110

Arg Gly Gly Arg Thr Pro Asp Val Ala Ala Ile Leu Val Val Met Asn
        115                 120                 125

Ala Ala Glu Glu Glu Ala Gly Asp Ala Asp Val Met Ala Pro Arg Lys
    130                 135                 140

Lys Leu Leu Ser Glu Ile Asp Ala Arg Ile Leu Glu Gly Ile Ala Ala
145                 150                 155                 160

Gly Val Ser Thr Ile Pro Leu Ala Ser Arg Leu Tyr Leu Ser Arg Gln
                165                 170                 175

Gly Val Glu Tyr His Val Thr Gly Leu Leu Arg Lys Leu Lys Val Pro
            180                 185                 190

Asn Arg Ala Ala Leu Val Ser Arg Ala Tyr Ser Met Gly Val Leu Lys
        195                 200                 205

Val Gly Thr Trp Pro Pro Lys Val Val Glu Asp Phe Ile Lys
    210                 215                 220


<210> SEQ ID NO 11
<211> LENGTH: 942
<212> TYPE: PRT
<213> ORGANISM: Streptomyces sp. FR-008

<400> SEQUENCE: 11

Met Leu Leu Glu Arg Thr Thr Glu Ile Ala Leu Val Asp Ala Ala Leu
 1               5                  10                  15
```

-continued

```
Gly Ala Ala Thr Glu Gly Arg Ser Ser Leu Val Leu Leu Thr Gly Pro
            20                  25                  30

Leu Gly Ile Gly Arg Ser Ala Leu Leu Gln Arg Leu Ser Cys Leu Ala
        35                  40                  45

Asp Asp Arg Asp Asp Val Arg Val Leu Arg Ala His Ala Ala Pro Met
    50                  55                  60

Glu Gln Asp Phe Ala Phe Gly Val Val Arg Gln Leu Phe Glu Thr Leu
65                  70                  75                  80

Leu Gly Asp Ser Pro Glu Asp Ala Arg Asp Arg Trp Met Asp Ala His
                85                  90                  95

Ala Ser Phe Ala Arg His Val Leu Ala Asp Asp Ala Ala Pro Pro Gly
            100                 105                 110

Ala Asp Gln Ala Ile Ala Ala Thr Glu Ala Val Leu His Gly Leu Leu
        115                 120                 125

Ser Leu Leu Ala Asn Val Ser Ala Asp Ser Arg Leu Leu Ile Leu Val
    130                 135                 140

Asp Asp Leu Gln Trp Ser Asp Val Pro Ser Leu Arg Trp Leu Thr Tyr
145                 150                 155                 160

Leu Ala Lys Arg Leu His Gly Leu Arg Ala Val Val Val Cys Ala Leu
                165                 170                 175

Arg Asp Gly Asp Pro Arg Ser His His Thr Leu Ala Arg Glu Ile Arg
            180                 185                 190

Glu Ala Gly Thr Gln Thr Leu Arg Pro Ala Ser Leu Ser Leu Thr Ala
        195                 200                 205

Thr His Glu Leu Val Arg Glu His Phe Gly Glu Ala Gly Asp Asp Glu
    210                 215                 220

Phe Val Gln Ala Cys His Glu Ala Ser Val Gly Asn Pro Leu Phe Leu
225                 230                 235                 240

Leu Ser Ile Leu Val Gly Thr Gly Phe Leu Gly Arg Arg Pro Leu Ala
                245                 250                 255

Glu His Ala Glu Thr Ala Arg Arg Leu Arg Pro Ser Gln Leu Arg Glu
            260                 265                 270

Arg Leu Ala Ser Ile Leu Arg Thr Gln Pro Ala Pro Val Arg Asp Leu
        275                 280                 285

Ala Ala Ala Ile Ala Ile Leu Gly Glu Gln Ser Asp Ala Pro Thr Leu
    290                 295                 300

Ala Arg Leu Ala Gly Leu Asp Ser Ile Gly Tyr Ala Gly Ala Leu Arg
305                 310                 315                 320

Ala Leu Gly Ala Leu Gly Ala Leu Ala Ala Pro Asp Glu Pro Arg Phe
                325                 330                 335

Ile His Arg Ser Val Arg Asp Ala Ala Glu Ser Thr Leu Thr Met Val
            340                 345                 350

Gln Arg Glu Arg Met His Asp Glu Ala Ala Ala Leu Leu Tyr Ala Ala
        355                 360                 365

Gly Ser Pro Ala Glu Gln Val Ala Ala Gln Leu Met Ala Val Val Thr
    370                 375                 380

Arg Arg Gln Pro Trp Ala Val Asp Val Leu Arg Ala Ala Ala Asp Thr
385                 390                 395                 400

Ala Leu Arg Arg Gly Ala Pro Asp Thr Ala Ala Gly Tyr Leu Cys Arg
                405                 410                 415

Ala Leu Leu Asp Ser Pro Ala Ala Gly Val Gly Arg Gly Arg Leu Leu
            420                 425                 430

Val Glu Leu Gly Thr Ala Glu Arg Gly Phe Asp Pro Leu Ala Cys Glu
```

-continued

```
        435                 440                 445

Arg His Ile Ala Gln Ala Met Thr Leu Leu Pro Glu Pro Arg Asp Arg
    450                 455                 460

Ala Val Ala Ala Leu Arg Ile Ser Pro Thr Ala Leu Gly Pro Ala Pro
465                 470                 475                 480

Leu Thr Ala Val Asp Leu Leu Arg Gln Ala Ala Glu Asp Leu Gly Pro
                485                 490                 495

Ala Asp Gly Leu Thr Gly Thr Asp Arg Asp Leu Ala Leu Arg Leu Glu
            500                 505                 510

Ala Arg Leu Arg His Cys Gly His Glu Asp Pro His Glu Leu Ala Ala
        515                 520                 525

Ser Ala His Arg Leu Lys Glu Leu Gly Pro Glu Pro Pro Val Asp Thr
    530                 535                 540

Gly Gly Glu Arg Glu Leu Thr Ile Ala Leu Leu Gly Ala Ala Thr Leu
545                 550                 555                 560

Gly Cys His Leu Pro Ala Ser Glu Val Val Arg Leu Ala Gly Arg Val
                565                 570                 575

Leu Asp Arg Glu Pro Ala Thr Ser Ala Arg Ile His Ser Thr Leu Pro
            580                 585                 590

Leu Ala Ile Ile Thr Met Ile Ala Ala Asp Ser Val Glu Ala Val Asp
        595                 600                 605

Ser Trp Leu Ala Val Glu His Arg Ala Asn Glu Arg Gly Thr Thr Pro
    610                 615                 620

Ala Asn Ala Leu Val His Ile Glu Gln Ala Leu Val His Leu Gly Arg
625                 630                 635                 640

Gly Arg Leu Ala Gln Ala Arg Glu Gln Ser Glu Thr Ala Leu Gly Met
                645                 650                 655

Thr Glu Pro Ala His Gln Gly Leu Asp Thr Ala Ala Thr Met Thr His
            660                 665                 670

Ala Ile Val Ala Leu Glu Ser Arg Asp Pro Ser Leu Ala Glu Lys Val
        675                 680                 685

Leu Arg Arg Ala Ser Arg Ile Arg Pro Gln Gly Leu Thr Leu Thr Gly
    690                 695                 700

Ile Leu Arg Leu Leu Glu Ala Thr Arg Glu Ile Ala Ala Gly Asp Gln
705                 710                 715                 720

Thr Gly Ala Leu Asp Ser Leu His Ser Cys Gly Arg Gln Leu Glu Ala
                725                 730                 735

Ala Gly Trp His Asn Pro Val Leu Phe Pro Trp Arg Pro Trp Ala Val
            740                 745                 750

Gly Val His Arg Arg Leu Gly Asp Ile Arg Thr Ala Arg Ser Leu Ala
        755                 760                 765

Glu Glu Glu Tyr Ala Arg Ala Glu Gln Trp Gly Ala Pro Val Gly Val
    770                 775                 780

Gly Arg Ala Leu Arg Leu Leu Gly Arg Leu Glu Asp Gly Gly Arg Gly
785                 790                 795                 800

Ile Gly Leu Leu Arg Glu Ala Val Thr Val Leu Arg Gly Ser Ala Asn
                805                 810                 815

Gln Leu Glu Leu Ala Arg Ala Leu Ser Thr Leu Ala Glu Arg Leu Gly
            820                 825                 830

Gly Gly Ala Glu Thr Glu Ala Leu Ala Arg Glu Ala Ala Thr Leu Ala
        835                 840                 845

Thr Ser Cys Gly Ala Pro Gly Leu Ala Glu Arg Ala Ala Arg Gly Ala
    850                 855                 860
```

-continued

```
Gly His Arg Ser Gly Pro Pro Ala Thr Pro Glu Asp Val Leu Thr Pro
865                 870                 875                 880

Thr Glu Arg Arg Val Val Gly Leu Ala Cys Arg Gly Leu Thr Asn Gln
                885                 890                 895

Glu Ile Ala Gly Ala Leu Gly Val Ser Ser Arg Ala Val Glu Lys His
            900                 905                 910

Leu Thr His Ala Tyr Arg Arg Leu Gly Ile Ser Gly Arg Arg Glu Leu
        915                 920                 925

Ile Val Leu Phe Ser Arg Ala Glu Tyr Ala Gly Thr Gly Asp
    930                 935                 940


<210> SEQ ID NO 12
<211> LENGTH: 1036
<212> TYPE: PRT
<213> ORGANISM: Streptomyces sp. FR-008

<400> SEQUENCE: 12

Met Arg Ser Gly Glu Ile His Arg Lys Asn Ser Gly Leu Gln Thr Pro
 1               5                  10                  15

Thr Cys Cys Thr Ala Gln Met Tyr Asp Leu His Met Pro Pro Ile Glu
            20                  25                  30

Leu Pro Leu Leu Glu Arg Asp Arg Glu Leu Ala Ala Leu Ser Ala Val
        35                  40                  45

Ile Gly Glu Leu Gly Ser Gly Arg Pro Ala Val Val Thr Val Thr Gly
    50                  55                  60

Glu Pro Gly Leu Gly Gln Asn Asp Leu Leu Arg Trp Ala Ala Ala Tyr
65                  70                  75                  80

Ala Thr Asp Ala Gly Leu Arg Val Leu Ser Ala His Ala Thr Pro Ala
                85                  90                  95

Glu His Glu Val Arg Tyr Gly Val Val Ala Gln Leu Leu Ala Glu Glu
            100                 105                 110

Asn Arg Ala Leu Ala Pro Arg Leu Phe Leu Thr Asp Glu Gln Pro Gly
        115                 120                 125

Gly Leu Pro Gly Leu Asn Gly Leu Leu Asn Ala Val Arg Asp Arg Pro
    130                 135                 140

Thr Leu Leu Val Val Arg Asp Thr Gln Trp Leu Asp Pro Ala Ser Leu
145                 150                 155                 160

Arg Trp Leu Glu Ala Leu Ala Arg Arg Leu Pro Arg Ala Pro Val Ala
                165                 170                 175

Leu Leu Thr Ser Thr Thr Gly Thr Ala Leu Thr Arg Pro Glu Trp Ser
            180                 185                 190

Val Gly Thr Pro Leu Thr Gly Leu Ala Thr Thr Ile Glu Leu Ala Leu
        195                 200                 205

Pro Pro Leu Thr Ser Gly Gly Thr Ala Thr Ala Val Leu Arg Ala Phe
    210                 215                 220

Gly Ala Pro Gly Asp Pro Ala Phe Thr Glu Ala Leu Ala Glu Ala Thr
225                 230                 235                 240

Arg Gly Ile Pro Ala Val Val His Asp Val Leu Asp Arg Phe Ala Arg
                245                 250                 255

Ala Gly Tyr Ser Pro Arg Ala Asp Arg Ile Asp Pro Leu Arg Ala Leu
            260                 265                 270

Thr Ala Glu Val Val Gly Asp His Ala Thr Arg Ala Leu Ser Asp Leu
        275                 280                 285

Arg Asp Pro Ala Ala Val Asp Ala Leu Arg Ala Leu Ala Val Cys Gly
```

-continued

```
    290                 295                 300

Asp Leu Leu Asp Phe Pro Leu Val Cys Thr Leu Ala Gly Pro His Ser
305                 310                 315                 320

Val Ser Glu Ser Arg Leu Arg Ala Ala Leu Ala Ala Ser Gly Leu Thr
                325                 330                 335

Thr Leu Arg Asp Gly His Pro Arg Val Gln Asp Ala Val Val Arg Ala
            340                 345                 350

Arg Val Leu Glu Glu Met Pro Ala Ala Asp Arg Ala Glu Leu Tyr Ala
        355                 360                 365

Arg Ala Ala Gly Leu Ala Gln Arg Val Ala Ala Asp Asp Gln Gly Ile
    370                 375                 380

Ala Asp Leu Leu Leu Leu Ala Arg Pro Val Gly Asp Pro Trp Ala Val
385                 390                 395                 400

Asp Thr Leu Arg Arg Gly Phe Thr Ser Ala Leu Arg Gly Gly Arg Arg
                405                 410                 415

Asp Leu Ala Val Ala Tyr Leu Ala Arg Ala Leu Asp Glu Pro Leu Ala
            420                 425                 430

Ala Glu Asp Arg Ala Arg Ile Glu Phe Gln Leu Ala Ser Val Glu Met
        435                 440                 445

Val Thr Ala Pro Thr Ala Ala Glu Arg Arg Leu Gly Gly Leu Ile Arg
    450                 455                 460

Ala Thr Arg Pro Gly Pro Gly Ala Gly Leu Arg Ala Arg Ala Thr Asp
465                 470                 475                 480

Leu Cys Leu Leu Gly Gly Asp Thr Arg Ala Ala Arg His Ala Leu Ala
                485                 490                 495

Gly Ala Ile Asp Ser Ala Pro Ala Ala Pro Glu Pro Arg Arg Gly Pro
            500                 505                 510

Thr Gly Ala Pro Ala Val Pro Pro Glu Ala Glu Pro Ala Ser Thr Pro
        515                 520                 525

Arg Thr His Leu Val Pro His Arg Pro Tyr Ala Gly Thr Pro Pro Gly
    530                 535                 540

Ala Thr Gly Pro Asp Gly Arg Arg Ser Ala Ala Pro Asp Leu Pro Gly
545                 550                 555                 560

Thr Pro Arg Ala His Asp Ala Pro Arg Ser Pro Gly Pro Glu Ala Ala
                565                 570                 575

Gly Arg Pro Asp Thr Ala Gly Pro Asp Glu Asp Pro Ala Val Ala Glu
            580                 585                 590

Arg His Glu Leu Thr Val Leu Cys Arg Val Ala Ser Phe Leu Arg His
        595                 600                 605

Asp Asp Ala Asp Leu Asp Val Leu Pro Val Pro Ala Leu Pro Asp Ala
    610                 615                 620

Val His Asn Pro Ala Val Ala Gly Val Trp Ala Trp Glu His Gly Val
625                 630                 635                 640

Ala Gly Val His Arg Glu Glu Val Arg Arg Leu Ala Arg Ser Ala Phe
                645                 650                 655

Val Pro Ala Ala Thr Gly Arg Pro Leu Leu Val Val Pro Arg Leu Leu
            660                 665                 670

Gly Cys Arg Ala Leu Leu Leu Thr Asp Asp Gly Asp Glu Ala Glu Asn
        675                 680                 685

His Leu Gly Ala Leu Leu Asp Glu Ser His Arg Glu Arg Ala Ala Ile
    690                 695                 700

Ser Val Ala His Ile Leu Thr Val Arg Ala Glu Leu His Ile Arg His
705                 710                 715                 720
```

-continued

```
Gly Arg Pro Asp Ala Ala Ala Arg Asp Leu Ala Ala Ala Gln Ala Glu
                725                 730                 735

Leu Pro Leu Asp Arg Leu His Pro Leu Phe Leu Pro Tyr Trp Leu Ala
            740                 745                 750

Leu Ser Met Ile Thr Asp Leu Gln Asn Gly His Thr Glu Arg Ala Arg
        755                 760                 765

Glu Thr Ala Ala Arg Pro Leu Pro Pro Leu Ala His Glu Ser Ala Thr
    770                 775                 780

Thr Ala Gln Leu Leu Phe Ala Arg Gly Val Leu Ala Arg Thr Asp Asp
785                 790                 795                 800

Glu Pro His Gln Ala Arg Glu His Phe Arg Ala Cys Gly Arg Trp Leu
                805                 810                 815

Leu Arg His Gly Cys Ala Asn Pro Ala Val Gln Pro Trp Arg Ser Leu
            820                 825                 830

Ala Ala Glu Ala Ala His Thr Leu Gly Asp Thr Glu Glu Ala Ala Arg
        835                 840                 845

Leu Val His Glu Glu Val Arg Leu Ala Arg Arg Trp Gly Ala Ala Ala
    850                 855                 860

Pro Leu Gly Arg Ala Gln Leu Ser Leu Ala Val Val Thr Glu Glu Asn
865                 870                 875                 880

Arg Val Glu Asn Leu Arg Ala Ala Val Thr Thr Leu Ser Ala Ala Ser
                885                 890                 895

Ala Arg Thr Ala Tyr Thr Arg Ala Val Ile Glu Leu Ala Ala Ala Glu
            900                 905                 910

Arg Glu Glu Asn Glu Arg Arg Thr Ala Val Ala Leu Gly Pro Ala Ala
        915                 920                 925

Thr Val Leu Pro Pro Val Ala Pro Pro Pro Gly Pro His Val Pro Ser
    930                 935                 940

Ala Val Ala Arg Pro Pro Gly Pro Arg Pro Ala Val Leu Thr Gly Arg
945                 950                 955                 960

Arg Thr Ala Lys Ala Pro Gly His Asp Ala Ala Val Trp His Gly Leu
                965                 970                 975

Thr Ala Val Glu Arg Glu Thr Ala Ala Leu Ala Ala Gln Gly Leu Gly
            980                 985                 990

Asn Arg Glu Ile Ala Thr Glu Leu Ala Val Thr Thr Arg Ala Val Glu
        995                 1000                1005

Leu Arg Leu Ser Gly Val Tyr Arg Lys Leu Arg Ile Arg Gly Arg Glu
   1010                1015                1020

Glu Leu Arg Ala Leu Val Gln Glu Ala Glu Gly Ser
1025                1030                1035


<210> SEQ ID NO 13
<211> LENGTH: 1005
<212> TYPE: PRT
<213> ORGANISM: Streptomyces sp. FR-008

<400> SEQUENCE: 13

Met Trp Leu Arg Trp Ala Gly Asp Arg Ser Arg Gly Ala Ala Pro Gly
 1               5                  10                  15

Arg Ser Gly Ser Ala Gly Pro Pro Ser Leu Ala Pro Ser Asp Ala Arg
            20                  25                  30

Glu Ser Pro Val Pro His Arg Ser Arg Ala Val Pro Pro Ala Pro Pro
        35                  40                  45

Leu Val Gly Arg Ala His Gln Leu Asp Val Leu Ala Arg His Ala Asp
```

```
    50                  55                  60

Ala Ala Arg Ala Gly Arg Pro Arg Leu Val Leu Leu Asp Gly Pro Ala
65                  70                  75                  80

Gly Ile Gly Lys Thr Ala Leu Leu Arg Ala Ala Leu Ala Glu Asp Gly
                85                  90                  95

Pro Leu Ala Gly Met Thr Thr Leu Tyr Gly Ser Cys Arg Ala Val Asp
            100                 105                 110

Val Ala Thr Gly Tyr Ser Gly Val Arg Ala Leu Phe Gly Gly Leu Gly
        115                 120                 125

Leu Thr Gly Arg Lys Gly Arg Thr Ser Pro Leu Leu Val Gly Gly Ala
    130                 135                 140

Arg Arg Ala Leu Pro Ala Leu Ala Ala Asp Pro Gly Glu Leu Asp Ala
145                 150                 155                 160

Asp Pro Gly Ser Thr Phe Ser Val Leu Gln Gly Leu Tyr Trp Leu Ala
                165                 170                 175

Ala Asn Leu Met Ala Asp Gly Pro Leu Val Leu Val Leu Asp Asp Val
            180                 185                 190

His Trp Cys Asp Glu Arg Ser Leu Arg Trp Leu Asp Phe Leu Leu Arg
        195                 200                 205

Arg Ala Asp Gly Leu Pro Leu Leu Val Val Ala Ala His Arg Thr Gly
    210                 215                 220

Thr Gly Leu Thr Ala Pro Asp Ala Leu Ala Asp Leu Val Ala His His
225                 230                 235                 240

Leu Pro Ala Ser Leu Gly Leu Gly Pro Leu Asp Thr Ala Glu Val Ala
                245                 250                 255

Glu Leu Thr Ala His Ser Phe Pro Glu Gln Asp Pro Leu Pro Ser Phe
            260                 265                 270

Val Gly Arg Leu Leu Ser Val Thr Gly Gly Ser Pro Leu Glu Ile Val
        275                 280                 285

Arg Leu Leu Arg Asp Leu Arg Ser Ala Gly Leu Gly Pro Asp Asp Thr
    290                 295                 300

Gly Thr Ala Arg Leu Ala Gln Ala Gly Gly Lys Val Val Ala Ala Ser
305                 310                 315                 320

Val Arg Gly Val Leu Glu His Gln Pro Asp Trp Val Arg Gln Val Ala
                325                 330                 335

Arg Ala Val Ala Val Leu Gly Asp Glu Asp Arg Thr Tyr Leu Ala Ala
            340                 345                 350

Leu Gly Arg Val Ser Val Val His Val Glu Glu Ala Val Glu Ile Leu
        355                 360                 365

Arg Asp Ala Gly Leu Ile His Pro Gly His Leu Glu Leu Ser His Asp
    370                 375                 380

Leu Val Arg Ala Ala Val Leu Asp Ala Val Gly Ala Ser Gly Val Ala
385                 390                 395                 400

Val Leu Arg Arg Arg Ala Ala Arg Leu Leu Ser Asp Val Gly Arg Ser
                405                 410                 415

Pro Glu Glu Ile Ala Thr Gln Leu Leu Leu Val Pro Gly Thr Pro Asp
            420                 425                 430

Asp Trp Ala Val Ser Val Leu Arg Asp Ala Ala Ala Gln Ala Glu Gln
        435                 440                 445

Arg Gly Ala Cys Glu Ala Ala Ala Arg Tyr Leu Glu Arg Val Arg Glu
    450                 455                 460

Ala Glu Pro Lys Asp Pro Asp Val Leu Ser Arg Leu Gly Lys Ala Leu
465                 470                 475                 480
```

-continued

```
Ala Glu Thr Asp Pro Ala Arg Ser Val Thr Leu Leu His Glu Ala His
                485                 490                 495

Ser Leu Thr Thr Asp Val Arg Ala Arg Ala Ala Thr Ala Val Gln Leu
            500                 505                 510

Gly Leu Thr Cys Leu Ala Val Gln Gln Ser Pro Asp Gly Ala Arg Ala
        515                 520                 525

Leu Thr Glu Ala Leu Asp Ala Leu Asp Ala Glu Leu Gly Pro Glu Pro
    530                 535                 540

Glu Pro Ala Asp Arg Glu Leu Arg Thr Leu Thr Glu Ser Ala Leu Leu
545                 550                 555                 560

Ile Val Gly Ser Asp Glu Lys Ala Thr Leu Pro Asp Ile Leu Arg Arg
                565                 570                 575

Thr Glu Gly Leu Thr Pro Gln Pro Gly Asp Thr Pro Ala Gln Arg Gln
            580                 585                 590

Gln Leu Ala Met Leu Ser Val Leu Ser Ala Ala Glu Gly Gly Gly Ala
        595                 600                 605

Glu Glu Thr Val Gly Arg Ala Arg Arg Ala Leu Arg Ala Pro Gly Val
    610                 615                 620

Pro Leu Gly Val Trp Ser Leu Leu Pro Thr Ser Leu Ala Leu Ser Leu
625                 630                 635                 640

Ala Asp Glu Asn Glu Ala Ala Glu Glu Val Leu Glu Thr Val Leu Arg
                645                 650                 655

Gly Ser Gly Asp Thr Ala Ala Val Trp Thr Tyr Val Leu Ala Leu Ser
            660                 665                 670

Thr Arg Ser Leu Phe Arg Leu Glu Asn Gly Ala Val Pro Asp Ala Met
        675                 680                 685

Ala Asp Ala Gln Thr Ala Leu Glu Ile Leu Gly Gln Glu Arg Trp Gly
    690                 695                 700

Asp Thr Ala Thr Met Pro His Thr Ala Tyr Ala Ser Val Leu Thr Glu
705                 710                 715                 720

Arg Gly Asp Pro Gly Arg Ala Leu Glu Ala Leu Asp Ala Ile Lys Arg
                725                 730                 735

Pro His Leu Asp Arg Phe Val Trp Glu Tyr His Trp Tyr Leu Met Ala
            740                 745                 750

Arg Gly Arg Ala Leu Ala Ala Asp Gly Asp Leu Asp Gly Ala Leu Gln
        755                 760                 765

Val Phe Gly Ser Cys Gly Ala Ser Met Ala Glu Ala Gly Leu Thr Asn
    770                 775                 780

Pro Val Leu Ala Pro Trp Trp Leu Glu Thr Ala Cys Leu Leu Gly Glu
785                 790                 795                 800

Ala Gly Arg Gly Glu Glu Ala Gly Arg Ala Ala Ala His Gly Thr Arg
                805                 810                 815

Leu Ala Glu Arg Trp Gly Thr Arg Arg Ala Leu Gly Tyr Ala Ala Leu
            820                 825                 830

Ala Arg Gly Ala Ala Ala Arg Gly Thr Ala Arg Thr Gly Ala Leu Arg
        835                 840                 845

Glu Ala Val Ala Leu Leu Ala Asp Ser Pro Ala Arg Ser Gly His Ala
    850                 855                 860

Arg Gly Leu Leu Leu Leu Gly Arg Ala Leu Val Glu Asp Gly Ala Val
865                 870                 875                 880

Arg Glu Gly Arg Glu His Leu Arg Glu Ala Val Gly Leu Ala Arg Arg
                885                 890                 895
```

-continued

Cys Gly Cys Val Ala Leu Ala Arg Arg Ala Arg Asp Glu Leu Ile Ala
900 905 910

Ala Gly Gly Arg Met Arg Glu Val Thr Ala Ser Pro Leu Asp Met Leu
915 920 925

Thr Gly Thr Glu Arg Thr Val Ala Gly Leu Val Ala Ser Gly Ala Gly
930 935 940

Asn Arg Glu Val Ala Glu Ser Leu Phe Val Thr Val Arg Thr Val Glu
945 950 955 960

Leu His Leu Thr Ser Val Tyr Arg Lys Leu Gly Val Ala Arg Arg Gly
965 970 975

Asp Leu Thr Glu Ala Leu Arg Glu Ala Gly Ala Thr Ala Arg Pro Ala
980 985 990

Ala Glu Arg Arg Pro Gly His Ala Lys Arg Arg Asn Pro
995 1000 1005

<210> SEQ ID NO 14
<211> LENGTH: 393
<212> TYPE: PRT
<213> ORGANISM: Streptomyces sp. FR-008

<400> SEQUENCE: 14

Met Thr Thr Ser Pro Gly Pro Thr Val Val Asp Phe Pro Arg Arg Thr
1 5 10 15

Pro Arg Glu Pro Leu Pro Leu Ser Gln Tyr Ala Glu His Arg Lys Gln
20 25 30

Asn Gly Leu Val Gln Thr His Leu Pro Asn Gly Arg Pro Ile Trp Leu
35 40 45

Val Thr Arg His Glu Asp Val Arg Ala Val Leu Thr His Pro Arg Ile
50 55 60

Ser Ala Asn Pro Asp Asn Glu Gly Phe Pro Asn Val Gly Glu Thr Met
65 70 75 80

Gly Val Pro Lys Gln Glu Gln Ile Pro Gly Trp Phe Val Gly Leu Asp
85 90 95

Ser Pro Glu His Asp Arg Phe Arg Lys Val Leu Ile Pro Glu Phe Thr
100 105 110

Val Arg Arg Val Arg Glu Leu Arg Pro Ala Ile Glu Arg Thr Val Asp
115 120 125

Glu Arg Ile Asp Ala Met Leu Ala Gly Gly Asn Thr Ala Asp Leu Val
130 135 140

Asn Asp Phe Ala Leu Pro Val Pro Ser Leu Val Ile Ser Ala Leu Leu
145 150 155 160

Gly Val Pro Ser Ala Asp Arg Asp Phe Phe Glu Ser Arg Thr Arg Thr
165 170 175

Leu Val Ala Ile Arg Thr Ser Thr Asp Glu Glu Arg Ala Glu Ala Thr
180 185 190

Arg Gln Leu Leu Arg Tyr Ile Asn Arg Leu Ile Val Ile Lys Lys Lys
195 200 205

Trp Arg Gly Glu Asp Leu Ile Ser Arg Leu Leu Ser Thr Gly Lys Leu
210 215 220

Ser Asp Glu Glu Leu Ser Gly Val Leu Leu Leu Leu Leu Ile Ala Gly
225 230 235 240

His Glu Thr Thr Ala Asn Asn Ile Gly Leu Gly Val Val Thr Leu Leu
245 250 255

Ser His Arg Glu Trp Ile Gly Asp Asp Arg Leu Val Glu Glu Leu Leu
260 265 270

-continued

```
Arg Leu His Ser Val Ala Asp Met Val Ala Leu Arg Val Ala Val Asp
        275                 280                 285

Asp Val Glu Ile Ala Gly Gln Thr Ile Arg Lys Gly Glu Gly Ile Val
    290                 295                 300

Pro Leu Leu Ala Ser Ala Asn His Asp Thr Glu Ala Phe Gly Cys Pro
305                 310                 315                 320

His Ala Phe Asn Pro Glu Arg Thr Glu Arg Arg His Val Ala Phe Gly
                325                 330                 335

Tyr Gly Val His Gln Cys Leu Gly Gln Asn Leu Val Arg Val Glu Met
            340                 345                 350

Glu Ile Ala Tyr Arg Lys Leu Phe Glu Arg Ile Pro Glu Leu Arg Leu
        355                 360                 365

Ala Val Pro Glu Asp Gln Leu Ala Tyr Lys Tyr Asp Gly Ile Leu Phe
    370                 375                 380

Gly Leu His Glu Leu Pro Val Arg Trp
385                 390


<210> SEQ ID NO 15
<211> LENGTH: 64
<212> TYPE: PRT
<213> ORGANISM: Streptomyces sp. FR-008

<400> SEQUENCE: 15

Met Arg Val Thr Val Asp Ser Glu Gln Cys Val Gly Ala Gly Gln Cys
 1               5                  10                  15

Val Leu Asn Ala Pro Glu Val Phe Asp Gln Asp Asp Asp Gly Val Val
            20                  25                  30

Val Leu Leu Arg Ala Glu Pro Asp Glu Arg Asp His Glu Ala Val Arg
        35                  40                  45

Thr Ala Gly Asp Leu Cys Pro Ser Ala Ser Val Val Leu Gln Glu Asp
    50                  55                  60


<210> SEQ ID NO 16
<211> LENGTH: 285
<212> TYPE: PRT
<213> ORGANISM: Streptomyces sp. FR-008

<400> SEQUENCE: 16

Met Pro Arg Pro Ala Arg Pro Ser His Pro Arg Thr Arg Arg Arg Arg
 1               5                  10                  15

Asn Thr Asp Arg Arg Gln Asn His Arg Arg Asp Ser Pro Val Thr Thr
            20                  25                  30

Ala Asp Asp Thr Ala Ala Arg Trp Leu Arg Arg Tyr His Pro Ala Glu
        35                  40                  45

Ala Asp Ala Val Arg Leu Val Cys Phe Pro His Ala Gly Gly Ser Ala
    50                  55                  60

Ser Phe Tyr His Pro Val Ser Ala Arg Phe Ala Pro Gly Ala Glu Val
65                  70                  75                  80

Val Ser Leu Gln Tyr Pro Gly Arg Gln Asp Arg Arg Lys Glu Pro Cys
                85                  90                  95

Val Pro Asp Leu Gly Thr Leu Ala Asp Leu Ile Thr Glu Gln Leu Leu
            100                 105                 110

Pro Leu Asp Glu Arg Pro Thr Val Phe Phe Gly His Ser Met Gly Ala
        115                 120                 125

Ala Leu Ala Phe Glu Thr Ala Trp Arg Leu Glu Gln Lys Gly Ala Gly
    130                 135                 140
```

```
Pro Arg Thr Val Ile Ala Ser Gly Arg Arg Gly Pro Ser Thr Thr Arg
145                 150                 155                 160

Ala Glu Arg Val His Thr Arg Asp Asp Asp Gly Ile Val Ala Glu Met
                165                 170                 175

Lys Arg Leu Asn Gly Thr Ala Ala Gly Val Leu Gly Asp Glu Glu Ile
            180                 185                 190

Leu Arg Met Ala Leu Pro Ala Leu Arg Gly Asp Tyr Arg Ala Ile Glu
        195                 200                 205

Thr Tyr Thr Cys Pro Pro Asp Arg Arg Leu Ala Cys Gly Leu Thr Val
    210                 215                 220

Leu Thr Gly Glu Asp Asp Pro Leu Thr Thr Val Glu Glu Ala Glu Arg
225                 230                 235                 240

Trp Arg Asp His Thr Thr Gly Pro Phe Arg Leu Arg Val Phe Thr Gly
                245                 250                 255

Gly His Phe Phe Leu Thr Gln His Leu Asp Ala Val Asn Thr Glu Ile
            260                 265                 270

Ala Gln Ala Leu His Pro Asp Arg Ala Ala Pro Ala Ala
        275                 280                 285


<210> SEQ ID NO 17
<211> LENGTH: 458
<212> TYPE: PRT
<213> ORGANISM: Streptomyces sp. FR-008

<400> SEQUENCE: 17

Met Asp Ser Ala Ala Arg Pro Ile Leu Phe Val Ser Leu Pro Glu Ser
 1               5                  10                  15

Gly Leu Leu Asn Pro Leu Leu Val Leu Ala Gly Glu Leu Ala Arg Arg
            20                  25                  30

Gly Val Pro Asp Leu Trp Phe Ala Thr Asp Glu His Arg Arg Glu Glu
        35                  40                  45

Val Glu Ala Leu Ser Asp Val Ser Lys Val Ser Phe Ala Ser Leu Gly
    50                  55                  60

Glu Val Val Pro Glu Leu Ser Ala Val Thr Trp Asp Asp Glu Val Tyr
65                  70                  75                  80

Arg Glu Val Thr Gln Ser Ser Arg Phe Lys Ala His Arg Ala Val Val
                85                  90                  95

Arg Gln Ser Tyr Arg Pro Ala Leu Gln Ala Arg Lys Tyr Arg Glu Leu
            100                 105                 110

Glu Gln Val Val Asp Glu Val Arg Pro Ala Leu Met Val Val Asp Cys
        115                 120                 125

Val Ala Gly Phe Gly Val Asp Leu Ala Leu Ala Arg Gly Ile Pro Tyr
    130                 135                 140

Val Leu Asn Val Pro Phe Val Ala Ser Asn Val Leu Thr Ser His Asn
145                 150                 155                 160

Pro Phe Gly Ala Ser Tyr Thr Pro Lys Ser Phe Pro Val Pro Asn Ser
                165                 170                 175

Gly Leu Pro Ala Arg Met Ser Val Arg Gln Lys Leu Ala Asn Thr Leu
            180                 185                 190

Phe Lys Trp Arg Thr Leu Gly Met Phe Leu His Pro Asp Met Ala Ala
        195                 200                 205

Leu Leu Arg Glu Asp Ala Ala Ile Arg Lys Glu Leu Gly Ile Ala Pro
    210                 215                 220

Pro Asn Ala Met Thr Arg Val Asp Glu Ala Ala Ala Val Val Cys Ser
```

-continued

```
225                 230                 235                 240

Ser Val Ala Glu Leu Asp Tyr Pro Phe Asp Ile Pro Asp Arg Val Ser
                245                 250                 255

Leu Val Gly Ala Val Leu Pro Pro Leu Pro Glu Ala Pro Asp Asp Asp
            260                 265                 270

Glu Val Thr Arg Trp Leu Asp Ala Gln Ser Ser Val Val Tyr Met Gly
        275                 280                 285

Phe Gly Thr Ile Thr Arg Leu Thr Arg Glu Glu Val Ala Ala Leu Val
    290                 295                 300

Glu Val Ala Arg Arg Met Ser Gly Thr His Gln Phe Leu Trp Lys Leu
305                 310                 315                 320

Pro Lys Glu Gln Gln His Leu Leu Pro Glu Ala Gly Ser Leu Pro Asp
                325                 330                 335

Asn Leu Arg Val Glu Ser Trp Val Pro Ser Gln Leu Asp Val Leu Ala
            340                 345                 350

His Pro Asn Val Ser Val Phe Phe Ser His Gly Gly Gly Asn Ala Tyr
        355                 360                 365

His Glu Gly Val Tyr Phe Gly Lys Pro Gln Val Val Arg Pro Leu Trp
    370                 375                 380

Val Asp Cys Phe Asp Gln Ala Val Arg Gly Arg Asp Phe Gly Ile Ser
385                 390                 395                 400

Leu Thr Leu Asp Lys Pro His Thr Val Asp Pro Asp Asp Val Val Asp
                405                 410                 415

Lys Leu Thr Arg Val Thr Ser Asp Pro Ala Phe Arg Thr Glu Ala Glu
            420                 425                 430

Arg Leu Gly Ala Leu Gln Arg Ala Ala Gly Gly Arg Ala Ala Ala Ala
        435                 440                 445

Asp Leu Val Thr Gly Leu Leu Pro Ala Ala
    450                 455


<210> SEQ ID NO 18
<211> LENGTH: 352
<212> TYPE: PRT
<213> ORGANISM: Streptomyces sp. FR-008

<400> SEQUENCE: 18

Met Ala Phe Thr His Pro Val Ser Arg Pro Ala Leu Asp Gly Arg Glu
 1               5                  10                  15

Leu Glu Tyr Val Ser Asp Ala Val Ser Gly Gly Trp Ile Ser Ser Gln
            20                  25                  30

Gly Pro Tyr Val Arg Arg Phe Glu Glu Ala Phe Ala Glu Trp Asn Gly
        35                  40                  45

Val Ala His Gly Val Ala Cys Ser Ser Gly Thr Ala Ala Leu Thr Leu
    50                  55                  60

Ala Leu Arg Ala Leu Asn Ile Gly Pro Gly Asp Glu Val Ile Val Pro
65                  70                  75                  80

Glu Phe Thr Met Val Ala Ser Ala Trp Ala Val Thr Tyr Thr Gly Ala
                85                  90                  95

Thr Pro Val Phe Val Asp Cys Gly Asp Asp Leu Asn Ile Asp Val Thr
            100                 105                 110

Arg Ile Glu Glu Lys Ile Thr Pro Arg Thr Arg Ala Val Met Pro Val
        115                 120                 125

His Val Tyr Gly Arg Arg Cys Asp Met Asp Ala Val Met Asp Leu Ala
    130                 135                 140
```

-continued

```
Leu Gln Tyr Asn Leu Arg Val Val Glu Asp Ser Ala Glu Ala His Gly
145                 150                 155                 160

Val Arg Pro Val Gly Asp Ile Ala Cys Phe Ser Leu Phe Ala Asn Lys
                165                 170                 175

Ile Ile Thr Ala Gly Glu Gly Gly Val Cys Leu Thr Asp Asp Pro Arg
            180                 185                 190

Leu Ala Glu Gln Leu Ala His Leu Arg Ala Met Ala Phe Thr Arg Asp
        195                 200                 205

His Ser Phe Leu His Lys Lys Leu Ala Tyr Asn Tyr Arg Met Thr Ala
    210                 215                 220

Met Gln Gly Ala Val Ala Leu Ala Gln Thr Glu Arg Leu Asp Glu Ile
225                 230                 235                 240

Leu Ala Thr Arg Arg Glu Ile Glu Ala Arg Tyr Asp Ala Gly Leu Lys
                245                 250                 255

Asp Leu Pro Gly Ile Thr Leu Met Pro Ala Arg Asp Val Leu Trp Met
            260                 265                 270

Tyr Asp Leu Arg Ala Glu Arg Arg Glu Glu Leu Arg Ala His Leu Asp
        275                 280                 285

Ala Arg Gly Ile Glu Thr Arg Leu Phe Phe Lys Pro Met Ser Arg Gln
    290                 295                 300

Pro Gly Tyr Leu Asp Pro Val Trp Pro Thr Leu Asn Ala His Arg Phe
305                 310                 315                 320

Ser Glu Asp Gly Leu Tyr Leu Pro Thr His Thr Gly Leu Thr Ala Ala
                325                 330                 335

Asp Gln Glu Tyr Ile Thr Gly Ala Val Arg Asp Phe Tyr Arg Ala Gly
            340                 345                 350


<210> SEQ ID NO 19
<211> LENGTH: 402
<212> TYPE: PRT
<213> ORGANISM: Streptomyces sp. FR-008

<400> SEQUENCE: 19

Met Ser Ala Thr Arg Thr Ala Arg Glu Arg Ser Arg Ala Ser Arg Ala
 1               5                  10                  15

Pro Glu Gly Gly Lys Ala Leu Pro Ser Ala Gly Ala Cys Gln Tyr Ala
            20                  25                  30

Trp Gly Ser Ile Ser Pro Pro Pro Pro Ala Arg Thr Pro Ala Arg Pro
        35                  40                  45

Val Leu Thr Val Ala Val Glu Arg Gly Lys Met Ser Lys Arg Ala Leu
    50                  55                  60

Ile Thr Gly Ile Thr Gly Gln Asp Gly Ser Tyr Leu Ala Glu His Leu
65                  70                  75                  80

Leu Asp Gln Gly Tyr Gln Val Trp Gly Leu Cys Arg Gly Gln Ala Asn
                85                  90                  95

Pro Arg Lys Asp Arg Ile Ala Lys Leu Ile Pro Glu Leu Ser Phe Val
            100                 105                 110

Asp Gly Asp Leu Met Asp Gln Gly Ser Leu Val Ser Ala Val Asp Leu
        115                 120                 125

Val Gln Pro Asp Glu Val Tyr Asn Leu Gly Ala Ile Ser Phe Val Pro
    130                 135                 140

Met Ser Trp Gln Gln Pro Glu Leu Val Thr Glu Val Asn Gly Thr Gly
145                 150                 155                 160

Val Leu Arg Met Leu Glu Ala Val Arg Ile Val Ser Gly Leu Thr Lys
                165                 170                 175
```

```
Ser Ser Gly Gly Ser Pro Arg Gly Gln Ile Arg Phe Tyr Gln Ala Ser
            180                 185                 190

Ser Ser Glu Met Tyr Gly Lys Val Ala Glu Ser Pro Gln Arg Glu Thr
        195                 200                 205

Thr Ser Phe His Pro Arg Ser Pro Tyr Gly Val Ala Lys Ala Phe Gly
    210                 215                 220

His Tyr Ile Thr Gln Asn Tyr Arg Glu Ser Tyr Gly Met Tyr Gly Val
225                 230                 235                 240

Ser Gly Ile Leu Phe Asn His Glu Ser Pro Arg Arg Gly Ala Glu Phe
                245                 250                 255

Val Thr Arg Lys Ile Ser Leu Ala Val Ala Gln Ile Lys Leu Gly Gln
            260                 265                 270

Met Asp Lys Leu His Leu Gly Asn Leu Asp Ala Glu Arg Asp Trp Gly
        275                 280                 285

Phe Ala Gly Asp Tyr Val Arg Ala Met His Leu Met Leu Gln Gln Glu
    290                 295                 300

Gln Ala Gly Asp Tyr Val Val Gly Thr Gly Ala Met His Gln Val Arg
305                 310                 315                 320

Asp Ala Ala Arg Ile Ala Phe Glu His Val Gly Leu Asp Trp Gln Glu
                325                 330                 335

His Val Val Val Asp Pro Gly Leu Val Arg Pro Ala Glu Val Glu Thr
            340                 345                 350

Leu Cys Ala Asp Ser Gly Asn Ala Arg Arg Glu Leu Gly Trp Glu Pro
        355                 360                 365

Glu Val Asp Phe Glu Gln Leu Met Arg Met Met Val Glu Ser Asp Leu
    370                 375                 380

Arg Gln Ala Ser Arg Glu Arg Asp Tyr Ser Gln Leu Leu Ala Thr Gly
385                 390                 395                 400

Ser Trp
```

<210> SEQ ID NO 20
<211> LENGTH: 458
<212> TYPE: PRT
<213> ORGANISM: Streptomyces sp. FR-008

<400> SEQUENCE: 20

```
Met Pro Ser Thr Cys Pro Ala Pro Thr Ser Ile Gly Phe Arg Gly Cys
 1               5                  10                  15

Pro His Arg Arg Lys Gly Arg Thr Ser Arg Gly Arg Arg Ile Ala Val
            20                  25                  30

Pro Thr Arg Pro Cys Gly Lys Val Arg Lys Gly His Gln His Ala Lys
        35                  40                  45

Lys Trp Arg Val Ser Met Arg Gly Gly Ser Val Ala Val Val Gly Gly
    50                  55                  60

Ser Ile Ala Gly Cys Ala Ala Ala Leu Ala Ala Ser Arg Gly Gly Ala
65                  70                  75                  80

Glu Arg Ile Thr Val Phe Glu Arg Ala Asp Ala Arg Leu Arg Asp Arg
                85                  90                  95

Gly Val Gly Ile Gly Val His Asp Ala Arg Tyr Ala Glu Leu Arg Asp
            100                 105                 110

Ala Gly Tyr Met Ala Asp Glu Met Pro Trp Ala Pro Leu Asn Arg Arg
        115                 120                 125

Val Trp Ser Val Arg Asp Gly Asp Ala Glu His Gly Arg Ala Ile Gly
    130                 135                 140
```

```
Thr Gln Pro Phe Pro Phe Arg Ala Tyr Asn Trp Gly Ser Leu Trp Ser
145                 150                 155                 160

Glu Leu Arg Arg Arg Val Pro Glu Thr Ala Thr Tyr Arg Ala Gly Ala
                165                 170                 175

Lys Val Glu Ala Val Glu Gln Asp Ala Asp Gly Val Thr Val Arg Leu
            180                 185                 190

Ala Asp Gly Glu Pro Glu Arg Phe Asp Leu Val Ile Gly Ala Asp Gly
        195                 200                 205

Tyr Arg Ser Val Val Arg Glu Ala Met Tyr Pro Gly Thr Gly Ala Ala
    210                 215                 220

Tyr Ala Gly Tyr Ile Gly Trp Arg Gly Thr Ser Pro Asp Val Ser Gly
225                 230                 235                 240

Leu Pro Ser Asp Gly Leu Asp Ala His Asn Ile Thr Phe Pro Gly Gly
                245                 250                 255

His Cys Met Ala Tyr Arg Ile Pro Asp Gly Ser Gly Gly His Arg Leu
            260                 265                 270

Asn Trp Val Leu Tyr Thr Ala Pro Pro Arg Ile Asp Gly Leu His Pro
        275                 280                 285

Asp Leu Arg Thr Pro Thr Ser Leu Pro Pro Gly Arg Leu Asn Ala Glu
    290                 295                 300

Leu Thr Glu His Leu Arg Ala Leu Val Ala Glu His Phe Pro Pro Phe
305                 310                 315                 320

Trp Ala Ala Lys Leu Leu Ser Thr Pro Ala Glu Thr Thr Phe Ile Gln
                325                 330                 335

Pro Ile Tyr Asp Leu Asp Val Pro His Tyr Ala Thr Asp Arg Met Val
            340                 345                 350

Leu Ile Gly Asp Ala Ala Ser Val Ala Arg Pro His Leu Gly Ala Gly
        355                 360                 365

Ser Val Lys Ala Leu Gln Asp Ala Thr Ala Leu Glu Ala Ala Trp Val
    370                 375                 380

Ala Gly Glu Ser Trp Lys Glu Ile Leu Glu Gly Tyr His Ala Ala Arg
385                 390                 395                 400

Gly Pro Val Gly Thr Ala Met Val Gly Leu Ala Arg Arg Met Gly Ser
                405                 410                 415

Ala Gln Val Glu Glu Thr Pro Asp Trp Ser Ala Met Gly Gln Ala Glu
            420                 425                 430

Phe Asp Ala Trp Trp Gln Glu Gln Asn Asn Gly Ser Asp Arg Arg Ser
        435                 440                 445

Gly Phe Gly Gly His Ser Leu Lys Ser Arg
    450                 455
```

<210> SEQ ID NO 21
<211> LENGTH: 723
<212> TYPE: PRT
<213> ORGANISM: Streptomyces sp. FR-008

<400> SEQUENCE: 21

```
Met Arg Thr Leu Leu Val Asp Asn Tyr Asp Ser Phe Thr Tyr Asn Leu
 1               5                  10                  15

Phe His Tyr Leu Ser Arg Ala Asn Gly Arg Glu Pro Glu Val Ile Arg
            20                  25                  30

Asn Asp Asp Pro Ala Trp Arg Pro Gly Leu Leu Asp Ala Phe Asp Asn
        35                  40                  45

Val Val Leu Ser Pro Gly Pro Gly Thr Pro His Arg Pro Ala Asp Phe
```

-continued

```
    50                  55                  60

Gly Leu Cys Ala Arg Ile Ala Glu Glu Gly Arg Leu Pro Val Leu Gly
65                  70                  75                  80

Val Cys Leu Gly His Gln Gly Met Ala Leu Ala His Gly Ala Arg Val
                85                  90                  95

Gly Arg Ala Pro Glu Pro Arg His Gly Arg Thr Ser Ala Val Arg His
            100                 105                 110

Asp Gly Thr Gly Leu Phe Glu Gly Leu Pro Gln Pro Leu Glu Val Val
        115                 120                 125

Arg Tyr His Ser Leu Ala Val Thr Glu Leu Pro Pro Glu Leu Glu Ala
    130                 135                 140

Thr Ala Trp Ser Glu Asp Gly Val Leu Met Ala Leu Arg His Arg Thr
145                 150                 155                 160

Leu Pro Leu Trp Gly Val Gln Phe His Pro Glu Ser Ile Gly Thr Gln
                165                 170                 175

Asp Gly His Arg Leu Leu Ala Asn Phe Arg Asp Leu Thr Glu Arg His
            180                 185                 190

Gly Arg Thr Arg Pro Gly Gly Arg Ala Gly His Gly Thr Leu Pro Pro
        195                 200                 205

Pro Ala Pro Ala Arg Glu Thr Thr Ala Thr Thr Gly Thr Pro Arg Arg
    210                 215                 220

Leu Arg Val Ile Ala Glu Ser Leu Pro Thr Arg Trp Asp Ala Glu Val
225                 230                 235                 240

Ala Phe Asp Ser Leu Phe Arg Thr Gly Asp His Pro Phe Trp Leu Asp
                245                 250                 255

Ser Ser Arg Pro Gly Gly Glu Leu Gly Gln Leu Ser Val Met Gly Asp
            260                 265                 270

Ala Ser Gly Pro Leu Ala Arg Thr Ala Lys Ala Asp Val His Ala Gly
        275                 280                 285

Thr Val Thr Val Arg Ala Asp Gly Ala Ser Ser Thr Val Glu Ser Ala
    290                 295                 300

Phe Leu Thr Trp Leu Glu Asn Asp Leu Ala Gly Leu Arg Thr Glu Val
305                 310                 315                 320

Pro Glu Leu Pro Phe Ala Phe Ala Leu Gly Trp Val Gly Cys Leu Gly
                325                 330                 335

Tyr Glu Leu Lys Ala Glu Cys Asp Gly Asp Ala Ala His Arg Ser Pro
            340                 345                 350

Asp Pro Asp Ala Val Leu Val Phe Ala Asp Arg Ala Leu Val Leu Asp
        355                 360                 365

His Arg Thr Arg Thr Thr Tyr Leu Leu Ala Leu Val Glu Asp Asp Ala
    370                 375                 380

Glu Ala Glu Ala Arg Ala Trp Leu Ala Ala Ala Ser Ala Thr Leu Glu
385                 390                 395                 400

Ala Ile Ala Gly Arg Glu Pro Glu Pro Cys Pro Glu Ala Pro Val Cys
                405                 410                 415

Thr Thr Gly Pro Val Glu Leu Arg His Asp Arg Asp Gly Tyr Leu Lys
            420                 425                 430

Leu Ile Asp Val Cys Gln Gln Glu Ile Ala Ala Gly Glu Thr Tyr Glu
        435                 440                 445

Val Cys Leu Thr Asn Met Ala Glu Ala Asp Thr Asp Leu Thr Pro Trp
    450                 455                 460

Ala Ala Tyr Arg Ala Leu Arg Arg Val Ser Pro Ala Pro Phe Ala Ala
465                 470                 475                 480
```

```
Phe Leu Asp Phe Gly Pro Met Ala Val Leu Ser Ser Ser Pro Glu Arg
                485                 490                 495

Phe Leu Arg Ile Asp Arg His Gly Arg Met Glu Ser Lys Pro Ile Lys
            500                 505                 510

Gly Thr Arg Pro Arg Gly Ala Thr Pro Gln Glu Asp Ala Ala Leu Val
        515                 520                 525

Arg Ala Leu Ala Thr Cys Glu Lys Asp Arg Ala Glu Asn Leu Met Ile
    530                 535                 540

Val Asp Leu Val Arg His Asp Leu Gly Arg Cys Ala Glu Val Gly Ser
545                 550                 555                 560

Val Val Ala Asp Pro Val Phe Gln Val Glu Thr Tyr Ala Thr Val His
                565                 570                 575

Gln Leu Val Ser Thr Val Thr Ala Arg Leu Arg Glu Asp Ser Ser Pro
            580                 585                 590

Val Ala Ala Val Arg Ala Ala Phe Pro Gly Gly Ser Met Thr Gly Ala
        595                 600                 605

Pro Lys Ile Arg Thr Met Gln Ile Ile Asp Arg Leu Glu Gly Gly Pro
    610                 615                 620

Arg Gly Val Tyr Ser Gly Ala Ile Gly Tyr Phe Ser Leu Thr Gly Ala
625                 630                 635                 640

Val Asp Leu Ser Ile Val Ile Arg Thr Val Val Leu Ser Gly Gly Arg
                645                 650                 655

Leu Arg Tyr Gly Val Gly Gly Ala Val Ile Ala Leu Ser Asp Pro Ala
            660                 665                 670

Asp Glu Phe Glu Glu Thr Ala Val Lys Ala Ala Pro Leu Leu Arg Leu
        675                 680                 685

Leu Asp Thr Ala Phe Pro Gly Arg Glu Ala Pro Gly Lys Asp Leu Asp
    690                 695                 700

Gly Glu Pro Asp Asp Gly Thr Asp Ala Gly Ala Pro Lys Asp Leu Val
705                 710                 715                 720

Leu Pro Gly


<210> SEQ ID NO 22
<211> LENGTH: 257
<212> TYPE: PRT
<213> ORGANISM: Streptomyces sp. FR-008

<400> SEQUENCE: 22

Met Ile Glu Leu Asp Gly Glu Pro Ala Gly Pro Glu Ala Leu Ala Ser
 1               5                  10                  15

Leu Ala Leu Thr Asn Tyr Gly His Phe Thr Thr Leu Leu Val Glu Asn
            20                  25                  30

Gly Arg Val Arg Gly Leu Asp Leu His Leu Glu Arg Leu Ile Arg Asp
        35                  40                  45

Cys Arg Thr Leu Phe Asp Ala Ala Leu Asp Pro Asp Arg Val Arg Lys
    50                  55                  60

Leu Ala Arg Arg Ala Ala Pro Thr Asp Gly Arg Ala Thr Val Arg Val
65                  70                  75                  80

Thr Val Phe Asp Pro Ala Leu Asn Leu Gly Asn Ile Ala Ala Asp Ala
                85                  90                  95

Arg Pro Gly Ile Leu Val Thr Ser Arg Pro Ala Pro Asp Lys Pro Pro
            100                 105                 110

Gly Pro Leu Arg Val Arg Ser Val Val His Arg Arg Asp Leu Pro Glu
        115                 120                 125
```

```
Val Lys Ser Val Gly Leu Cys Pro Thr Leu Arg Leu Arg Arg Gln Ala
    130                 135                 140

Gln Arg Ala Gly Tyr Asp Asp Val Leu Phe Thr Gly Pro Asp Gly Asp
145                 150                 155                 160

Ile Leu Glu Gly Gly Thr Trp Asn Val Gly Leu Val Arg Asp Gly Glu
                165                 170                 175

Val Val Trp Pro Gly Gly Glu Val Leu Ala Gly Thr Thr Arg Gln Leu
            180                 185                 190

Leu Arg Arg Gly His Arg Arg Ser His Arg Thr Gly Arg Pro Arg Gly
        195                 200                 205

Pro Arg Leu Ser Arg Gly Gly Leu Arg Asp Gln Arg Arg Val Gly Val
    210                 215                 220

Arg Pro Val Thr Gly Ile Asp Asp Arg Glu Phe Pro Ala Ala His His
225                 230                 235                 240

Ser Val Thr Arg Leu Ala Glu Ile Tyr Gln Ala Leu Pro Gly Ser Pro
                245                 250                 255

Leu


<210> SEQ ID NO 23
<211> LENGTH: 17
<212> TYPE: DNA
<213> ORGANISM: Artificial Sequence
<220> FEATURE:
<223> OTHER INFORMATION: PCR Primer

<400> SEQUENCE: 23

tgccgcgctc gccgaca                                                      17


<210> SEQ ID NO 24
<211> LENGTH: 17
<212> TYPE: DNA
<213> ORGANISM: Artificial Sequence
<220> FEATURE:
<223> OTHER INFORMATION: PCR Primer

<400> SEQUENCE: 24

cgcgtccggt gctcacg                                                      17


<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25

gatcctcttc gtcagtctcc                                                   20


<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26

catgtagacc accgacgact                                                   20


<210> SEQ ID NO 27
<211> LENGTH: 20
<212> TYPE: DNA
```

-continued

```
<213> ORGANISM: Artificial Sequence
<220> FEATURE:
<223> OTHER INFORMATION: PCR Primer

<400> SEQUENCE: 27

gacctgaaca tcgacgtcac                                                 20


<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28

aggtcgtaca tccacaggac                                                 20
```

GENES FOR SYNTHESIS OF FR-008 POLYKETIDES

REFERENCE TO SEQUENCE LISTING SUBMITTED ON COMPACT DISC

The present application includes a Sequence Listing filed on one (1) CD-R disc, containing a single file named PO13-B015 (Sequence) Copy Sent to USPTO.doc, having 980 kilobytes, last modified on Jan. 30, 2004 and recorded on Jan. 30, 2004. The Sequence Listing contained in said file on said disc is incorporated herein by reference in its entirety.

FIELD OF THE INVENTION

The present invention relates to genes for the synthesis of an FR-008 polyketide derived from *Streptomyces* sp. FR-008.

BACKGROUND OF THE RELATED ART

Polyketides, which are compounds synthesized from 2-carbon units by the action of polyketide synthases through a series of condensations and subsequent modifications, are produced in several bacteria, including molds or actinomycetes (Robinson, J. A., *Philos. Trans. R. Soc. Lond. B. Biol. Sci.,* 332:107-14, 1991; Hopwood, D. A., *Curr. Opin. Biotechnol.,* 4:531-537, 1993). The polyketides are physiologically active molecules having highly various structures and the species thereof includes many compounds having various activities.

Generally, a production method using such natural polyketides has encountered a difficulty in industrial application because of its low efficiency, and also faced many economic and technical difficulties in producing polyketide compounds by the prior chemical method.

Owing to such concerns, studies to efficiently biosynthesize the natural polyketides were conducted, and a recombinant production method using related genes started to be developed. Namely, studies, including cloning, assay and operation using a recombinant technology of genes coding for polyketide synthases, were performed, and owing to such technologies, the production of polyketides at a higher level than those occurring in an environment or host, which does not produce polyketides, became possible (WO 93/13663; 95/08548; 96/40968; 97/02358; 98/27203; 98/49315; U.S. Pat. Nos. 4,874,748, 5,063,155; 5,098,837; 5,149,639; 5,672,491; 5,712,146; 5,830,750; 5,843,718; Fu, H. et al., *Biochem.,* 33:9321-6, 1994; McDaniel, R. et al., *Science,* 262:1546-50, 1993; Kuhstoss, S. et al., *Gene,* 183:231-6, 1996).

The natural polyketides is synthesized by the continuous activity of about 50 species of enzymes, so-called polyketide synthases (PKSs), and carrier proteins, in a similar manner as the synthesis of fatty acids (Robinson, J. A., *Philos. Trans. R. Soc. Lond. B. Biol. Sci.,* 332:107-14, 1991; Hopwood, D. A., *Curr. Opin. Biotechnol.,* 4:531-7, 1993). For example, the core structure of erythromycin is made by about 25 continuous enzymatic reactions. PKSs include two types, one of which is a modular type and the other one is an iteractive type (Khosla, C., *Chem. Rev.,* 97:2577-90, 1997).

In the modular PKSs (type I), all steps for the assembly and modification of carbon chains occur by different catalytic sites, but in the iteractive PKSs (type II), one catalytic site is utilized one or more times on biosynthetic pathway. A typical modular PKS consists of several large peptides, which are divided into a loading module, multiple extension modules and a releasing module in the direction from the N-terminal end to the C-terminal end (Hopwood and Sherman, *Annu. Rev. Genet.,* 24:37-66, 1990).

The loading module consists of acyl-transferase (AT) and acyl carrier protein (ACP). Furthermore, the multiple extension modules basically comprise ketosynthase (KS), AP and ACP, and often comprise an enzyme for modifying the β-carbon of the extended polyketide chain in addition to such basic modules. Finally, the releasing module comprises thioesterase (TE) and in some cases, cyclase activity.

Generally, the loading module binds to a first building block used in synthesizing polyketides, and acts to transfer the building block to the first extension module. AT on the multiple extension modules recognize a certain acyl-CoA (acetyl or propionyl) and transfer it to ACP in the form of thiol ester. At the same time, AT on each module transfers the malonyl group of a certain malonyl-CoA (malonyl or α-substituted malonyl) to ACP on the module in a thiol ester form. Then, the acyl group on the loading module is transferred to KS on the first module by transesterification. The transferred acyl group covalently binds to the α-carbon of the malonyl group, and dicarboxylation occurs to produce a new acyl group with a backbone two carbons longer than the loaded unit (extension or elongation).

The polyketide chain grown by two carbon atoms of each extension module is transferred from the extension module to the next extension module in the form of covalently bonded thiol ester, and subjected to the above-mentioned procedure. In addition to KS, AT and ACP involved in the formation of the C—C bonds, each module often comprises enzymes for modifying the β-keto group of 2-carbon units just added to the extended polyketide chain before this chain is transferred to the next module. These modifier enzymes include ketoreductase (KR) reducing a keto group into alcohol, dehydroreductase (DH) forming a double bond by dehydration of alcohol, and enoyl reductase (ER) converting a double bond into a single bond.

There are modules having no modifier enzymes, and modules comprising KR(1), KR+DH(2) or KR+DH+ER(3). According to such modifier enzymes, the oxidation state of the β-carbon of each 2-carbon unit is determined (0=ketone; 1=alcohol; 2=double bond; and 3=single bond). Polyketide products will vary depending on the specificity of AT of each module and the kind of the modifier enzymes. If the extended polyketide chain is transferred to the last module of PKS, it will meet the releasing module or thioesterase active site in which polyketide is truncated into a ring form. Furthermore, polyketide can be further modified by adding a carbohydrate or methyl group to the core molecule thereof or by a tailoring enzyme (TE) inducing other modifications.

As described above, polyketides are formed by the condensation of carboxylic acid units using the continuous action of PKS. Most of PKS genes in microorganisms are known as being present in a cluster form in the microbial chromosome (Hopwood, Chem. Rev., 97:2465-97, 1997). In 1960, DEBS genes involved in the formation of 6-deoxyerythronolide B (6 dEB) were first reported (Cortes et al., Nature, 348:176-8, 1990; Donadio et al., Science, 252:675-9, 1991), and then, the cloning and base sequence of whole or partial genes for the synthesis of eleven polyketides were reported up to now. The genetic information of the polyketides reported up to now is summarized in Table 1 below.

TABLE 1

Genetic information of polyketides reported up to now.

| Polyketide | Size | Open Reading Frames (ORFs) | References |
|---|---|---|---|
| Avermectin | 80 kb | 18 ORFs (containing 4 PKSes) | U.S. Pat. No. 5,252,474; Ikeda, et al., PNAS USA, 96: 9509-14, 1999 |
| FK506 | 60 kb | 6 ORFs (containing 3 PKSes) | Motamedi & Shafiee, Eur. J. Biochem., 256: 528-34, 1998 |
| Rapamycin | 110 kb | 26 ORFs (containing 3 PKSes) | Schwecke, et al., PNAS USA., 92: 7839-43, 1995 |
| Rifampicin | 90 kb | 34 ORFs (containing 5 PKSes) | August, et al., Chem. Biol., 5: 69-79, 1998 |
| Tylosin | 85 kb | 41 ORFs (containing 5 PKSes) | Cundliffe, et al., Ant. van Leeuwen., 79: 229-34, 2001 |
| Nystatin | 124 kb | 22 ORFs (containing 6 PKSes) | Brautaset, et al., Chem. Biol., 7: 395-403, 2000 |
| Pimaricin | 85 kb | 17 ORFs (containing 5 PKSes) | Aparicio, et al., Chem. Biol., 7: 895-905, 2000 |
| Amphotericin | 113 kb | 17 ORFs (containing 6 PKSes) | Caffrey, et al., Chem. Biol., 8: 713-23, 2000 |
| Candicidin D | 70 kb (partial) | 16 ORFs (containing 4 PKSes) | Campelo & Gil, Microbiol., 148: 51-9, 2002 |

FR-008 polyketide produced in *Streptomyces* sp. FR-008 is a heptaene macrolide having aglycone containing 4-aminoacetophenone, as in candicidin D (Yuan and Zhou, *J. Huazhong Agricult. Univ.,* 9:209, 1990). Since the FR-008 polyketide has antifungal activity and also high toxicity against mosquito larva, they are highly useful in agricultural and medical fields (Liang and Zhou, *Chinese J. Biotech.,* 3:130-6, 1987). The FR-008 polyketide has the following formula:

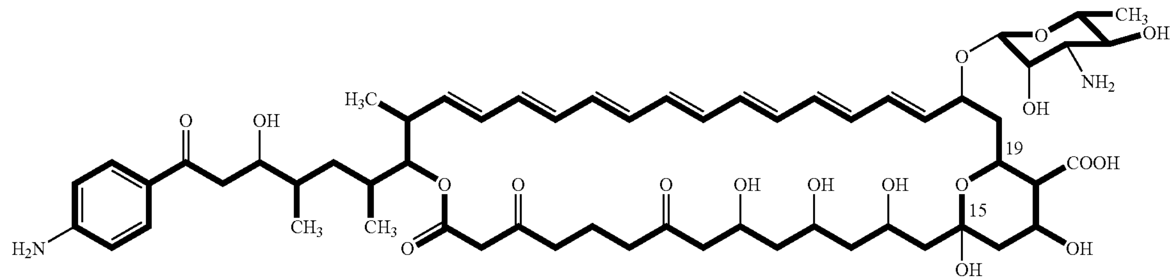

Genes for the synthesis of the FR-008 polyketide was first cloned in 1994 (Hu et al., *Mol. Microbiol.,* 14:163-72, 1994). Hu et al. constructed a chromosomal library of *Streptomyces* sp. FR-008 using a cosmid vector and screened 16 cosmid clones containing PKS genes from the same, but the base sequence of the genes was not reported.

SUMMARY OF THE INVENTION

Therefore, the present inventors have cloned genes for the biosynthesis of FR-008 polyketides derived from *Streptomyces* sp. FR-008, and identified their base sequence, thereby reaching the present invention.

Accordingly, a primary object of the present invention is to provide the base sequence of genes coding for proteins involved in the biosynthesis of FR-008 polyketides derived from *Streptomyces* sp. FR-008.

Another object of the present invention is to provide a method for producing FR-008 polyketide variants comprising the step of cultivating a mutant strain where one or more of the genes in the just above-mentioned base sequence were deleted or inactivated.

BRIEF DESCRIPTION OF THE INVENTION

In FIG. 2, the open read frames (ORF) of A to F represent modular PKR genes, active domains are represented by black blocks, the symbol * in transparent blocks represent inactive domains, and italic types represent silent domains.

DETAILED DESCRIPTION OF THE INVENTION OF THE PREPARED EMBODIMENT

Figure 1:
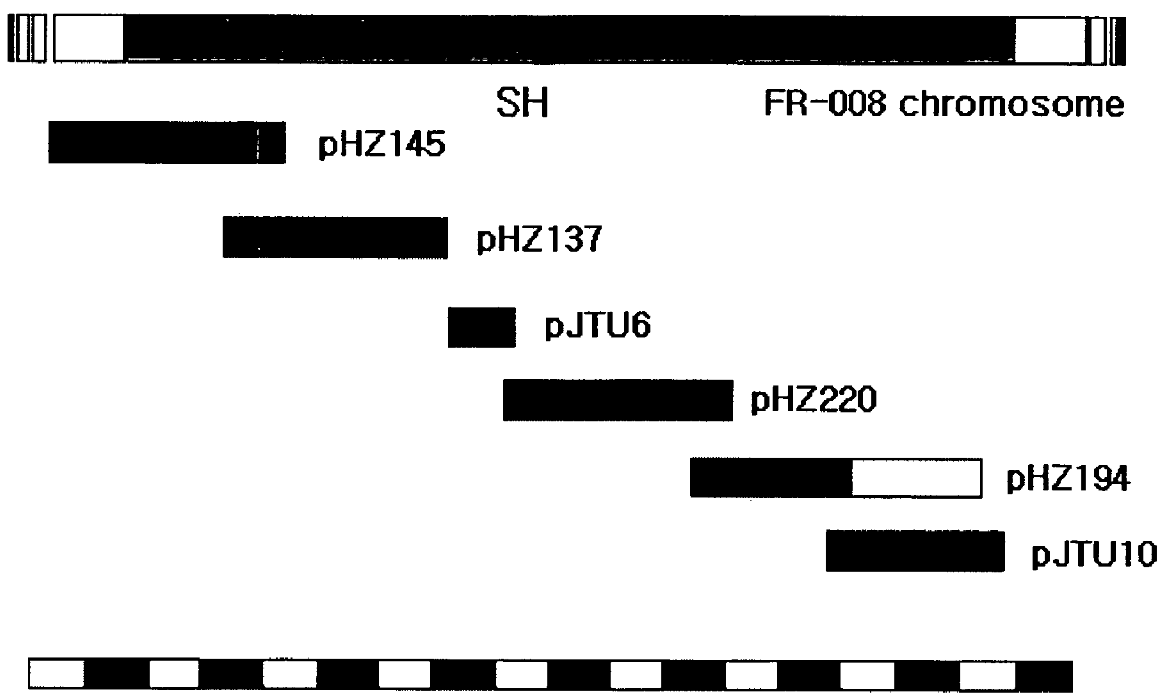
FIG. 1 is a drawing where genes contained in each cosmid clone used in the present invention are shown in a whole gene cluster.

In the present invention, the base sequence of whole genes (138,203 bp) coding for proteins involved in the biosynthesis of FR-008 polyketides derived from *Streptomyces* sp. FR-008 was analyzed. This base sequence comprises genes coding for ketosynthase (KS), acyl transferase (AT), acyl carrier protein (ACP), ketoreductase (KR), dehydratase (DH) and enoyl reductase (ER) domains involved in FR-008 polyketide biosynthesis, and also genes coding for modifier enzymes, such as ABC transporter, cytochrome P-450 monooxygenase, ferredoxin, thioesterase, sugar biosynthetic protein, FAD-dependent monooxygenase, 4-amino-4-deoxychorismate (ADC) synthase and ADC lyase.

In one embodiment, the present invention provides the whole base sequence (SEQ ID NO: 1) of a gene cluster for the biosynthesis of FR-008 polyketides. SEQ ID NO. 1 is a 138,203 bp gene base sequence having 21 open reading frames consisting of fscA, fscB, fscC, fscD, fscE, fscF, fscTI, fscTII, fscRI, fscRII, fscRIII, fscRIV, fscP, fscFE, fscTE, fscMI, fscMII, fscMIII, fscO, pabAB and pabC involved in FR-008 polyketide biosynthesis.

In the present invention, FscA, FscB, FscC, FscD, FscE and FscF represent modular (type I) polyketide synthase, FscTI and FscTII represent ABC transporter protein, FscRI, FscRII, FscRIII and FscRIV represent regulator protein, FscP represents cytochrome P-450 monooxygenase, FscFE represents ferredoxin protein, FscTE represents thioesterase, FscMI represents glycosyltransferase, FscMII represents GDP-ketosugar aminotransferase, FscMIII represents GDP-mannose-4,6-dehydratase, FscO represents FAD-dependent monooxygenase, ADC represents 4-amino-4-deoxychorismate synthase, and PabC represents ADC lyase.

In another embodiment, the present invention provides a method for producing FR-008 polyketide variants comprising the step of cultivating a mutant strain where one or more genes in the above-mentioned base sequence were deleted or inactivated, as well as FR-008 polyketide variants produced by this method.

In this embodiment, the FR-008 polyketide variants are preferably FR-008-V, FR-008-VI, FR-008-VII, FR-008-VIII, FR-008-IX, FR-008-X, FR-008-XI and FR-008-XII, the variants having the following formula:

FR-008-V

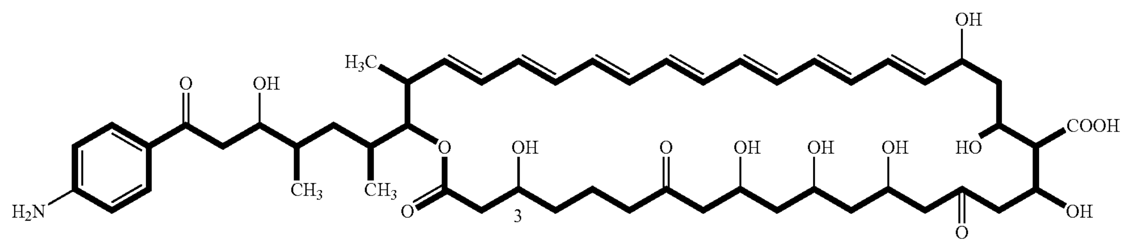

FR-008-VI

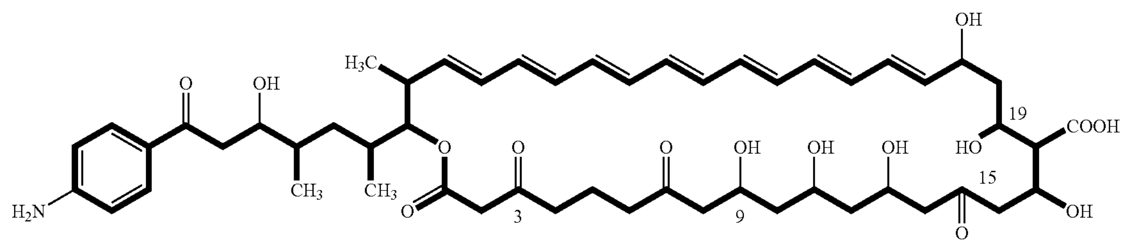

FR-008-VIII

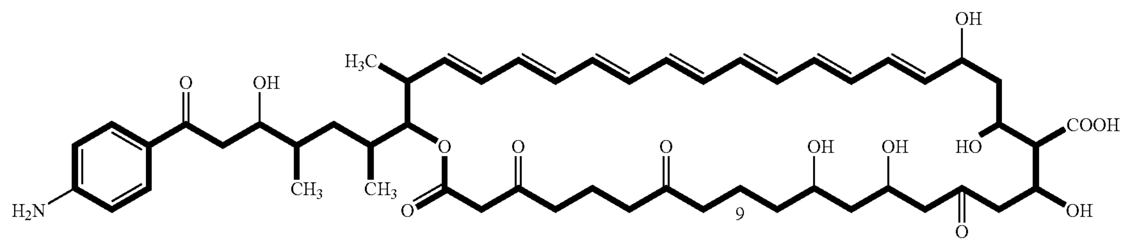

-continued

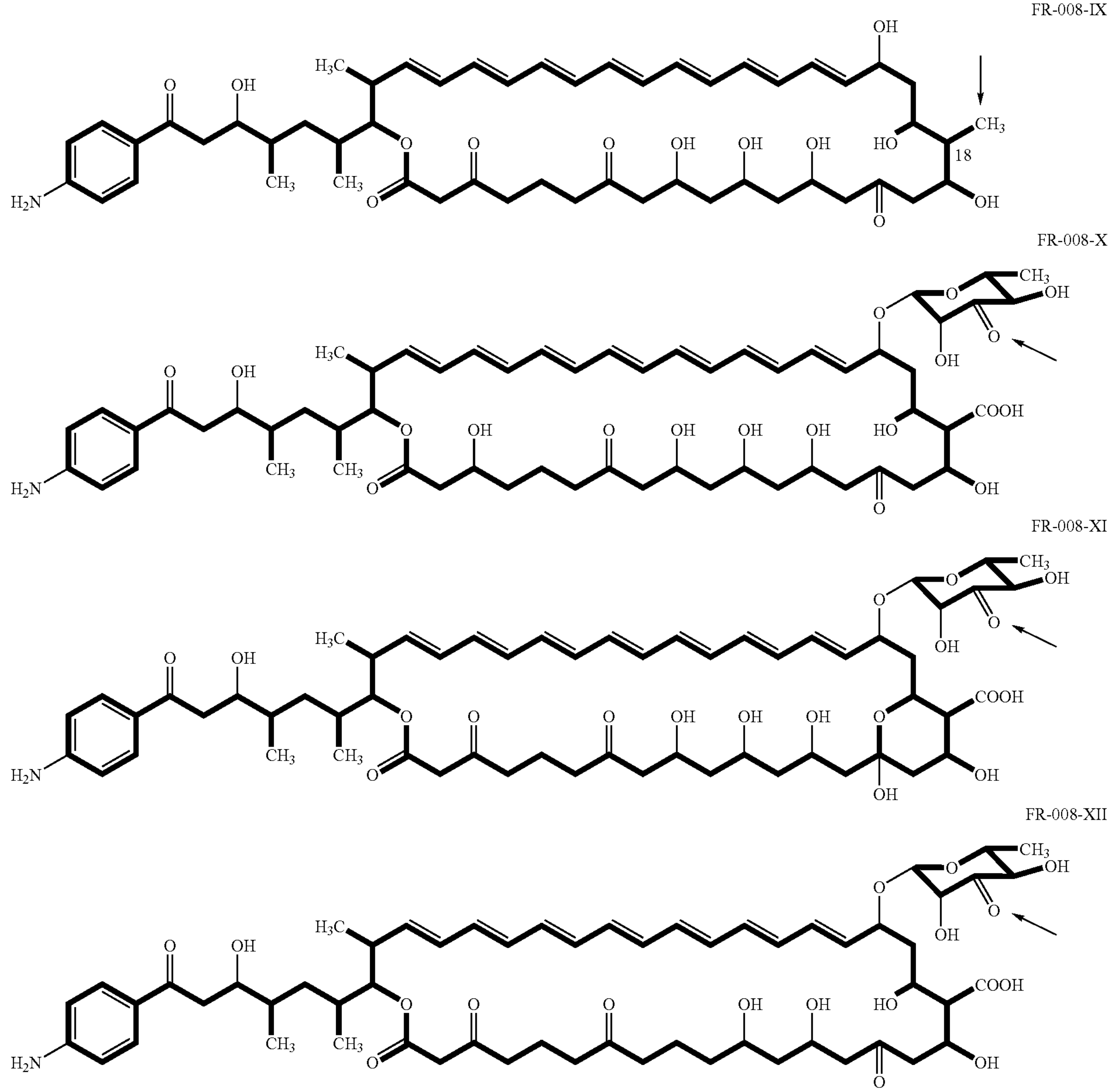

In another embodiment, the present invention provides a modular polyketide synthase (PKS) of FR-008 comprising the following amino acid sequences (a)-(f), as well as a gene coding for the same:

(a) an amino acid sequence consisting of SEQ ID NO: 2, residues 51-465 (ATP-dependent carboxylic acid; CoA ligase (CoL)), 581-647 (ACPL), 661-1,094 (KS1), 1,202-1,509 (AT1) and 1,596-1,662 (ACP1): 2; (b) an amino acid sequence consisting of SEQ ID NO: 3, residues 8,808-9,221 (KS10), 9,330-9,627 (AT10), 9,680-9,867 (DH10), 10,183-10,366 (KR10), 10,469-10,536 (ACP10), 6,966-7,383 (KS9), 7,490-7,792 (AT9), 7,845-8,029 (DH9), 8,331-8,514 (KR9) 8,618-8,685 (ACP9), 5,253-5,675 (KS8), 5,775-6,074 (AT8), 6,127-6,310 (DH8), 6,590-6,773 (KR8), 6,874-6,941 (ACP8), 3,529-3,954 (KS7), 4,059-4,356 (AT7), 4,407-4,595 (DH7), 4,884-5,063 (KR7), 5,163-5,230 (ACP7), 1,787-2,212 (KS6), 2,318-2,617 (AT6), 2,670-2,859 (DH6), 3,155-3,338 (KR6), 3,438-3,505 (ACP6), 34-460 (KS5), 576-875 (AT5), 928-1,112 (DH5), 1,417-1,596 (KR5) and 1,696-1,763 (ACP5); (c) an amino acid sequence consisting of SEQ ID NO: 4, residues 3,703-4,103 (KS4), 4,247-4,550 (AT4), 4,600-4,722 (DH4), 5,103-5,286 (KR4), 5,389-5,456 (ACP4), 1,597-2,023 (KS3), 2,139-2,442 (AT3), 2,494-2,684 (DH3), 2,970-3,322 (ER3), 3,325-3,508 (KR3), 3,610-3,677 (ACP3), 33-460 (KS2), 571-874 (AT2), 1,224-1,406 (KR2) and 1,508-1,574 (ACP2); (d) an amino acid sequence consisting of SEQ ID NO: 5, residues 33-456 (KS21), 545-851 (AT21), 903-1,083 (DH21), 1,378-1,561 (KR21), 1,668-1,735 (ACP21) and 1,814-2,018 (TE21); (e) an amino acid sequence consisting of SEQ ID NO: 6, residues 5,642-6,069 (KS20), 6,158-6,463 (AT20), 6,515-6,693 (DH20), 7,017-7,322 (ER20), 7,330-7,512 (KR20), 7,615-7,682 (ACP20), 4,117-4,544 (KS19), 4,633-4,936 (AT19), 5,263-5,445 (KR19), 5,552-5,619 (ACP19), 2,071-2,498 (KS18), 2,590-2,896 (AT18), 2,948-3,127 (DH18) 3,428-3,733 (ER18), 3,741-3,924 (KR18), 4,025-4,092 (ACP18), 34-460 (KS17), 548-850 (AT17), 902-1,081 (DH17), 1,384-1,689 (ER17), 1,697-1,880 (KR17) and 1,982-2,049 (ACP17); and an amino acid sequence consisting of SEQ ID NO: 7, residues 7,935-8,352 (KS16), 8,464-8,767 (AT16), 9,099-9,280 (KR16), 9,387-9,452 (ACP16), 6,425-6,845 (KS15), 6,935-7,241 (AT15), 7,559-7,725 (KR15), 7,838-7,898 (ACP15), 4,872-5,297 (KS14), 5,408-5,720 (AT14), 6,049-6,225 (KR14), 6,331-6,398 (ACP14), 3,342-3,765 (KS13), 3,872-4,170 (AT13), 4,499-4,676 (KR13), 4,782-4,849 (ACP13), 1,788-2,209 (KS12), 2,313-2,621 (AT12), 2,972-3,150 (KR12), 3,254-3,314 (ACP12), 38-452 (KS11), 563-864 (AT11), 921-1,105 (DH11), 1,410-1,592 (KR11) and 1,694-1,760 (ACP11).

In this embodiment, the above-mentioned gene preferably has the base sequence of SEQ ID NO: 1, residues 20,927-26,158 (fscA), 28,983-60,860c (fscC), 60,962-77,587c (fscB), 77,983-84,132c (fscF), 84,170-107,485c (fscE) and 107,496-136,148c (fscD). The indication “c” on the sequence according to the present invention shows that transcription occurs in a complementary strand in the opposite direction.

In yet another embodiment, the present invention provides an ABC transporter having the amino acid sequence of SEQ ID NO: 8 or 9, as well as a gene (fscTI or fscTII) coding for the same. The fscTI and fscTII genes preferably have the base sequences of residues 26,333-27,340 and 27,561-28,280 of SEQ ID NO: 1, respectively.

In still another embodiment, the present invention provides a regulator protein having the amino acid sequence of SEQ ID NO: 10, 11, 12 or 13, and a gene (fscRI, fscRII, fscRIII or fscRIV) coding for the same. The fscRI, fscRII, fscRIII and fscRIV genes preferably have the base sequences of residues 3,150-3,818c, 4,377-7,205c, 7,210-10,320c and 10,298-13,315c of SEQ ID NO: 1, respectively.

Furthermore, the present invention provides a cytochrome P-450 monooxygenase having the amino acid sequence of SEQ ID NO: 14, as well as a gene (fscP) coding for the same. The fscP gene preferably has the base sequence of residues 16,106-17,287 of SEQ ID NO: 1.

In another embodiment, the present invention provides a ferredoxin protein having the amino acid sequence of SEQ ID NO: 15, as well as a gene (fscFE) coding for the same. The fscFE gene preferably has the base sequence of residues 17,334-17,528 of SEQ ID NO: 1.

In still another embodiment, the present invention provides a thioesterase having the amino acid sequence of SEQ ID NO: 16, and a gene (fscTE) coding for the same. The fscTE gene preferably has the base sequence of residues 17,556-18,413 of SEQ ID NO: 1.

In further another embodiment, the present invention provides a glycosyltransferase having the amino acid sequence of SEQ ID NO: 17, and a gene (fscMI) coding for the same. The fscMI gene preferably has the base sequence of residues 13,522-14,898 of SEQ ID NO: 1.

In yet another embodiment, the present invention provides a GDP-ketosugar aminotransferase having the amino acid sequence of SEQ ID NO: 18, and a gene (fscMII) coding for the same. The fscMII gene preferably has the base sequence of residues 14,953-16,011 of SEQ ID NO: 1.

In still another embodiment, the present invention provides a GDP-mannose-4,6-dehydratase having the amino acid sequence of SEQ ID NO: 19, and a gene (fscMIII) coding for the same. The fscMIII gene preferably has the base sequence of residues 136,558-137,766c of SEQ ID NO: 1.

Moreover, the present invention provides a FAD-dependent monooxygenase having the amino acid sequence of SEQ ID NO: 20, and a gene (fscO) coding for the same. The fscO gene preferably has the base sequence of residues 574-1,950c of SEQ ID NO: 1.

In another embodiment, the present invention provides an ADC synthase having the amino acid sequence of SEQ ID NO: 21, and a gene (pabAB) coding for the same. The pabAB gene preferably has the base sequence of residues 18,610-20,781 of SEQ ID NO: 1.

Also, the present invention provides an ADC lyase having the amino acid sequence of SEQ ID NO: 22, and a gene (pabC) coding for the same. The pabC gene preferably has the base sequence of residues 2,264-3,037c of SEQ ID NO: 1.

Hereinafter, the present invention will be described in further detail.

As a result of prior studies on the cloning of genes for the synthesis of FR-008 polyketides, a chromosomal library of *Streptomyces* sp. FR-008 was constructed using a cosmid vector, and 16 cosmid clones containing PKS genes were screened from the chromosomal library (Hu et al., *Mol. Microbiol.,* 14:163-72, 1994). Meanwhile, a *Streptomyces* sp. FR-008 strain used in the present invention was deposited under the accession number KCTC 10529BP on Oct. 20, 2003 with the Korean Collection for Type Cultures (KCTC), Korea Research Institute of Bioscience and Biotechnology, 52, Oun-dong, Yusong-Ku, Taejon 305-333, Republic of Korea.

In the present invention, all of the gene base sequences of cosmid clones pHZ145, pHZ137, pHZ220 and pHZ194 among 16 cosmid clones constructed in the prior art and also plasmid clone pJTU6 were analyzed. Also, the gene base sequence of a new plasmid clone pJTU10 was analyzed. On the basis of this sequencing, a gene base sequence (138,203 bp) involved in the biosynthesis of FR-008 polyketides was identified from base sequences other than the cosmid and plasmid DNA base sequences (see, FIG. 1).

The present invention will hereinafter be described in further detail by examples. It will however be obvious to a person skilled in the art that these examples are given for illustrative purpose only, and the scope of the present invention is not limited to or by these examples.

EXAMPLE 1

Base Sequence Analysis of PKS Genes from Cosmid Clones pHZ145, pHZ137, pHZ220 and pHZ194 among 16 cosmid clones constructed by Hu et al. (Hu et al., *Mol. Microbiol.,* 14:163-72, 1994) and also plasmid clone pJTU6 were used in gene sequencing.

Cosmid DNA was fragmented by ultrasonic treatment and then subjected to agrose gel electrophoresis. The produced DNA fragments of suitable sizes were isolated from agarose gels, and their both ends were polished with T4 DNA polymerase and T4 DNA kinase. The polished DNA fragments were cloned into plasmid pUC19 digested with restriction enzyme SmaI. For cosmids pHZ145, pHZ137 and pJTU6, the isolated DNA fragments of about 5 kb size were used. For pHZ220 and pHZ194, the isolated DNA fragments of about 1 kb size were used.

Gene sequencing reaction was carried out in each pUC19 clone using a BigDye Terminator Cycle Sequencing kit, version 2 (Applied Biosystems, USA) by dye terminator sequencing chemistry. For gene sequencing, an ABI Prism 3700 DNA analyzer (Applied Biosystems, USA) was used.

As an analysis program, the phrap version 0.990329 was used. For contig viewing and editing, the consed version 11 was used. The gene sequencing was performed at least six times for each base.

A whole base sequence analyzed by the method as described above was 138,203 bp in length. The G+C content in the whole base sequence was about 74.6%, and whole open reading frames were 20 in number. Gaps in shotgun sequencing were filled either by primer walking or extra clone sequencing. Gene base sequences for open reading frame analysis and conserved domain database search were analyzed with FramePlot 2.3.2.

This gene sequencing revealed that parts of FR-008 polyketide biosynthetic genes were deleted in the four cosmid clones resulted from the study of Hu et al. and the one-plasmid clone. Hu et al. reported that the fourth plasmid pHZ194 contained the latest part of the FR-008 polyketide biosynthetic genes (Hu et al., *Mol. Microbiol.,* 14:163-72, 1994), but the actual gene sequencing revealed that the pHZ194 cosmid clone had parts of the FR-008 polyketide biosynthetic genes, parts of chromosomes derived from *Streptomyces* sp. FR-008, and two backbone cosmids pHZ132.

Thus, in order to secure the whole base sequence of the FR-008 polyketide biosynthetic genes, a cosmid clone containing the last part of the FR-008 polyketide biosynthetic genes was searched from a cosmid library reported on the article of Hu et al. In a search method, Southern hybridization was performed using probes constructed by polymerase chain reaction (PCR) from parts of the FR-008 polyketide biosynthetic genes contained in the pHZ194 cosmid clone. Namely, PCR was performed using primers of SEQ ID NOs: 23 and 24 as described below, thereby obtaining a PCR product of a 218 bp length. This PCR product was subjected to Southern hybridization using probes, and as a result, two cosmid clones (pJTU10 and pJTU11) could be identified. The cosmid clone pJTU10 was selected and selected to gene sequencing as described above, thereby securing a whole gene sequence (138,203 bp) involved in FR-008 polyketide biosynthesis.

```
5' TGCCGCGCTCGCCGACA 3'      (SEQ ID NO: 23)

5' CGCGTCCGGTGCTCACG 3'      (SEQ ID NO: 24)
```

The analysis result of each gene is as follows. The base sequences of residues 20,927-26,158 and 28,983-107,485 of SEQ ID NO: 1 code for PKS genes involved in the synthesis of FR-008 macrolide backbones. In such two regions, there are present six open reading frames (fscA, fscB, fscC, fscD, fscE and fscF), and between the two regions, there are present genes coding for two ABC transporters. The base sequence and amino acid sequence position of each of the PKS genes are summarized in Table 2 below.

TABLE 2

Base sequence and amino acid sequence position of each of PKS genes.

| Genes | Amino acid sequence positions of SEQ ID NO: 1 | Corresponding Amino acid Sequence |
|---|---|---|
| fscA | 20,927-26,158 | SEQ ID NO: 2 |
| fscC | 28,983-60,860c | SEQ ID NO: 3 |
| fscB | 60,962-77,587c | SEQ ID NO: 4 |
| fscF | 77,983-84,132c | SEQ ID NO: 5 |
| fscE | 84,170-107,485c | SEQ ID NO: 6 |
| fscD | 107,496-136,148c | SEQ ID NO: 7 |

fscA codes for a loading module and extension module 1. Each of amino acid sequences for PKS domains of the loading module and extension module in fscA is summarized in Table 3 below.

fscC codes for six extension modules (extension modules 5, 6, 7, 8, 9 and 10). Each of amino acid sequences for PKS domains of the six extension modules in fscC is summarized in Table 4 below.

fscB codes for three extension modules (extension modules 4, 3 and 2). Each of amino acid sequences for PKS domains of the three extension modules in fscB is summarized in Table 5.

TABLE 3

Amino acid sequence positions for PKS domains of loading module and extension modules in fscA.

| Domain | Amino acid sequence positions of SEQ ID NO: 2 | Domain | Amino acid sequence positions of SEQ ID NO: 2 |
|---|---|---|---|
| CoL | 51-465 | AT1 | 1,202-1,509 |
| ACPL | 581-647 | ACP1 | 1,596-1,662 |
| KS1 | 661-1,094 | | |

TABLE 4

Amino acid sequence positions for PKS domains of six extension modules in fscC.

| Domain | Amino acid sequence positions of SEQ ID NO: 3 | Domain | Amino acid sequence positions of SEQ ID NO: 3 |
|---|---|---|---|
| KS10 | 8,808-9,221 | KS7 | 3,529-3,954 |
| AT10 | 9,330-9,627 | AT7 | 4,059-4,356 |
| DH10 | 9,680-9,867 | DH7 | 4,407-4,595 |
| KR10 | 10,183-10,366 | KR7 | 4,884-5,063 |
| ACP10 | 10,469-10,536 | ACP7 | 5,163-5,230 |
| KS9 | 6,966-7,383 | KS6 | 1,787-2,212 |
| AT9 | 7,490-7,792 | AT6 | 2,318-2,617 |
| DH9 | 7,845-8,029 | DH6 | 2,670-2,859 |
| KR9 | 8,331-8,514 | KR6 | 3,155-3,338 |
| ACP9 | 8,618-8,685 | ACP6 | 3,438-3,505 |
| KS8 | 5,253-5,675 | KS5 | 34-460 |
| AT8 | 5,775-6,074 | AT5 | 576-875 |
| DH8 | 6,127-6,310 | DH5 | 928-1,112 |
| KR8 | 6,590-6,773 | KR5 | 1,417-1,596 |
| ACP8 | 6,874-6,941 | ACP5 | 1,696-1,763 |

Table 5. Amino acid sequence positions for PKS domains of three extension modules in fscB.

TABLE 5

Amino acid sequence positions for PKS domains of three extension modules in fscB.

| Domain | Amino acid sequence positions of SEQ ID NO: 4 | Domain | Amino acid sequence positions of SEQ ID NO: 4 |
|---|---|---|---|
| KS4 | 3,703-4,103 | ER3 | 2,970-3,322 |
| AT4 | 4,247-4,550 | KR3 | 3,325-3,508 |
| DH4 | 4,600-4,722 | ACP3 | 3,610-3,677 |
| KR4 | 5,103-5,286 | KS2 | 33-460 |
| ACP4 | 5,389-5,456 | AT2 | 571-874 |
| KS3 | 1,597-2,023 | KR2 | 1,224-1,406 |
| AT3 | 2,139-2,442 | ACP2 | 1,508-1,574 |
| DH3 | 2,494-2,684 | | |

FscF codes for one extension module (extension module 21) and one thioesterase. Each of amino acid sequences for PKS domains of the one extension module and one thioesterase in FscF is summarized in Table 6 below.

FscE codes for four extension modules (extension modules 17, 18, 19 and 20). Each of amino acid sequences for PKS domains of the four extension modules in fscE is summarized in Table 7 below.

TABLE 6

Amino acid sequence positions for PKS domains of one extension module and one thioesterase in fscF.

| Domain | Amino acid sequence positions of SEQ ID NO: 5 | Domain | Amino acid sequence positions of SEQ ID NO: 5 |
|---|---|---|---|
| KS21 | 33-456 | KR21 | 1,378-1,561 |
| AT21 | 545-851 | ACP21 | 1,668-1,735 |
| DH21 | 903-1,083 | TE21 | 1,814-2,018 |

TABLE 7

Amino acid sequence positions for PKS domains of four extension modules in fscE.

| Domain | Amino acid sequence positions of SEQ ID NO: 6 | Domain | Amino acid sequence positions of SEQ ID NO: 6 |
|---|---|---|---|
| KS20 | 5,642-6,069 | AT18 | 2,590-2,896 |
| AT20 | 6,158-6,463 | DH18 | 2,948-3,127 |
| DH20 | 6,515-6,693 | ER18 | 3,428-3,733 |
| ER20 | 7,017-7,322 | KR18 | 3,741-3,924 |
| KR20 | 7,330-7,512 | ACP18 | 4,025-4,092 |
| ACP20 | 7,615-7,682 | KS17 | 34-460 |
| KS19 | 4,117-4,544 | AT17 | 548-850 |
| AT19 | 4,633-4,936 | DH17 | 902-1,081 |
| KR19 | 5,263-5,445 | ER17 | 1,384-1,689 |
| ACP19 | 5,552-5,619 | KR17 | 1,697-1,880 |
| KS18 | 2,071-2,498 | ACP17 | 1,982-2,049 |

fscD codes for six extension modules (extension modules 16, 15, 14, 13, 12, and 11). Each of amino acid sequences for PKS domains of the six extension modules in fscD is summarized in Table 8.

There are the total 15 open reading frames for PKS enzymes, and such open reading frames comprise modifier enzymes, transcription regulatory proteins, and ABC transporters. The base sequence and amino acid sequence position of each gene are summarized in Table 9 below.

TABLE 8

Amino acid sequence positions for PKS domains of six extension modules in fscD.

| Domain | Amino acid sequence positions of SEQ ID NO: 7 | Domain | Amino acid sequence positions of SEQ ID NO: 7 |
|---|---|---|---|
| KS16 | 7,935-8,352 | AT13 | 3,872-4,170 |
| AT16 | 8,464-8,767 | KR13 | 4,499-4,676 |
| KR16 | 9,099-9,280 | ACP13 | 4,782-4,849 |
| ACP16 | 9,387-9,452 | KS12 | 1,788-2,209 |
| KS15 | 6,425-6,845 | AT12 | 2,313-2,621 |
| AT15 | 6,935-7,241 | KR12 | 2,972-3,150 |
| KR15 | 7,559-7,725 | ACP12 | 3,254-3,314 |
| ACP15 | 7,838-7,898 | KS11 | 38-452 |
| KS14 | 4,872-5,297 | AT11 | 563-864 |
| AT14 | 5,408-5,720 | DH11 | 921-1,105 |
| KR14 | 6,049-6,225 | KR11 | 1,410-1,592 |
| ACP14 | 6,331-6,398 | ACP11 | 1,694-1,760 |
| KS13 | 3,342-3,765 | | |

TABLE 9

Gene base sequences and amino acid sequence positions of fifteen PKS modifier enzymes.

| ORFs | Gene Residues of SEQ ID NO: 1 | Corresponding Amino acid sequence |
|---|---|---|
| fscTI | 26,333-27,340 | SEQ ID NO: 8 |
| fscTII | 27,561-28,280 | SEQ ID NO: 9 |
| fscRI | 3,150-3,818c | SEQ ID NO: 10 |
| fscRII | 4,377-7,205c | SEQ ID NO: 11 |
| fscRIII | 7,210-10,320c | SEQ ID NO: 12 |
| fscRIV | 10,298-13,315c | SEQ ID NO: 13 |
| fscP | 16,106-17,287 | SEQ ID NO: 14 |
| fscFE | 17,334-17,528 | SEQ ID NO: 15 |
| fscTE | 17,556-18,413 | SEQ ID NO: 16 |
| fscMI | 13,522-14,898 | SEQ ID NO: 17 |
| fscMII | 14,953-16,011 | SEQ ID NO: 18 |
| fscMIII | 136,558-137,766c | SEQ ID NO: 19 |
| fscO | 574-1,950c | SEQ ID NO: 20 |
| pabAB | 18,610-20,781 | SEQ ID NO: 21 |
| pabC | 2,264-3,037c | SEQ ID NO: 22 |

The function of the proteins that are coded by genes involved in FR-008 biosynthesis is summarized in Tables 10 and 11 below.

TABLE 10

Function of PKS proteins coded by genes involved in FR-008 biosynthesis.

| Gene | Protein | Function |
|---|---|---|
| fscA | Type I PKS | Loading module and module 1 |
| fscB | Type I PKS | Module 2-4 |
| fscC | Type I PKS | Module 5-10 |
| fscD | Type I PKS | Module 11-16 |
| fscE | Type I PKS | Module 17-20 |
| fscF | Type I PKS | Module 21 and TE |

TABLE 11

Function of proteins coded by genes involved in FR-008 biosynthesis.

| Gene | Protein | Function |
|---|---|---|
| fscRI | Transcriptional regulator | regulation |
| fscRII | Transcriptional regulator | regulation |

TABLE 11-continued

| Function of proteins coded by genes involved in FR-008 biosynthesis. | | |
|---|---|---|
| Gene | Protein | Function |
| fscRIII | Transcriptional regulator | regulation |
| fscRIV | Transcriptional regulator | regulation |
| fscMI | Glycosyltransferase | Attachment of mycosamine |
| fscMII | GDP-ketosugar aminotransferase | Mycosamine biosynthesis |
| fscMIII | GDP-mannose-4,6-dehydratase | Mycosamine biosynthesis |
| fscP | Cytochrome P450 monooxygenase | Formation of a carboxyl group at C-18 |
| fscFE | Ferredoxin | electron transfer in P450 system |
| fscTE | Type II thioesterase | Remove aberrant intermediates |
| pabAB | ADC synthase | Biosynthesis of starter unit PABA |
| pabC | ADC lyase | Biosynthesis of starter unit PABA |
| fscO | FAD-dependent monooxygenase | Putative tailoring enzyme |
| fscTI | ABC transporter | Efflux of FR-008 |
| fscTII | ABC transporter | Efflux of FR-008 |

EXAMPLE 2

Function of PKS Genes Involved in FR-008 Biosynthesis

Figure 2:
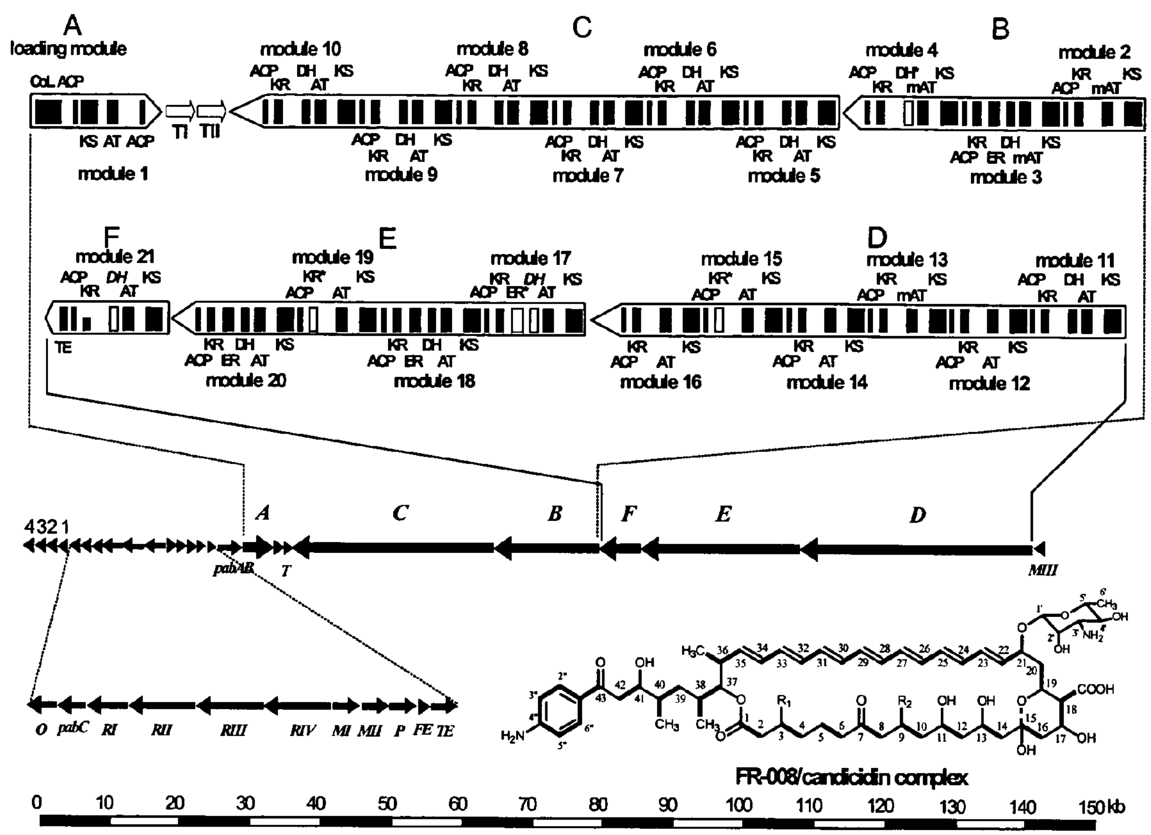
FIG. 2 shows the direction of a FR-008 gene cluster, and an imaginative diagram of a FR-008 polyketide biosynthesis model.

The amino acid sequence of proteins for which fscA through fscF genes code was analyzed by comparison with the amino acid sequence of the existing type I PKS protein. As a result, the function of each gene is shown in FIG. 2.

The transcription of the fscA gene occurred in the opposite direction to the fscC, fscB, fscF, fscE and fscD genes, and 21 condensation reactions were required in FR-008 polyketide biosynthesis. Thus, it could be found that there were the total 21 modules within the fscA through fscF genes (see, FIG. 2).

The FscA protein has a loading module involved in the starting of FR-008 aglycone biosynthesis and also a first condensation module consisting of KS-AT-ACP. The loading module has CoA ligase (CoL) and ACP domains. The CoL domain was also found in genes for the biosynthesis of rifamycin, pimaricin and candicidin (Schwecke, T. et al., *Proc. Natl. Acad. Sci. USA,* 92:7839-43, 1995; Aparicio, J. F. et al., *J. Biol. Chem.,* 274:10133-9, 1999; Campelo and Gil, *Microbiology,* 148:51-9, 2002).

The FscB protein has 2-4 extension modules involved in 2-4 extension procedures of FR-008 agylcone biosynthesis. Three AT domains within FscB have residues of the amino acid sequence of RVDVVxxxxxxxMxS(A)xAxxW of SEQ ID NO: 4 as a conservative sequence at the N-terminal end of the active site GHSxG, of SEQ ID NO: 4, in which this amino acid sequence is specific for methylmalonate (Tang, L. et al., *Gene,* 216:255-65, 1998; Haydock, S. F. et al., *FEBS Lett.,* 374:246-8, 1995). Module 2 has KS, mAT, KR and ACP domains, and module 3 has a DH-ER-KR reduction loop. DH4 within module 4 is found to be deleted for residues of the conservative sequence HPLL of SEQ ID NO: 4 at its N-terminal end and also 56 amino acids shorter at its C-terminal end, and thus, regarded as having no activity. However, a CanP2 protein involved in 2-4 extension procedures of candicidin aglycone biosynthesis was reported to have no inactive DH domain described above, although the N-terminal end of a KS domain was not identified.

FscC and FscD proteins provide two other examples of hexamodular proteins. FscC has a 10,625-amino acid length, and FscD has a 9,550-amino acid length. FscC combines six double bonds of the total seven double bonds. Modules 5-10 involved in condensation steps 5-10 all have a DH-KR reduction loop. The total six DH domains have residues of the conservative active site GXGXXGXXXA of SEQ ID NO: 3. All the AT domains within FscC are specific for acetate. FscC that is a protein having the same six DH-KR reduction loops, is in a form which was not found up to date. On the other hand, NysC, Raps2 and AmphC all have five DH-KR reduction loops and also DH-ER-KR reduction loops.

FscD consists of modules 11-16 involved in extension procedures 11-16 in the formation of the FR-008 macrolactone ring. The module 11 combines a KS-AT-DH-KR-ACP domain structure with the last double bond. The extension procedures 10-11 are involved in the formation of two adjacent double bonds (last two of seven double bonds), but interestingly, a gene for the module 11 on the *Streptomyces* FR-008 chromosome is located about 110-kb apart from the gene for the module 10.

The module 13 has a methylmalonate-specific AT domain, and acts to construct a KS-mAT-KR-ACP domain in the extension procedure so as to insert a methylmalonate-CoA extender. The modules 12, 14, 15 and 16 all have the same KS-AT-KR-ACP domain structure, but exceptionally KR15 is inactivated. Furthermore, KR15 is deleted of two conservative G amino acid residues at its NADP-binding site, and also deleted of 10 amino acids at its inside. In a similar manner to nystatin, amphotericin B, and pimaricin, the inactive KR domain is a carboxyl group at C-28. This illustrates the formation of six ketalic rings between positions C-25 and C-28 of most polyketides (Brautaset et al., *Chem. Biol.,* 7:395-403, 2000; Caffrey et al., *Chem. Biol.,* 8:713-23, 2001; Aparicio et al., *Chem. Biol.,* 7:895-905, 2000).

An FscE protein forms modules 17-20 which is involved in extension procedures 17-20 of FR-008 polyketide biosynthesis. The ER domain of the module 17 is 67 amino acids shorter than the N-terminal end of the ER domain of the modules 3, 18 and 20, and thus becomes inactive. The module 19 has the domain structure of KS-AT-KR-ACP. At the active site of the KR domain of the module 19, tyrocine is replaced with leucine, so that the active site becomes inactive.

FscF forms the module 21, which has a chain terminator thioesterase domain at the C-terminal end. The activity of a DH domain in FscF is not required in the last extension procedure. This inactivity also appears in Nystanin (NysK), rifamycin (RifB and RifC) and amphotericin (AmphJ) polyketides. The KS-AT-KR-ACP domain of FscF adds an —OH group to position C-40 of the FR-008 macrolactone ring. Furthermore, a TE domain enables FscF involved in the release of FR-008 polyketides to form lactone. The KR domain of the module 21 has no difference in active motifs and residues from the known KR domain, but it is guessed from the structure of FR-008 that this KR domain is inactive.

The TE domain of FscF and also an fscTE gene upstream of a pabAB gene were known as coding for thioesterase. Like two other TE activities present in gene clusters for antibiotic biosynthesis, such as pikromycin (PicAV), tyrosine (TylO), nystatine (NysE) and pimaricin (PimI), FscTE has high homology with TEII. However, FscTE has low homology with the TEI domain.

TEII is known as serving to remove a bad intermediate which may also interfere with extension procedures in polyketide biosynthesis. This maintains antibiotic production at a normal level (Butler, et al., *Chem. Biol.,* 6:287-92, 1999; Tang, et al., *Chem. Biol.,* 6:553-8, 1999). This is also supported by recent study results on the action of tyrosine TEII.

EXAMPLE 3

Function of p-Aminobenzoic Acid Synthase Gene p-aminobenzoic acid(PABA) is a precursor substance of p-aminoacetophenone acting as a starting unit of FR-008 biosynthesis. Between fscTE and fscA, there is a pabAB gene which codes for 4-amino-4-deoxychorismate (ADC) synthase (see, FIG. 2). This exhibits significant homology with PabABs. Namely, it shows 93% homology with PabAB of *S. griseus* IMRU3570, and 46% homology with PabAB of *S. venezuelae.* pabC upstream of the transcription regulatory gene fscRI consists of 257 amino acids and codes for 4-amino-4-deoxychorismate (ADC) lyase. It is presumed that PabC acts to convert ADC produced by PabAB into PABA or pyruvic acid or acts as aminotransferase or pyridoxal-5'-phosphate-dependent enzyme.

EXAMPLE 4

Function of Genes Involved in Transcription Regulatory Mechanism

Four transcription regulatory genes (fscRI, fscRII, fscRIII, and fscRIV) are involved in FR-008 polyketide biosynthesis. All proteins for which such genes code belong to LuxR family transcription regulatory proteins. FscRI consists of 222 amino acids and has 60% homology with PleR present in a gene cluster for *Streptomyces avermitilis* polyene macrolide biosynthesis (GenBank accession number AB070949), and 59% homology with proteins coded by ORF4 regarded as being involved in the regulation of nystadin biosynthesis (Brautaset et al., *Chem. Biol.,* 7:395-403, 2000). Also, it shows homology with several two-component response regulatory proteins.

The FscRII protein (942 amino acids) shows more than 84% homology with the first 595 amino acid sequence of a *Streptomyces griseus*-derived cho-pseudo protein known as being involved in candicidin synthesis. It is surprising that, in spite of the fact the FscRII protein is 347 amino acids longer than the cho-pseudo protein, this high homology is shown in the N-terminal 595 amino acids. FscRII exhibits 42% homology with a NysRII regulator protein (927 amino acids) involved in nystatin biosynthesis.

FscRIII has 1,036 amino acids and shows significant homology to NysRII (953 amino acids). An FscRIV protein has 1,005 amino acids and shows high homology to NysRI (966 amino acids). It is noteworthy that FscRII, FscRIII and FscRIV have homology to a transcription regulatory protein found in regions adjacent to a cholesterol oxydase-cytochrome P450 operon derived from *Streptomyces* sp. SA-COO, as in NysRIII, NysRII and NysRI.

EXAMPLE 5

Function of Genes Involved in Biosynthesis of Undetermined Sugar

FscMI(458 amino acids) shows high homology with UDP-glucuronosyltransferase of eukaryotic cells, and is presumed to be involved in the attachment of sugar to aglycone of FR-008 at position C-21 (see, FIG. 2).

FscMII(352 amino acids) is similar to aminotransferase involved in the biosynthesis of perosamine (4,6-dideoxy-4-aminomannose). An fscMIII gene codes for 402 amino acids similar to GDP-mannose-4,6-dehydratase. It was reported that the biosynthetic pathway of mycosamine (3,6-dideoxy-3-amino-D-mannose) included the isomerization of GDP-6-deoxy-4-ketomannose into GDP-6-deoxy-3-ketomannose and the production of GDP-mycosamine by amino group transfer (Caffrey et al., *Chem. Biol.,* 8:713-23, 2001). Thus, each of FscMIII and FscMII is presumed to be involved in the biosynthetic pathway of mycosamine.

As a result of searching in the GenBank database, FscMI has 54.7% homology with AmphDI, 52.4% homology with NysDI and 60.5% homology with PimK, FscMII has 92% homology with CanA, and 74-76% homology with AmphDII, NysDII and PimC, and FscMIII has 77-79% homology with AmphDIII, NysDIII and PimJ.

All the proteins as described above are presumed to be involved in the biosynthesis and attachment of mycosamine in the amphotericin, nystatin, pimaricin or candicidin gene cluster. This agrees with the fact that FscMI, FscMII and FscMIII are involved in the biosynthesis and attachment of mycosamine in the FR-008 gene cluster.

EXAMPLE 6

Function of Modifier Gene and Transporter Gene

An fscP gene and an fscFE gene code for cytochrome P450 monooxygenase and ferredoxin, respectively. These genes form a P450 monooxygenase system, and it is presumed that FscP acts to produce a carboxyl group at position C-18, and FscFE is involved in electron transfer in the P450 system (O'Keefe & Harder, *Mol. Microbiol.,* 5:2099-105, 1991).

An fscO gene downstream of a pabC codes for FAD-dependent monooxygenase (see, FIG. 2). This has 34% homology with FAD-dependent monooxygenase from *Agrobacterium tumefaciens* C58. Between fscA and fscC genes, there are located fscTI and fscTII genes (FIG. 2). They show very high homology with proteins belonging to the ATP-dependent ABC transporter super-family, and are presumed to be involved in the efflux of FR-008 polyketides. This is regarded as one of self-resistance mechanisms caused by the efflux of FR-008 polyketides from cytoplasm to the outside. It is very interesting that all polyene clusters reported up to date have two transporter proteins that act as a homodimer together (Bolhuis et al., *FEMS Microbiol. Rev.,* 21:55-84, 1997).

It is noteworthy that FscFE (64 amino acids) has 100% homology with CanF involved in candicidin biosynehtsis. FscP shows 96% homology with CanC. FscTI and FscTII show 85% and 76% homology to CanRA and CanRB, respectively. Such a high homology between the candicidin and the protein involved in FR-008 polyketide biosynthesis suggests that two synthetic gene clusters have a relatively recent common origin.

EXAMPLE 7

Comparison Between Genes for FR-008 Polyketide and Candicidin Biosynthesis

FR-008 polyketides have aglycone containing the same 4-aminoacetophenone as that of candicidin D which is a polyketide produced in *Streptomyces griseus* (Yuan and Zhou, *Chinese J. Biotechnol.,* 7:142-7, 1991; Yuan and Zhou, J. Huazhong *Agricult.* Univ. 9:209, 1990). *Streptomyces* sp. FR-008 shows significant biological differences from the candicidin-producing *Streptomyces griseus* IMRU3570, in that *Streptomyces* sp. FR-008 has two linear plasmids pHZ227 (130 kb) and pHZ228 (30 kb) whereas *Streptomyces griseus* IMRU3570 has no any linear plasmid, and in that sporulation easily occurs in the *Streptomyces* sp. FR-008 but does not easily occur in the *Streptomyces griseus* IMRU3570. In spite of such significant differences between the two strains, polyketides produced by the two strains have aglycones containing the same 4-aminoacetophenone, respectively, and thus have very high homology with genes involved in aglycone synthesis.

Campelo et al. reported the gene base sequence of parts (39,314 bp) of genes for candicidin synthesis (Campelo and Gil, *Microbiology,* 148:51-9, 2002). The result of the comparison between this gene base sequence and the base sequence of the present invention showed a very high homology between the two sequences. The comparison results are summarized in Table 12 below.

TABLE 12

Comparison between FR-008 polyketide and candicidin synthetic genes (positions with homology).

| Identity (%) | FR-008 gene base sequences (SEQ ID NO: 1) | Candicidin gene base sequences (GenBank accession No AJ300302) |
|---|---|---|
| 98.73 | 5,421–5,970 | 2–551 |
| 99.10 | 6,024–7,468 | 605–2,049 |
| 98.19 | 7,528–7,693 | 2,109–2,274 |
| 99.17 | 7,757–8,118 | 2,338–2,699 |
| 99.76 | 8,167–3,,171 | 2,748–3,172 |
| 98.54 | 8,646–10,764 | 3,227–5,336 |
| 99.33 | 10,826–13,228 | 5,398–7,801 |
| 100.0 | 13,292–13,420 | 7,865–7,993 |
| 99.47 | 13,488–18,382 | 8,061–12,963 |
| 99.06 | 18,445–20,785 | 13,026–15,366 |
| 98.88 | 20,842–23,973 | 15,423–18,553 |
| 95.52 | 23,996–24,259 | 18,576–18,843 |
| 98.80 | 24,357–26,349 | 18,852–20,845 |
| 99.59 | 26,374–27,350 | 20,870–21,846 |
| 98.10 | 27,394–44,804 | 21,890–39,314 |
| 95.65 | 28,473–23,548 | 23,460–23,415 |

At the intervals between the compared positions in Table 12, the two gene base sequences did not show high homology with each other. The results of the comparison between the two gene base sequences at such intervals are given in Table 13 below. A 39,414 bp gene of candicidin codes for proteins corresponding to the KR domain of the module 4 in fscRII, fscRIII, fscRIV, fscMI, fscMII, fscP, fscFE, fscTE, pabAB, fscA, fscTI, fscTII and fscB present in positions 5,421-44, 805 of SEQ ID NO: 1 for FR-008. This codes for canA (aminotransferase), canC (cytochrome P450), canF (ferredoxine), canT (thioesterase), pabAB (PABA synthase), canRA (ABC transporter), canRB (ABC transporter) and moiety orf1 (Cho-like protein).

TABLE 13

Comparison between FR-008 polyketide and candicidin synthetic genes (positions without homology).

| Intervals | Positions of SEQ ID NO: 1 | FR-008 gene | Candicidin gene |
|---|---|---|---|
| 52bp | 5,972–6,024 | fscRII | orf1 |
| 58bp | 7,470–7,528 | fscRIII | orf2 |
| 62bp | 7,695–7,757 | fscRIII | orf2 |
| 47bp | 8,120–8,167 | fscRIII | orf2 |
| 53bp | 8,593–8,646 | fscRIII | orf2 |
| 60bp | 10,757–10,817 | fscRIV | orf3 |
| 62bp | 13,222–13,284 | fscRIV | orf3 |
| 55bp | 20,787–20,842 | Position between pabAB and PKS gene | |
| 21bp | 23,974–23,995 | KS1 of fscA Domain | KS Domain |
| 9bp | 24,262–24,271 | KS1 of fscA Domain | KS Domain |
| 23bp | 26,284–26,289 | fscTI | canRA |
| 42bp | 27,267–27,309 | fscTII | canRB |

Figure 3:
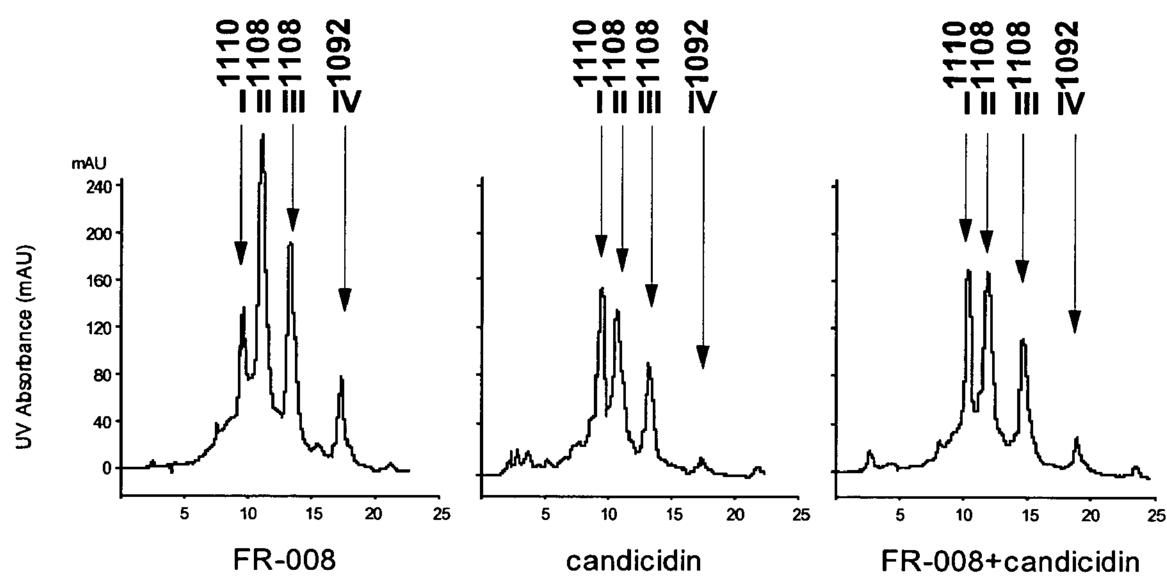
FIG. 3 shows the comparison between FR-008, candicidin, and FR-008/candicidin.

FR-008 produced by *Streptomyces* sp. and candicidin complex produced by *Streptomyces griseus* were analyzed by HPLC. The analysis results showed that the two antibiotics could not be definitely distinguished from each other (see, FIG. 3). Also, the results of HPLC analysis for a mixture of the two antibiotics showed that the retention time of four main peaks of each antibiotic was not changed (FIG. 3), and the UV spectrum of FR-008-I, II, III and IV was precisely identical to that of the candicidin complex. Equal results were also obtained in LC/MS1/MS2 analysis. Thus, *Streptomyces* sp. FR-008 can seem to produce four components identical to those of the candicidin complex produced by *S. griseus*.

Figure 4:
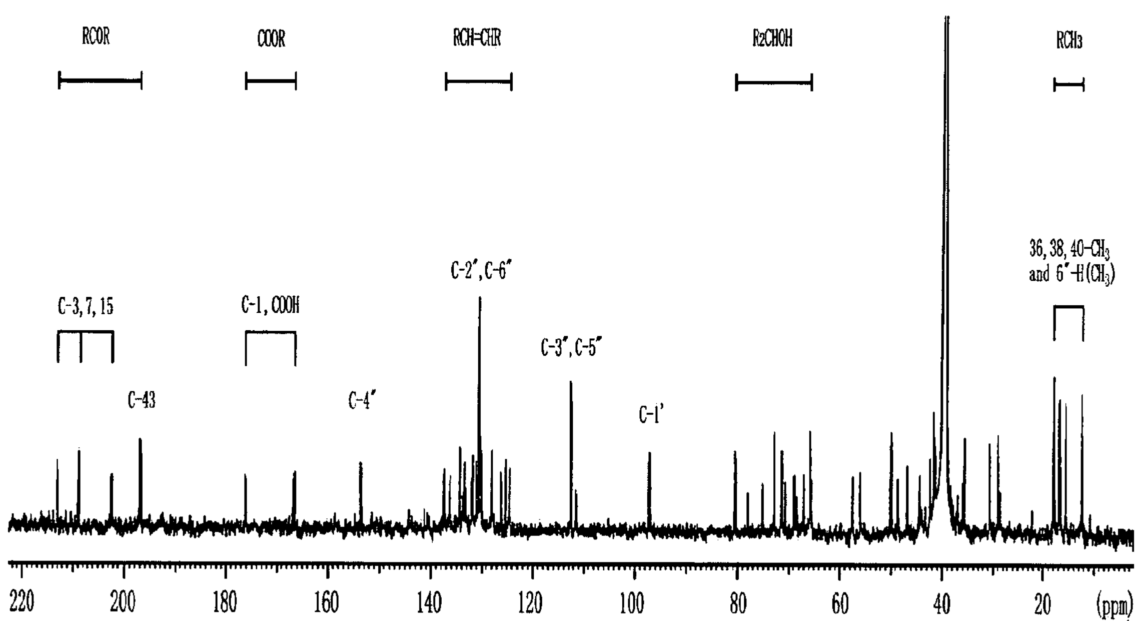
FIG. 4 shows $^{13}C$ NMR data for FR-008-II.

Since the m/z 1108 of FR-008II is equal to the m/z 1108 of FR-008III, FR-008II is regarded as the isomer of FR-008III. Moreover, the two substances showed the same peaks as those of candicidin-II and candicidin-III (m/z 1108) (FIG. 3), and also their theoretical molecular weight (MW 1109) was the same as the molecular weight ($C_{59}H_{94}N_2O_{18}$) of candicidin D. The main functional groups of FR-008-II were analyzed by $^1H—^1H$ COSY spectrums. The structure of FR-008-II was analyzed by $^{13}C$ NMR (FIG. 4).

It was found that the hemiketal ring was not found between positions C-15 and C-19 of FR-008II, ketal at δ96.9 was located at position C-1 of mycosamine, and four ketone groups between δ202.2 and δ196.7 were located at positions C-3, C-7, C-15 and C-43, respectively. Moreover, it was found that six hemiketal rings attributed to the isomer FR-008-III which equilibrates in the FR-008 complex.

That amphotericin B, polyhydroxy ketone, is present in a structure equilibrating in the form of various cyclic ketals was demonstrated by the fact that a six-membered ring cyclic ketal structure and a structure having no six-membered ketal ring are present together.

A difference in molecular weight between FR-008-I and FR-008-II (III) is 2 Daltons, and this difference can be explained by the fact that a mixture having a keto group and a hydroxy group occurs at position C-3, since K21 activity is insufficient to catalyze keto reduction and thus incompletely reduced polyketide chains are passed to a stage mediated by TE(thioesterase), or TE can not distinguish the polyketides of a form reduced by KR21 from the polyketides of a oxidized form before cyclization.

FR-008-IV/candicidin-IV with $MS_1$ m/z 1092 shows a molecular weight difference of 16 Daltons from FR-008-II (III)/candicidin-II(III)($MS_1$ m/z 1108). There are several alternative possibilities for the structural between the FR-008-IV/candicidin-IV and the FR-008-II(III)/candicidin-II(III) functioning as FscO (FAD-dependent monooxygenase).

EXAMPLE 8

Test for Disruption of Glycotransferase (FscMI)

To disrupt FscMI, a 6.6 kb KpnI fragment of pHZ145 containing fscMI was inserted into pIJ2925 (Janssen and Bribb, Gene, 124:133-4, 1993) so as to construct pJTU26. A 1.4 kb EcoRV-SmaI DNA fragment containing an apramycine-resistant gene was inserted into the BalI site (located 564 bp downstream of the start codon of fscMI) of the pJTU26 so as to construct pJTU38. A 8.0 kb BglII DNA fragment of the pJTU38 was inserted into the BamHI site of pHZ1358 (Sun et al, *Microbiology,* 148:361-71, 2002) so as to construct pJTU56. *Streptomyces* sp. FR-008 was transformed with pJTU56 by conjugation using *E. coli* ET12567 (MacNeil et al., *Gene,* 115:119-25, 1992; and Mazodier et al., *J. Bacteriol.,* 171:3583-5, 1989) containing RP4 derivative pUZ8002, thereby giving mutant strain C101. This mutant strain was identified by PCR using primers of CS3 (SEQ ID NO: 25) and CS4 (SEQ ID NO: 26).

```
5'-GATCCTCTTCGTCAGTCTCC-3'    (SEQ ID NO: 25)

5'-CATGTAGACCACCGACGACT-3'    (SEQ ID NO: 26)
```

When the chromosomal DNA of a wild-type *Streptomyces* sp. FR-008 gene was used as a template, a 840 bp fragment was produced, but when its mutant strain was used, a 2.2 kb fragment was produced by insertion of a 1.4 kb apramycine-resistant gene (acc(3)IV).

A culture medium of this mutant strain was analyzed by LC/MSn, and the results showed that polyketides V, VI, VII, VIII and IX having no sugar attached thereto were produced, in addition to polyketides produced in wild-type *Streptomyces* sp. FR-008 (see, FIG. 5). From such results, it could be found that FscMI was a gene coding for proteins with glycotransferase activity in polyketide production.

EXAMPLE 9

Test for Disruption of Transaminase (FscMII)

To disrupt FscMII, a 5.5 kb SacI-KpnI fragment of pHZ145 containing an fscMII gene was inserted into pIJ2925 so as to construct pJTU27. A 1.4 kb PstI DNA fragment of the pJTU27 containing an apramycine-resistant gene of pHZ1358 was inserted into the PstI site (located 436 bp downstream of the start codon of fscMII) of the pJTU27 so as to construct pJTU31. A 6.9 kb BglII DNA fragment of the pJTU31 was inserted into the BamHI site of pHZ1358 so as to construct pJTU58. *Streptomyces* sp. FR-008 was transformed with pJTU58 by conjugation using *E. coli* ET12567 containing RP4 derivative pUZ8002, thereby giving mutant strain CS102. This mutant strain was identified by PCR using primers of CS5 (SEQ ID NO: 27) and CS6 (SEQ ID NO: 28).

```
5'-GACCTGAACATCGACGTCAC-3'    (SEQ ID NO: 27)

5'-AGGTCGTACATCCACAGGAC-3'    (SEQ ID NO: 28)
```

When the chromosomal DNA of a wild-type *Streptomyces* sp. FR-008 gene was used as a template, a 508 bp fragment was produced, but when its mutant strain was used, a 1.9 kb fragment was produced by insertion of a 1.4 kb apramycine-resistant gene (acc(3)IV).

A culture medium of this mutant strain was analyzed by LC/MSn, and the results showed that polyketides V, VI, VII, VIII and IX having no sugar attached thereto and also polyketites X, XI and XII where amine transfer did not occur were produced, in addition to polyketides produced in wild-type *Streptomyces* sp. FR-008 (see, FIG. 5 and FIG. 6). From such results, it could be found that FscMII was a gene coding for proteins with transaminase activity in a polyketide biosynthesis process.

EXAMPLE 10

Antifungal Activity of Polyketide Variants

Figure 7:
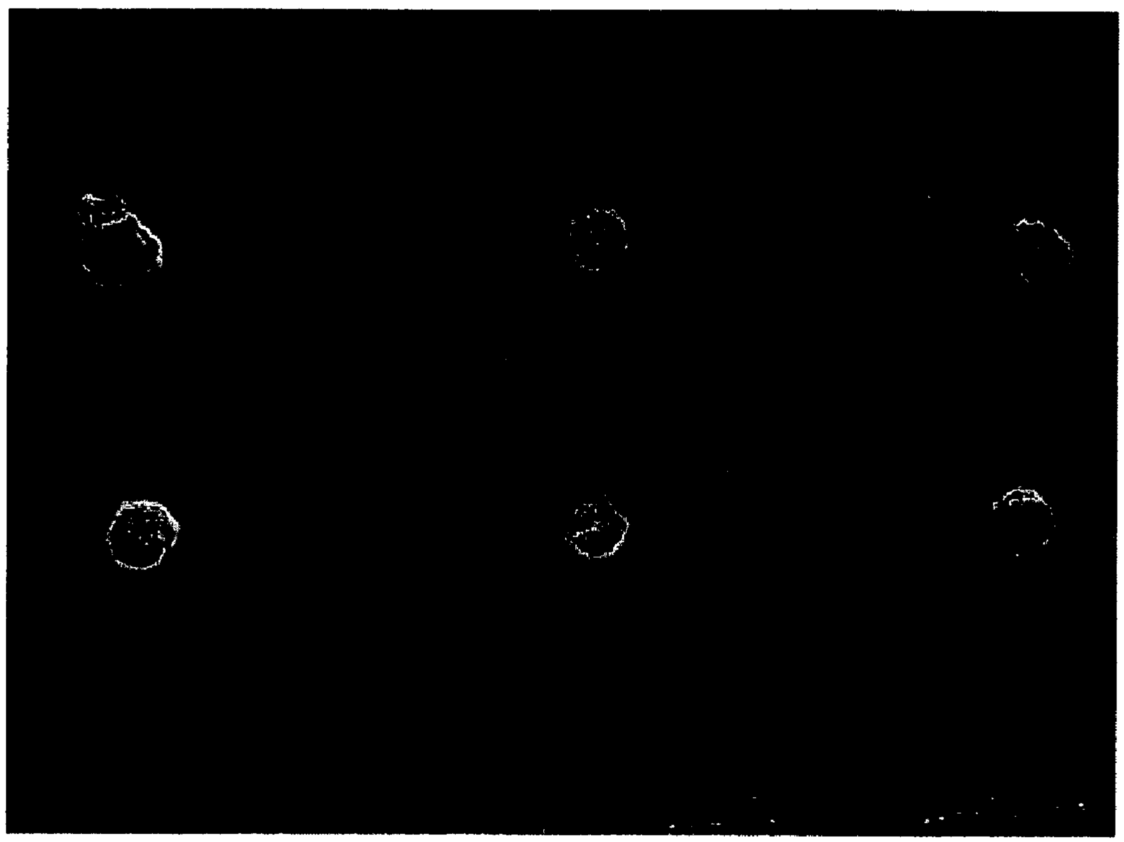
FIG. 7 shows the antifungal activity of polyketide variants V, VI, VIII, IX, X, XI and XII.

The polyketide variants produced in Examples 8 and 9 were tested for antifungal activity, and the results showed that turbid inhibition zones where the growth of *Saccharomyces cerevisiae* is inhibited were formed at sites to which the culture mediums of the *Streptomyces* sp. FR-008 mutant strains CS101 and CS102 were added (see, FIG. 7). In FIG. 7, the left turbid zone is a zone added with *Streptomyces* sp. FR-008, the middle is a zone added with the mutant strain CS101, and the right is a zone added with the mutant strain CS102. As shown in FIG. 7, the culture mediums of the mutant strains CS101 and CS102 also exhibited antifungal activity. This is caused by the polyketide variants V, VI, VIII, IX, X, XI and XII, which are produced in the mutant strains.

EXAMPLE 11

Test for Replacement of Transcription Regulatory Genes

To disrupt transcription regulatory genes fscRII and fscRIII and moiety fscRI (6,414 bp DNA; 3,811-10,225 of GenBank accession number AY310323), cosmid pHZ2007 derived from cosmid pHZ1358 was constructed. The cosmid pHZ2007 was constructed in such a manner that 2.8 kb of an apramycine (aac(3)IV)- and erythromycin (ermE)-resistant gene cassette derived from cosmid pHZ1358 (Hu et al, Mol. Microbiol., 14:163-72, 1994) is interposed between a 1,518 bp BglII-BamHI DNA fragment serving as a left arm and a 1,952 bp SacI-BamHI DNA fragment serving as a right arm. This cosmid was transformed into *Streptomyces* sp. FR-008 by conjugation in the same manner as in Example 8, thereby giving a mutant strain. In this mutant strain, a 4.3 kb BglII-BamHI DNA fragment was identified by Southern hybridization using left and right arms derived from pHZ2007, and an acc(3)IV/ermE gene cassette, as probes. This mutant strain did not produce substances related with FR-008. From this result, it could be found that fscRII, fscRIII and fscRI were involved in FR-008 biosynthesis.

EXAMPLE 12

Test for PabAB Deletion

A 4.6 kb BamHI fragment was obtained from a pHZ145 cosmid and cloned into suicide vector pOJ260. Then, it was digested with FscPI and ligated to delete a 1,491 bp fragment containing a pabAB gene (in frame deletion, 497 amino acid). The resulting cosmid was transformed into *Streptomyces* sp. FR-008 by conjugation in the same manner as in Example 8. The pabAB-deleted mutant strain was analyzed by Southern hybridization. FR-008 polyketides were not biosynthesized by culturing of this mutant strain, and when p-aminobenzoic acid was added, the biosynthetic capability of the mutant strain was restored. From this result, it could be found that pabAB is a gene coding for enzymes for the synthesis of p-aminobenzoic acid.

EXAMPLE 13

Prediction of Two Cis Double Bonds Based on Sequencing

When comparing KR domains related with double bonds, it can be seen that, in KR8 and KR9, aspartate (D) residues that are conserved amino acids known as producing D configuration (Tang et al, *Chem. Biol.,* 6:553-8, 1999), are changed into glycine (G) and asparagine (N) by reduction, respectively. KR having conserved aspartate forms trans double bonds by dehydratase activity after reduction. The presence of two double bonds in KR was found by the NMR analysis of vacidin A (Altschul et al, *Trends Biochem. Sci.,* 23:444-7, 1998), and it was reported that a KR domain was connected with the planar structure of double bonds (Tang et al, *Chem. Biol.,* 6:553-8, 1999). As a result, it is predicted that two double bonds of C28-C29 and C30-C31 of FR-008 is in cis as in other similar KRs (Pearson, *Methods Enzymol.,* 183:63-98, 1990; August et al, *Chem. Biol.,* 5:69-79, 1998).

INDUSTRIAL APPLICABILITY

As described and demonstrated in detail as described above, the present invention provides the base sequence of genes involved in the biosynthesis of new FR-008 polyketides. The whole or parts of the gene base sequence provided in the present invention can be used to develop recombinant microorganisms capable of producing FR-008 polyketides or to search for the active site of FR-008 polyketides from *Streptomyces* sp. FR-008 or other species. Moreover, the whole or parts of the gene base sequence provided in the present invention can be applied to increase the productivity of the existing FR-008 polyketides or to produce new FR-008 polyketide variants, by its modification.

In particular, the whole or parts of the gene base sequence provided in the present invention can be used to produce FR-008 polyketides or variants thereof in cells other than source producer strain *Streptomyces* sp. FR-008. In addition, it can be used in molecular evolution by DNA shuffling between the DNA fragments of the whole or parts of the gene base sequence according to the present invention and other genes having similar homology, and allows new polyketides to be produced using such a procedure.

While the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An isolated gene cluster for the biosynthesis of FR-008 polyketides having the nucleotide sequence of SEQ ID NO:1.

Figure 5:
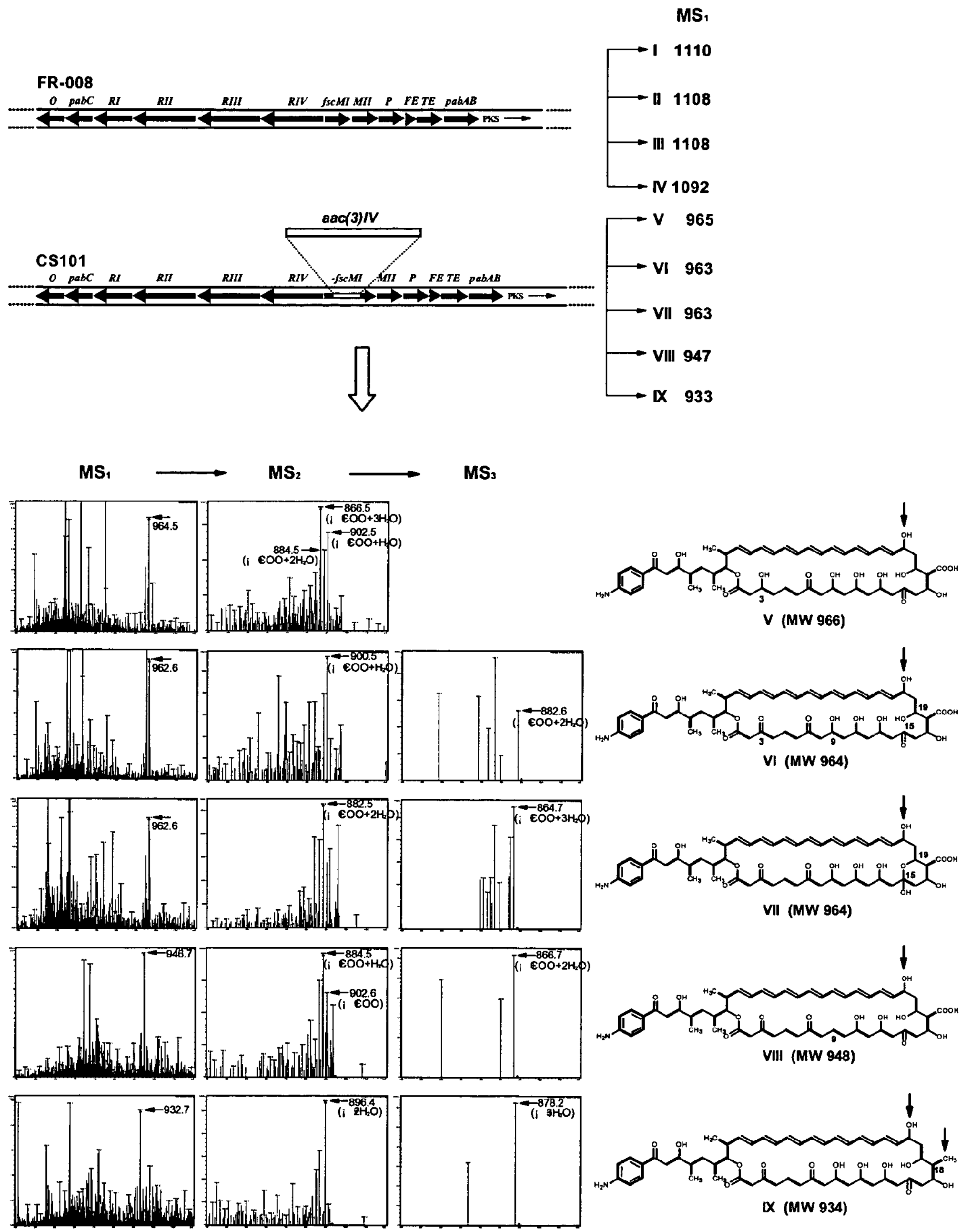
FIG. 5 shows polyketides V, VI, VII, VIII and IX having no sugar attached thereto, which were produced in an fscMI gene-disrupted mutant strain.
Figure 6:
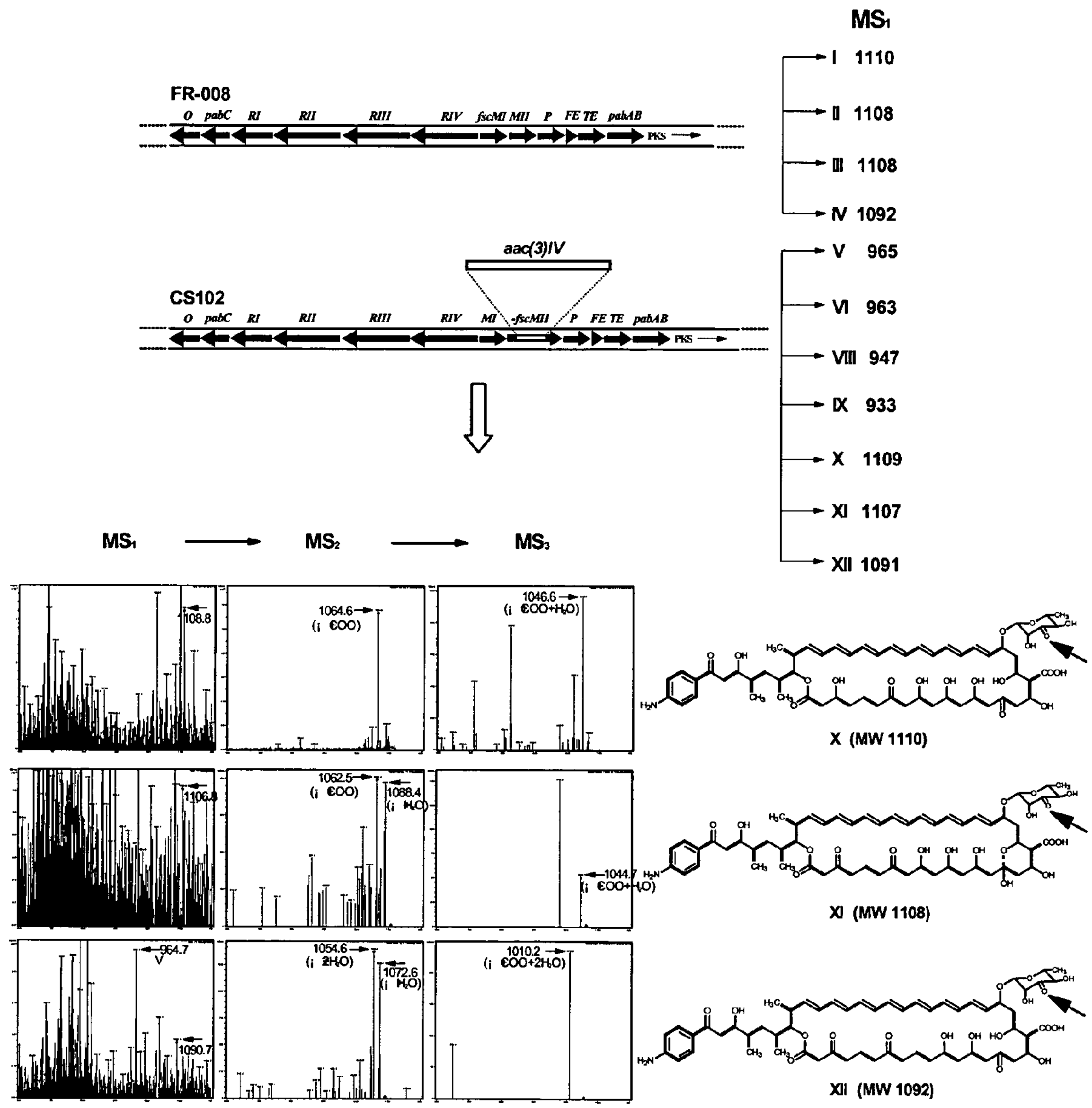
FIG. 6 shows polyketides X, XI and XII where amino group transfer did not occur and which were produced in an fscMII gene-disrupted mutant strain.

2. A method for producing FR-008-V, FR-008-VI, FR-008-VII, FR-008-VIII or FR-008-IX polyketide variant as shown in FIGS. 5 and 6, the method comprising the steps of:

preparing a mutant strain of *Streptomyces* sp. FR-008 in which the fscMI gene, having the nucleotides 13,522-14,898 of SEQ ID NO: 1, is deleted or inactivated by insertion of a 1.4 kb apramycin-resistant gene;

cultivating the mutant strain of *Streptomyces* sp. FR-008 so as to produce a cultivated resultant comprising FR-008-V, FR-008-VI, FR-008-VII, FR-008-VIII and FR-008-IX polyketide variants; and separating the cultivated resultant into FR-008-V, FR-008-VI, FR-008-VII, FR-008-VIII or FR-008-IX polyketide variant.

3. A method for producing FR-008-V, FR-008-VI, FR-008-VIII, FR-008-IX, FR-008-X, FR-008-XI or FR-008-XII polyketide variant as shown in FIGS. 5 and 6 the method comprising the steps of:

preparing a mutant strain of *Streptomyces* sp. FR-008 in which the fscMII gene, having the nucleotides 14,953-16,011 of SEQ ID NO: 1, is deleted or inactivated by insertion of a 1.4 kb apramycin-resistant gene;

cultivating the mutant strain of *Streptomyces* sp. FR-008 so as to produce a cultivated resultant comprising FR-008-V, FR-008-VI, FR-008-VIII, FR-008-IX, FR-008-X, FR-008-XI and FR-008-XII polyketide variants; and separating the cultivated resultant into FR-008-V, FR-008-VI, FR-008-VIII, FR-008-IX, FR-008-X, FR-008-XI or FR-008-XII polyketide variant.

4. An isolated FR-008 polyketide variant selected from the group consisting of FR-008-V, FR-008-VI, FR-008-VII, FR-008-VIII, FR-008-IX, FR-008-X, FR-008-XI and FR-008-XII as shown in FIGS. 5 and 6.

* * * * *

UNITED STATES PATENT AND TRADEMARK OFFICE

CERTIFICATE OF CORRECTION

PATENT NO. : 7,595,156 B2
APPLICATION NO. : 10/819386
DATED : September 29, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1132 days.

Signed and Sealed this

Twenty-eighth Day of September, 2010

David J. Kappos

*Director of the United States Patent and Trademark Office*